US006410775B1

(12) United States Patent
Victoria et al.

(10) Patent No.: US 6,410,775 B1
(45) Date of Patent: Jun. 25, 2002

(54) APL IMMUNOREACTIVE PEPTIDES, CONJUGATES THEREOF AND METHODS OF TREATMENT FOR APL ANTIBODY-MEDIATED PATHOLOGIES

(75) Inventors: Edward Jess Victoria, San Diego; David Matthew Marquis, Encinitas; David S. Jones; Lin Yu, both of San Diego, all of CA (US)

(73) Assignee: La Jolla Pharmaceutical Company, San Diego, CA (US)

( * ) Notice: Subject to any disclaimer, the term of this patent is extended or adjusted under 35 U.S.C. 154(b) by 0 days.

(21) Appl. No.: 09/160,513

(22) Filed: Sep. 24, 1998

Related U.S. Application Data

(63) Continuation of application No. 08/760,508, filed on Dec. 5, 1996, now abandoned, which is a continuation-in-part of application No. 08/660,092, filed on Jun. 6, 1996, now Pat. No. 6,207,160, which is a continuation-in-part of application No. 08/482,651, filed on Jun. 7, 1995, now Pat. No. 5,874,409.

(51) Int. Cl.$^7$ ............................................. C07C 321/16

(52) U.S. Cl. ........................ 560/15; 560/142; 560/145

(58) Field of Search ................................. 562/426, 465; 560/9, 147, 15, 142, 145; 558/270, 275

(56) References Cited

U.S. PATENT DOCUMENTS

| | | | |
|---|---|---|---|
| 3,335,165 A | * | 8/1967 | Johnson et al. |
| 4,625,057 A | * | 11/1986 | Springmann et al. |
| 5,082,967 A | * | 1/1992 | Heuckeroth et al. |
| 5,120,748 A | * | 6/1992 | Caprathe et al. |
| 5,162,515 A | | 11/1992 | Conrad et al. |
| 5,268,454 A | | 12/1993 | Barstad et al. |
| 5,276,013 A | | 1/1994 | Conrad et al. |
| 5,344,758 A | | 9/1994 | Krilis et al. |
| 5,393,751 A | * | 2/1995 | Sendai et al. |
| 5,472,883 A | | 12/1995 | Matsuura et al. |
| 5,498,538 A | | 3/1996 | Kay et al. |
| 5,506,110 A | | 4/1996 | Matsuura et al. |
| 5,552,391 A | | 9/1996 | Coutts et al. |

FOREIGN PATENT DOCUMENTS

| | | | |
|---|---|---|---|
| EP | 411409 | * | 11/1968 |
| EP | 0 498 658 A2 | | 8/1992 |
| EP | 0 642 798 A | | 3/1995 |
| GB | 1134314 | * | 11/1968 |
| WO | WO 91 15722 A | | 10/1991 |
| WO | WO 96 40197 A | | 12/1996 |

OTHER PUBLICATIONS

Kunz, Chem. Abst. 1977: 536379.*
Friesen et al, Chem. Abst. 1981: 84487.*
Bliznyuk et al, Chem. Abst. 1984: 138768.*
Laduranty et al, Chem. Abst. 1988: 5540.*
Kitano et al., Chem. Abst. 1995: 716757, 1977.*

Aichele et al., "Peptide–induced T–cell tolerance to prevent autoimmine diabetes in a transgenic mouse model," *Proc. Natl. Acad. Sci. USA* 91:444–448 (1994).
Arvieux et al., "Platelet activating properties of murine monoclonal antibodies to $\beta_2$–glycoprotein 1," *Thromb. Haemostas.* 70:336–341 (1993).
Bakimer et al., "Induction of primary antiphospholipid syndrome in mice by immunization with a human monoclonal anticardiolipin antibody (H–3)," *J. Clin. Invest.* 89:1558–1563 (1992).
Balass et al., "Identification of a hexapeptide that mimics a conformation–dependent binding site of acetylcholine receptor by use of a phage–epitope library," *Proc. Natl. Acad. Sci. USA* 90:10638–10642 (1993).
Barbas III et al., "Assembly of combinatorial antibody libraries on phage surfaces: The gene III site," *Proc. Natl. Acad. Sci. USA* 88:7978–7982 (1991).
Blank et al., "Induction of anti–phospholipid syndrome in naive mice with mouse lupus monoclonal and human polyclonal anti–cardiolipin antibodies," *Proc. Natl. Acad. Sci. USA* 88:3069–3073 (1991).
Brighton et al., "Antiphospholipid antibodies and thrombosis" *Balliere's Clin. Haematol.* 7(3):541–557. (1994).
Cesareni, "Peptide display on filamentoud phage capsids," *FEBS Lett.* 307:66–70 (1992).
Cwirla et al., "Peptides on phage: A vast library of peptides for identifying ligands," *Proc. Natl. Acad. Sci. USA* 87:6378–6382 (1990).
Dower et al., "High efficiency transformation of *E. coli* by high voltage electroporation," *Nucleic Acid Res.* 16:6127–6145 (1988).
Elliott, "Anergy and suppression in B–cell responses," *Scand. J. Immunol.* 36:761–767 (1992).
Galli et al., "Antiocardiolipin antibodies (ACA) directed not to cardiolipin but to a plasma protein cofactor," *Lancet* 1544–1547 (1990).
Gharavi et al., "Induction of antiphospholipid antibodies by immunization with a 15–amino acid peptide spanning the phospholipid binding site of $\beta_2$ glycoprotein I" *J Invest. Med.* 44:69A. (1996).
Haas et al., "Rapid sequencing of viral DNA from filamentous bacteriophage," *BioTechniques* 15:422–423, 426, 428–429 (1993).

(List continued on next page.)

*Primary Examiner*—Mary E. Ceperley
(74) *Attorney, Agent, or Firm*—Morrison & Foerster LLP

(57) ABSTRACT aPL analogs that (a) bind specifically to B cells to which an aPL epitope binds and are disclosed. Optimized analogs lack T cell epitope(s) are useful as conjugates for treating aPL antibody-mediated diseases. Conjugates comprising aPL analogs and nonimmunogenic valency platform molecules are provides as are novel nonimmunogenic valency platform molecules and linkers. Methods of preparing and identifying said analogs, methods of treatment using said analogs, methods and compositions for preparing conjugates of said analogs and diagnostic immunoassays for aPL antibodies are disclosed.

5 Claims, 32 Drawing Sheets

OTHER PUBLICATIONS

Harris et al. (eds.) *Phospholipid–Binding Antibodies,* CRC Press, Boca Raton, FL (1991).

Harris, "Antiphospholipid antibodies," *Brit. J. Haemotol.* 74:1–9 (1990).

Hasselaar et al., "Crossreactivity of antibodies directed against cardiolipin, DNA, endothelial cells and blood platelets," *Thromb. Haemostas.* 63:169–173 (1990).

Holmes et al., "A rapid boiling method for the preparation of bacterial plasmids," *Anal. Biochem.* 144:193–197 (1981).

Hunt et al., "The fifth domain of $\beta_2$glycoprotein 1 contains a phospholipid binding site (cys281–cys288) and a region recognized by anticardiolipin antibodies," *J. Immunol.* 152:653–659 (1994).

Jones et al., "Antigenic specificity of anticardiolipin antibodies appears to depend on a conformation of $\beta_2$–glycoproetin 1," Proc. 5th Intl. Symp. Antiphospholipid Antibodies (Sep. 9–12, 1992) Hyatt Regency San Antonio, Texas (Abstract S5) (4 pages total).

Kandiah et al., "Epitope mapping studies of antiphospholipid antibodies and $\beta_2$–GPI using synthetic peptides" *Lupus* 4(Suppl 1):S7–S11. (1995).

Kato et al., "Amino acid sequence and location of the disulfide bonds in bovine $\beta_2$–glycoprotein 1: The presence of five sushi domains," *Biochem.* 30:11687–11694 (1991).

Lauer et al., "Amino acid sequence of the region of $\beta_2$–glycoprotein 1 (gp1) which mediated binding of autoantibodies to the cardiolipin–gp1 complex in humans," *Immunol.* 80:22–28 (1993).

Luzzago et al., "Mimicking of discontinuous epitopes by phage–displayed peptides, I. Epitope mapping of humam H ferritin using a phage library of constrained peptides," *Gene* 128:51–57 (1993).

McCarty–Farid "Antiophospholipid antibodies in systemic lupus erythematosus and Sjorgen's syndrome" *Current Opinion in Rheumatology* 5:596–603. (1993).

McConathy et al., "Isolation and characterization of other apolipoproteins," *Meth. Enzymol.* 128:296–310 (1986).

McNeil et al., Anti–phospholipid antibodies are directed against a complex antigen that includes a lipid–binding inhibitor of coagulation: $\beta_2$–glycoprotein 1 (apoliprotein H) *Proc. Natl. Acad. Sci.* 87:4120–4124 (1990).

McNeil et al., "Immunology and clinical importance of antiphospholipid antibodies," *Adv. Immunol.* 49:193–280 (1991).

Moos et al., "Recent advances in the generation of molecular diversity," *Ann. Reports Med. Chem.* 28:315–324 (1993).

Nonaka et al., "Molecular cloning of mouse $\beta_2$–glycoprotein 1 and mapping of the gene to chromosome 11," *Genomics* 13:1082–1087 (1992).

Petri et al., "Diagnosis of antiphospholipid antibodies" *Rheumatic Disease Clinics of North America,* 20(2):443–469 (1994).

Posnett et al., "A novel method for producing anti–peptide antibodies," *J. Biol. Chem.* 263:1719–1725 (1988).

Powell, "Peptide stability in drug development: In vitro peptide degradation in plasma and serum," *Ann. Reports Med. Chem.* 28:285–294 (1993).

Reber et al., "Multicenter evaluation of nine commercial kits for the quantitation of anticardiolipin antibodies," *Thrombosis and Haemostat.* 73:444–452 (1995).

Roubey et al., "Comparison of an enzyme–linked immunosorbent assay for antibodies to $\beta_2$–glycoprotein I and a conventional anticardiolipin immunoassay" *Arthritis & Rheumatism* 39(9):1606–1607 (1996).

Sambrook et al., *Molecular Cloning: A Laboratory Manual* 2nd ed., Cold Spring Harbor Laboratory Press, Cold Spring Harbor, New York (1989). The title page and table of contents were included therewith.

Sanger et al., "DNA sequencing with chain–terminating inhibitors," *Proc. Natl. Acad. Sci. USA* 74:5463–5467 (1977).

Scott et al., "Searching for peptide ligands with an epitope library," *Science* 249:386–390 (1990).

Scott, J.K., "Identifying lead peptides from epitope libraries," *Biological Approaches to Rational Drug Design* GN (CRC Press, Weiner, D.B. and Williams, W.V., eds., Boca Raton, FL, 1994), Chapter 1, pp. 1–28. The title page and table of contents were enclosed therewith.

Smith et al., "Libraries of peptides and proteins displayed on filamentous phage," *Meth. Enzymol.* 217:228–257 (1993).

Steinkasserer et al., "Activity, disulphide mapping and structural modelling of the fifth domain of human $\beta_2$–glycoprotein 1," *FEBS Lett.* 313:193–197 (1992).

Steinkasserer et al., "Complete nucleotide and deduced amino acid sequence of human $\beta_2$–glycoprotein 1," *Biochem. J.* 277:387–391 (1991).

Valesini et al., "A new player in the antiphospholipid syndrome: the $\beta_2$–glycoprotein I cofactor" *Autoimmunity* 14:105–110 (1992).

Vermylen et al., "Is the antiphospholipid syndrome caused by antibodies directed against physiologically relevant phospholipid–protein complexes?" *J. Clin. Lab. Med.* 120:10–12 (1992).

Wagenknecht et al., "Changes in $\beta_2$–glycoprotein 1 antigenicity induced by phospholipid binding," *Thromb. Haemostas.* 69:361–365 (1993).

Wang et al., "Epitope specificity of monoclonal anti–$\beta_2$–glycoprotein I antibodies derived from patients with the antiphospholipid syndrome" *J. Immunol.* 155:1629–1636 (1995).

Lenstra et al. (1992). "Isolation of Sequences From a Random–Sequence Expression Library that Mimics Viral Epitopes," *J. Immunol. Methods* 152: 149–157.

* cited by examiner

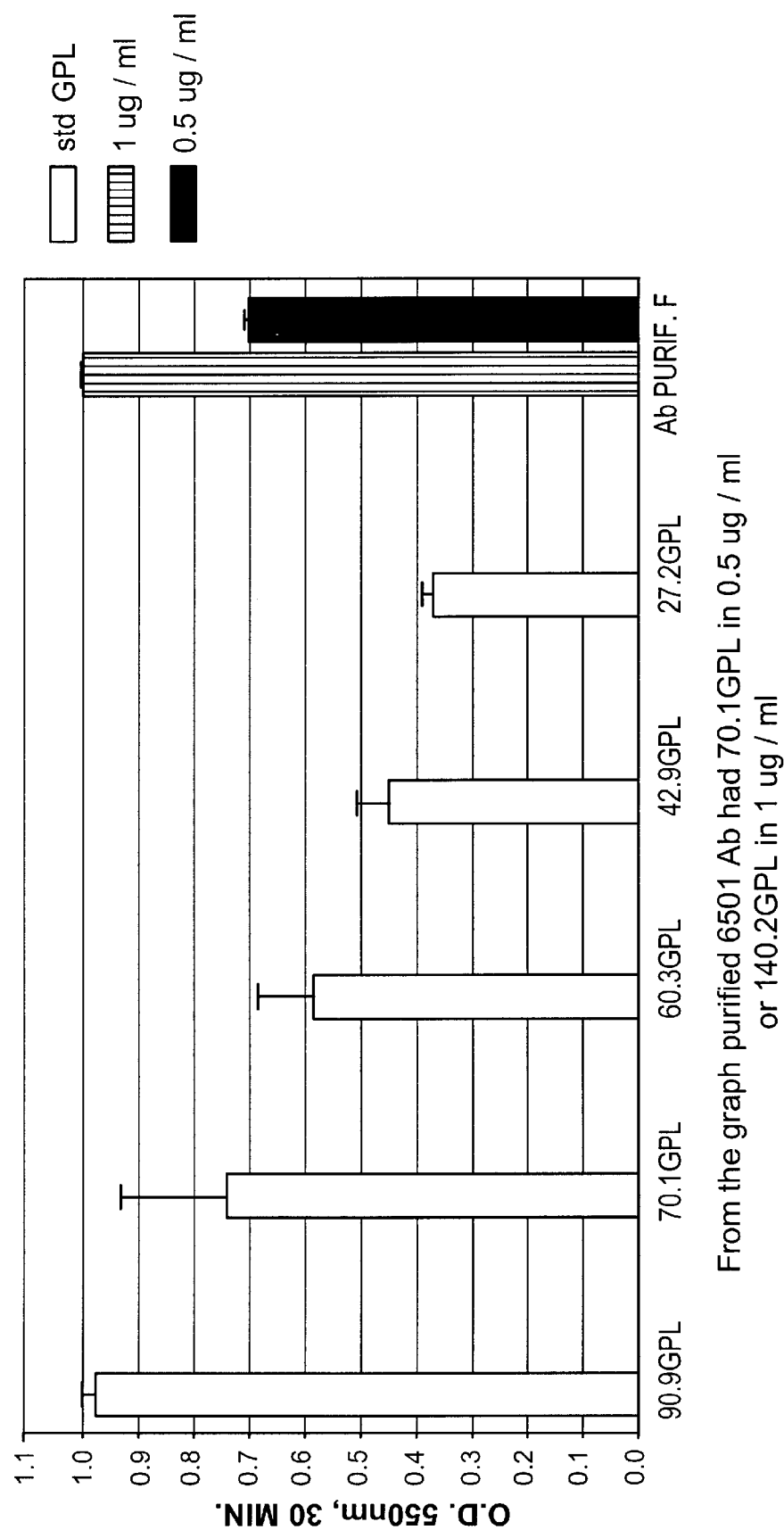

APL IMMUNOREACTIVE PEPTIDES, CONJUGATES THEREOF AND METHODS OF TREATMENT FOR APL ANTIBODY-MEDIATED PATHOLOGIES

CROSS-REFERENCE APPLICATIONS

This application is a continuation application of U.S. Ser. No. 08/760,508, abandoned, filed Dec. 5, 1996, which is a continuation-in-part application of U.S. Ser. No. 08/660, 092, filed Jun. 6, 1996, now U.S. Pat. No. 6,207,160 which is a continuation-in-part of U.S. Ser. No. 08/482,651, filed Jun. 7, 1995, now U.S. Pat. No. 5,874,409.

TECHNICAL FIELD

This invention is in the field of immunology and relates to compositions and methods for treating and diagnosing antiphospholipid (aPL) antibody-mediated pathologies. More specifically, the invention relates to conjugates of chemically-defined nonimmunogenic valency platform molecules and immunospecific analogs of aPL-binding epitopes as well as methods and compositions for producing these conjugates. Optimized analogs lack T cell epitopes. In addition, the invention relates to diagnostic assays for detecting the presence of and quantitating the amount of antiphospholipid antibodies in a biological sample. The invention also relates to a method of utilizing random peptide libraries to identify immunospecific analogs of aPL-binding epitopes.

BACKGROUND OF THE INVENTION

Antiphospholipid antibodies occur in autoimmune diseases such as systemic lupus erythematosus (SLE) and antiphospholipid antibody syndrome (APS) as well as in association with infections and drug therapy. APS is characterized by one or more clinical features such as arterial or venous thrombosis, thrombocytopenia and fetal loss. APS may be primary or it may be associated with other conditions, primarily SLE. (Phospholipid-Binding Antibodies (Harris et al., eds., CRC Press, Boca Raton, Fla., 1991); McNeil et al. Advances in Immunology, Vol. 49, pp. 193–281 (Austen et al., eds., Academic Press, San Diego, Calif., 1991)). Approximately 30–40% of patients with SLE have aPL, however, 50% of patients with aPL antibodies do not have SLE. This 50% may have other autoimmune rheumatic diseases, miscellaneous conditions or they may have been subjected to drug therapy, particularly chlorpromazine. In one study of 70 patients, 26 males and 44 females, with primary APS (PAPS) but no evidence of SLE, the following features were observed: deep venous thrombosis (DVT) in 31; arterial occlusion in 31, particularly stroke or transient ischemia; myocardial infarctions in 15; recurrent fetal loss in 24; thrombocytopenia (TCP) in 32; 10 had a positive Coombs' test; Evans' syndrome in 7; antinuclear antibody (ANA) in 32, but less than 1:160 in 29; and antimitochondrial antibody (AMA) in approximately 24. (McNeil et al., supra.). Estimates vary but in about 5% of all stroke patients, aPL antibodies are thought to be an important contributing factor.

Transient aPL antibodies, such as those detected in a VDRL test, occur during many infections. Approximately 30% of patients possessing persistent aPL antibodies have suffered a thrombic event. The presence of aPL antibodies defines a group of patients within SLE who display a syndrome of clinical features consisting of one or more of thrombosis, TCP, and fetal loss. The risk of this syndrome in SLE overall is around 25%; this risk increases to 40% in the presence of aPL antibodies and decreases to 15% in their absence. Because aPL antibodies were thought to be directed at phospholipids in plasma membranes, it has been postulated that they may exert direct pathogenic effects in vivo by interfering with hemostatic processes that take place on the phospholipid membranes of cells such as platelets or endothelium. In patients with PAPS, the fact that aPL antibodies appear to be the only risk factor present is further evidence that these antibodies have a direct pathogenic role. Induction of PAPS by immunizing mice with human anticardiolipin antibodies is the best evidence yet that aPL antibodies are directly pathogenic (Bakimer et al. 1992 *J. Clin. Invest.* 89:1558–1563; Blank et al. 1991 *Proc. Natl. Acad. Sci.* 88:3069–3073).

Measurement of aPL antibodies in the clinical environment is still an imperfect art. A commercially available set of standard antisera (APL Diagnostics, Inc., Louisville, Ky.) allow generation of a standard curve for comparison of assays performed in various laboratories. A great deal of inconsistency exists, however, between the results obtained at these laboratories regarding the exact GPL and MPL, the unit of measurement for IgG and IgM antiphospholipid antibodies, respectively, ratings for given sera and the levels of GPL and MPL that are categorized as high, medium or low titer. The available commercial kits vary greatly in the values assigned to the commercially available standards (Reber et al. (1995) *Thrombosis and Haemostat.* 73:444–452). In spite of these limitations, there is general agreement that the epitopes recognized by antibodies in APS, PAPS and other aPL antibody-mediated diseases including recurrent stroke and recurrent fetal loss are located in the 5th domain of $\beta_2$-GPI and are exposed to the antibody following binding of $\beta_2$-GPI to cardiolipin.

It is now generally accepted that aPL antibodies recognize an antigenic complex comprised of $\beta_2$-glycoprotein I ($\beta_2$-GPI) and negatively-charged phospholipid, e.g., cardiolipin (McNeil et al. (1990) *Proc. Natl. Acad. Sci.* 87:4120–4124; Galli et al. (1990) *Lancet* 1:1544–1547) (hereinafter "aPL immunogen"). $\beta_2$-GPI is a minor plasma glycoprotein found free and in association with lipoprotein lipids where it is also known as apolipoprotein H (apo H). It consists of five independently folding domains referred to as Sushi or short consensus repeat domains that resemble similar domains in other proteins. $\beta_2$-GPI has been reported to undergo antigenic and conformational changes upon binding phospholipid (Wagenkneckt et al. (1993) *Thromb. Haemostas.* 69:361–365; Jones et al. (1992) *Proc. 5th Intl. Symp. Antiphospholipid Antibodies* (Abstract S5)). The fifth domain contains the putative sites of lipid binding and aPL antibody binding (Hunt J. and S. Krilis, (1994) *J. Immunol* 152:653–659; Lauer et al. (1993) *Immunol.* 80:22–28). The pathological mechanism for aPL is unknown (McNeil et al., supra). Most explanations invoke endothelial cell function or platelet involvement (Haselaar et al. (1990) *Thromb. Haemostas.* 63:169–173). These explanations suggest that following blood vessel endothelial cell injury or platelet activation, the exposure or transbilayer migration of anionic phospholipid to the plasma-exposed surface may lead to $\beta_2$-GPI-binding and trigger aPL antibody formation.

aPL antibodies may be directly prothrombotic by reducing prostacyclin formation (Vermylen, J. and J. Arnout (1992) *J. Clin. Lab. Med.* 120:10–12); by direct interference with the action of coagulation proteins; or by blocking the ability of $\beta_2$-GPI to inhibit the intrinsic blood coagulation pathway, platelet prothrombinase activity, and ADP-mediated platelet aggregation (Arvieux et al. (1993) *Thromb. Haemostas.* 60:336–341).

A major new tool in medicinal chemistry in the search for lead compounds has been the advent of combinatorial libraries providing vast molecular diversity. Molecular diversity may arise from chemical synthesis or from biological systems (Scott., J. K. Rational Drug Design (CRC Press, Weiner, D. B. and W. V. Williams, eds., Boca, Raton, Fla., 1994); Moos et al. (1993) *Ann. Reports Med. Chem.* 28:315–324). By displaying random peptides on the surface of filamentous phage, epitope libraries containing hundreds of millions of clones for probing by clinically significant antibodies have been created (Scott, J. K. and G. P. Smith (1990) *Science* 249:286–390; Cesareni, G. (1992) *FEBS Lett.* 307:66–70). Such phage libraries are prepared by incorporating randomized oligonucleotide sequences into the phage genome, usually the pIII gene, which encode unique peptide sequences on the surface of each phage. Following sequential rounds of affinity purification and amplification, those phage that bind antibody are propagated in *E. coli* and the binding peptides identified by sequencing the corresponding coding region of viral DNA. In most cases, subsequent study will involve corresponding synthetic peptides after establishing their ability to bind antibody. Phage-based libraries have been used to mimic discontinuous epitopes (Luzzago et al. (1993) *Gene* 128:51–57; BaLass et al. (1993) *Proc. Natl. Acad. Sci.* 90:10638–10642). The potential plasma instability of peptide-based drugs has been successfully overcome by N-terminal blocking or by the judicious use of amino acid analogs (Powell, M. F. (1993) *Ann. Reports Med. Chem.* 28:285–293).

At present there is no selective, immunospecific therapy for patients showing high titers of aPL antibodies. In many cases use of drugs such as aspirin, steroids, and warfarin has proven to be largely inadequate (Phospholipid-Binging Antibodies (Harris et al., eds., CRC Press, Boca Raton, Fla., 1991); McNeil et al., supra). Synthetic mimetic peptides, characterized by (i) the inability to activate T cells while (ii) retaining the ability to bind immune B cells, are used to tolerize B cells in an antigen-specific manner. This technology is disclosed in co-owned, co-pending U.S. patent application, Ser. No. 08/118,055, filed Sep. 8, 1993, and U.S. Pat. No. 5,268,454, which are incorporated by reference herein in their entirety. As disclosed in the application and patent cited above, B cell tolerance entails administering such peptides conjugated to multivalent, stable, non-immunogenic valency platforms in order to abrogate antibody production via B cell anergy or clonal deletion after cross-linking surface immunoglobulin.

Although the exact molecular nature of the target epitopes recognized by aPL antibodies is unknown, the use of peptides derived from epitope libraries will allow for the construction of successful tolerogens. B cell tolerogens for the treatment of human systemic lupus erythematosus-related nephritis have also been disclosed in co-owned U.S. Pat. Nos. 5,276,013 and 5,162,515 which are incorporated by reference herein in their entirety.

DISCLOSURE OF THE INVENTION

This invention resides in the discovery of a method for identifying analogs of key epitopes recognized by aPL antibodies in patients suffering from PAPS, APS and other aPL antibody-mediated diseases, such as recurrent stroke and recurrent fetal loss, using random peptide phage libraries.

Accordingly, one aspect of the invention is an improved method for screening random peptide phage libraries in order to identify the peptide sequences which best mimic the epitopes recognized by aPL antibodies. This method comprises the steps of: (a) biopanning the library using methods modified from those known in the art; (b) eliminating very weakly-binding phage by micropanning the phage screened from step (a) by (i) incubating the phage in microplate wells coated with aPL antibody bound to Protein G, (ii) washing the microplate wells to remove unbound phage, (iii) eluting the bound phage, and (iv) infecting a microorganism such as *E. coli* with the eluted phage and counting the number of infected microorganisms by plating on agar; (c) determining the strongest-binding clones recovered in (b) by evaluation via phage-capture ELISA by (i) coating the wells of a microplate with aPL antibody, (ii) incubating the strongest-binding clones identified by micropanning in (b) in the coated wells and washing away unbound phage, (iii) quantitating the number of phage bound to the antibody using an enzyme-conjugated goat anti-phage antibody in a colorimetric ELISA assay and, if several equivalent strongly-binding clones are identified, an additional round of (d) phage-ELISA on the strongest-binding phage-capture-ELISA clone.

In this regard, the invention encompasses a method for identifying analogs of epitopes which specifically bind aPL antibodies isolated from humans suffering from an aPL antibody-mediated disease comprising: (a) preparing phage random peptide libraries; (b) screening said libraries with aPL antibodies to identify aPL mimetic epitopes, wherein said screening comprises (i) screening said libraries by biopanning; (ii) further screening phage isolated by biopanning in (i) by micropanning; and (iii) identifying phage containing aPL antibody high-affinity binding peptides recovered in (ii) by immunoassay.

The invention also encompasses a method of biopanning phage random peptide libraries to identify and isolate peptides which bind to aPL antibody comprising: (a) reacting affinity-purified aPL antibody with phage bearing random peptide inserts; (b) recovering phage bearing random peptide inserts which bind to the aPL antibody; (c) infecting a microorganism with phage recovered in (b); and (d) culturing the infected microorganism in an antibiotic-containing medium in order to isolate the phage.

The invention further encompasses a method of micropanning phage random peptide libraries to identify and isolate peptides having a high binding affinity to aPL antibodies comprising: (a) isolating phage bearing random peptide inserts by biopanning; (b) incubating the phage recovered in step (a) in microplate wells coated with aPL antibody bound to Protein G; (c) washing the microplate wells to remove unbound phage; (d) eluting bound phage; and (e) infecting a microorganism with phage recovered in (d); and (f) culturing the infected microorganism in an antibiotic-containing medium in order to isolate the phage.

The invention also encompasses the above method described wherein the immunoassay is a phage-capture ELISA comprising: (a) incubating phage bearing random peptide inserts isolated by micropanning in the microplate wells coated with aPL antibody; (b) washing away unbound phage;(c) incubating an enzyme-labeled anti-phage antibody to the wells; (d) washing away unbound enzyme-labeled anti-phage antibody; (e) adding a colorimetric substrate; and (f) measuring the absorbance of the substrate to identify high affinity-binding phage.

Also encompassed by the invention is the method described above and further comprising performing an additional phage-capture ELISA assay of the high affinity-binding phage comprising: (a) coating a uniform amount of the phage on microplate wells; (b) incubating aPL antibody in the wells; (c) washing away unbound antibody; (e) incubating an enzyme-labeled anti-aPL antibody with the bound aPL antibody; (f) washing away unbound enzyme-labeled anti-aPL antibody; (g) adding a colorimetric substrate to the wells; and (h) measuring the absorbance of the substrate to measure the relative binding affinity of the phage.

The invention also encompasses the method described above wherein the immunoassay is a colony-blot immunoassay comprising: (a) culturing a microorganism infected with phage bearing random peptide inserts on a nitrocellulose membrane atop an agar-containing culture medium; (b) replicate transferring the microorganism cultured in (a) by blotting the microorganism on a second nitrocellulose membrane atop an agar-containing culture medium; (c) incubating the transferred microorganism;(d) lysing the microorganism; (e) digesting the microorganism with lysozyme; (f) blocking the membrane with a gelatin solution; (g) incubating the membrane with aPL antibody; (h) washing away unbound aPL antibody; (i) incubating a enzyme-labeled anti-aPL antibody with the nitrocellulose membrane; (j) washing away unbound enzyme-labeled anti-aPL antibody; (k) adding a colorimetric substrate; and (l) measuring the absorbance of the substrate to identify high affinity-binding phage.

A method for assaying and ranking, for affinity-binding characteristics, epitopes which specifically bind aPL antibodies isolated from humans suffering from an aPL antibody-mediated disease is also encompassed, the method comprising: (a) coating wells of a microtitration plate with cardiolipin; (b) adding adult bovine or human serum as a source of $\beta_2$-GPI to bind to the cardiolipin and to prevent non-specific binding to the wells of the plate; (c) incubating a solution of monomeric analog and a high-titered aPL antibody for a pre-determined time; (d) adding the aPL antibody/analog mixture to wells of the microtitration plate and incubating for a pre-determined time; (e) washing the wells to wash away unbound aPL antibody; (f) adding anti-human IgG conjugated with a label (e.g., an enzyme) to the wells of the plate and incubating for a pre-determined time; (g) washing the wells to wash away unbound anti-human IgG conjugate; (h) adding a substrate for the labeled conjugate and developing the substrate/label reaction for a pre-determined time;(i) measuring the end-product of the substrate/label reaction to quantitate the amount of aPL antibody bound to the well; (j) calculating the percentage inhibition, if any, of binding of the aPL antibody to determine the affinity of the analog to the aPL antibody.

Another aspect of the invention encompasses a fluorescence polarization peptide binding assay for determining the dissociation constants for peptides that bind to aPL antibodies. This assay detects direct binding of peptides to aPL antibodies.

The invention also encompasses a diagnostic immunoassay for determining the presence of aPL antibody in body fluids taken from subjects suspected of suffering from an aPL antibody-mediated disease comprising contacting a sample of a body fluid with an analog of an epitope which specifically binds aPL antibodies and determining by methods well known in the art whether aPL antibodies are present in the body fluid and, if present, quantitating the amount of aPL antibodies present in the fluid. One such immunoassay comprises: (a) coating wells of a microtitration plate with an analog of an epitope which specifically binds aPL antibodies; (b) washing the wells to wash away unbound analog; (c) adding a test sample of a body fluid to the wells and incubating for a pre-determined time; (d) washing the wells to remove unbound test sample; (e) adding anti-human IgG conjugated with a label to the wells of the plate and incubating for a pre-determined time;(f) washing the wells to wash away unbound anti-human IgG conjugate; (g) adding a substrate for the labeled conjugate and developing the substrate/label reaction for a pre-determined time; (h) measuring the end-product of the substrate/label reaction to determine the presence of anti-aPL antibody in the test sample. A diagnostic immunoassay as described above wherein the immunoassay is quantitative is also encompassed.

The phage-ELISA assay consists of (i) coating a uniform amount of different clones on wells of a microtitration plate followed by (ii) identifying the peptide inserts which most strongly bind aPL antibody by adding antibody to the wells and developing the reaction with an enzyme-labeled anti-human IgG conjugate. The random peptides displayed by the phage which have a high binding affinity to aPL antibody as measured by phage-ELISA, colony blot or phage-capture-ELISA represent the analogs of the aPL-specific epitope. These peptides are then synthesized and ranked for strength of binding using competition assays.

Another aspect of the invention is aPL antibody-binding analogs that bind specifically to B cells to which an aPL epitope binds. Optimized analogs lack T cell epitope(s).

Yet another aspect of the invention is a composition for inducing specific B cell tolerance to an aPL immunogen comprising a conjugate of a nonimmunogenic valency platform molecule and an aPL antibody-binding analog that (a) binds specifically to B cells to which an aPL immunogen binds and (b) lacks T cell epitope(s).

BRIEF DESCRIPTION OF THE DRAWINGS

FIGS. 4 and 5 illustrate that while the ACA-6501/5A12 and ACA-6626/4D3 aPL antibody-binding analogs derived from screening with methods within the instant invention bind preferentially with the screening antibody, a significant degree of crossreactivity was detected.

FIG. 7 shows the activity of affinity-isolated ACA-6501 compared to GPL standard sera.

As used herein "pharmacophore" means the three dimensional orientation and chemical properties of key groups involved in binding of an aPL analog to the antibody target.

Figure 1:
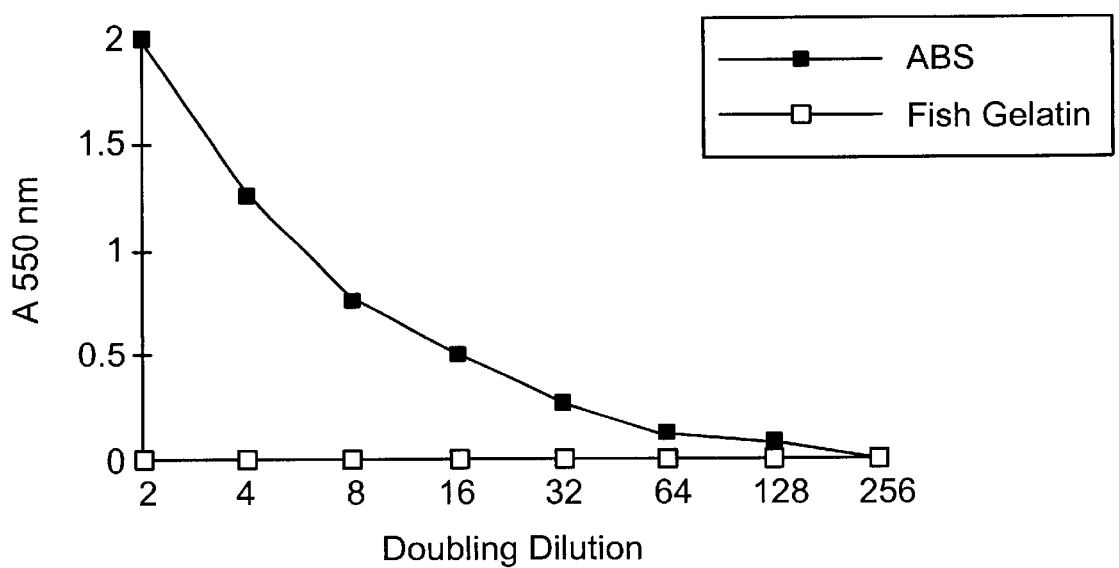
FIG. 1 shows that the substitution of fish gelatin for adult bovine serum abolished all anticardiolipin (ACA) activity in an ELISA assay of a commercial aPL antibody standard. This result supported the findings of McNeil et al., supra, and Galli et al., supra, concerning the importance of $\beta_2$-glycoprotein I ($\beta_2$-GPI) in defining the target epitope(s) of ACA.

B. Identification of aPL Antibody-binding Analogs aPL antibody-binding analogs may be identified by screening candidate molecules to determine whether or not they (a) bind specifically to aPL antibodies and (b) lack T cell epitopes. Specific binding to aPL antibodies may be determined using conventional immunoassays such as the ELISA assays described in the examples below and the presence or absence of T cell epitopes may be determined by conventional T cell activation assays also described in the examples. In this regard, an analog which "binds specifically" to serum antibodies to the immunogen exhibits a reasonable affinity thereto, e.g, $10^7$ $M^{-1}$. The presence or absence of T cell epitopes may be determined using a tritiated thymidine incorporation assay disclosed in Ser. No. 08/118,055. The presence of T cell epitopes can also be determined by measuring secretion of T cell-derived lymphokines by methods well known in the art. Analogs that fail to induce statistically significant incorporation of thymidine above background are deemed to lack T cell epitopes. It will be appreciated that the quantitative amount of thymidine incorporation may vary with the immunogen. Typically a stimulation index below about 2–3, more usually about 1–2, is indicative of a lack of T cell epitopes.

C. Preparation of Conjugates

The aPL antibody-binding analogs are coupled to a non-immunogenic valency platform molecule to prepare the conjugates of the invention. Preferred valency platform molecules are biologically stabilized, i.e., they exhibit an in vivo excretion half-life often of hours to days to months to confer therapeutic efficacy, and are preferably composed of a synthetic single chain of defined composition. They will normally have a molecular weight in the range of about 200 to about 200,000, usually about 200 to about 20,000. Examples of valency platform molecules within the present invention are polymers such as polyethylene glycol (PEG), poly-D-lysine, polyvinyl alcohol and polyvinylpyrrollidone. Preferred polymers are based on polyethylene glycols (PEGs) having a molecular weight of about 200 to about 8,000.

Other valency platform molecules suitable for use within the present invention are the chemically-defined, non-polymeric valency platform molecules disclosed in co-owned, co-pending U.S. patent application Ser. No. 08/152,506, filed Nov. 15, 1993, which is incorporated by reference herein in its entirety. Particularly preferred homogeneous chemically-defined valency platform molecules suitable for use within the present invention are derivatized 2,2'-ethylenedioxydiethylamine (EDDA) and triethylene glycol (TEG).

Additional suitable valency platform molecules include tetraaminobenzene, heptaaminobetacyclodextrin, tetraaminopentaerythritol, 1,4,8,11-tetraazacyclotetradecane (Cyclam) and 1,4,7,10-tetraazacyclododecane (Cyclen).

Conjugation of the aPL antibody-binding analog to the valency platform molecule may be effected in any number of ways, typically involving one or more crosslinking agents and functional groups on the analog and valency platform molecule.

Polypeptide analogs will contain amino acid sidechain moieties containing functional groups such as amino, carboxyl, or sulfhydryl groups that will serve as sites for coupling the analog to the carrier. Residues that have such functional groups may be added to the analog if the analog does not already contain these groups. Such residues may be incorporated by solid phase synthesis techniques or recombinant techniques, both of which are well known in the peptide synthesis arts. In the case of carbohydrate or lipid analogs, functional amino and sulfhydryl groups may be incorporated therein by conventional chemistry. For instance, primary amino groups may be incorporated by reaction with ethylenediamine in the presence of sodium cyanoborohydride and sulfhydryls may be introduced by reaction of cysteamine dihydrochloride followed by reduction with a standard disulfide reducing agent. In a similar fashion, the valency platform molecule may also be derivatized to contain functional groups if it does not already possess appropriate functional groups.

Hydrophilic linkers of variable lengths are useful for connecting peptides or other bioactive molecules to valency platform molecules. Suitable linkers include linear oligomers or polymers of ethyleneglycol. Such linkers include linkers with the formula $R^1S(CH_2CH_2O)_nCH_2CH_2O(CH_2)_mCO_2R^2$ wherein n=0–200, m=0 to 10, for example m=1 or 2 or m=0 to 2, $R^1$=H or a protecting group such as trityl, and $R^2$=H or alkyl or aryl, e.g., 4-nitrophenyl. These linkers are useful in connecting a molecule containing a thiol reactive group such as haloacyl, maleiamide, etc., via a thioether to a second molecule which contains an amino group via an amide bond. These linkers are flexible with regard to the order of attachment, i.e., the thioether can be formed first or last.

The conjugates will normally be formulated for administration by injection (e.g., intraperitoneally, intravenously, subcutaneously, intramuscularly, etc.). Accordingly, they will typically be combined with pharamceutically acceptable vehicles such as saline, Ringer's solution, dextrose solution, and the like. The conjugate will normally constitute about 0.01% to 10% by weight of the formulation. The conjugate is administered to an individual in a "therapeutically effective amount", i.e., an amount sufficient to produce B cell anergy to the involved immunogen and effect prophylaxis, improvement or elimination of the antibody-mediated condition being addressed. The particular dosage regimen, i.e., dose, timing and repetition, will depend on the particular individual and that individual's medical history. Normally, a dose of about 1 μg to about 100 mg conjugate/kg body weight, preferably about 100 μg to about 10 mg/kg body weight, will be given weekly. Other appropriate dosing schedules would be as frequent as daily or 3 doses per week, or one dose per week, or one dose every two to four weeks, or one dose on a monthly or less frequent schedule depending on the individual or the disease state. Repetitive administrations, normally timed according to B cell turnover rates, may be required to achieve and/or maintain a state of humoral anergy. Such repetitive administrations will typically involve treatments of about 1 μg to about 10 mg/kg body weight or higher every 30 to 60 days, or sooner, if an increase in antibody titer is detected. Alternatively, sustained continuous release formulations of the conjugates may be indicated for some pathologies. Various formulations and devices for achieving sustained release are known in the art.

Anti-helper T cell treatments may be administered together with the conjugates. Such treatments usually employ agents that suppress T cells such as steroids or cyclosporin.

D. Nature of the Antigen for aPL Antibodies

Initial studies on aPL antibodies by the inventors coincided with the publication of reports questioning the nature of the antigenic site recognized by these antibodies. Initially these antibodies were thought to recognize the cardiolipin molecule much like those antibodies detected in a VDRL test. As shown in FIG. 1, substitution of fish gelatin for adult bovine serum in the anticardiolipin antibody (ACA) solid phase ELISA essentially abolished all ACA activity of an antibody preparation obtained commercially as an ACA standard. This finding indicated the ACA antibodies recognized a determinant on a serum protein as proposed by McNeil et al., supra and Galli et al., supra, rather than cardiolipin itself. This protein was shown by these authors to be $\beta_2$-GPI and, thus, the terms "ACA" or "anti-cardiolipin antibodies" are really misnomers but are still used today to refer to these antibodies.

The majority of autoimmune, IgG aPL antibodies recognize determinants on the $\beta_2$-GPI molecule. These epitopes may be formed or exposed on $\beta_2$-GPI only upon its binding to cardiolipin (a neo epitope). Alternatively, the epitope on $\beta_2$-GPI may exist in a single copy per $\beta_2$-GPI molecule and may have low affinity for aPL antibodies. Sufficient avidity to maintain an antibody-antigen interaction might be reached only with the alignment of two of these sites on adjacent $\beta_2$-GPI molecules by their binding to cardiolipin.

Additional insight into the $\beta_2$-GPI epitope structure has been gained by nuclear magnetic resonance (NMP) analygig of aPL analogs within the present invention which mimic the native epitope(s) of $\beta_2$-GPI. For, example, a comparison of the NMR solution structure of two peptide aPL analogs that are highly cross-reactive with aPL antibodies showed that both peptides have turns at approximately the same positions in the peptide sequence (see FIGS. 18 and 19).

E. ACA ELISA

The necessity of large-scale testing in connection with GPL scoring of clinical samples and chromatographic purifications of research antibodies and $\beta_2$-GPI led to the development of an ELISA assay for aPL antibodies with performance in close agreement with a commercial kit and similar to the design found to have the best reproducibility (Reber et al., supra). A modified ACA ELISA has also been performed wherein $\beta_2$-GPI bound directly to certain microplates is used to bind aPL IgG directly in the absence of any cardiolipin first added to the microplate wells. (See, Roubey et al. (1996) *Arthritis & Rheumatism* 39;1606–1607R. A. S. Roubey (1996) *Arthritis & Rheumatism* 39:1444–1454).

F. Immunoaffinity Purification of aPL Antibodies

In order to isolate the aPL antibodies, multilamellar, cardiolipin-containing dispersions (liposomes; also containing cholesterol and dicetylphosphate) are incubated with aPL plasma (or serum). These liposomes are pelleted from the serum by centrifugation. After washing, the liposome mixture is disrupted by 2% octylglucoside detergent and applied to a protein A-agarose column. Following extensive washings to first remove lipids and then to remove non-IgG components, IgG aPL antibody is eluted from protein A with mild acid, neutralized, buffer-exchanged, and tested in the ACA ELISA. This procedure yields aPL antibody enriched up to 10,000-fold that is devoid of any contaminating $\beta_2$-GPI as shown by western blotting with rabbit IgG anti-human $\beta_2$-GPI antisera. An additional affinity-purification step is performed by chromatography of the affinity-purified antibody on solid phase $\beta_2$-GPI. This second affinity-purification step is recommended as a result of the new awareness regarding the greater clinical relevance of aPL antibodies that directly bind to $\beta_2$-GPI. It also serves to further ensure a final preparation devoid of contaminants, in particular $\beta_2$-GPI.

G. Construction of Filamentous Phage Random Peptide Libraries

Eleven different fUSE 5 filamentous phage random peptide libraries on the p-III protein (five copies of p-III with peptide per phage) are constructed. These libraries provide a vast array of shapes and structures for the discovery of mimetic epitopes. Four libraries, designated "x" libraries, have peptide inserts that are 8, 10, 12, and 15 residues in length, respectively, and are flanked by proline residues on both the amino and carboxyl ends. The purpose of these proline residues is to disrupt any contribution to secondary structure that might arise from the native p-III protein and to project the insert into the solvent. The "y'" libraries contain cysteine-bounded inserts that are 6, 7, 8, 9, 11, and 13 amino acids long. The "y" library is the same as the "y'" library except that it lacks the 6 and 8 amino acid inserts. These peptide inserts for both "y" and "y'" libraries are flanked by cysteine residues at both the amino and carboxyl ends to form cyclic, more rigid structures. Proline residues are incorporated outside these cysteine residues for reasons similar to those for the "x" libraries above. The "x," "y'", and "y" libraries are located five residues from the amino terminus of the native p-III protein. The "z" library consists of random eight amino acid inserts located at the amino terminus of the p-III protein and do not contain any flanking proline or cysteine residues. A combination of the "x," "y'" and "z" libraries represents eleven different libraries each with approximately one hundred million different peptide inserts.

These libraries are constructed by incorporation of random oligonucleotide sequences of the length appropriate to give the desired length insert into the p-III gene of fUSE 5 using standard molecular biology techniques. Following restriction endonuclease digestion of the fUSE 5 DNA, an excess of kinased oligonucleotides provided as gapped duplexes is added and ligated. The DNA is then electroporated into *E. coli* and inserts are selected by culturing in tetracycline-containing media. The phage from this culture (which contain the peptide insert) are isolated from the supernatant, washed and resuspended in buffer. Typically libraries are shown to have $7 \times 10^8$ independent clones at $8 \times 10^{12}$ transducing units per mL.

H. Phage-screening Methodology

The essence of screening phage display peptide libraries lies in the ability to collapse billions of potential candidate phage to a relative few with outstanding properties. The original screening protocols recommended by Scott, J. K. and G. P. Smith, (1990) *Science* 249:315–324 are significantly modified to facilitate the selection of the best epitopes for various aPL antibodies. These procedures are designed to apply greater stringency of selection as the screen progressed until a point is reached where a useful number of clones representing the best sequences can be thoroughly investigated. With some antibodies, the library does not appear to have sequences which bind very tightly and if a method with a high degree of stringency is applied to the screen, no clones survive that are specific. On the other hand, the library frequently yields many clones that represent good analogs of the antigen and it is necessary to employ a method with a high degree of stringency to identify the best epitopes. For that reason, assays were developed with varying degrees of stringency in order to identify the best epitopes from an epitope library screen. The assays are listed here in order of increasing stringency: Biopanning<Micropanning<Phage-Capture ELISA<Phage ELISA=Colony Blot=Peptide ELISA.

(i) Biopanning

"Biopanning" describes the technique wherein affinity-purified aPL antibody and phage bearing random peptide inserts are allowed to mix, following which antibody-specific recovery captures the bound phage. The phage confer tetracycline resistance to *E. coli* that are propagated in a tetracycline-containing medium and then isolated. Multiple rounds of biopanning enrich the number of immunospecific phage in a sample. Phage are always recovered at the end of three to five rounds of selection but may represent only sequences that are nonspecifically bound at low affinities for the selecting antibodies. A method for further evaluating these phage (micropanning) is required.

(ii) Micropanning

An estimation of the relative strength of binding of the phage to the aPL antibody can be determined by "micropanning." Micropanning is carried out following three or more rounds of biopanning and uses the same antibody as employed in the biopanning method. The method consists of dilution of the phage from the last round of biopanning and analyzing fifty or more of these clones by micropanning. Micropanning is accomplished by growing each clone to a similar density and then incubating dilute phage at an optimal single concentration in microtitration wells previously coated with a constant amount of antibody. The optimal single concentration of phage is that concentration most likely to reveal the widest range of micropanning scores (from 0 to 4+) and, thus, permit the greatest discrimination among the clones being tested. It is based on the micropanning behavior of six randomly selected clones where the score is determined at each of several concentrations of phage obtained by serial dilution. Following the incubation with antibody, the unbound phage are washed away and the amount of bound phage is used as an indication of the affinity of the phage insert for the antibody. The amount of bound phage is determined by elution with mild acid followed by neutralization and infection of *E. coli*. The number of infected *E. coli* are then quantitated by plating the microorganisms on agar plates containing tetracycline and then determining colony densities achieved by each clone.

(iii) Phage-Capture ELISA

The phage-capture ELISA test was developed to provide an intermediate level assay to bridge the gap between the relatively low stringency of the micropanning assay and the high stringency of the phage- or peptide-ELISA assays. Preliminary studies show that some antibody preparations give too many positive clones by micropanning but none by phage-ELISA or peptide-ELISA. The limitation of the phage-ELISA described below is that only five copies of p-III are located on each phage and even with a large number of phage coated on a well, few copies of the insert are represented and detection requires that the antibody have a very high affinity for the insert. With the phage-capture ELISA, the signal is amplified many times which facilitates the detection of lower affinity, stable interactions between the antibody and the insert.

The phage-capture ELISA consists of the following steps. Microtitration wells are coated with aPL antibody and phage clones are added as in the micropanning assay. Unbound phage are washed away and the amount of bound phage is quantitated using an enzyme-conjugated goat antiserum which binds the major coat protein of the phage. Phage screened using phage-capture ELISA react with many aPL antibodies and provide a strong signal in subsequent ELISA assays. This intermediate level of sensitivity allows for greater efficiency in the peptide synthesis effort since few micropanning-positive phage are phage-capture ELISA positive. As a result, peptides synthesized from positive phage-capture ELISA phage are generally immunoreactive.

(iv) Phage-ELISA

This method of selecting phage requires very tight binding of the insert to the screening antibody. Phage are directly coated onto wells of a microtitration plate and incubated with the screening antibody. Following washes to remove unbound antibody, an anti-human IgG alkaline phosphatase conjugate is added to bind any aPL antibodies bound to the phage. APL antibodies are then detected by adding a colorimetric substrate to the well which will react with alkaline phosphatase according to methods well known in the art.

(v) Colony Blot

This assay allows large-scale colony screening of *E. coli* infected by biopanned phage. This procedure is an alternative to phage-ELISA for identifying immunoreactive clones and exhibits a comparable level of sensitivity without requiring culturing of individual phage clones prior to testing. In this assay, *E. coli* infected with phage from a round of biopanning are spread on a large diameter nitrocellulose (NC) membrane and cultured overnight on the surface of an agar plate containing tetracycline (Barbas et al. (1991) *Proc. Natl. Acad. Sci. USA* 88:7978–7982). Each colony results from infection by phage containing identical sequences. Several replicate transfer blots on NC are made using this NC "master" and are allowed to grow on the surface of an agar plate. Following the chemical and enzymatic disruption of phage-infected colonies on the blots, the phage may be probed by the techniques commonly used in Western blotting, i.e., staining or immunoblotting. Blots that have been blocked may be incubated with the screening aPL antibody. Following washes to remove unbound antibody, an anti-human IgG horseradish peroxidase conjugate is added to bind to any aPL-antibody that is bound to phage. The addition of a colorimetric substrate allows one to localize the discrete colonies in the master plate which represent immunospecific phage that may be cloned for further study.

(vi) Peptide-ELISA

Following DNA sequencing to determine the peptide insert sequences of the best-reacting phage in the assays described above, the corresponding peptides are made using standard Fmoc peptide chemistry as is well known in the art. For the peptide-ELISA assay, the peptides can be made, for example, as branched tetravalent molecules, i.e., each molecule has four copies of the insert. Such a molecule can coat the well of a microtitration plate and still have epitopes exposed to the solution to allow binding by an antibody. The tetravalent peptides are synthesized by incorporating lysines as branch points at the first two couplings analogous to the methods used for Multiple Antigenic Peptides (MAPS) (Posnett et al. (1988) *J. Biol. Chem.* 263:1719–1725). A spacer consisting of glycine-serine-glycine-serine (SEQ ID NO:3) is added on each arm after the lysines and then the insert, including the framework amino acids found in the phage, proline-glycine at the carboxyl terminus and alanine-glycine-proline at the amino terminus. All amino acids in this synthesis are added one at a time using standard Fmoc methods.

These peptides are then assayed by ELISA which is carried out by coating the peptides on microtitration wells and then assaying their reactivity with aPL antibody in a standard ELISA format. In practice, the peptides usually bind very strongly to the original screening antibody and show some cross-reactivity with other aPL antibodies. Controls of non-aPL antibodies are included to eliminate non-specific binding peptides.

(vii) Competitive Binding Peptide-ELISA

Once ELISA-positive peptides are identified, it is necessary to quantitate their relative binding affinity to the aPL antibodies and to determine whether or not two peptides bind the same population of antibodies in a given patient serum via a peptide-competition ELISA assay. In this assay, various monomeric peptides compete with tetravalent peptides coated on a microtitration plate well. To perform the assay, the peptides to be evaluated are synthesized as monomers, i.e., without the lysine branches employed in the synthesis of the tetravalent peptides, using standard Fmoc chemistry. The monomeric peptides are then purified and dissolved at known concentrations. Wells of a microtitration plate are coated with a tetravalent peptide known to bind to the aPL antibody. Serial dilutions of the monomeric peptides are incubated with a constant dilution of the aPL antibody. The dilution of the aPL antibody was previously determined by titering the antibody against the tetravalent peptide and selecting a dilution on the downslope of the titration curve. After incubating the antibody and monomeric peptides for one hour, the antibody/peptide solutions are added to the microtitration wells and a standard colorimetric ELISA is performed. The concentration of each monomeric peptide that decreases binding of the aPL antibody with the tetravalent peptide is determined by plotting the colorimetric readings obtained for each well. The 50% inhibition point is used as the measure of the relative strength of binding for the monomeric peptides.

A variation of this assay uses microtitration plates coated with human $\beta_2$-glycoprotein I/cardiolipin ($\beta_2$-GPI/CL) instead of tetravalent peptide and tests the ability of monomeric peptides to block the binding of aPL antibody to the epitope(s) on $\beta_2$-GPI/CL. In this assay, IgG-depleted human serum at an optimized concentration is used as a source of $\beta_2$-GPI. The monomeric peptides at several concentrations are incubated with an optimized concentration of aPL antibody in a manner analogous to the assay which employs tetravalent peptide as a plate substrate. Following the incubation of aPL/peptide in ($\beta_2$-GPI/CL) plates, antibody binding and the peptide concentration required for 50% inhibition is determined at half-maximal absorbance as in the tetravalent assay.

An additional variation of this assay tests the ability of monomeric peptides to block the binding of aPL antibody to $\beta_2$-GPI coated directly on the wells of Nunc Maxisorp microtitration plates. In this variation, the use of cardiolipin is omitted and instead of fish gelatin, the reagent diluent and blocker used is nonfat milk/Tween.

(viii) Fluorescence Polarization Peptide Binding Assay

This assay detects direct binding of the peptide to aPL antibody. Since aPL antibodies bind to $\beta_2$-GPI (the antigen), the ELISA competitive inhibition assay can show inhibition due to binding to $\beta_2$-GPI as well inhibition due to binding of the peptide to the aPL antibody. Because binding to antibodies is required in order for the peptide to function as a Toleragen, it is essential to establish that a peptide can directly bind to an aPL antibody. This assay is used to determine the dissociation constants for peptides that bind to two aPL antibodies, ACA-6501 and ACA-6701. While the ELISA assay is useful for high throughput screening because it requires less antibody than the Fluorescence Polarization assay, however, ELISA-positive peptides should be further evaluated by the Fluorescence Polarization assay to determine whether they are capable of directly binding with aPL antibody.

(ix) Evaluation of amino acid contributions to binding by substitution and deletion synthesis The desired epitope for tolerance induction should have as strong an interaction with as many of the aPL antibodies as possible but not contain any unnecessary residues. In order to deduce the minimum constitution of an epitope, analogs of each peptide are made (i) that lack given residues, for example, the framework residues at the carboxyl and/or amino termini are deleted, or (ii) in which amino acid substitutions have been made which differ from sequences found in the epitope library screen. These amino acid substitutions may be either natural, e.g., isoleucine for leucine, or unnatural, e.g., alpha methyl proline for proline. The effect of these deletions and/or substitutions are then measured via peptide-competition ELISA.

(x) Grouping of aPL Sera Specificities by Mutagenesis of the 5th domain of $\beta_2$-GPI For a Tolerogen to be generally effective, it must bind a major portion of the aPL antibodies in the majority of patients. It is important to determine if several antibodies from different patients bind identical residues within the eighty-four amino acid 5th domain of $\beta_2$-GPI which has been suggested by others to contain the target epitope. If several antibodies bind identical residues, a single mimotope derived from the structural data of the peptides can be constructed which will react with all the antibodies. On the other hand, if the antibodies bind to different residues, a unique tolerogen would be required for each antibody. Site-directed mutagenesis was performed to identify if key residues involved in aPL antibody binding reside in the 5th domain of $\beta_2$-GPI. The resulting mutant $\beta_2$-GPIs were assayed for reactivity with several aPL antibodies. The results were inconclusive. A fusion protein comprising the 5th domain of $\beta_2$-GPI and glutathionine S transferase (GST) was obtained from A. Steinkasserer and expressed in *E. coli* (Steinkasserer et al. (1992) *FEBS Lett.* 313:193–197). This fusion protein was successfully substituted for native $\beta_2$-GPI in the ACA ELISA. Amino acid substitutions are engineered using standard site-directed mutagenesis.

I. Isolation of Synthetic aPL Epitopes

Antibody ACA-6501, from a patient with a GPL score of 151 (high titer) and a history of recurrent stroke, fetal loss, lupus and three aortic valve replacements was immunoaffinity purified on cardiolipin liposomes. The antibody was used in four separate phage library screens, using the xy, the xyz, the xy'z, and a special pro/cys-bounded 7-mer library where, based on the previous screens, Arg was fixed at the seventh position. As shown in Table 1, 36 sequences were obtained in phage that micropanned (out of 140 tested). These appear quite homologous and the conserved DR residues at positions 6 and 7 are notably striking. The consensus sequence is CLLLAPDRC (SEQ ID NO:9). Despite this homology, only seven phage (see Table 2) were positive after phage-ELISA colorimetric testing. Screening the xy'z phage with affinity purified ACA-6626 (from a patient with a high, but lower than ACA-6501, titer) yielded five unique sequences that were phage-ELISA tested. None were color positive but two were positive when the ELISA immunoconjugate was developed with a chemiluminescent substrate. The sequence motif associated with ACA-6626 appears related but is different from that seen with ACA-6501 (see Table 3). Both antibodies preferred the cys-bounded (probably cyclized and constrained) epitopes over the open pro-bounded sequences.

TABLE 1

ACA-6501 Phage Library Sequences

| Clone | Sequence | Clone | Sequence |
|---|---|---|---|
| xy Library | | | |
| 2101 (SEQ ID NO: 10) | CNILVLDRC | | |
| xyz Library | | | |
| 5A12 (SEQ ID NO: 11) | CLILAPDRC | 3C10 (SEQ ID NO: 17) | CILLAKNRC |
| 2D7 (SEQ ID NO: 12) | CLLLAPDRC | 3C5 (SEQ ID NO: 18) | CIVLVPDRC |
| 3B6 (SEQ ID NO: 13) | CLVLALDRC | 2F4 (SEQ ID NO: 19) | CLVIALDRC |
| 3E4 (SEQ ID NO: 14) | CLFVALDRC | 5B1 (SEQ ID NO: 20) | CWFRSQSSC |
| 3E7 (SEQ ID NO: 15) | CILLAHDRC | 3E11 (SEQ ID NO: 21) | CSPILRGNC |
| 2H1 (SEQ ID NO: 16) | CIILAPGRC | 3E8 (SEQ ID NO: 22) | CHKFFWLTC |
| xy'z Library | | | |
| 2A10 (SEQ ID NO: 23) | CTILAPDRC | 2D12 (SEQ ID NO: 28) | CLVLAADRC |
| 2G12 (SEQ ID NO: 24) | CLLITPDRC | 3B10 (SEQ ID NO: 29) | CLLLAPDRC |
| 2G11 (SEQ ID NO: 25) | CLLITHDRC | 3F2 (SEQ ID NO: 30) | CFFHFDHSC |
| 2F10 (SEQ ID NO: 26) | CNILVLDRC | 2D3 (SEQ ID NO: 31) | CPLHTHHTC |
| 2E3 (SEQ ID NO: 27) | CPLITHDRC | | |
| Custom (X)₆R Library | | | |
| G11 (SEQ ID NO: 32) | CTILTPDRC | 1A4 (SEQ ID NO: 40) | CNLLALDRC |
| 2H5 (SEQ ID NO: 33) | CTILTPDRC | 2H6 (SEQ ID NO: 41) | CNLLAIDRC |
| 2H2 (SEQ ID NO: 34) | CTILTLDRC | 1C3 (SEQ ID NO: 42) | CLLLAIDRC |
| 2H10 (SEQ ID NO: 35) | CTLLTPDRC | 1D10 (SEQ ID NO: 43) | CTIITQDRC |
| 2E10 (SEQ ID NO: 36) | CIQLTPDRC | 2H4 (SEQ ID NO: 44) | CNIITRDRC |
| 1B7 (SEQ ID NO: 37) | CHLLTPDRC | 2G12 (SEQ ID NO: 45) | CILHAAHRC |
| 2H1 (SEQ ID NO: 38) | CLILTPDRC | 1A9 (SEQ ID NO: 46) | CSSKSYWRC |
| 2H12 (SEQ ID NO: 39) | CSILAPDRC | | |
| xy'z Library, Colony Blot Screening Assay | | | |
| CB2 (SEQ ID NO: 218) | CILLARDRC | | |

TABLE 2

ACA-6501 Colorimetric ELISA-positive Phage

| Clone | Sequence | Clone | Sequence |
|---|---|---|---|
| 5A12 (SEQ ID NO: 11) | CLILAPDRC | 3B6 (SEQ ID NO: 13) | CLVLALDRC |
| 2H1 (SEQ ID NO: 38) | CLILTPDRC | 2G11 (SEQ ID NO: 32) | CTILTPDRC |
| 3B10 (SEQ ID NO: 29) | CLLLAPDRC | *3E7 (SEQ ID NO: 15) | CILLAHDRC |
| 2H2 (SEQ ID NO: 34) | CTILTLDRC | | |

*Corresponds to consensus or average sequence

TABLE 3

ACA-6626 xy'z Phage Library Sequences

| Clone | Sequence | Clone | Sequence |
|---|---|---|---|
| 4B11 (SEQ ID NO: 47) | CGNAADARC | 4G7 (SEQ ID NO: 50) | CTNLTDSRC |
| 4D3 (SEQ ID NO: 48) | CTNWADPRC | 4A2 (SEQ ID NO: 51) | CGNPTDVRC |
| 4C7 (SEQ ID NO: 49) | CGNIADPRC | | |

ACA-6644 is another high-titered aPL antibody that was used to screen the pooled p-III phage libraries according to methods described herein. The following sequences were discovered:

```
ACA-6644/CBc      GILLNEFA
                  (SEQ ID NO: 52)
ACA-6644/CBd      GILTIDNL
                  (SEQ ID NO: 53)
ACA-6644/CBf      GILALDYV
                  (SEQ ID NO: 54)
```

These sequences all were derived from the component "z" epitope library that lacks phage framework residues at the N-terminus. When synthesized as peptides the sequences were immunoreactive with several ACA sera including ACA-6644 and ACA-6501. Analysis revealed unsuspected homologies with the sequences previously obtained with ACA-6501 as illustrated in Table 4.

TABLE 4

```
ACA-6644/CBd      GILTIDNL
                  (SEQ ID NO: 53)
ACA-6501/2H2      CTILTLDRC
                  (SEQ ID NO: 34)
ACA-6644/CBf      GILALDYV
                  (SEQ ID NO: 54)
ACA-6501/2F10     CNILVLDRC
                  (SEQ ID NO: 10)
ACA-6644/CBc      GILLNEFA
                  (SEQ ID NO: 52)
ACA-6501/1D10     CTIITODRC
                  (SEQ ID NO: 43)
```

The convergent sequence homology from two very dissimilar source libraries screened by these two aPL antibodies suggests that the sequences may mimic a major, perhaps immunodominant, region in the native target antigen.

Screening of the p-III libraries with ACA-6701 yielded two unique sequences with a high degree of internal homology but unlike others previously obtained with other aPL antibody. The sequences are as shown:

ACA-6701/3B1 LSDPGYVRNIFH (SEQ ID NO:55)
ACA-6701/3E1 LTDPRYTRDISNFTD (SEQ ID NO:56)

As resin-bound peptides, the sequences were strongly immunoreactive with the parent serum (ACA-6701) but were minimally cross-reactive with other aPL antibodies.

Continued screening of random pill phage libraries with affinity purified ACA antibody resulted in the discovery of a peptide that displayed significant crossreactivity with all nine affinity purified ACA antibodies against which it was initially tested. The performance of this peptide as well as four others is shown in Table 5. Peptide sequences for all five peptides immediately follow the table. All were tested using the competitive binding peptide ACA ELISA using CL/β2-GPI plates as described herein.

TABLE 5

Percent Inhibition of AffACA by Peptide Monomers

| Peptide | 6626 | 6638 | 6641 | 6644 | 6701 | 7004 | 7005 | 6903 | 6501 | Ave. |
|---|---|---|---|---|---|---|---|---|---|---|
| 6641/3G3 1 mg/mL | 100 | 100 | 93 | 100 | 100 | 100 | 95 | 100 | 86 | 97 |
| 6501/3B10 1 mg/mL | 76 | 87 | 52 | 55 | 51 | 87 | 47 | 69 | 60 | 65 |
| 6626/4C7 1 mg/mL | 88 | 96 | 45 | 45 | 69 | 99 | 54 | 77 | 39 | 68 |
| 6701/3B1 1 mg/mL | 43 | 65 | 43 | 37 | 96 | 72 | 23 | 51 | 41 | 52 |
| 6644/CBf 200µg/mL | 37 | 60 | 28 | 18 | 22 | 54 | 57 | 43 | 37 | 39 |

| Peptide | Sequence |
|---|---|
| ACA-6641/3G3: | AGP CLGVLGKLC PG (SEQ ID NO: 57) |
| ACA-6501/3B10: | AGP CLLLAPDRC PG (SEQ ID NO: 219) |
| ACA-6626/4C7: | AGP DGNIADPRC PG (SEQ ID NO: 220) |
| ACA-6701/3B1: | AGP LSDPGYVRNIFH PG (SEQ ID NO: 221) |
| ACA-6444/CBf: | GILALDYV GG (SEQ ID NO: 222) |

Subsequent testing determined that this peptide, ACA-6641/3G3 having the sequence AGP-CLGVLGKLC-PG (LJP 688)(SEQ ID NO:58) was cross-reactive with a number of ACA antiser. Chemical optimization of this peptide was pursued by truncation, systematic amino acid substitution, and non-disulfide cyclization studies.

The motifs of several peptides selected from the random phage library screening is set forth below.

TABLE 6

| ACA Antibody | Phage Insert Sequence |
|---|---|
| 6501 (SEQ ID NO:29) | CLLLAPDRC (3B10) |
| 6626 (SEQ ID NO: 48) | CTNWADPRC |
| 6641 (SEQ ID NO: 58) | CLGVLGKLC (3G3) |
| 6644 (SEQ ID NO: 54) | GILALDYV |
| 6701 (SEQ ID NO: 56) | LTDPRYTRDISNFTD |
| 6707 (SEQ ID NO: 225) | CAHPDWDRC |

Figure 2:
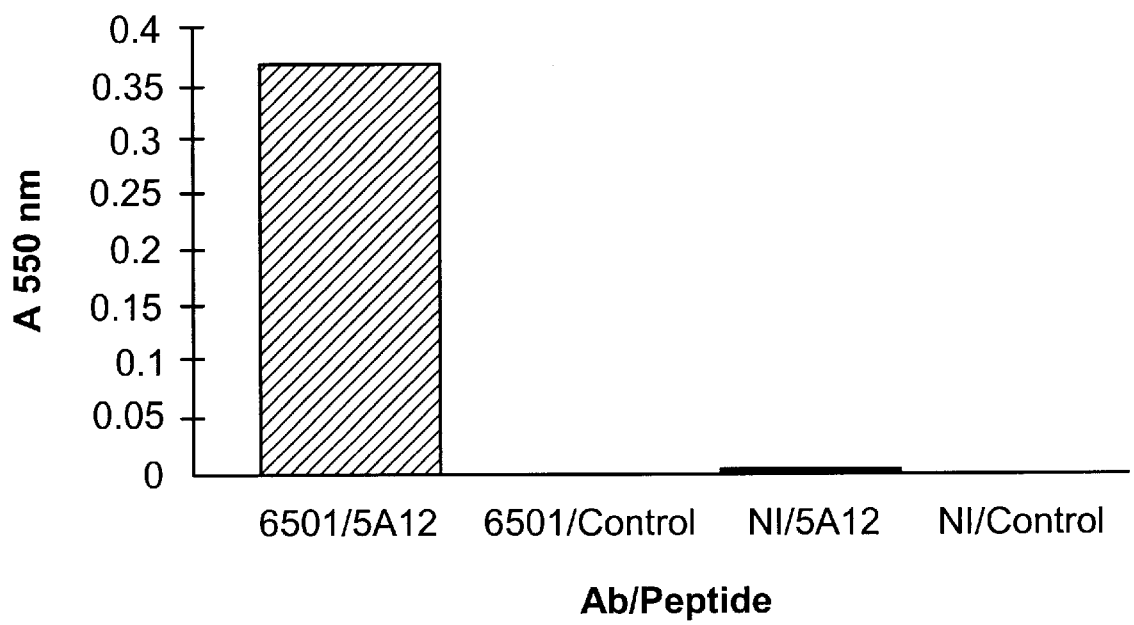
FIG. 2 shows that resin-bound analog 5A12 immunospecifically binds to affinity-purified IgG designated ACA-6501.

J. Immunoreactivity of aPL-related Peptides with Affinity Purified IgG aPL Antibody Phage sequences obtained with affinity-purified ACA-6501 and found to be phage-ELISA-positive were synthesized on a solid support recently developed for synthetic peptide libraries. This support, a Rapp resin, has a high peptide density and uses a hydrophilic polyethylene glycol spacer before the first amino acid is coupled. The synthesis resulted in resin-bound peptide that was ideally suited for antibody binding studies. As shown in FIG. 2, peptide 5A12

(sequence CLILAPDRC)(SEQ ID NO:11) dramatically outperformed an unrelated control peptide while not significantly binding normal IgG. Similar results were obtained with the other phage-ELISA-positive peptides tested. In the experiment shown, resin peptide-bound affinity-purified ACA-6501 aPL antibody was detected by an immunoconjugate color reaction.

K. aPL Serum Antibody Reactivity with Synthetic Peptides

Figure 3:
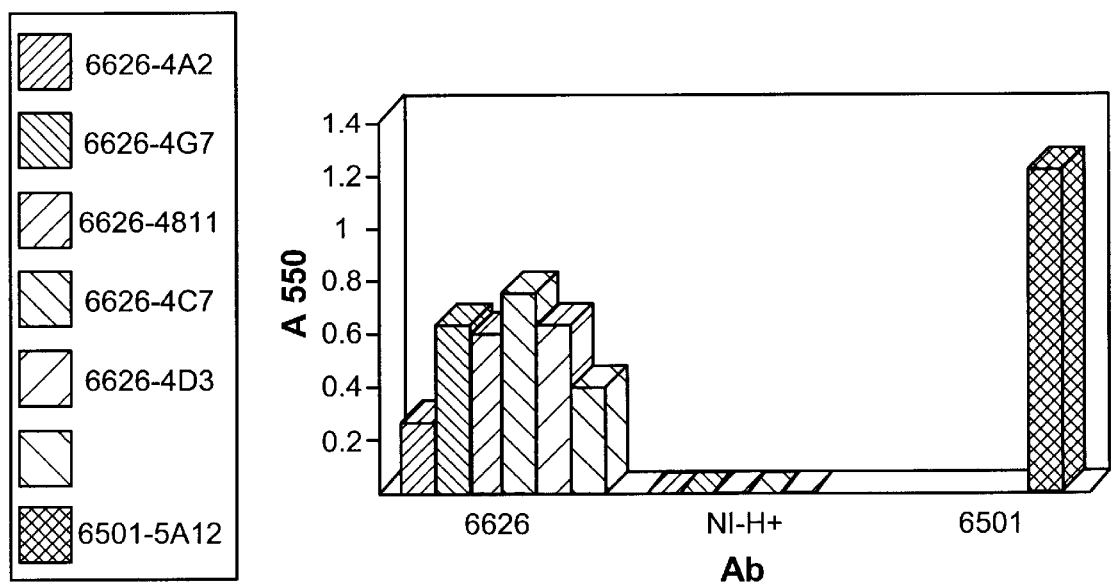
FIG. 3 illustrates that the aPL antibody-binding analogs derived from screening with ACA-6626 bound aPL antisera but did not bind normal sera.

The discovery that resin-bound peptides could bind aPL immunospecifically using serum significantly enhanced the ability to test aPL antibodies. As shown in FIG. 3, the peptide derived from screening with ACA-6626 bound aPL antiserum but did not demonstrate significant binding of normal serum. FIG. 3 also illustrates the immunospecific-binding behavior of ACA-6501-5A12 peptide towards aPL serum. Binding of normal serum to peptide 5A 1 2 was nil in data not shown.

Figure 4:
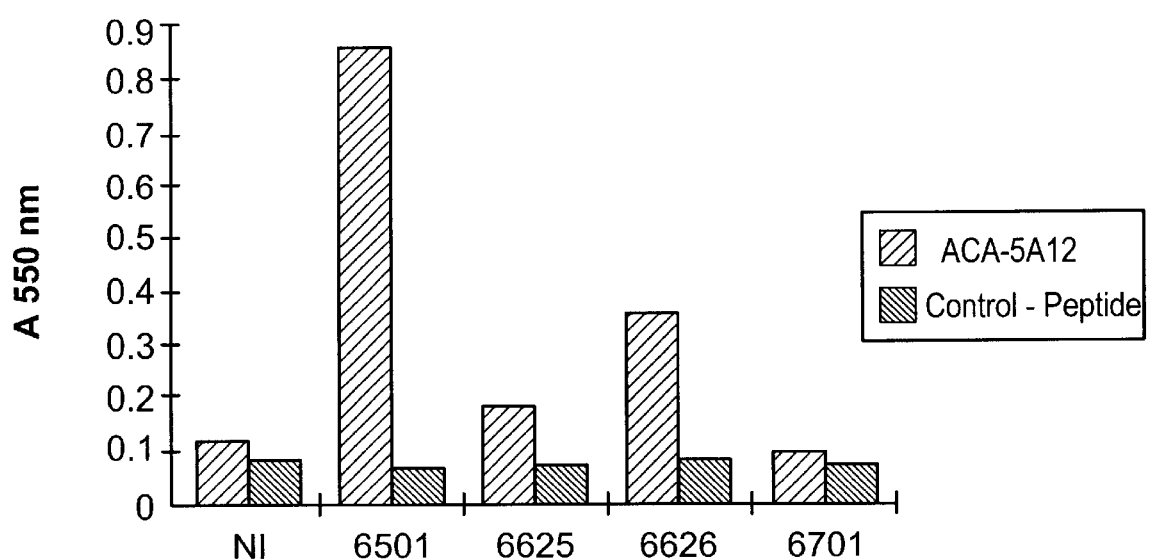
FIG. 4 also illustrates that the ACA-6501/5A12 analog immunospecifically binds ACA-6501 antiserum and is crossreactive with ACA-6626.
Figure 5:
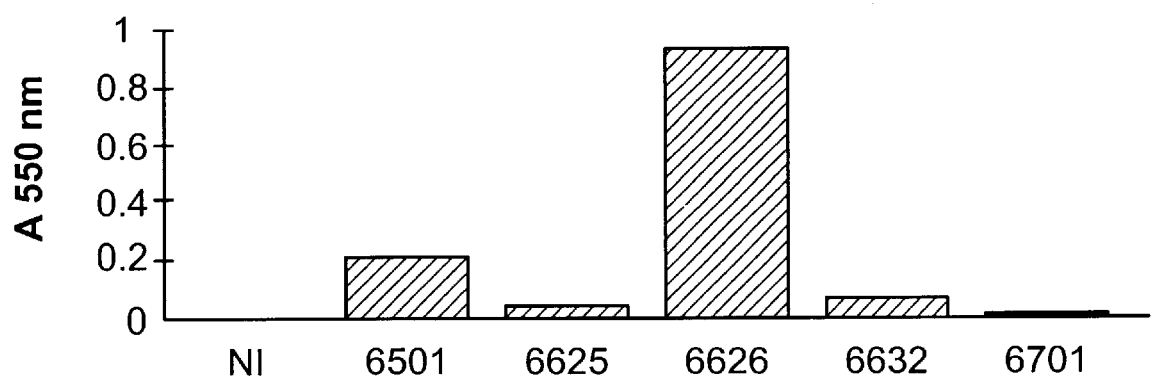
Figure 6B:
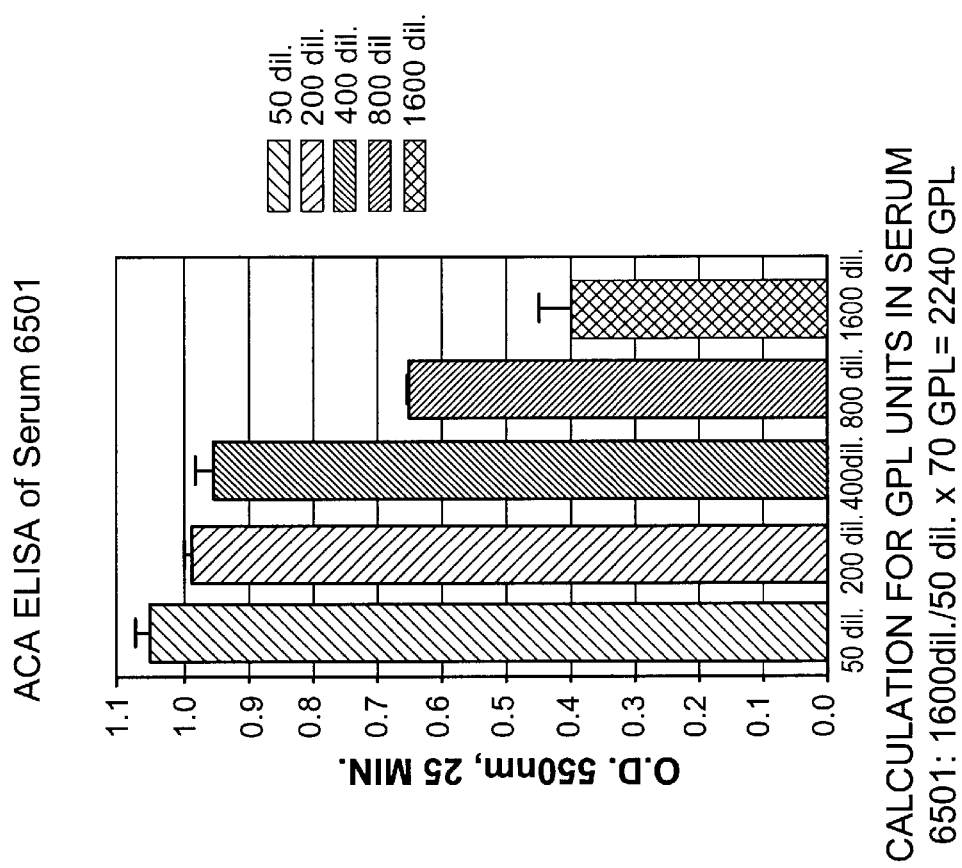
FIG. 6 illustrates method for calculating the GPL value for ACA-6501 aPL antibody.
Figure 6A:
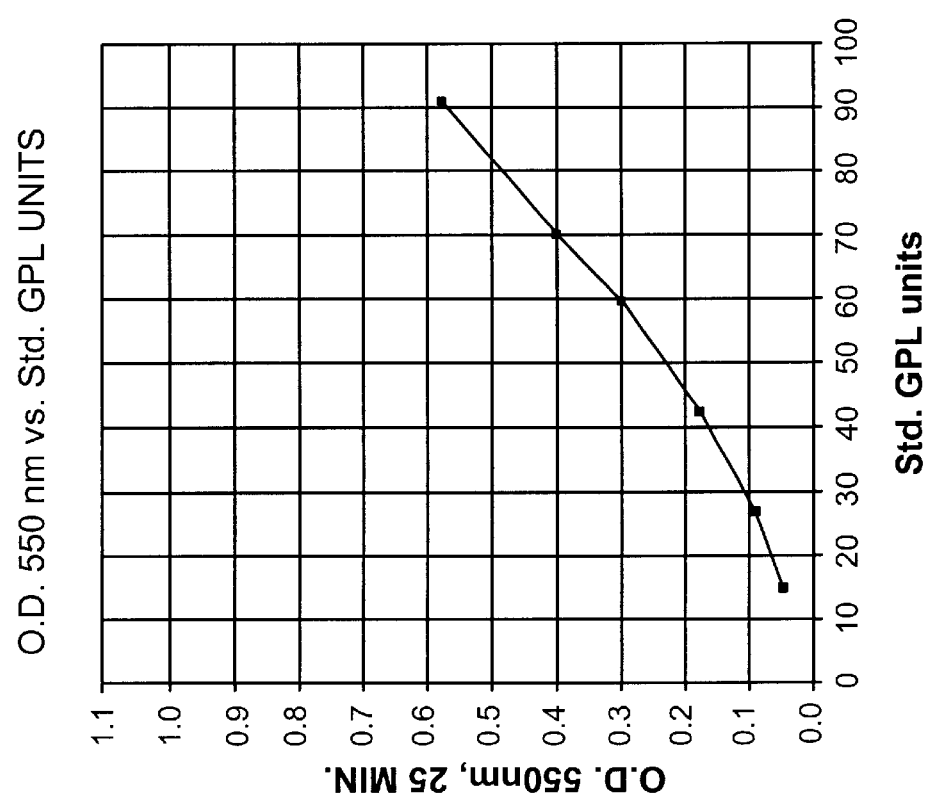

L. Crossreactivity of Synthetic Peptides Towards aPL Antiserum that was Not the Source of the Library Screening Antibody Two peptides were selected for aPL sera testing, one (5A12) representing the ACA-6501 screen and another one (4D3) representing the ACA-6626 screen. As shown in FIGS. 4 and 5, each of the peptides reacted preferentially with the parent serum of the screening antibody. However, a significant degree of crossreactivity was detectable especially between ACA-6501 and ACA-6626. A survey of 19 patient sera with low or no GPL score and of 13 pathologic sera with moderate to high GPL carried out with the 5A12 resin-bound peptide showed 8 of the 13 pathologic samples with detectable peptide binding while only 2 out of 19 control samples showed low peptide binding. These results evidence that synthetic peptides are useful for diagnostic or prognostic assays in stroke patient care.

Figure 14:
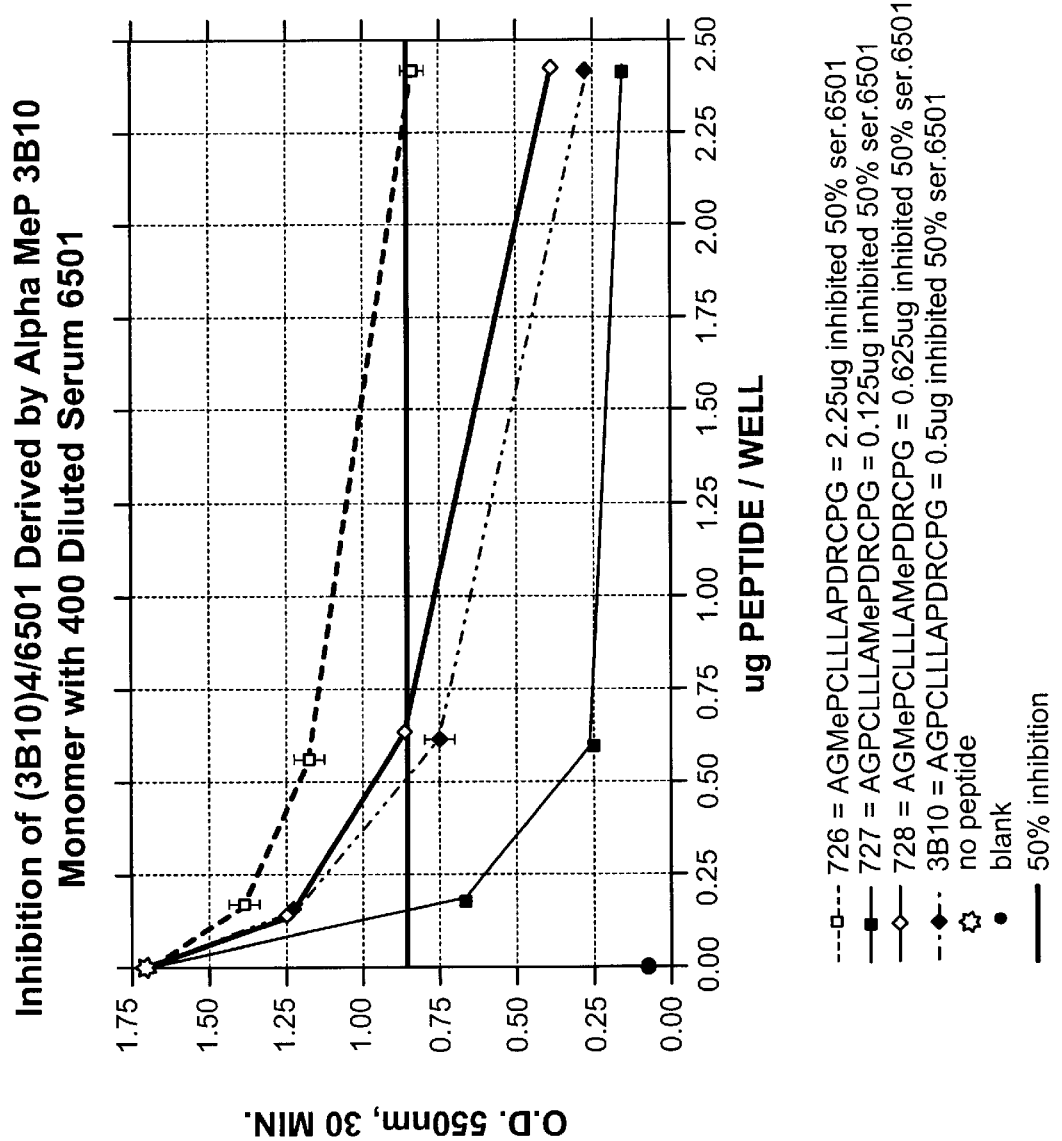
FIG. 14 (SEQ ID NOS:4–7) illustrates the effects of substituting α-Me-Pro at positions 3, 9 and both 3 and 9 in peptide 3B10. Substitution of α-Me-Pro at position 9 increased activity of the peptide four-fold compared to the "native" peptide.
Figure 15:
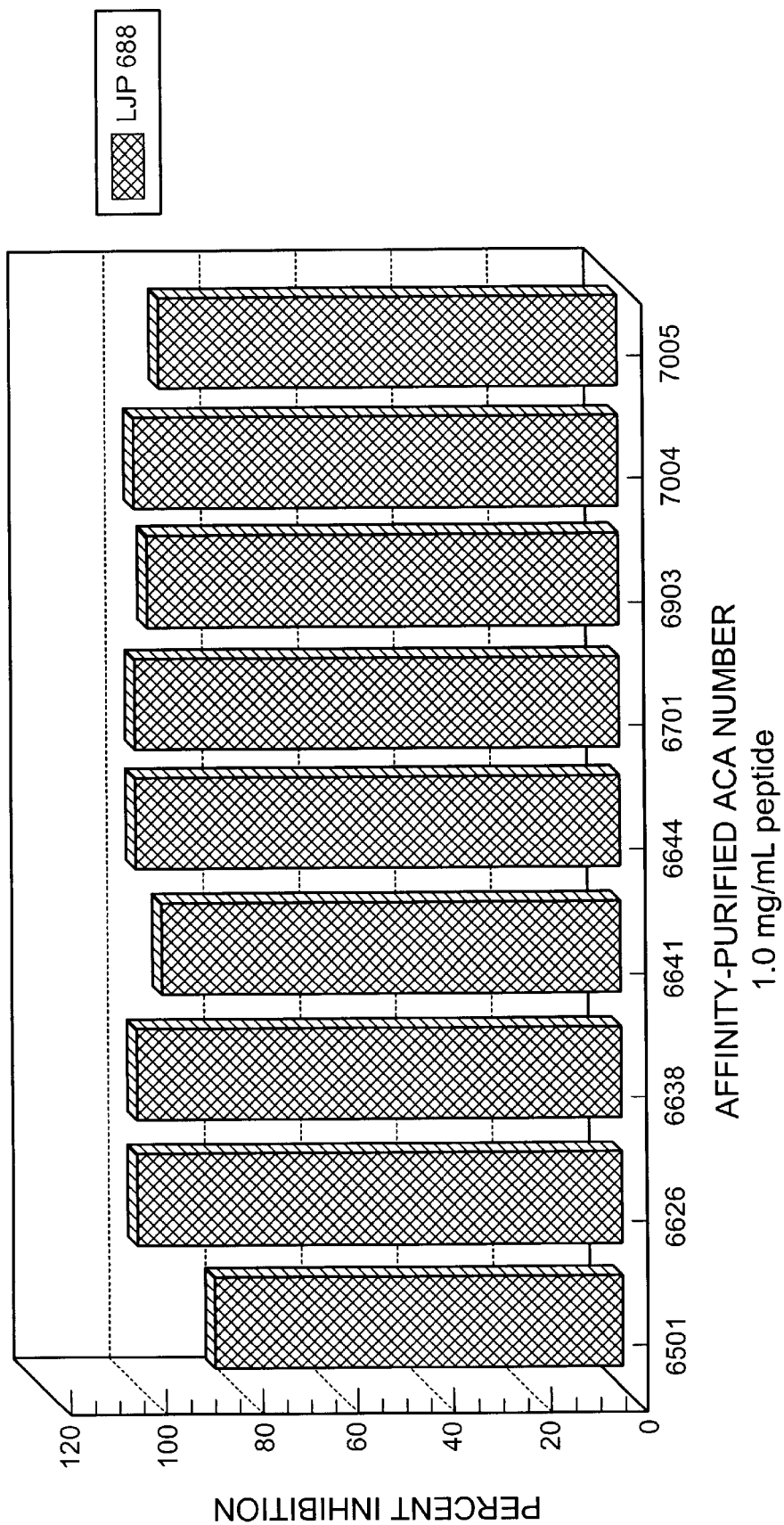
FIG. 15 shows that peptide 6641/3G3 (LJP 688) is highly cross-reactive with nine affinity-purified ACA antibodies.

As noted in Section I above, one synthetic peptide, 6641/3G3 was tested against several high titer ACA antisera. This peptide appeared to be crossreactive with the vast majority of ACA antisera tested as illustrated in FIG. 14. 6641/3G3 demonstrated dose-dependent cross-reactivity with 10 of 10 ACA antibodies with complete inhibition (>80%) at 1.8 mg/mL and appeared to be specific for ACA antibodies as demonstrated in Table 7 below.

TABLE 7

CROSSREACTIVITY DATA FOR
AGP-CLGVLGKLC-PG (LJP 688) (SEQ ID NO:57)
ACA SERA WITH CARDIOLIPIN/β2-GPI-COATED PLATES

| ACA SERUM Nr. | $IC_{50}$, mg/mL, for peptide LJP 688 |
|---|---|
| [1] 6501 RS, RFL | 0.89, 1.1 |
| [2] 6626 RS | 1.09 |
| [3] 6635 RS | 1 |
| [4] 6638 RS | 0.81 |
| [5] 6641 RS | 0.89, 0.51 |
| [6] 664 RS | 0.76 |
| [7] 6701 RS | 1.07 |
| [8] 6903 RS | 0.8 |
| [9] 7004 RFL | 0.67 |
| [10] 7005 RFL | 0.75 |
| mean ± sd | 0.86 ± 0.16 |

RS = recurrent stroke
RFL = recurrent fetal loss

M. New Synthetic Peptide Methodologies

The identification of new candidate sequences by aPL library screening required testing of the new synthetic peptides for antibody binding. With Rapp resin of known peptide substitution, it is possible to carry out quantitative binding studies such as saturation binding analysis and equilibrium measurements using radiolabeled aPL IgG.

Peptide synthesis allows the molecular dissection of the mimotope by selective synthesis. This includes the modification of each amino acid along the chain with the goal of enhancing antibody binding. Selective synthesis reveals the relative importance of each amino acid in the sequence. If necessary, selective substitution at particular residue locations can be designed to maintain B cell reactivity while abolishing any T cell proliferative reactivity discovered during T cell assays.

Peptide 6641/3G3 (LJP 688) was subjected to a number of analyses. The analyses included truncation at both the N-terminus and the C-terminus, disulfide substitution, substitution of alanine and glycine for amino acids in positions 2 through 8, substitution of branched aliphatic amino acids in positions 2, 4, 5 and 8, substitution of amino acids affecting conformation of the peptide, including substitution of α-methyl amino acids, substitution of basic amino acids in position 7, substitution of D-amino acids in positions 2 through 9, and the substitution of N-α-methyl amino acids in positions 1 through 9. The results are shown below in Table 9. The structure/activity relationship of these substitutions and truncations is shown in Table 8.

TABLE 8

Optimization of Peptide 3G3

Total Peptides 144
with ACA 6501

3/28/96 Position Number

| | -2 | -1 | 0 | 1 | 2 | 3 | 4 | 5 | 6 | 7 | 8 | 9 | A | B | std 150, µg/mL |
|---|---|---|---|---|---|---|---|---|---|---|---|---|---|---|---|

Truncation analysis (SEQ ID NOS:60–65)

| | -2 | -1 | 0 | 1 | 2 | 3 | 4 | 5 | 6 | 7 | 8 | 9 | A | B | std |
|---|---|---|---|---|---|---|---|---|---|---|---|---|---|---|---|
| 1 | A | G | P | C | L | G | V | L | G | K | L | C | P | G | 850 |
| 2 | | G | P | C | L | G | V | L | G | K | L | C | P | G | 180 |
| 3 | | | P | C | L | G | V | L | G | K | L | C | P | G | 420 |
| 4 | | | | C | L | G | V | L | G | K | L | C | P | G | 460 |

TABLE 8-continued

Optimization of Peptide 3G3

| | | | | | | | | | | | | | | | |
|---|---|---|---|---|---|---|---|---|---|---|---|---|---|---|---|
| | 5 | A | G | P | C | L | G | V | L | G | K | L | C | G | 450 | |
| | 6 | | | | C | L | G | V | L | G | K | L | C | | 10 | #906 (LJP 690) |
| Disulfide surrogates (SEQ ID NOS:66–69) | | | | | | | | | | | | | | | | |
| | 1 | | | | C | L | G | V | L | G | K | L | C | | 110 | #952 = 100 |
| | 2 | | | | Hc | L | G | V | L | G | K | L | C | | 46 | |
| | 3 | | | | C | L | G | V | L | G | K | L | Hc | | 92 | |
| | 4 | | | | Hc | L | G | V | L | G | K | L | Hc | | 80 | |
| Ala scan (SEQ ID NOS: 70–76) | | | | | | | | | | | | | | | | |
| | 1 | | | | C | A | G | V | L | G | K | L | C | | 200 | #952 = 80 |
| | 2 | | | | C | L | A | V | L | G | K | L | C | | 170 | |
| | 3 | | | | C | L | G | A | L | G | K | L | C | | 260 | |
| | 4 | | | | C | L | G | V | A | G | K | L | C | | inf | |
| | 5 | | | | C | L | G | V | L | A | K | L | C | | 40 | |
| | 6 | | | | C | L | G | V | L | G | A | L | C | | inf | |
| | 7 | | | | C | L | G | V | L | G | K | A | C | | 360 | |
| Gly scan (SEQ ID NOS:77–81) | | | | | | | | | | | | | | | | |
| | 1 | | | | C | G | G | V | L | G | K | L | C | | 310 | #952 = 120 |
| | 2 | | | | C | L | G | G | L | G | K | L | C | | inf. | |
| | 3 | | | | C | L | G | V | G | G | K | L | C | | inf | |
| | 4 | | | | C | L | G | V | L | G | G | L | C | | inf | |
| | 5 | | | | C | L | G | V | L | G | K | G | C | | 500 | |
| Sequence optim. | Branched aliphatic amino acids (SEQ ID NOS: 82–69) | | | | | | | | | | | | | | | |
| | 1 | | | | C | I | G | V | L | G | K | L | C | | 60 | #910 = 40 |
| | 2 | | | | C | V | G | V | L | G | K | L | C | | 130 | |
| | 3 | | | | C | M | G | V | L | G | K | L | C | | | |
| | 4 | | | | C | Cy | G | V | L | G | K | L | C | | | |
| | 5 | | | | C | tL | G | V | L | G | K | L | C | | | |
| | 6 | | | | C | mL | G | V | L | G | K | L | C | | | |
| | 7 | | | | C | Iv | G | V | L | G | K | L | C | | | |
| | 8 | | | | C | L | G | L | L | G | K | L | C | | | |
| | 9 | | | | C | L | G | I | L | G | K | L | C | | | |
| | 10 | | | | C | L | G | M | L | G | K | L | C | | | |
| | 11 | | | | C | L | G | Cy | L | G | K | L | C | | | |
| | 12 | | | | C | L | G | tL | L | G | K | L | C | | | |
| | 13 | | | | C | L | G | mL | L | G | K | L | C | | | |
| | 14 | | | | C | L | G | Iv | L | G | K | L | C | | | |
| | 15 | | | | C | L | G | V | I | G | K | L | C | | | |
| | 16 | | | | C | L | G | V | V | G | K | L | C | | | |
| | 17 | | | | C | L | G | V | M | G | K | L | C | | | |
| | 18 | | | | C | L | G | V | Cy | G | K | L | C | | | |
| | 19 | | | | C | L | G | V | tL | G | K | L | C | | | |
| | 20 | | | | C | L | G | V | mL | G | K | L | C | | | |
| | 21 | | | | C | L | G | V | Iv | G | K | L | C | | | |
| | 22 | | | | C | L | G | V | L | G | K | I | C | | | |
| | 23 | | | | C | L | G | V | L | G | K | V | C | | | |
| | 24 | | | | C | L | G | V | L | G | K | M | C | | | |
| | 25 | | | | C | L | G | V | L | G | K | Cy | C | | | |
| | 26 | | | | C | L | G | V | L | G | K | tL | C | | | |
| | 27 | | | | C | L | G | V | L | G | K | mL | C | | | |
| | 28 | | | | C | L | G | V | L | G | K | Iv | C | | | |
| | Conformational scan amino acids (SEQ ID NOS: 110–140) | | | | | | | | | | | | | | | |
| | 1 | | | | C | L | P | V | L | G | K | L | C | | | |
| | 2 | | | | C | L | mP | V | L | G | K | L | C | | | |
| | 3 | | | | C | L | mA | V | L | G | K | L | C | | | |
| | 4 | | | | C | L | cG | V | L | G | K | L | C | | | |
| | 5 | | | | C | L | G | V | L | P | K | L | C | | | |
| | 6 | | | | C | L | G | V | L | mP | K | L | C | | | |
| | 7 | | | | C | L | G | V | L | mA | K | L | C | | | |
| | 8 | | | | C | L | G | V | L | cG | K | L | C | | | |
| | 9 | | | | C | L | dA | V | L | G | K | L | C | | | |
| | 10 | | | | C | L | G | V | L | dA | K | L | C | | | |
| | 11 | | | | C | P | G | V | L | G | K | L | C | | 160 | #952 = 100 |
| | 12 | | | | C | L | P | V | L | G | K | L | C | | 340 | #(Pro Scan) |
| | 13 | | | | C | L | G | P | L | G | K | L | C | | 180 | |
| | 14 | | | | C | L | G | V | P | G | K | L | C | | Inf. | |
| | 15 | | | | C | L | G | V | L | P | K | L | C | | 350 | |
| | 16 | | | | C | L | G | V | L | G | P | L | C | | 160 | |
| | 17 | | | | C | L | G | V | L | G | K | P | C | | 550 | |
| | 18 | | | | C | pG | G | V | L | G | K | L | C | | 130 | #910 = 40 |
| | 19 | | | | C | L | pG | V | L | G | K | L | C | | 70 | |
| | 20 | | | | C | L | G | pG | L | G | K | L | C | | 70 | |
| | 21 | | | | C | L | G | V | pG | G | K | L | C | | 35 | |
| | 22 | | | | C | L | G | V | L | pG | K | L | C | | 30 | #910 = 5 |
| | 23 | | | | C | L | G | V | L | G | pG | L | C | | 230 | |
| | 24 | | | | C | L | G | V | L | G | K | pG | C | | 80 | |
| alpha Me AA | 25 | | | | C | aiB | G | V | L | G | K | L | C | | 370 | #910 = 40 |
| | 26 | | | | C | L | aiB | V | L | G | K | L | C | | 80 | |

TABLE 8-continued

Optimization of Peptide 3G3

| | | | | | | | | | | | | |
|---|---|---|---|---|---|---|---|---|---|---|---|---|
| | 27 | | C | L | G | aiB | L | G | K | L | C | | 110 | |
| | 28 | | C | L | G | V | aiB | G | K | L | C | | inf. | |
| | 29 | | C | L | G | V | L | aiB | K | L | C | | 110 | |
| | 30 | | C | L | G | V | L | G | aiB | L | C | | 460 | |
| | 31 | | C | L | G | V | L | G | K | aiB | C | | >470 | |
| | Basic amino acid (SEQ ID NOS: 141–143) | | | | | | | | | | | | | |
| | 1 | | C | L | G | V | L | G | R | L | C | | 160 | #952 = 120 |
| | 2 | | C | L | G | V | L | G | Or | L | C | | 40 | 910 = 60 |
| | 3 | | C | L | G | V | L | G | mK | L | C | | | |
| | D amino acids (lower case d) (SEQ ID NOS: 144–166) | | | | | | | | | | | | | |
| | 1 | dP | C | L | G | V | L | G | K | L | C | | 120 | #952 = 100 |
| | 2 | | C | dL | G | V | L | G | K | L | C | | 180 | #952 = 30 |
| | 3 | | C | L | G | dV | L | G | K | L | C | | 260 | #952 = 30 |
| | 4 | | C | L | G | V | dL | G | K | L | C | | 230 | #952 = 30 |
| | 5 | | C | L | G | V | L | G | dK | L | C | | 170 | #952 = 50 |
| | 6 | | C | L | G | V | L | G | K | dL | C | | 140 | #952 = 30 |
| | 7 | | C | dL | G | dV | L | G | K | L | C | | | |
| | 8 | | C | dV | G | dV | L | G | K | L | C | | | |
| | 9 | | C | dL | G | dL | L | G | K | L | C | | | |
| | 10 | | C | L | G | dV | dL | G | K | L | C | | 50 | #952 = 30 |
| | 11 | | C | L | G | dL | dV | G | K | L | C | | | |
| | 12 | | C | L | G | dV | dV | G | K | L | C | | | |
| | 13 | | C | L | G | dL | dL | G | K | L | C | | | |
| | 14 | | C | L | G | V | dL | G | dK | L | C | | | |
| | 15 | | C | L | G | V | dK | G | dL | L | C | | | |
| | 16 | | C | L | G | V | cL | G | dL | L | C | | | |
| | 17 | | C | L | G | V | dK | G | dK | L | C | | | |
| | 18 | | C | L | G | V | L | G | dK | dL | C | | 150 | #952 = 50 |
| | 19 | | C | L | G | V | L | G | dL | dK | C | | | |
| | 20 | | C | L | G | V | L | G | dK | dK | C | | | |
| | 21 | | C | L | G | V | L | G | dL | dL | C | | 140 | #952 = 30 |
| | 22 | | C | L | G | V | L | dA | K | L | C | | 140 | #952 = 50 |
| | | | C | L | G | V | L | G | K | L | dC | | | |
| | N—Me amino acids (SEQ ID NOS: 167–175) | | | | | | | | | | | | | |
| | 1 | | nC | L | G | V | L | G | K | L | C | | | |
| | 2 | | C | L | G | V | L | G | K | L | C | | | |
| | 3 | | C | L | nG | V | L | G | K | L | C | | 70 | #952 = 50 |
| | 4 | | C | L | G | nV | L | G | K | L | C | | 220 | |
| | 5 | | C | L | G | V | nL | G | K | L | C | | 180 | |
| | 6 | | C | L | G | V | L | nG | K | L | C | | 550 | |
| | 7 | | C | L | G | V | L | G | nK | L | C | | | |
| | 8 | | C | L | G | V | L | G | K | nL | C | | 240 | #952 = 50 |
| | 9 | | C | L | G | V | L | G | K | L | nC | | | |
| | Others (SEQ ID NOS: 176–181) | | | | | | | | | | | | | |
| | 1 | | C | L | G | V | L | G | K | L | C | ATU-Y | 300 | #952 = 50 |
| | 2 | Y ATU | C | L | G | V | L | G | K | L | C | | 170 | |
| | 3 | | C | L | G | V | L | G | K | L | C | TGR resin | 500 | |
| | 4 | | C | L | G | V | L | G | K | L | C | dC TGR resin | 620 | |
| | 5 | | dC | L | G | V | L | G | K | L | C | | | |
| | 6 | | cC | L | G | V | L | G | K | L | C | dC TGR resin | | |
| Thioethers: | single deletion (SEQ ID NOS: 182–189) | | | | | | | | | | | | | |
| | 1 | | Hc | L | G | V | L | A | K | L | C | | | |
| | 2 | | Hc | | G | V | L | A | K | L | C | | | |
| | 3 | | Hc | L | | V | L | A | K | L | C | | | |
| | 4 | | Hc | L | G | | L | A | K | L | C | | | |
| | 5 | | Hc | L | G | V | | A | K | L | C | | | |
| | 6 | | Hc | L | G | V | L | | K | L | C | | | |
| | 7 | | Hc | L | G | V | L | A | | L | C | | | |
| | 8 | | Hc | L | G | V | L | A | K | | C | | | |
| | shrink minimization (SEQ ID NOS: 190–192) | | | | | | | | | | | | | |
| | 1 | | Hc | | | V | L | A | K | L | C | | | |
| | 2 | | Hc | | | | L | A | K | L | C | | | |
| | 3 | | Hc | | | | L | A | K | | C | | | |
| | branched (SEQ ID NOS: 193–197) | | | | | | | | | | | | | |
| | 1 | | Hc | L | G | V | L | G | K | L | Pe | | | |
| | 2 | | Hc | L | G | V | L | G | K | L | dPe | | | |
| | 3 | | Pe | L | G | V | L | G | K | L | Hc | | | |
| | 4 | | dPe | L | G | V | L | G | K | L | Hc | | | |
| | 5 | | dPe | L | G | V | L | G | K | L | dPe | | | |
| | D amino acids (SEQ ID NOS: 198–200) | | | | | | | | | | | | | |
| | 1 | | dHc | L | G | V | L | G | K | L | C | | | |
| | 2 | | dHc | L | G | V | L | G | K | L | dC | | | |
| | 3 | | Hc | L | G | V | L | G | K | L | dC | | | |

TABLE 8-continued

Optimization of Peptide 3G3

Des amino (SEQ ID NOS: 201–204)

| | | | | | | | | | | | |
|---|---|---|---|---|---|---|---|---|---|---|---|
| 1 | | By | L | G | V | L | G | K | L | Hc | desamino HHTE |
| 2 | | By | L | G | V | L | G | K | L | C | desamino HCTE |
| 3 | | Pp | L | G | V | L | G | K | L | Hc | desamino CHTE |
| 4 | | Pp | L | G | V | L | G | K | L | C | desamino CHTE |

| Abbreviations | | |
|---|---|---|
| | Hc | homocysteine |
| | Cy | cyclohexyl alanine |
| | tL | tertiary leucine |
| | mL | alpha methyl leucine |
| | Iv | alpha methyl, alpha amino butyric acid |
| | mP | alpha methyl proline |
| | mA | alpha methyl alanine |
| | aiB | aminoisobutryic acid |
| | pG | phenylglycine |
| | cG | cyclopropyl glycine |
| | dA | D alanine |
| | dP | D proline |
| | dL | D leucine |
| | dV | D valine |
| | dK | D lysine |
| | nC | N alpha-methyl cysteine |
| | nL | N alpha-methyl leucine |
| | nG | N methyl glycine |
| | nV | N alpha-methyl valine |
| | nK | N alpha-methyl lysine |
| | mK | N epsilon-methyl lysine |
| | Pe | penicillamine |
| | By | butyroyl |
| | Pp | proprionyl |
| | Or | ornithine |

TABLE 9

Structure Activity Relationship of the Crossreactive ACA Epitope

| Structure | Relative Activity |
|---|---|
| AGPCLGVLGKLCPG (3G3) (LJP 688)(SEQ ID NO:60) | 100 |
| CLGVLGKLC (LJP 690)(SEQ ID NO:65) | 3.5 |
| CLGVLAKLC(SEQ ID NO:74) | 1.8 |
| CLGVL$_p$GKLC(SEQ ID NO:131) | 1.4 |
| CLG$_d$V$_d$LGKLC(SEQ ID NO:153) | 5.9 |
| HcLGVLGKLC(SEQ ID NO:205) (thioether) | 1.6 |
| SLGVLGKLS(SEQ ID NO:206) | ∞ |
| CLGVAGKLC(SEQ ID NO:207) | ∞ |
| CLGVLGALC(SEQ ID NO:208) | ∞ |

N. Use of α-methyl Amino Acids Substitutions and Unnatural Amino Acids to Enhance Peptide Immunoreactivity and Confer Resistance to Protease Attack Proline residues have a special significance due to their influence on the chain conformation of polypeptides. They often occur in reverse turns on the surface of globular proteins. In the phage epitope libraries of the present invention, all random peptide inserts are flanked by boundary prolines. In addition, most of the mimotopes discovered with ACA-6501 have a third proline which, based on computer-based predictions, likely exists as part of a β-turn. β-turn mimetics can be used to enhance the stability of reverse turn conformations in small peptides. Such a mimetic is (S)-α-methyl proline (α-MePro), a proline analog that, in addition to stabilizing turn conformations, confers resistance to protease degradation. Protease resistance is a desirable property for a potential drug designed to act in the plasma. Peptide ACA-6501/3B10 AGPCLLLAPDRCPG (SEQ ID NO:219) (insert highlighted) is a consensus peptide. It has a sequence featuring the most prevalent residue at each position based on a comparison with 35 other homologous sequences. Due to its representative character, the sequence was subjected to a number of systematic modifications and deletions and its activity subsequently evaluated by aPL antibody binding. Among the most important findings was the discovery that the prolines at the 3 and 9 positions are important for activity. Proline-3 is derived from the phage framework and is not part of the random insert. The most dramatic effect was obtained by the substitution of α-MePro for proline at the 9-position. This substitution led to a six-fold enhancement in immunoreactivity.

The results of α-methyl and N-α-methyl amino acid substitution studies carried out on peptide 6641/3G3 are shown above in Table 8.

In addition to the twenty naturally-occurring amino acids and their homoanalogs and noranalogs, several other classes of alpha amino acids can be employed in the present invention. Examples of these other classes include d-amino acids, N$^α$-alkyl amino acids, alpha-alkyl amino acids, cyclic amino acids, chimeric amino acids, and miscellaneous amino acids. These non-natural amino acids have been widely used to modify bioactive polypeptides to enhance resistance to proteolytic degradation and/or to impart conformational constraints to improve biological activity (Hruby et al. (1990) *Biochem. J.* 268:249–262; Hruby and Bonner (1995) *Methods in Molecular Biology* 35:201–240).

The most common $N^\alpha$-alkyl amino acids are the $N^\alpha$-methyl amino acids, such as $N^\alpha$-methyl cysteine (nK), $N^\alpha$-methyl glycine (nG), $N^\alpha$-methyl leucine (nL), $N^\alpha$-methyl lysine (nK), and $N^\alpha$-methyl valine (nV). Examples of alpha-alkyl amino acids include alpha-methyl alanine (mA), alpha-aminoisobutyric acid (aiB), alpha-methyl proline (mP), alpha-methyl leucine (mL), alpha-methyl valine (mV), alpha-methyl-alpha-aminobutyric acid (ty), diethylglycine (deG), diphenylglycine (dpG), and dicyclohexyl glycine (dcG) (Balaram (1992) *Pure & Appl. Chem.* 64:1061–1066; Toniolo et al. (1993) *Biopolymers* 33:1061–1072; Hinds et al. (1991) *Med. Chem.* 34:1777–1789).

Examples of cyclic amino acids include 1-amino-1-cyclopropane carboxylic acid (cG), 1-amino-1-cyclopentane carboxylic acid (Ac5c), 1-amino-1-cyclohexane carboxylic acid (Ac6c), aminoindane carboxylic acid (ind), tetrahydroisoquinoline carboxylic acid (Tic), and pipecolinic acid (Pip) (C. Toniolo (1990) *Int'l. J. Peptide Protein Res.* 35:287–300; Burgess et al. (1995) *J. Am. Chem. Soc.* 117:3808–3819). Examples of chimeric amino acids include penicillamine (Pe), combinations of cysteine with valine, 4R- and 4S-mercaptoprolines (Mpt), combinations of homocysteine and proline and 4R- and 4S-hydroxyprolines (hyP) and a combination of homoserine and proline. Examples of miscellaneous alpha amino acids include basic amino acid analogs such as ornithine (Or), $N^\epsilon$-methyl lysine (mK), 4-pyridyl alanine(pyA), 4-piperidino alanine (piA), and 4-aminophenylalanine; acidic amino acid analogs such as citrulline (Cit), and 3-hydroxyvaline; aromatic amino acid analogs such as 1-naphthylalanine (1-Nal), 2-naphthylalanine (2-Nal), phenylglycine (pG), 3,3-diphenylalanine (dpA), 3-(2-thienyl)alanine (Thi), and halophenylalanines (e.g., 2-fluorophenylalanine and 4-chlorophenylalanine); hydrophobic amino acid analogs such as t-butylglycine (i.e., tertiary leucine (tL)), 2-aminobutyric acid (Abu), cyclohexylalanine (Cy), 4-tetrahydropyranyl alanine (tpA), 3,3-dicyclohexyl alanine (dcA), and 3,4-dehydroproline.

In addition to alpha-amino acids, others such as beta amino acids can also be used in the present invention. Examples of these otlher amino acids include 2-aminobenzoic acid (Abz), β-aminopropanoic acid (β-Apr), γ-aminobutyric acid (γ-Abu), and 6-aminohexanoic acid (ε-Ahx). Carboxylic acids such as 4-chlorobutyric acid (By) and 3-chloropropionic acid (Pp) have also been used as the first residue on the N-terminal in the synthesis of cyclic thioether peptides.

O. Preparation of Cyclic Thioether Analogs

The mimetic peptides identified by the methods of the instant invention can be further modified to contain thioether substitutions. Modification of cyclic disulfide analogs to cyclic thioether analogs will extend the plasma half-life of the analog conjugates and, therefore, require a lower dosage. Cyclic thioether analogs also eliminate the problem of disulfide bond exchange which often occurs with cyclic disulfide polypeptides. In addition, the cyclic thioether analogs may also interfere with MHC Class II presentation to T cells and, thus, facilitate induction of anergy. Finally, the cyclic thioether analogs are useful in the thiol-dependent conjugation reactions used in the production of valency platform molecule conjugates.

Four cyclic thioether analogs were prepared according to the methodology described in co-owned, co-pending U.S. Pat. No. 5,817,752, which is incorporated herein in its entirety. Using either a Rink™ amide 4-methyl benzhydrylamino resin or MBHA resin, full length peptide analogs of 6641/3G3 were prepared, converted into chloro-peptides, cleaved from a solid support and then cyclized. See Thioether Reaction Scheme below. Suitable cyclic thioether analogs include the analogs shown below.

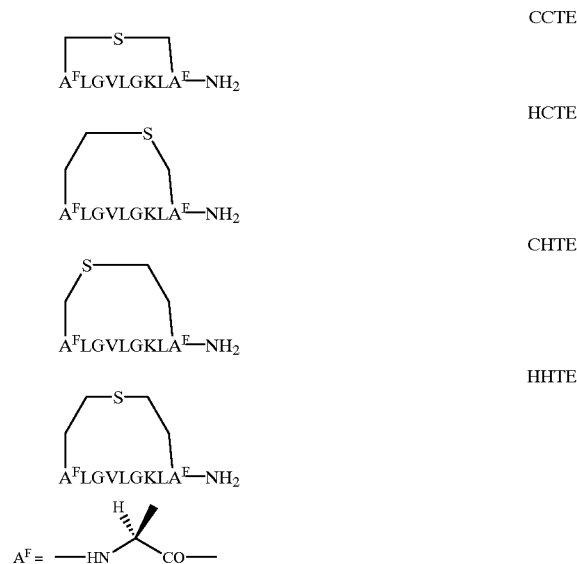

CYCLIC THIOETHER REACTION SCHEME 1

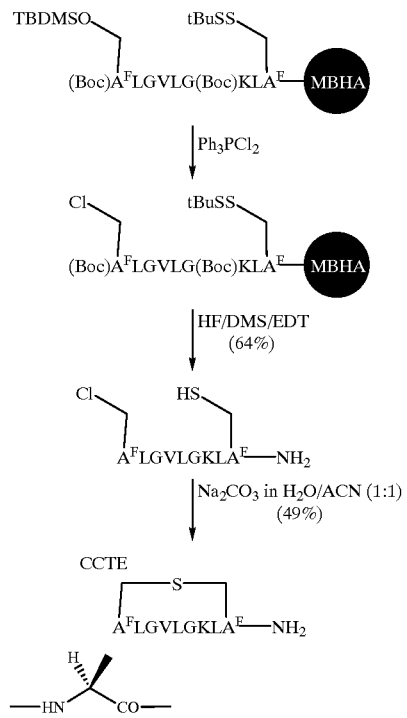

Alternatively, thioether analogs are prepared according to the reaction scheme below.

CYCLIC THIOETHER REACTION SCHEME 2

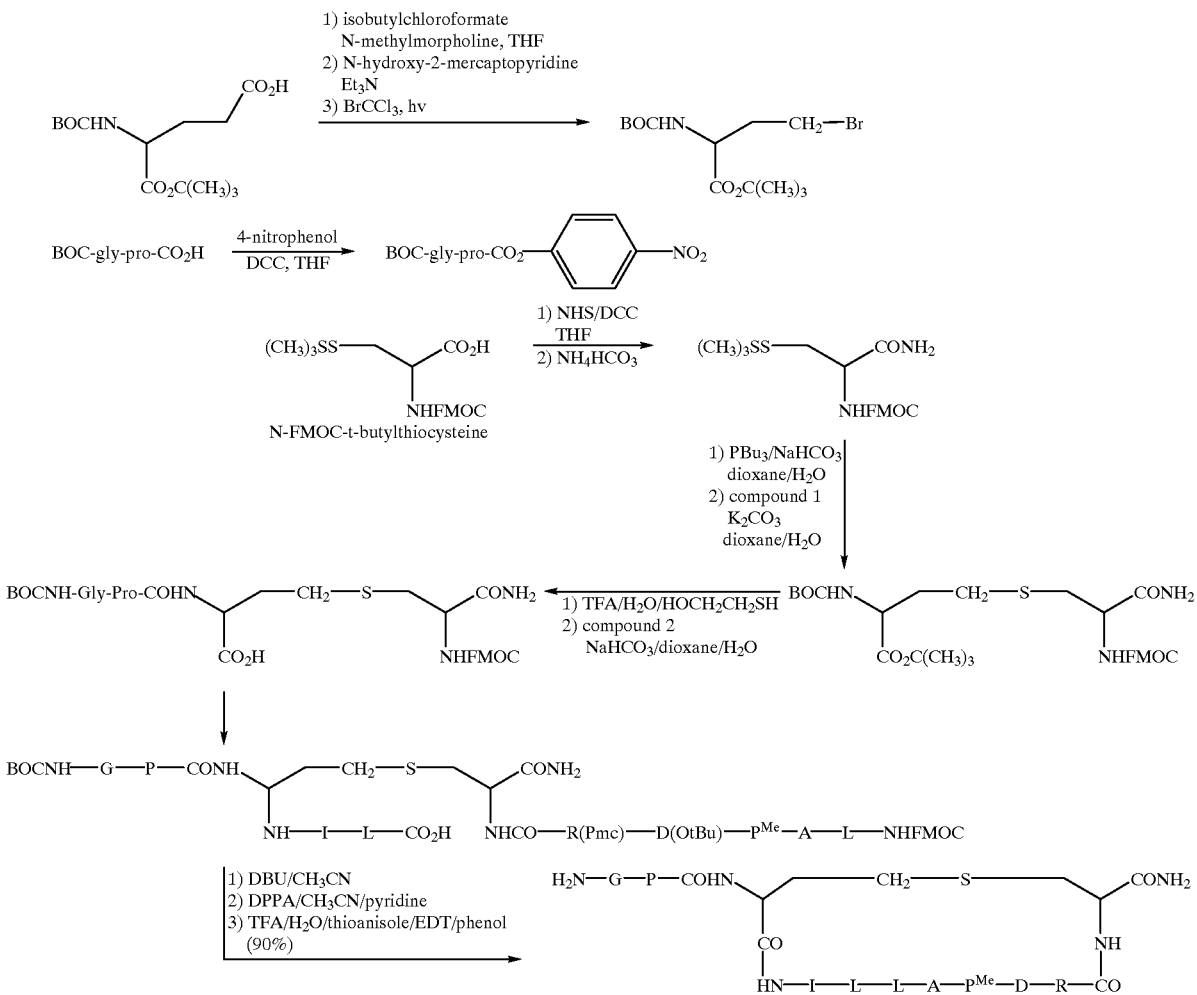

The following analogs are representative as analogs made according to cyclic thioether reaction scheme 2.

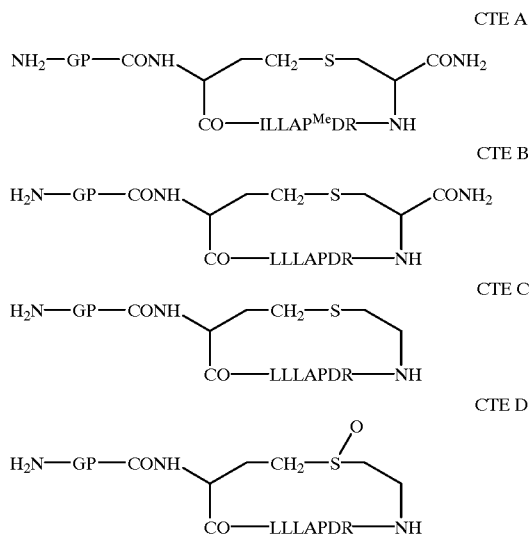

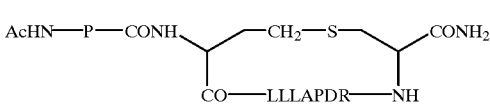

Exemplary cyclic thioether analogs were tested for activity against ACA antibodies ACA-6501 and ACA-6701. The results are shown in Table 10 below.

TABLE 10

| Thioether | IC$_{50}$ Values ($\mu$g/0.1 mL) | |
|---|---|---|
|  | ACA-6501 | ACA-6701 |
| CCTE, LJP 698 | 11.0 | 5.0 |
| HCTE, LJP 699 | 4.6 | 3.0 |
| CHTE, LJP 702 | 9.2 | 3.2 |
| HHTE, LJP 703 | 8.0 | 3.6 |
| LJP 690 | 10.0 | 4.0 |
| CTE A | 0.08 |  |
| CTE B | 0.5 |  |
| CTE C | 0.9 |  |

TABLE 10-continued

| | IC$_{50}$ Values ($\mu$g/0.1 mL) | |
|---|---|---|
| Thioether | ACA-6501 | ACA-6701 |
| CTE D | 3.2 | |
| CTE E | 6.3 | |

The HCTE analog, LJP 699, outperformed the reference peptide, UJP 690, which is the truncated version, CLGV-LGKLC (SEQ ID NO:65), of LJP 688, AGPCLGVLGKL-CPG (SEQ ID NO:60).

All articles, documents, patents and patent applications cited herein are incorporated by reference herein in their entirety. The following examples are intended to further illustrate the invention and its uniqueness. These examples are not intended to limit the scope of the invention in any manner.

EXAMPLES

Example 1
Measurement of Anticardiolipin Antibodies (ACA) in Serum 6501

Even numbered wells of an Immulon I microtitration plate (Dynatech Laboratories, Inc., Chantilly, Va.) were coated with 50 $\mu$g cardiolipin (Sigma Chemical, St. Louis, Mo.) in 30 $\mu$L ethanol per well. The plate was dried overnight at 4° C. and blocked with 200 $\mu$L of 10% adult bovine serum (ABS) (Irvine Scientific Co., Santa Ana, Calif.) in phosphate-buffered saline (ABS/PBS) for 2 hours at room temperature (RT). The plates were washed 5 times with Tris-buffered saline (TBS) prior to the addition of 10 $\mu$L of aPL standards and the test serum, ACA-6501. The aPL standards (APL Diagnostics, Inc., Louisville, Ky.) were reconstituted according to the manufacturer's instructions and diluted 1:50 with 10% ABS-PBS. The test serum, ACA-6501, diluted 1:50 to 1:2,000 in serial dilutions with 10% ABS-PBS, was added to selected duplicate wells and incubated for 2 hours at RT. The plate was washed five times with TBS and 100 $\mu$L of 1:1,000 goat-anti-human-IgG/alkaline phosphatase conjugate (Zymed, South San Francisco, Calif., Cat. No. 62,8422), in 10% ABS-PBS was added and incubated for 1 hour at RT. Again, the plate was washed five times with TBS and the assay was developed by adding 100 $\mu$L phenolphthalein monophosphate (PPMP) substrate solution (Sigma, Cat. No. P-5758), prepared from a stock solution of 0.13 M PPMP and 7.8 M 2-amino-2-methyl-1-propanol, adjusted to pH 10.15 with HCl, after a dilution of 1:26 with deionized water. After approximately 30 minutes, the reaction was stopped with 50 $\mu$L of 0.2 M dibasic sodium phosphate (Mallinckrodt, Analytical Reagent) added per well. The optical density was read at 550 nm in a microplate autoreader (Bio-Tek Instruments, Winooski, Vt., Model EL311). The optical density of the odd-numbered control wells (blank, without cardiolipin (CL)) was subtracted from the optical density of the even-numbered wells. The absorbance readings of the aPL standards were plotted using Graph Pad Prizm (Graph Pad Software, Inc., San Diego, Calif.) to generate the GPL (IgG phospholipid) standard curve. The diluted 6501 test serum absorbance readings were used to calculate GPL scores based on the GPL standard curve.

In the modified ACA ELISA, Nunc Maxisorp microtitration plates were coated with 100 $\mu$L/mL $\beta_2$-GPI made up in PBS following incubation at 1 hour at room temperature. Following this step, microplates were blocked with PBS containing 2% nonfat milk and 0.4% (w/v) Tween 80 for 2 hours at room temperature. Except for the use of nonfat milk/Tween as reagent diluent and blocking agent, the Nunc microplates coated with $\beta_2$-GPI directly were used for ACA IgG binding studies as previous described for the Dynatech microplates coated first with cardiolipin before the $\beta_2$-GPI was added.

Example 2
Anticardiolipin Antibody (ACA) Purification from Serum 6501

In a 25 mL round-bottom flask (Kontes Scientific Co., Vineland, N.J.) a mixture of 1.2 mL cardiolipin (Sigma Chemical, St. Louis, Mo., #C-1649), 0.464 mL cholesterol (Sigma Diag., St. Louis, Mo., #965–25), 0.088 mL of 5 mg dicetylphosphate (Sigma Chemical, St. Louis, Mo, D-2631) per mL chloroform was dried for approximately 5 minutes in a Rotavap (Buchi, Switzerland). Following the removal of solvent, 2 mL of 0.96% (wt./vol.) NaCl (J. T. Baker, Inc., Phillipsburg, N.J.) Baker analyzed reagent) was added and mixed in a Vortex Genie Mixer (Scientific Industries, Inc., Bohemia, N.Y.) for 1 minute. The liposome suspension was incubated for 1 hour at 37° C. Meanwhile, serum 6501 was spun at 600×g in a Sorvall RT 6000 centrifuge (Dupont Co. Wilmington, Del.) for 10 minutes at 8° C. Four mL of the supernatant was placed in a 25 mL round-bottom flask with 1 mL of the prepared liposome suspension and the mixture was incubated with agitation at medium speed in an orbital shaker, Tektator V (Scientific Products, McGraw Park, Ill.) for 48 hours at 4° C., and an additional 2 hours at 37° C. Twenty mL of cold TBS was added and the mixture was transferred into a 50 mL polycarbonate centrifuge tube (Nalge Co., Rochester, N.Y.) and centrifuged at 27,000×g for 15 minutes at 4° C. in an RC3 centrifuge in a SS-34 rotor (Sorvall-Dupont, Wilmington, Del.). The precipitate was washed 3 times with 25 mL of cold 0.96% NaCl using the RC3 centrifuge. The pellet was dissolved in 1 mL of 2% (wt/vol) solution of n-octyl-$\beta$-D-glucopyranoside (Calbiochem, La Jolla, Calif.) in TBS and applied to a 0.6 mL protein A/cross-linked agarose (Repligen Corporation, Cambridge, Mass.) column which had been pre-washed with 15 times bed volume of 1 M acetic acid and equilibrated with 15 times bed volumes of TBS. The antibody-protein A/agarose column was washed with 40 times bed volume of 2% octylglucopyranoside to remove lipids, followed by extensive washings with TBS until the optical density of the eluate at 280 nm approached the baseline. The bound antibody was eluted with 1 M acetic acid. One mL fractions were collected, neutralized immediately with 0.34 mL 3 M Tris (Bio-Rad, electrophoresis grade reagent) per fraction and kept in an ice bath. The optical density of each fraction was determined at 280 nm in a spectrophotometer (Hewlett-Packard, 8452A Diode Array Spectrophotometer, Palo Alto, Calif.). Fractions containing antibody were pooled, concentrated and washed 4 times with TBS in Centricon-30 concentrators (Amicon Division, W. R. Grace & Co., Beverly, Mass.) per manufacturer's protocol. The final yield of purified antibody from 4 mL of serum 6501 was determined by reading the optical density at 280 nm of an aliquot from the concentration, where 1 mg=1.34 OD$_{280}$. The average yield obtained was 750 $\mu$g antibody from 4 mL of serum 6501. The purified antibody was tested for ACA activity and checked for purity with Laemmli SDS-PAGE. An affinity adsorbent containing $\beta_2$-GPI was prepared using CNBr-activated agarose )Pharmacia, Inc., Piscataway, N.J.) or Affi-Gel 10 (BioRad, Richmond, Calif.) in accordance with the manufacturer's instructions using purified $\beta_2$-GPI obtained commercially (PerImmune, Rockville, Md.). To a 1 mL gel column containing the $\beta_2$-GPI affinity adsorbent, up to 100 $\mu$g of liposome-purified aPL IgG in 1 mL TBS was added. After 1 hour, the column was extensively washed with buffer to displace contaminants and any IgG that did not bind $\beta_2$-GPI. The $\beta_2$-GPI-binding IgG was displaced with 1 M HOAc and the fractions neutralized with Tris as described above. Fractions containing IgG were pooled, concentrated and subjected to buffer exchange as previously described.

Example 3
Construction of a p-III Library Vector Preparation fUSE 5 (Scott, J. K. and G. Smith, supra) was used as the vector for the construction of p-III libraries, and a variation of the method of Holmes, D. S. and M. Quigley (1981), *Anal. Biochem.* 144:193) was employed to generate the double-stranded replicative form (RF). Briefly, an 800 mL culture of *E. coli* K802, harboring fUSE 5, was grown in 2YT medium (Difco Labs, Ann Arbor, Mich.) containing 20 micrograms/mL tetracycline for 18 hours at 37 degrees with vigorous shaking. Cells were collected by centrifugation and resuspended in 75 mL STET. STET consists of 8% sucrose in 50 mM Tris/HCl pH 8.0, 50 mM EDTA and contains 0.5% Triton X-100. Lysozyme, 10 mg/mL in STET, was added to a final concentration or 1 mg/mL. After 5 minutes at RT, three equal aliquots were placed in a boiling water bath with occasional shaking for 3.5 minutes. The viscous slurry was centrifuged for 30 minutes at 18000×G and an equal volume of isopropanol was added to the supernatant. The solution was cooled to −20° C. and the nucleic acids were collected by centrifugation. The RF was isolated from a CsCl gradient as described by Sambrook et al. Molecular Cloning: A Laboratory Manual (Cold Spring Harbor Laboratory Press, Cold Spring Harbor, N.Y., 2d ed., 1989).

Preparation of the Random Insert

The DNA for insertion was generated by the "gapped duplex" method described by Cwirla et al. (1990) *Proc. Natl. Acad. Sci. USA* 87:6378–6382. In this method, an oligonucleotide containing a degenerate region in the middle is surrounded by short constant regions on each end of the oligonucleotide. Two shorter, complementary oligonucleotides are annealed to form a "gapped duplex" possessing overhangs that are complementary to the sticky ends produced by the restriction endonuclease used to digest the vector. In this case, the longer degenerate oligonucleotide has the sequence: 5' GGGCTGGACCC(NNK)$_x$CCGGGGGCTGCTG 3' (SEQ ID NO:209) where N=A or C or G or T, K=G or T, and x is the number of codons in the random regions. EpiGS2 was designed to base pair to the 5' end of the degenerate oligonucleotide and has the sequence 5' GGGTCCAGCCCCGT 3' (SEQ ID NO:210). Similarly EpiGS3 was designed to anneal to the 3' end of the degenerate oligonucleotide and has the sequence 5' CAGCCCCCGG 3' (SEQ ID NO:211). When correctly annealed, the three oligonucleotides form a "gapped duplex" which, when inserted into fUSE 5 digested with Sfi1, restores the reading frame of p-III with the random insert near the 5' end.

Oligonucleotides described above were prepared by excision from polyacrylamide gels. One nanomole of EpiGS2, EpiGS3, and 50 picomoles of the degenerate oligonucleotide were kinased separately in 66 microliter volumes. The three oligonucleotides were then pooled, NaCl was added to 50 mM and the mixture was heated to 65° C. for 5 minutes followed by slow cooling to RT. The annealed oligonucleotides were then cooled on ice and used immediately in the ligation reaction with fUSE 5. The ligation reaction consisted of 10 micrograms of fUSE 5 DNA digested to completion with Sfi1, 30 $\mu$L of the "gapped duplex" solution and 1000 U of T4 ligase in a total volume of 450 microliters. The ligation was incubated for 18 hours at 16° C. The mixture was then phenol-chloroform extracted, precipitated with ethanol and the precipitate dissolved in 20 $\mu$L of water.

Generating and Amplifying the Library

The ligated DNA was introduced into *E. coli* by electroporation (Dower et al. (1988) *Nucleic Acid Res.* 16:6127–6145). Frozen electrocompetent MC 1061 cells (0.1 mL) were mixed with 4 $\mu$of ligated DNA in a cold 2 mm cuvette and subjected to 2.5 kV, 5.2 mS pulse by a BTX electroporation device (BTX Corp., San Diego, Calif.). Immediately after the pulse, 1 mL of SOC, a cell growth medium (see Dower et al., supra) was added. Five separate electroporations were carried out, pooled, and incubated at 37° C. for 1 hour. At that time, samples were removed and diluted to determine the total number of clones generated. The balance of the mixture was diluted in 1L of 2YT (1.6% Peptone, 140, 1% Yeast Extract, and 0.5% NaCl, Difco Labs, Ann Arbor, Mich.) containing 20 micrograms per mL of tetracycline and grown for 18 hours at 37° C. while shaken at 275 rpm. Phage were purified by 2 rounds of PEG/NaCl precipitation and resuspension in 1.2 mL TBS containing 0.02% sodium azide. Particle number was estimated by absorbance at 269 nm. The titer of the phage was determined by mixing 10 $\mu$L of dilutions of phage with 10 microliters of starved *E. coli*.

Example 4
Screening a p-III Library with aPL Antibody

Affinity-purified ACA-6501 (affACA-6501, 10 $\mu$g; 7 $\mu$L of 1.44 mg/mL stock solution) was incubated for 2 hours at RT in siliconized 1.4 mL microfuge polypropylene tubes with pooled phage from the x, y and z libraries (epi$^{xyz}$) [11 $\mu$L+8.5 $\mu$L+2 $\mu$L, respectively; total volume=21.5 $\mu$L, ~10$^{10}$ clones] in a final volume of 100 $\mu$L TBS, pH 7.4, with 0.5% bovine serum albumin (BSA). During this incubation, the final steps in preparing freshly starved *E. coli*, strain K-91, were carried out. A suspension of *E. coli* freshly grown in 2YT medium for about 5 hours with 250 rpm shaking at 37° C. was spun at 1000×g for 10 minutes at RT in 50 mL polypropylene tubes. Twenty mL of 80 mM NaCl was added to the packed *E. coli* pellet and then incubated for 45 minutes at 37° C. at 100 rpm. Following centrifugation as above, the starved *E. coli* pellet was suspended in 1 mL of 50 mM ammonium phosphate/80 mM NaCl and used later for phage amplification. Protein G-agarose beads were washed 2× in TBS/BSA and 2 times in TBS/0.5% Tween-20 and stored at 4° C. as a 50% suspension in TBS/Tween.

Two hundred $\mu$L of the protein G-agarose bead suspension was then added to the ACA-6501/phage mixture and incubation continued for an additional 1 hour at RT. At this point, the mixture was chilled and washed 3 times with cold TBS/Tween and the precipitate was collected in a microfuge in a cold room. The washed beads were transferred to new microfuge tubes prewashed with TBS/BSA and TBS/Tween to prevent non-specific adherence. After three additional washes with TBS/Tween, the beads with bound ACA-6501-bearing phage were eluted with 300 $\mu$L 0.2 N HCl/glycine, pH 2.1 by tumbling for 10 minutes at RT. Following centrifugation at 16,000×g, the acidic eluate supernatant was collected and an additional 100 $\mu$L of elution solution was added to the bead pellet and the procedure repeated. After 10 minutes, the phage-containing eluates (representing the unamplified first round phage) were pooled (~400 $\mu$L) and placed in a sterile 17×100 mm polypropylene cell culture tube to which was added 50 $\mu$L 0.5 M NaCl followed by pH neutralization with 2.5 M Tris base (usually ~25–35 $\mu$L). An equal volume of the starved *E. coli* suspension was added immediately and then incubated for 10 minutes at 37° C. at 100 rpm. The mixture was then transferred to a 250 mL sterile culture flask containing 25 mL 2YT with 20 μg/mL tetracycline (Tet) and incubated overnight at 37° C. at 250 rpm.

To isolate amplified phage from overnight cultures, the suspension was centrifuged at 12,000×g for 10 minutes in polycarbonate tubes and the pellet discarded. After heating the supernatant at 70° C. for 30 minutes in polypropylene tubes, the material was spun again in polycarbonate tubes and the supernatant saved. To the supernatant, ¼ volume of 20% (w/v) polyethylene glycol, molecular weight 8000 (PEG 8000) was added to precipitate phage. The solution was mixed by inversion 100 times and then incubated at 4° C. for 2 hours. After centrifugation at 35,000×g for 30 minutes at 4° C., the phage-containing pellet was resuspended in ~0.5 mL of TBS/BSA and transferred to a 1.4 mL microfuge tube. After a 1 minute spin in a microfuge at 16,000×g, the supernatant was transferred to a clean tube and labeled first round amplified phage.

During second, third and fourth rounds of biopanning, 75 μL of amplified phage from the preceding round was incubated with 7 μL affACA-6501 in a final volume of 100 μL. For fifth round phage, affACA-6501 was diluted first at 1:1000, then treated as described for the other rounds. All subsequent steps were carried out as described for the first round. Phage from five rounds of biopanning were spot-titered on 2YT/Tet plates to determine phage concentration. The spot titer of amplified phage requires an initial phage dilution of $1 \times 10^6$ in TBS/BSA or 2YT media. For each round, 10 μL of the dilute phage was incubated with 40 μL of starved *E. coli* for 10 minutes at 37° C. with no shaking. Following the addition of 950 μL of 2YT/dilute Tet (0.2 μg/mL), the mixture was incubated for 30–45 minutes at 37° C. with 250 rpm shaking. Ten μL aliquots of neat and diluted phage solutions, 1:10, 1:100, and 1:1000, were spotted in 2YT/dilute Tet using agar plates containing 20 μg/mL Tet.

Micropanning

Immulon type 2 plates were coated with protein G. Protein G was prepared at 10 μg/mL in 0.1 M NaHCO$_3$ and 100 μL per well was added to the wells of microtitration plates and incubated overnight at 4° C. After discarding excess protein G solution from plates, each well was blocked with 250–300 μL 2YT for 1 hour at RT with agitation on an oscillating platform. Tris-buffered saline, pH 7.4/0.5% Tween 20 (TBS/Tween), was used with an automatic plate washer to wash the wells 4 times with 200 μL. One hundred μL affACA-6501 (or control normal IgG), diluted to 2.5 μg/mL with 2YT, was added to washed wells. The plate was transferred to a cold room rotator near the end of a 1 hour incubation at RT on a rotating platform.

Phage to be tested by micropanning were obtained from the agar plates generated by biopanning. Each clone to be tested was transferred using sterile toothpicks to a separate well of a round-bottom 96-well microtitration plate (Corning, Corning, N.Y.) containing 250 μL 2YT/Tet per well and cultured overnight at 37° C. Clone designations are based on the screening antibody, the biopanning round of origin, and the location of the clone in the overnight culture plate, e.g., ACA-6501/3B10 refers to the clone isolated by ACA-6501 in the third round located in the well designated B10 on the microtitration plate. Following overnight incubation, phage cultures were centrifuged using a microtitration plate holder at 1300×g for 10 minutes at RT. Supernatants constituted the source of "neat" phage.

Figure 8:
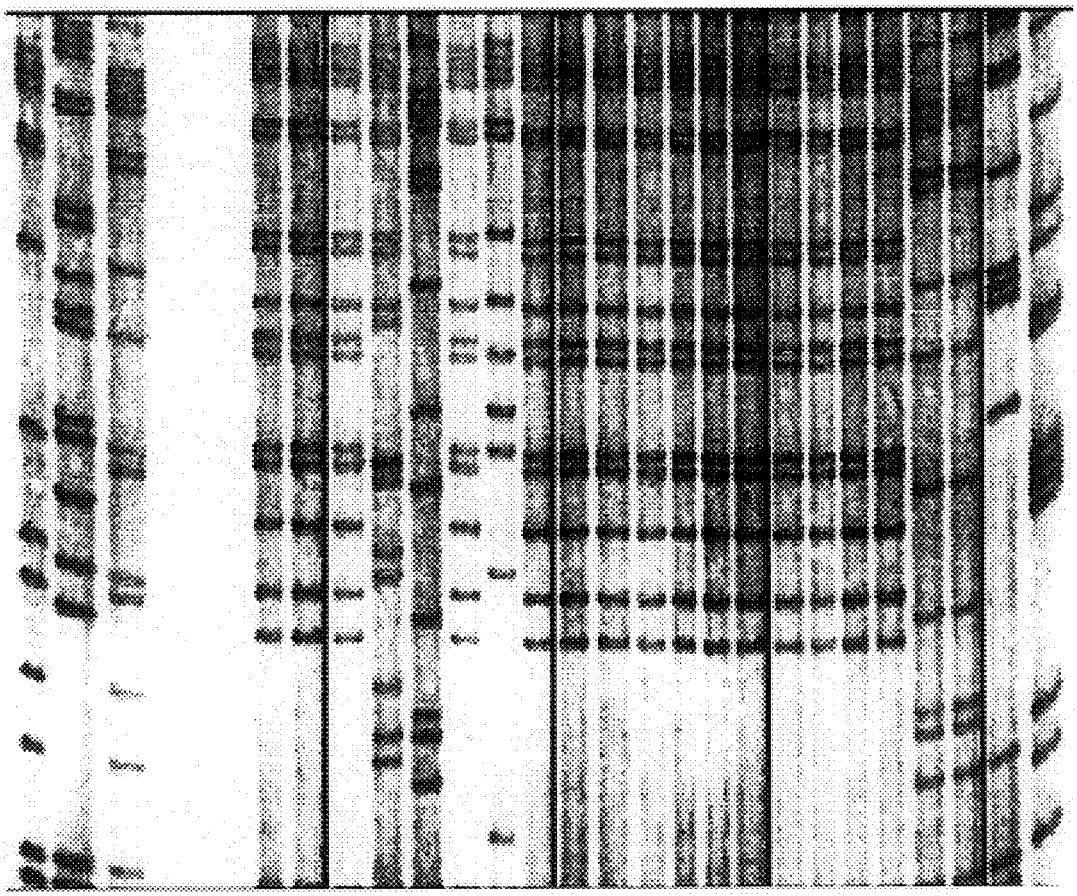
FIG. 8 illustrates the dramatic drop in sequence diversity of the isolated clones by the fourth round of biopanning.

Initial micropanning was restricted to six clones which were tested at dilutions expanded by factors from 1:10 to $1:10^6$. The results from these pilot clones were used to suggest the appropriate single dilution that would yield gradable results for clones in the source plate for each round. Plates representing cultured, randomly chosen clones from the 3rd, 4th, and 5th rounds of biopanning were diluted to 1:100,000 from the "neat" solution using 2YT in microtitration plates with a final volume per well of 250 μL. From the last plate representing the desired dilution, 100 μL was added to the plate containing protein G-bound ACA-6501 and normal IgG prepared as described above. The incubation of dilute phage with aPL antibody or control IgG was carried out for 2 hours at 4° C. on a flat rotator. After 9 washes with TBS/Tween in an automated plate washer, the IgG-bound phage was eluted with 20 μL of 0.2 N HCl-glycine/0.1% BSA, pH 2.2. The elution incubation continued for 10 minutes at RT, during which time a new Corning microtitration plate was prepared containing 20 μL of freshly starved *E. coli* per well and kept chilled. One hundred forty μL of 29 mM Tris was added to the plate containing the phage eluates in order to neutralize the pH, following which 20 μL of phage suspension was transferred from each well to the corresponding well in the plate containing starved *E. coli*. After a 10 minute incubation at 37° C., 200 μL 2YT/dil Tet was added and incubation carried out an additional 30 minutes at 37° C. Using multichannel pipettors, 10 μL from each well was spotted on a large 2YT/Tet agar plate while retaining the original 8×12 well pattern and orientation from the last microtitration plate. After allowing the spots to dry for 30 minutes, the plate was incubated overnight at 37° C. The following day, colonies were semiquantitatively scored from 0 to 4+, with 0 symbolizing <10 colonies; +/−, 10–20; 1+, 20–50; 2+, 50–70% confluent; 3+, 70–90% confluent; and 4+ representing >90% confluent colonies. Of the 94 clones that were examined at a dilution of $1:10^5$ [representing 81 third, 6 fourth, and 7 fifth round clones], six clones had micropanning scores of zero, three scored 1+, 14 scored 2+, 62 scored 3+, and 9 scored 4+. A survey of random clones from the plates representing the second through fifth rounds of biopanning was carried out by G-track DNA sequencing as described below. The results showed a dramatic drop in sequence diversity by the fourth round of biopanning (see FIG. 8), therefore, a second plate was micropanned using phage at a dilution of $1:3 \times 10^5$, this time including clones from an earlier (second) round. A total of 94 clones were tested, including 29 which had scored high at $1 \times 10^5$ dilution [26 from the 3rd round, 1 from the 4th found, and 2 from the 5th round] plus 65 clones from the 2nd round that had not been previously tested. Of the 94 clones tested at a dilution of $1:3 \times 10^5$, 26 scored zero, 11 scored +/−, 10 scored 1+, 13 scored 2+, 34 scored 3+, and zero scored 4+.

G-track DNA Sequencing

Single-stranded viral DNA was isolated from cultures incubated overnight at 37° C. To prepare cultures, 2YT/Tet, either as 2 mL in tubes or 250 μL in microtitration plate round-bottom wells, was inoculated with individual phage from spread plates of previously grown cultures in microtitration plates. The purification of phage by 20% PEG/2.5 M NaCl precipitation of culture supernatants as well as the isolation or release of virion DNA by phenol-chloroform extraction or by alkali denaturation was performed as described in Smith, G. P. and J. K. Scott, "Libraries of peptides and proteins displayed on filamentous phage" (1993) *Meth. Enzymol.* 217:228–257 for cultures in tubes and as described in Haas, S. J. and G. P. Smith G. P., "Rapid sequencing of viral DNA from filamentous phage" (1993) *BioTechniques* 15:422–431 for phage in microtitration plates. The dideoxy nucleotide chain termination DNA sequencing technique of Sanger et al. (Sanger et al., "DNA sequencing with chain terminating inhibitors" (1970) *Proc. Natl. Acad. Sci.* 74:5463–5467) was carried out using a commercial Sequenase kit (U.S. Biochemical/Amersham, Arlington Heights, Ill.) as described by Smith and Scott, supra, for tube culture phage DNA and as in Haas and Smith, supra, for phage DNA from microtitration plates. By using only the ddCTP termination mixture, G tracking or the sequence pattern suggested by a single base (G) was obtained following electrophoresis on 7% polyacrylamide/urea sequencing gels and exposure by autoradiography. Standard gel electrophoresis and autoradiography procedures were followed (Sambrook et al., supra).

G-tracking of 76 clones from the micropanning plate tested at a phage dilution of 1:1×10$^5$ from the ACA-6501 library screen revealed 11 unique sequences, while 64 clones from the second micropanning plate tested at a phage dilution of 1:3×10$^5$ showed 30 unique sequences. Conventional DNA sequencing using all four dideoxynucleotide triphosphates was applied to the phage clones with the highest micropanning scores and unique sequences and resulted in the 12 sequences shown in Table 1 for the xyz library.

Phage-Capture ELISA

Figure 9:
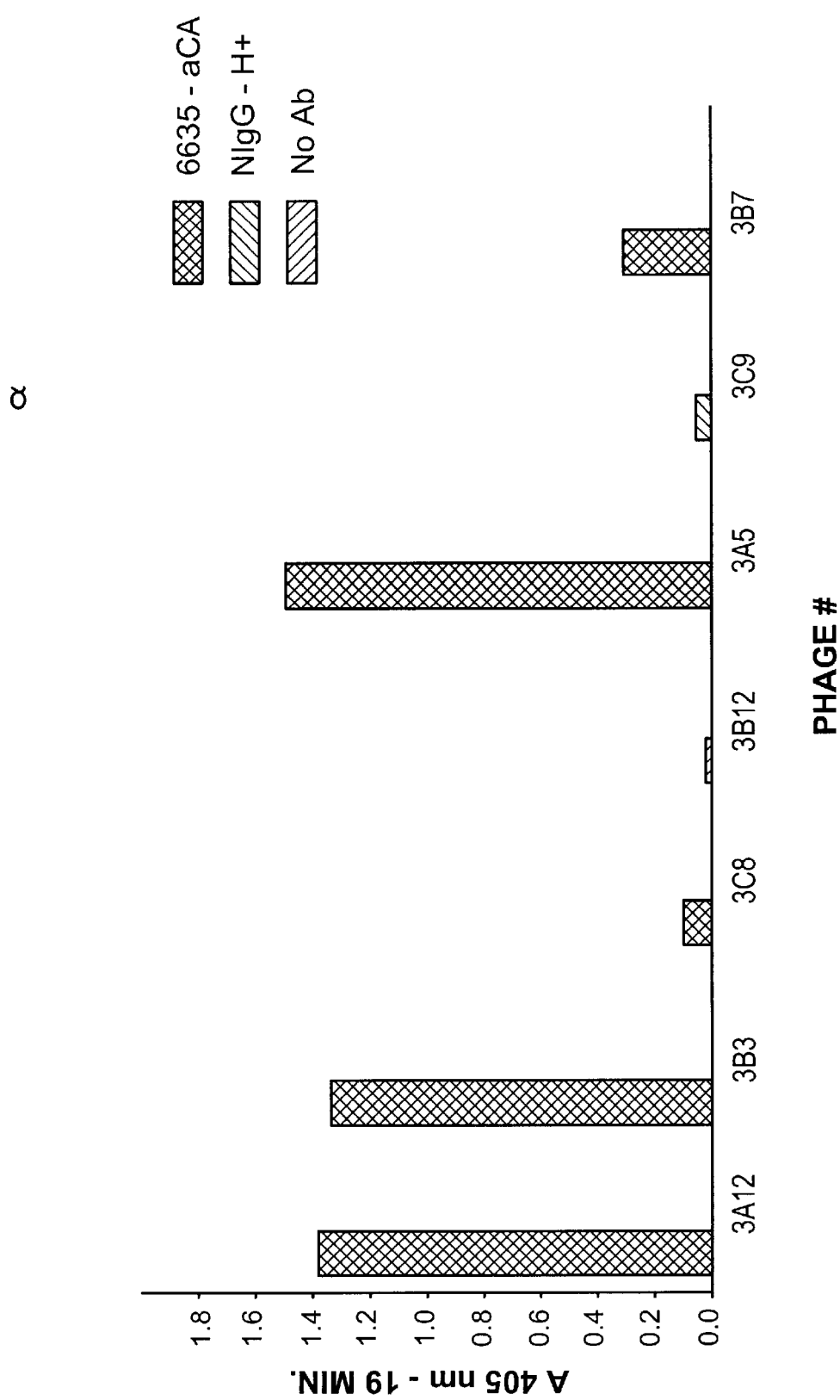
FIG. 9 illustrates that three clones (3A12, 3B3 and 3A5) exhibited a very strong immunospecific signal in the phage-capture ELISA using ACA-6635 whereas all clones tested were unreactive with normal IgG.

Clones ACA-6635/3A12, 3B3, 3C8, 3A5, 3C9, and 3B7 were grown as 3 mL cultures. Affinity purified ACA-6635 was diluted to 2.5 $\mu$/mL in phosphate-buffered saline, pH 7.2, and 100 $\mu$L added to Immulon-2 microtitration plate wells. After 2 hours, the plates were washed 3 times with TBS/Tween in an automated plate washer with no shaking. The plate was then blocked with 150 $\mu$L 0.1 % BSA (globulin-free) in PBS per well. After 1 hour at 4° C., the plate was washed 3 times as previously described. After centrifuging each phage culture 3 minutes at 17,000×g, each supernatant was diluted 1:10 in 0.1 % BSA/PBS and 100 $\mu$L added to each of the wells coated with affinity purified ACA-6635 and then incubated for 2 hours at 4° C. Plates were then washed with TBS/Tween as before. Horseradish peroxidase-conjugated sheep IgG anti-M 13 phage antibody (Pharmacia, Inc., Piscataway, N.J.) was diluted 1:5,000 in 0.1% BSA/PBS and 100 $\mu$L applied to each well. Following incubation for 1 hour at 4° C., the plate was washed 4 times as before. One hundred $\mu$L of substrate prepared according to the conjugate manufacturer's instructions was added to each well. After 19 minutes, the absorbance at 405 nm of each well was read in the automated microplate absorbance reader (Biotek, Winooski, Vt.) The seven clones tested from the ACA-6635 phage library screen were selected because of their high micropanning scores and negative phage-ELISA scores (see below). As shown in FIG. 9, three clones (3A12, 3B3, and 3A5) out of the seven tested exhibited a very strong immunospecific signal in the phage-capture ELISA.

Phage-ELISA

Figure 10:
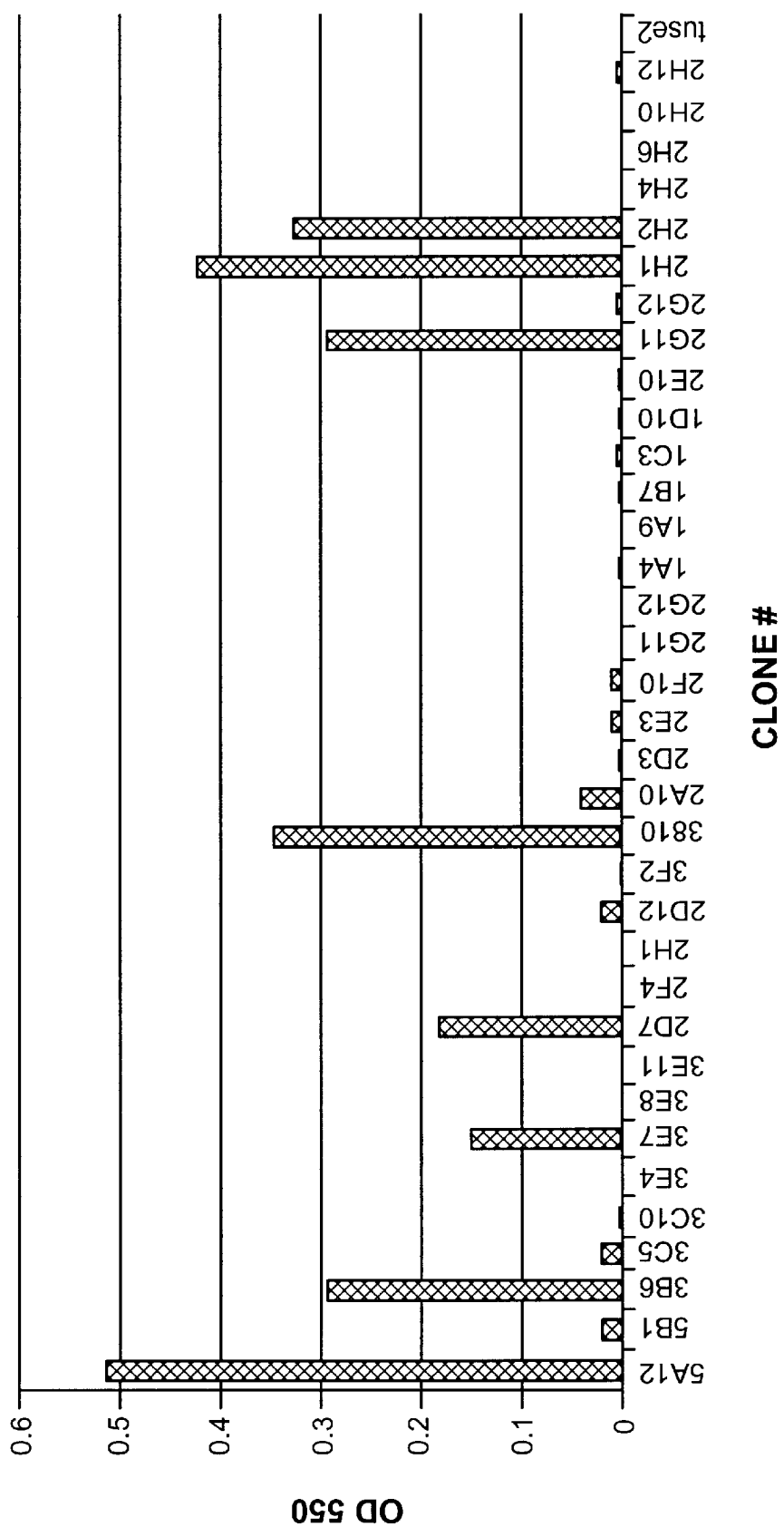
FIG. 10 shows the strong signal exhibited by seven clones in a phage-ELISA using ACA-6501.

Three mL cultures were prepared from 35 clones previously isolated with affinity purified ACA-6501 in several phage library screens as well as one fUSE 2 phage clone lacking a peptide insert which was used as a control. After centrifugation for 3 minutes at 17,000×g, 100 $\mu$L from each phage supernatant (adjusted to ~2×10$^{11}$ particles/mL, based on absorbance) was added to microtitration plate wells (Falcon, Becton-Dickinson Labware, Lincoln Park, N.Y.) and allowed to incubate overnight at 4° C. Following four washes with TBS 7.4, the plate was blocked with 125 $\mu$L of 0.5% BSA/TBS for 1 hour at RT. After another four TBS washes, 100 $\mu$L of affACA-6501 previously diluted to 2.5 $\mu$g/mL in TBS/BSA was added to each well and allowed to incubate 1 hour at 37° C. Following an additional four washes, 100 $\mu$L anti-human IgG diluted 1:1000 in TBS/0.5% Tween was added to each well. After 1 hour at RT, enzyme substrate was added and the incubation allowed to proceed for 2 hours. Following the addition of 50 $\mu$L 0.2 M Na$_2$HPO$_4$ to stop the reaction, absorbance was measured at 550 nm in the automated plate absorbance reader. As shown in FIG. 10, seven of the clones had significant signals in the phage-ELISA with ACA-6501: 5A12, 3B6, 3E7, 3B10 (same sequence as 2D7), 2G11, 2H1, and 2H2. The sequences for these clones are shown in Table 2.

Peptide-ELISA

In the standard protocol, stock solutions of tetrameric peptide in dimethylformamide were diluted 1000 times to 10 $\mu$g/mL in pH 9.5 carbonate buffer. Each microtitration plate well was coated overnight at 4° C. with 100 $\mu$L of dilute peptide followed by blocking with buffered albumin. Peptide-coated microtitration plates were incubated 1–2 hours at room temperature with aPL sera at several dilutions starting at 1:50. Following washes, the presence of peptide-bound human IgG was determined with enzyme-conjugated anti-human IgG according to standard ELISA procedures.

Competitive Binding Peptide-ELISA (A) Each well of an Immulon II plate (Dynatech Laboratories, Inc., Chantilly Va.) was coated with 100 $\mu$L of a solution containing 10 $\mu$g tetravalent peptide ACA 6501/3B10 in 50 mM sodium carbonate, pH 9.5, containing 35 mM sodium bicarbonate (Fisher Scientific, Pittsburgh, Pa., reagent grade) for at least 1 hour at RT, except for three wells used as blank controls. The liquid was then removed from the wells and 200 $\mu$L of 0.5% (wt/vol) BSA (Sigma Chemical, St. Louis, Mo., #A7638) in TBS was added per well including the blank wells for blocking and incubated for at least 1 hour at RT. Four 1.5 mL microfuge tubes were numbered 1 to 4. The following reagents were mixed in the first microfuge tube (Brinkman Instruments, Westbury, N.Y.): 30 $\mu$L of 5% BSA; 284 $\mu$L TBS; 8 $\mu$L of a stock solution of approximately 400–500 $\mu$g/mL of monomeric peptide (ACA-5A12 or -CB2 or -3B10 or scrambled -3B10 as negative control) in TBS; and 8.2 $\mu$L of 1:10 diluted serum 6501 in 0.5% BSA-TBS. The following reagents were mixed in the second microfuge tube: 30 $\mu$L of 5% BSA; 290 $\mu$L TBS; 2 $\mu$L of a stock solution of approximately 400–500 $\mu$g/mL of monomeric peptide (ACA-5A12 or -CB2 or -3B10 or scrambled -3B10 as negative control) in TBS; and 8.2 $\mu$L of 1:10 diluted serum 6501 in 0.5% BSA-TBS. The following reagents were mixed in the third microfuge tube: 30 $\mu$L of 5% BSA, 287 $\mu$L of a 1:10 dilution of approximately 400–500 $\mu$g/mL of monomeric peptides (5A12, CB2, 3B10, or scrambled sequence 3B10 control), and 8.2 $\mu$L of ACA-6501 serum previously diluted 1:10 in 0.5% BSA-TBS. The following reagents were mixed in the fourth Eppendorf microfuge tube: 60 $\mu$L 5% BSA; 584 $\mu$L TBS and 16.5 $\mu$L of 1:10 diluted serum 6501 in 0.5% BSA-TBS. The blocked plate was washed 5 times with TBS. The solution in the first microfuge tube was added to triplicate wells, 100 $\mu$L per well. Identical amounts of the solutions in the second, third and fourth microfuge tubes were also added to triplicate wells. An aliquot of 100 $\mu$L of the solution in the fourth microfuge tube was added to each of the three blocked blank wells of the microtitration plate. The plate was incubated for 1 hour at RT with agitation at 40 rpm in an orbital shaker (American Dade, Miami, Fla., Rotator V) and then washed 5 times with TBS. An aliquot of 100 $\mu$L of 1:1000 diluted goat-anti-human-IgG/alkaline phosphatase conjugate (Zymed, South San Francisco, Calif., Cat. no. 62-8422) in 0.5% BSA-TBS was added and incubated for 1 hour at RT.

The plate was then washed 5 times with TBS and the assay was developed by adding 100 μL PPMP diluted substrate solution as described in Example 1. After 20 minutes, the reaction was stopped by adding 50 μL of 0.2 M $Na_2HPO_4$ (Mallinckrodt, St. Louis, Mo., reagent grade) per well. The optical density was read at 550 nm in a microplate reader (Bio-Tek Instruments, Winooski, Vt., Model EL 311). The optical density at 550 nm versus the amount of the peptide per well was plotted in Graph Pad Prizm (Graph Pad Software, Inc., San Diego, Calif.). The amount of peptide required for 50% inhibition of binding of serum 6501 to tetravalent 3B10 was calculated from the graph.

(B) Immulon I® 96-well, flat-bottom, polystyrene microtitration plates (Dynatech Laboratories, Inc., Chantilly, Va.) were coated with 30 μL/well of cardiolipin (CL, 50 μg; Sigma Chemical Co., St. Louis, Mo.) in ethanol. Two control wells received 30 μL ethanol only. After overnight evaporation at 4° C., each well was blocked with 200 μL of 5% (w/v) fish gelatin in PBS for 2 hours at RT. The CL-coated, blocked plate was washed 5 times with TBS and then to each well was added $β_2$-GPI as 100 μL of 2.3% (v/v in PBS) IgG-depleted human serum (Sigma Chemical Co., St. Louis, Mo.) and incubated 2 hours at RT.

During this incubation, variable amounts of each of six peptides were mixed with 22 μL ACA-6501 serum diluted with 3% fish gelatin in 1:1 TBS/PBS (final dilution of 1:400) in a final volume of 220 μL using Eppendorf microcentrifuge tubes. Specifically, in tube #1 were mixed 181.3 μL of 3% fish gelatin in TBS-PBS, 16.7 μL of peptide stock solution plus 22 μL of ACA-6501 serum diluted 40 times in 3% fish gelatin/TBS-PBS. Stock solutions ranged from 450–800 μg/mL for peptides #951 (diserine non-cyclized negative control), #952 (a lot of LJP 690), and thioethers CCTE-3G3, CHTE-3G3, HCTE-3G3 and HHTE-3G3. To tube #2 the following were added: 148 μL fish gelatin/TBS-PBS, 50 μL of peptide stock solution, plus 22 μL of 40 times diluted ACA-6501 serum. Tube #3 contained 48 μL fish gelatin/TBS-PBS, 50 μL of peptide stock solution, plus 22 μL of 40 times diluted ACA-6501 serum. The control tube #4 received 396 μL fish gelatin/TBS-PBS and 44 μL of 40 times diluted ACA-6501 serum (no peptide). Each of the tubes incubated for approximately 1 hour at RT.

Figure 12:
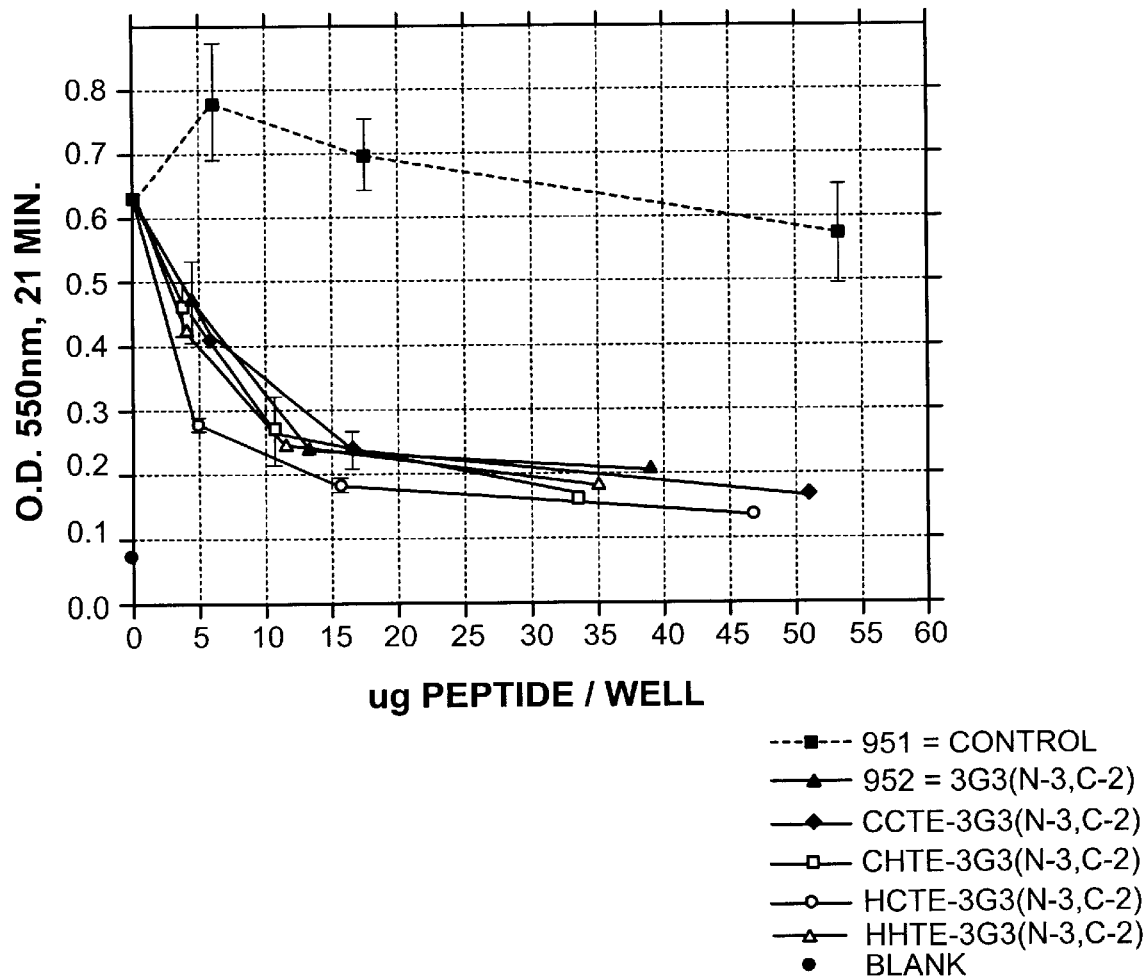
FIG. 12 illustrates the comparative activity of modified ACA-6641/3G3 analogs.

The CL/β2-GPI microtitration plate was washed 5 times with TBS and 100 μL aliquots in duplicate from Eppendorf tubes #1, 2, 3, and 4 containing the antibody-peptide (or no peptide mixtures) were added to the wells. A volume of 100 μL from tube #4 was added to the duplicate control wells containing no cardiolipin. The microtitration plate was incubated for 1 hour at RT with agitation at 40 rpm in an orbital shaker (American Scientific, Rotator V), washed 5 times with TBS and then 100 μL of 1:1000 goat anti-human IgG alkaline phosphatase conjugate (Zymed, Cat No. 62–8422) in 0.5% (w/v) BSA-TBS was added. Following incubation for 1 hour at RT, the microtitration plate was again washed 5 times with TBS and the calorimetric enzyme detection developed by adding 100 μL of PMPP solution (7.8 g phenolphthalein monophosphate plus 69.5 g of 2-amino-2-methyl-1-propanol in 100 mL water stock solution diluted 1:26 with water). After 21 minutes, the reaction was stopped by adding 50 μL of 0.2 M $Na_2HPO_4$ (Mallinckrodt) to each well. Absorbance at 550 nm was read in a microplate reader (Bio-Tek Instruments, Model EL 311). Absorbance vs. peptide added was plotted on Graph Pad Prism (Graph Pad Software, Inc.) as shown in FIG. 12. The amount of peptide that inhibited ACA-6501 binding by 50%, the $IC_{50}$, was calculated from the graph at the intersection of half-maximal absorbance with amount of peptide added.

(C) Nunc Maxisorp® 96-well, flat-bottom microtitration plates were coated with 100 μL/well of purified human $β_2$-glycoprotein I (PerImmune, Rockville, Md.) at 10 μg/well in PBS. Two control wells received 100 μL PBS only. After two hours incubation at room temperature, the liquid was removed. The coated plate was blocked for 2 hours at room temperature with 200 μL/well of PBS containing 2% (w/v) nonfat dry milk (Carnation, Glendale, Calif.) and 0.4% (w/v) Tween 80 (Calbiochem, San Diego, Calif.). The blocking solution was also used as a reagent diluent.

During the second hour of incubation, variable amounts of each of four test peptides were mixed with 22 μL of ACA-6501 serum diluted with sample diluent in a final volume of 220 μL using Eppendorf microcentrifuge tubes. Specifically, in tube #1, 188 μL of sample diluent, 10 μL of peptide stock solution (2 mg–4 mg/mL diluent), and 22 μL of AC-6501 serum diluted 1:35 in sample diluent were added. To tube #2, 158 μL sample diluent, 40 μL peptide stock solution and 22 μL of 1:35 diluted ACA-6501 serum were added. Tube #3 contained 38 μL sample diluent, 160 μL peptide stock solution and 22 μL of 1:35 diluted ACA-6501 serum. The control tube, tube #4, contained 396 μL sample diluent and 44 μL of 1:35 diluted ACA-6501 serum (no peptide). Each of the tubes was incubated for approximately 1 hours at room temperature.

Figure 21:
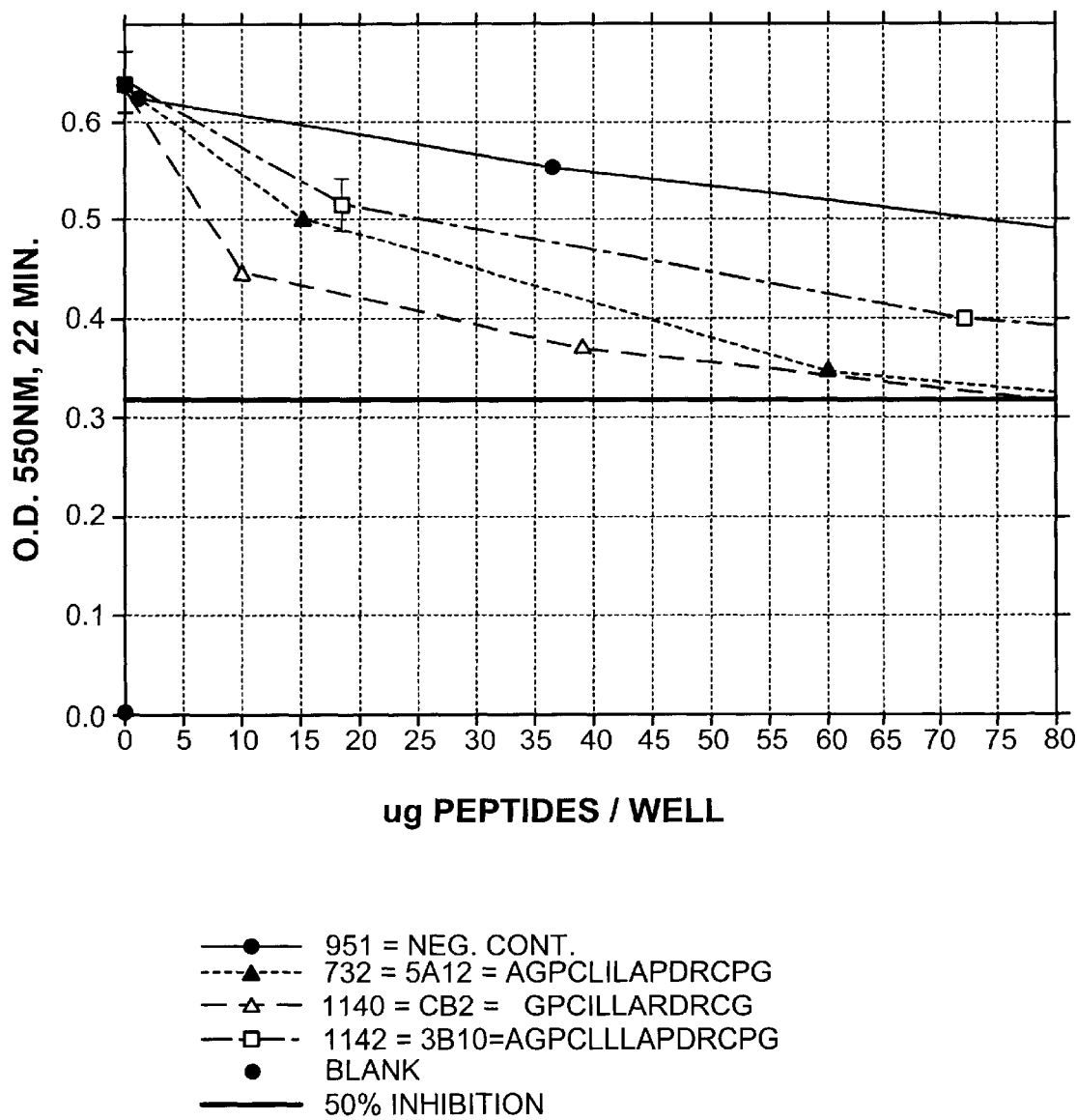

The $β_2$-GPI microplate was washed 5 times with TBS and 100 μL of the mixtures contained in Eppendorf tubes #1, 2, 3 and 4 was added to duplicate wells of the microplate. 100 μL of the contents of tube #4 was added to each of the duplicate control wells that were not coated with $β_2$-GPI. The plate was incubated for 1 hour at room temperature, washed 5 times with TBS and 100 μL of 1:1000 goat anti-human IgG/AP conjugate (Zymed, Cat. No. 62–8422) diluted in sample diluent buffer was added. Following incubation for 1 hour at room temperature, the plate was again washed 5 times with TBS and the colorimetric enzyme detection developed by adding 100 μL PPMP solution (7.8 g phenolphthalein monophosphate and 69.5 g 2-amino-2-methyl-1-propanol in 100 mL water stock solution diluted 1:26 with water). After 22 minutes, the reaction was stopped with 50 μL of 0.2 M $Na_2HPO_4$ (Mallinckrodt) added per well. $A_{550\ nm}$ was read in a microplate reader (Bio-Tek Instruments, Model EL 311). Absorbance vs. peptide added was plotted on Graph Pad Prism (Graph Pad Software, Inc.) as shown in FIG. 21. The amount of peptide that inhibited ACA-6501 binding by 50%, the IC-50, was calculated from the graph at the intersection of half-maximal absorbance with the amount of peptide added.

Example 5

Truncation Experiments of Peptide 3B10 and the Resulting Peptide Competition ELISA Results Microtitration plates (96-well, flat bottom polystyrene, Immulon-2, Dynatech Laboratories, Inc., Chantilly, Va.) were coated with 100 μL/well for 1 hour at RT with tetrameric ACA-6501/3B10 peptide at 10 μg/mL in carbonate buffer, pH 9.6 (15 mM $Na_2CO_3$/35 mM $NaHCO_3$). After the liquid from the wells was removed, each well was blocked for 1 hour at RT with 200 μL 0.5% (wt/vol) BSA (globulin-free, cat. no. A7638, Sigma Chemical Co., St. Louis, Mo.) in TBS. Three wells on the plate were left uncoated by tetravalent peptide to serve as blank control wells.

During the blocking step, each soluble, monomer peptide to be tested was set up in three test tubes (Eppendorf micro test tubes, Brinkrmann Instruments, Westbury, N.Y.) each containing 30 μL 5% BSA/TBS, 8.2 μL ACA-6501 serum (at 1:10 dilution with 0.5% BSA/TBS), plus a variable volume of the peptide/TBS stock and the necessary volume of TBS buffer to yield a final volume of 330 μL. The 330 μL volume was sufficient to generate triplicate 100 μL samples for each peptide concentration that was tested for its ability to block ACA-6501 binding to the tetravalent peptide-coated plate. For peptide 139, which was truncated at the amino terminus and lacks the framework ala-gly contribution normally tested, the concentration of the stock solution was approximately 340–400 μg/mL TBS and aliquots of 19 μL, 75 μL, and 292 μL were removed to prepare the three peptide concentration tubes. For peptide 142 (lacking only the N-terminal ala) and peptide 143 (not truncated), stock solution concentrations were 400–500 μg/mL in TBS. Aliquots from each stock solution of 1 μL, 4 μL, and 16 μL were removed to set up the three concentration tubes for each peptide. For the peptide monomer control tube (lacking peptide), a tube with a final volume of 660 μL was prepared containing 60 μL 5% BSA, 16.5 μL of a 1:10 dilution of ACA-6501 and 583.5 μL TBS, i.e., the same final concentrations (0.5% BSA and ACA-6501 serum at 1:400) as the 330 μL tubes but with twice the volume and without peptide.

Figure 11:
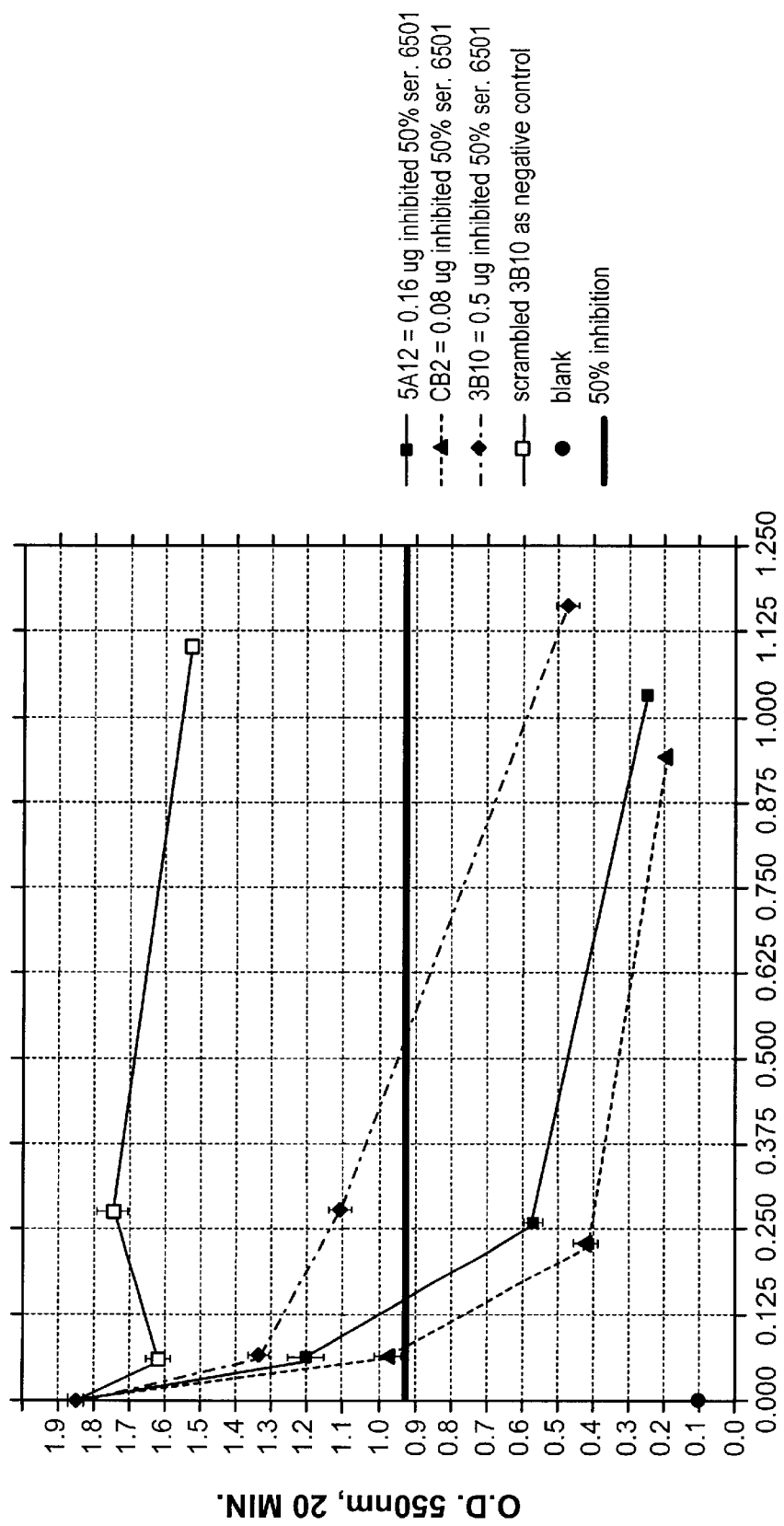
FIG. 11 shows the results of a competitive-binding ELISA obtained with peptides 5A12, CB2 and 3B10 using ACA-6501. 0.16 μg of Peptide 5A12 produced 50% inhibition of binding of ACA-6501 aPL antibody to tetravalent peptide ACA-6501/3B10 bound to polystyrene microplate wells, whereas 0.08 μg of CB2 and 0.5 μg of 3B 10 were required to produce 50% inhibition.

Following the blocking incubation, the plate coated with tetravalent peptide was washed 5 times with TBS. From each 330 μL tube containing peptides 139, 142 and 143 at different concentrations, 100 μL was added to coated triplicate wells. Three 100 μL aliquots from the 660 μL control tube without peptide were each added to coated wells and three additional 100 μL aliquots were each added to uncoated blank wells. The plate was incubated at 40 rev/min on a rotary orbital shaker (Rotator V, American Dade, Miami, Fla.) for 1 hour at RT and then washed 5 times with TBS. One hundred μL/well of goat antihuman IgG/alkaline phosphatase conjugate (Cat. no. 62-8422, Zymed, South San Francisco, Calif.) diluted 1:1000 in BSA/TBS was added to the microplate. After incubation for 1 hour at RT, the plate again was washed 5 times with TBS. Color development followed the addition of 100 μL/well of freshly prepared dilute PPMP substrate solution. A dilute solution of PPMP (phenolphthalein monophosphate, cat. no. P-5758, Sigma Chemical Co., St. Louis, Mo.) was prepared by making a 1:26 dilution with water of the PPMP stock solution (0.13 M PPMP, 7.8 M amino-2-methyl-1-propanol adjusted to pH 10.15 with HCl). After 30 minutes, the reaction was stopped by adding 50 μL/well of 0.2M $Na_2HPO_3$ (reagent grade, Mallinckrodt, St. Louis, Mo.). Absorbance measurements at 550 nm were carried out on a microplate reader (Bio-Tek Instruments, Winooski, Vt.) and the $A_{500\ nm}$ Vs. peptide added per well results plotted using Graph Pad Prizm (Graph Pad Software, Inc., San Diego, Calif.). As shown on FIG. 11, a horizontal line has been drawn corresponding to half-maximal the binding reaction obtained in the absence of monomer peptide competitive inhibition. The amount of peptide necessary for 50% inhibition can be read at the intersection of this line with the plot for each peptide tested. The 50% inhibition values are shown on FIG. 12. The results indicate that while the loss of the N-terminal Ala had no negative consequences, the additional loss of Gly increased by about 8-fold the concentration necessary to achieve 50% inhibition.

Example 6

Substitution of Alpha Methyl Proline Into 3B10 and the Resulting ELISAs

Testing of peptides ACA-6501/3B10 and analogs in which prolines at the 3 and 9 position were replaced by α-Me-Pro was carried out using the methodology described in Example 5. Peptides 3B10, 726 (αMe-Pro substituted at the 3 position), 727 (αMe-Pro substituted at the 9 position), and 728 (αMe-Pro substituted at both the 3 and 9 positions) were tested as soluble monomer peptides in a competitive-binding ELISA using tetramer peptide 3B10-coated microtitration plates and ACA-6501 serum.

Microtitration plates were coated with tetramer 3B10 peptide as described for Example 5. For each of the four peptides tested, three peptide concentrations were prepared in tubes. As in Example 5, these twelve tubes had final concentrations of 0.5% BSA/TBS and ACA-6501 serum at a final dilution of 1:400 in a final volume of 330 μL. All peptide stock solutions were at 400–500 μg/mL TBS. To tubes containing 30 μL of 5% BSA/TBS and 8.2 μL of ACA-6501 serum (diluted 1:10 with 0.5% BSA/TBS), aliquots of 1 μL, 4 μL, or 16 μL of each of the four peptide stock solutions were added in addition to an appropriate volume of TBS to achieve a final volume of 330 μL. A control tube with no competitor peptide present was prepared with a final volume of 660 μL as described in Example 5.

Figure 13:
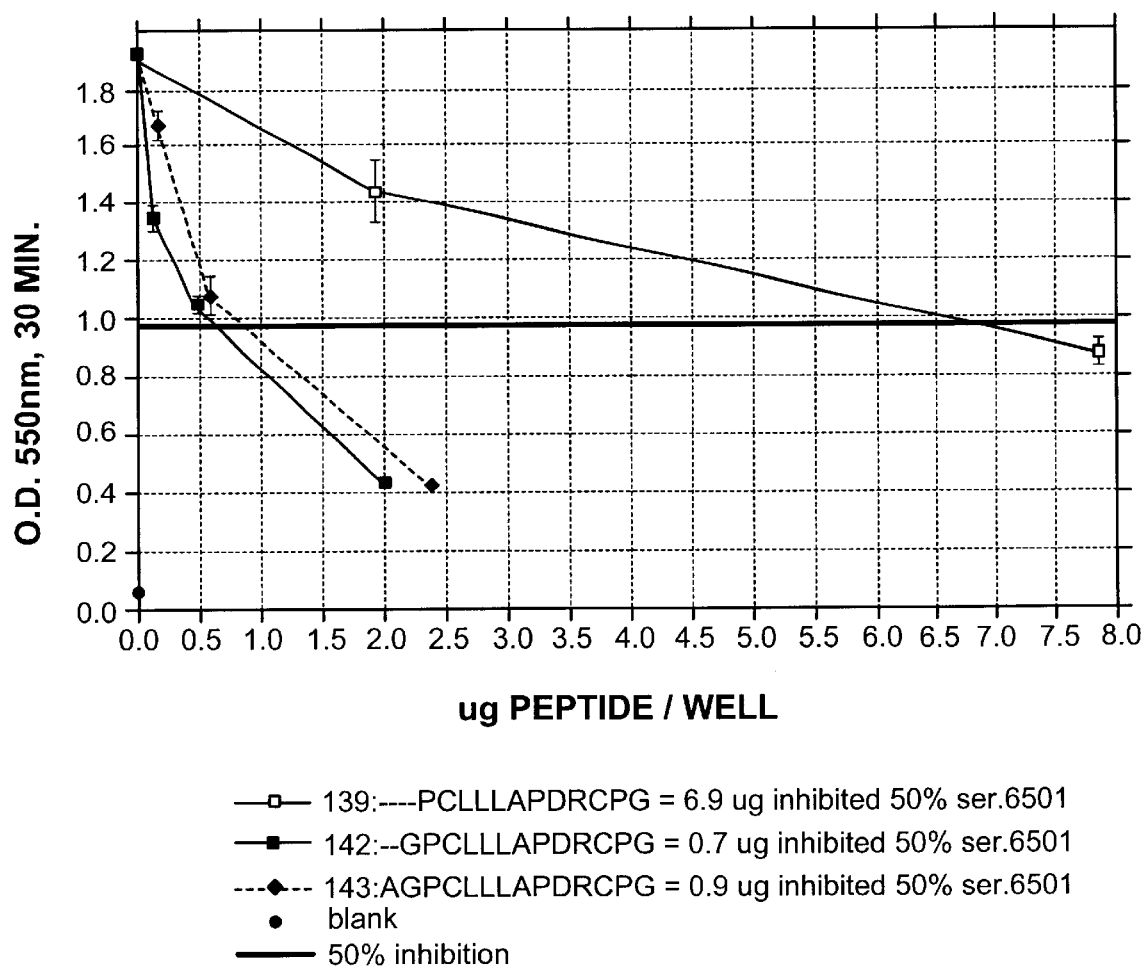
FIG. 13 (SEQ ID NOS:1–3) illustrates that the 50% inhibition values for peptides 139, 142 and 143 in a competitive-binding ELISA using ACA-6501 aPL antibody were 6.9, 0.7 and 0.9 μg, respectively.

Following the blocking incubation of the tetravalent peptide-coated plate, three 100 μL aliquots from each of the peptide concentration tubes for each of the four peptides as well as the control tube containing no peptide and blank controls were tested as described in Example 5. The microtitration plate ELISA procedures as well as the data handling were performed as described in Example 5. As shown in FIG. 13, peptide 727, where α-Me-Pro was substituted at the 9 position, was significantly more active than unmodified peptide 3B10 or the analog with both prolines changed (peptide 728). Peptide 726, which was substituted at position 3, lost activity as a result of the substitution.

Example 7

Abbreviated Description of Screen with 6626 Antibody and the Corresponding Sequences Affinity purified ACA-6626 (AffACA-6626) was isolated by affinity purification from 8 mL of ACA-6626 plasma as previously described. AffACA-6626 (10 μg) was incubated with the epitope $xy^z$ phage library consisting of a pool of all p-III component libraries in a final volume of 100 μL as previously described for ACA-6501 biopanning. Following three rounds of biopanning, randomly selected phage from the second and third rounds were tested by micropanning. Only a few clones were weakly immunopositive at a 1:1000 dilution. An additional 4th round of biopanning was carried out. Micropanning of 94 fourth round clones revealed 43 immunopositives, some at phage dilutions as high as 1:100,000. G-Tracking DNA sequencing of the 43 immunopositive clones carried out as previously described for ACA-6501 revealed 5 unique sequences. After conventional four base DNA sequencing, the translated amino acid sequences of Table 3 were obtained.

Example 8

Identification of Sequences Specific for the ACA from Patient 6644

The $epi^{xyz}$ phage display library was screened using methods similar to those in Example 4 with ACA affinity purified antibody from patient number 6644. A colony blot assay as described previously was employed as the final identification step prior to peptide synthesis. Approximately 150 colonies were plated on the original nitrocellulose membrane and assayed. Antibody from patient 6644 was used at a concentration of 1 μg/mL. Of the 150 colonies plated on the nitrocellular membrane and assayed, only 4 were strongly positive and 2 weakly positive in this screen. Sequencing of the inserts of the six positive phage selected by this screen revealed that the inserts were all derived from the 8-mer library with a free amino-terminus (epi[z]):

Gly-Ile-Leu-Ala-Leu-Asp-Tyr-Val-Gly-Gly (SEQ ID NO:212) (3 inserts)

Gly-Ile Leu-Tlu-Ile-Asp-Asn-Leu-Gly-Gly (SEQ ID NO:213) (1 insert)

Gly-Ile-Leu-Leu-Asn-Glu-Phe-Ala-Gly-Gly (SEQ ID NO:214) (2 inserts)

Example 9
Summary of Phage Library Screen with ACA-6641

AffACA-6641 was isolated from 4 mL of plasma taken from patient number 6641. AffACA-6641 (10 $\mu$g) was incubated with the pooled p-III phage libraries in a final volume of 100 $\mu$L as described previously. Following four rounds of biopanning, 45 clones from the 3rd and 4th rounds were tested by micropanning. Of the 45, 23 scored negative. The 3rd round phage yielded two clones that scored 4+, two that scored 3+ and two that scored 2+. From the 4th round, one clone scored 4+, one scored 3+ and three scored 2+. G-tracking DNA sequencing revealed six unique sequences. Only one, clone 3G3, was strongly positive in the phage-capture ELISA. Four base DNA sequencing gave the following translated peptide sequence:

CLGVLGKLC (SEQ ID NO:58).

Example 10
Peptide Conjugation to Non-immunogenic, Multivalent Carriers

Several tetravalent platforms for the development of B cell tolerogens have been developed as described in co-owned and co-pending U.S. patent applications, Ser. Nos., 08/118,055, filed Sep. 8, 1993, 08/152,506, filed Nov. 15, 1993, and U.S. Pat. Nos. 5,268,454, 5,276,013 and 5,162,515 which are incorporated by reference herein in their entirety. Candidate peptides selected by aPL antibody screens of epitope libraries are conjugated and tested for modifications of immunochemical behavior such as antibody binding.

Non-inmmunogenic multivalent platforms with amine groups are synthesized as shown in the following scheme.

Amine on Platform—Carboxyl on Peptide

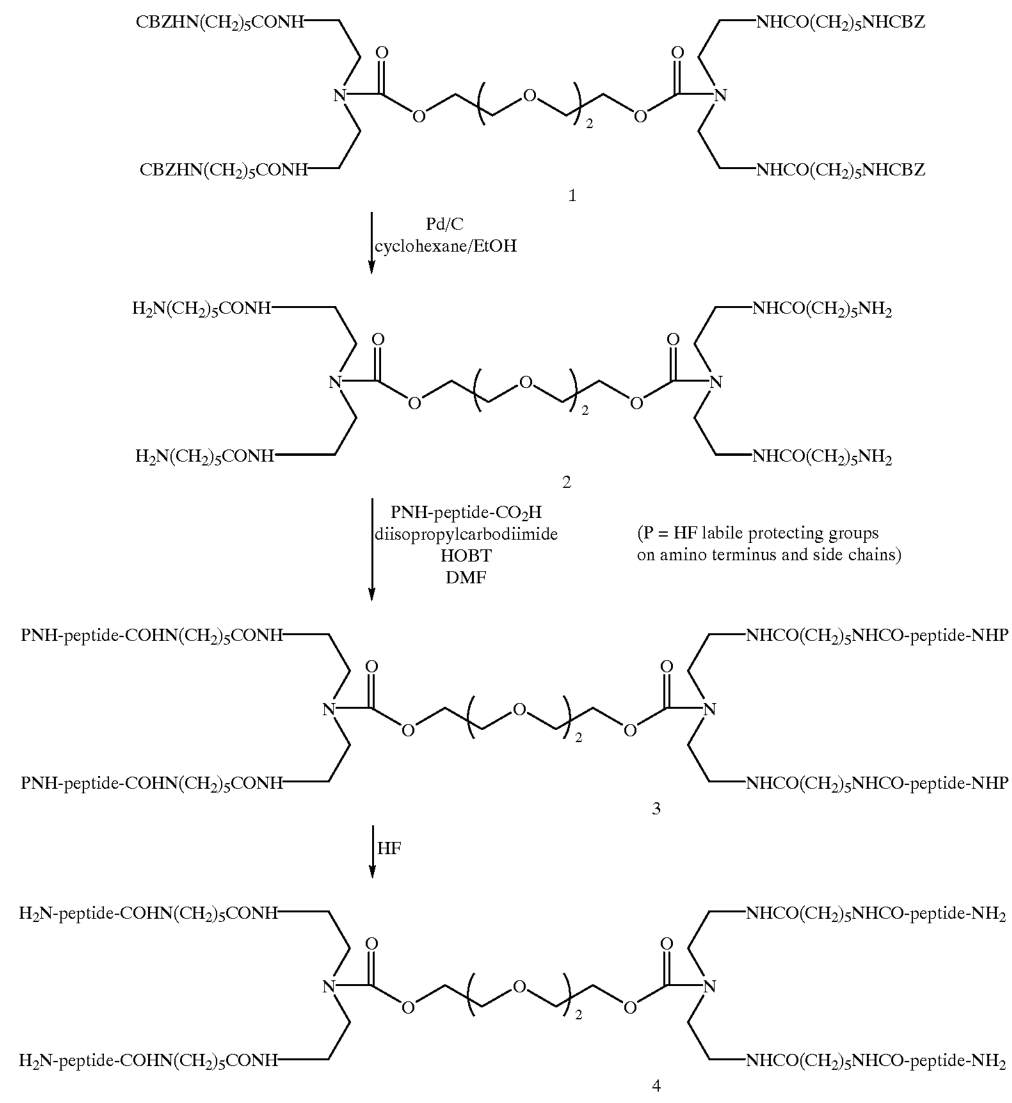

Compound 2

A solution of 8.0 g (5.7 mmol) of 1 in 50 mL of absolute EtOH and 35 mL of cyclohexene was placed under nitrogen, and 500 mg of 10% Pd on carbon was added. The mixture was refluxed with stirring for two hours. When cool, the mixture was filtered through Celite and concentrated to give 5.0 g of 2 as an oil. $^1$H NMR (50/50 CDCl$_3$/CD$_3$OD) d 1.21 (m, 8H), 1.49 (m, 8H), 1.62 (m, 8H), 2.19 (t, J=7.4 Hz, 8H), 2,67 (t, J=7.4 Hz, 8H), 3.36 (bd s, 16H), 3.67 (s, 4H), 3.71 (m, 4H), 4.21 (m, 4H).

Protected peptide with free carboxyl (PHN-peptide-CO$_2$H

A peptide is synthesized with standard solid phase methods using FMOC chemistry on a Wang (p-alkoxybenzyl) resin, using trifluoroacetic acid (TFA) stable protecting groups (benzyl ester or cyclohexyl ester on carboxyl groups and carbobenzyloxy (CBZ) on amino groups). Amino acid residues are added sequentially to the amino terminus. The peptide is removed from the resin with TFA to provide a peptide with one free carboxyl group at the carboxy terminus and all the other carboxyls and amines blocked. The protected peptide is purified by reverse phase HPLC.

Peptide—Platform Conjuaate, 4

The protected peptide (0.3 mmol) is dissolved in 1 mL of dimethylformamide (DMF), and to the solution is added 0.3 mmol of diisopropylcarbodiimide and 0.3 mmol of 1-hydroxybenzotriazole hydrate (HOBT). The solution is added to a solution of 0.025 mmol tetraamino platform, 2 in 1 mL of DMF. When complete, the DMF is removed under vacuum to yield a crude fully protected conjugate 3. The conjugate, 3, is treated with hydrofluoric acid (HF) in the presence of anisole for 1 hour at 0° to give conjugate 4. Purification is accomplished by preparative reverse phase HPLC.

The following scheme shows the attachment of an amino group of a peptide to a carboxy group on a platform.

Carboxyl on Platform—Amine on Ligand

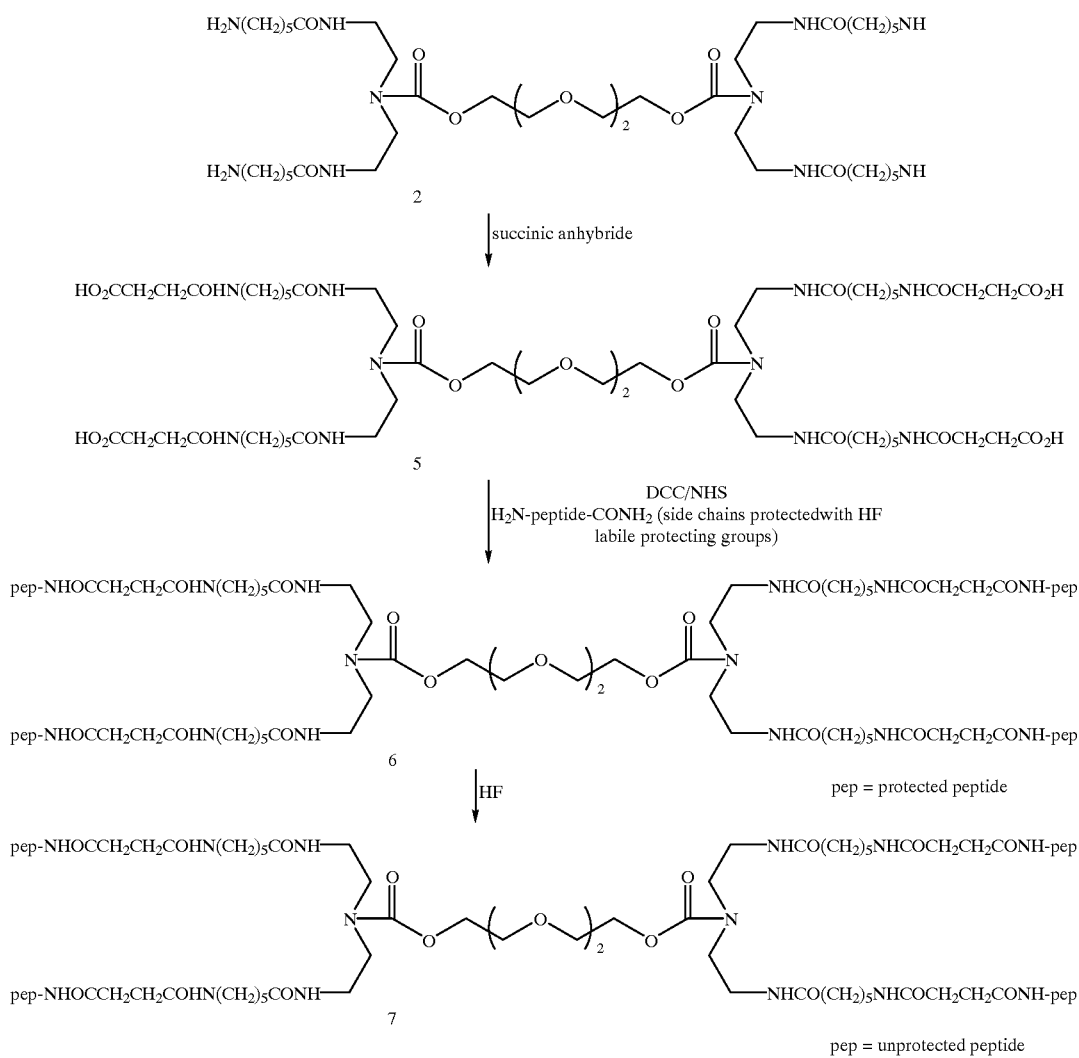

Compound 5—Platform with Four Carboxylic Acid Groups

Succinic anhydride (1.0 g, 10 mmol) is added to a solution of 861 mg (1.0 mmol) of 2 and 252 mg (3.0 mmol) of NaHCO$_3$ in 20 mL of 1/1 dioxane/H$_2$O, and the mixture is stirred for 16 hours at RT. The mixture is acidified with 1N HCl and concentrated. The concentrate is purified by silica gel chromatography to provide 5.

Protected peptide with free amine (H$_2$N-peptide-CONH$_2$)

A peptide is synthesized with standard solid phase methods on an amide resin, which resulted in a carboxy terminal amide after cleavage from the resin, using TFA stable protecting groups (benzyl ester or cyclohexyl ester on carboxyl groups and CBZ on amino groups). Amino acid residues are added sequentially to the amino terminus using standard FMOC chemistry. The peptide is removed from the resin with trifluoroacetic acid to provide a protected peptide with a free amine linker. The protected peptide is purified by reverse phase HPLC.

Peptide—Platform Conjugate, 7

A solution of 0.05 mmol of protected peptide with free amine, (H$_2$N-peptide-CONH$_2$), 0.1 mmol of diisopropyl-ethyl amine, and 0.01 mmol of 5 in 1 mL of DMF is prepared. BOP reagent (benzotriazol-1-yloxy-tris(dimethylamino)phosphonium hexafluorophosphate) (0.1 mmol) is added, and the mixture is stirred until the reaction is complete as evidenced by analytical HPLC. The peptide protecting groups are removed by treatment with HF in the presence of anisole at 0° to give conjugate with protecting groups removed, 7. Compound 7 is purified by preparative reverse phase HPLC.

The following scheme shows how to attach a sulfhydryl linker to the amino terminus of a peptide and, in turn, attach the peptide/linker to a tetrabromoacetylated platform to give compound 13.

Haloacetyl on Platform and Sulfhydryl on Peptide 35 mL of EtOAc. The mixture was stirred at 60° C. for 10 minutes, allowed to cool to room temperature (RT), and placed on ice for 1 hour. The resulting white solid was collected by filtration to give 4.52 g (75%) of 9.

Compound 10

Dicyclohexyl carbodiimide (DCC) (2.41 g, 11.7 mmol) was added to a 0° C. solution of 2.72 g (7.8 mmol) of 9 and 1.08 g (7.8 mmol) of p-nitrophenol in 41 mL of CH$_2$Cl$_2$. The mixture was stirred for 16 hours allowing it to come to RT. The mixture was filtered to remove N,N-dicyclohexylurea (DCU), and the filtrate was concentrated. The residue was crystallized from hexane/CH$_2$Cl$_2$ to give 3.17 g (86%) of 10 as pale yellow crystals.

Compound 11—Cyclic Thioether Peptide with Mercaptopropionyl Linker Attached

A solution of a cyclic thioether peptide (an analogue of a disulfide cyclized peptide in which one sulfur was replaced with a CH$_2$) and sodium bicarbonate in water and dioxane was treated with p-nitrophenyl ester 10. If the peptide contains lysine, it must be appropriately blocked. The resulting modified peptide was treated with trifluoroacetic acid to provide thiol linker modified peptide 11.

Compound 13—Conjugate of Cyclic Thioether Peptide and Bromoacetylated Platform

To a He sparged solution of 0.10 mmol of thiol modified peptide 11 in 100 mM sodium borate pH 9, was added 0.025

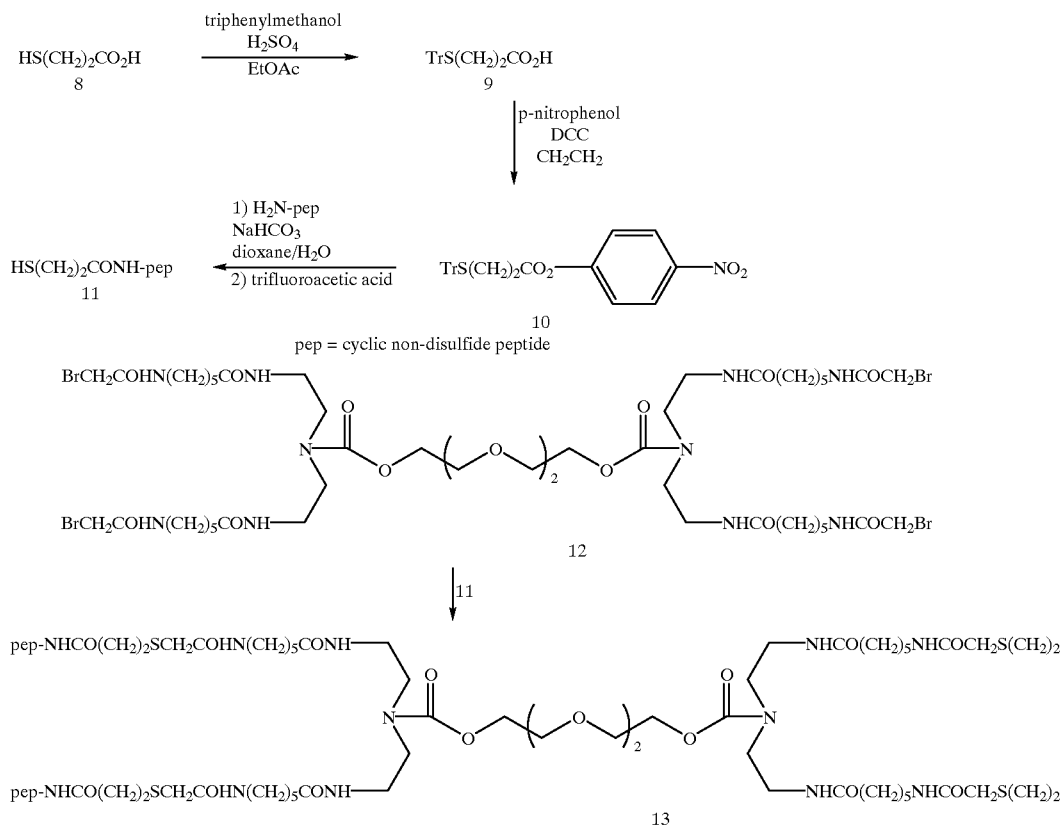

Compound 9

Concentrated sulfuric acid (100 uL) was added to a 60° C. solution of 4.48 g (17.2 mmol) of triphenyl methanol and 1.62 g (15.3 mmol, 1.3 mL) of 3-mercaptopropionic acid in of bromoacetylated platform 12 as a 40 mg/mL solution in 9/1 MeOH/H$_2$O). The solution was allowed to stir under N$_2$ atmosphere until conjugation was complete as evidenced by HPLC. The conjugate was purified by reverse phase HPLC.

Example 12
Synthesis of LJP 685

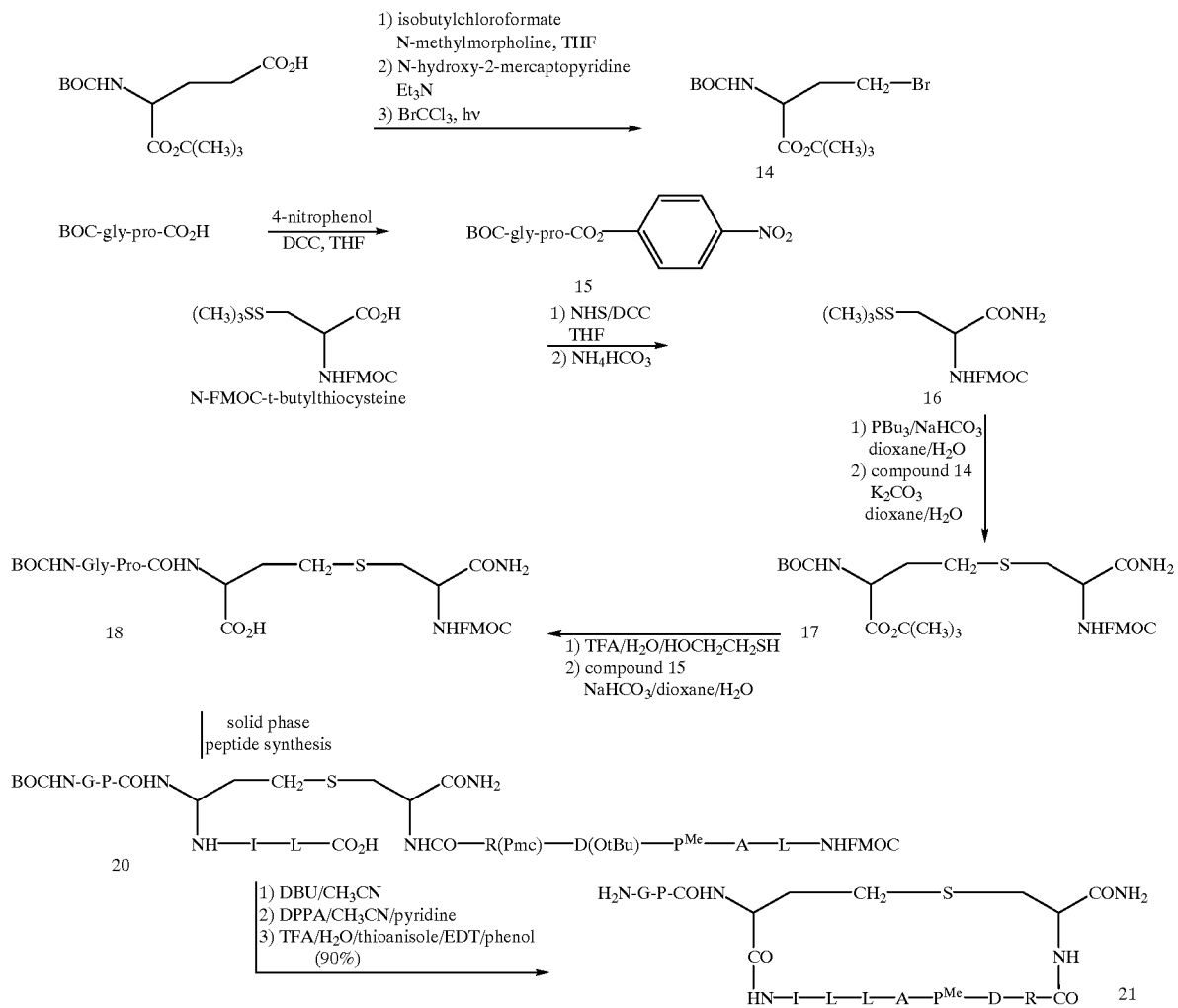

γ-bromo-N-BOC-α-aminobutryic Acid t-butyl Ester, Compound 14

A solution of 4.03 g (13.3 mmol) of N-BOC-glutamic acid-α-t-butyl ester and 1.61 mL (1.48 g, 14.6 mmol) of N-methylmorpholine in 40 mL of dry THF under $N_2$ atmosphere was cooled to 15°. Isobutylchloroformate (1.73 mL, 1.82 g, 13.3 mmol) was added to the mixture dropwise. The mixture was stirred for 10 minutes and a solution of 2.03 g (16.0 mmol) of N-hydroxy-2-mercaptopyridine in 8 mL of THF was added followed by 2.23 mL (1.62 g, 16.0 mmol) of $Et_3N$. The mixture was covered with foil to keep out light and allowed to stir at room temperature for 1 hour. The mixture was filtered and the filtrate was concentrated on the rotary evaporator taking care to minimize exposure to light. The concentrate was dissolved in 20 mL of $BrCCl_3$ and the solution was cooled to −70° C. The solid was placed under vacuum, then purged with $N_2$, allowed to come to room temperature, placed in a 20° water bath, and irradiated from above at close range with a 500 W sunlamp for 5 minutes. The mixture was concentrated on the rotary evaporator and purified by silica gel chromatography (40 mm×150 mm, toluene was used as eluent until UV active material finished eluting, 2% EtOAc/toluene (500 mL), 5% EtOAc/toluene (500 mL). Impure fractions were repurified. Pure fractions by TLC ($R_f$ 0.23, 5% EtOAc/toluene) were combined and concentrated to give 3.23 g (72%) of compound 14 as a waxy solid.

N-BOC-glycylproline-4-nitroplhenyl Ester, Compound 15

A solution of 3.0 g (11.6 mmol) of N-BOC-glycylproline and 1.93 g (13.9 mmol) of 4-nitrophenol in 82 mL of dry THF was cooled to 0° C. and 3.34 g (16.2 mmol) of DCC was added. The mixture was stirred at 0° C. for 1 hour, the ice bath was removed, and the mixture was stirred for 16 hours at room temperature. HOAc (579 μL) was added to the mixture and it was allowed to stir for 30 minutes. The mixture was kept in the freezer for 30 minutes and filtered under vacuum. The filtrate was concentrated and purified by silica gel chromatography (18×150 mm bed, 2.5% EtOAc/ 97.5% $CH_2Cl_2$/1%HOAc). Traces of acetic acid were removed by concentrating from dioxane several times on the rotary evaporator. The concentrate was triturated with 3/1 hexane $Et_2O$ and the resulting white solid was collected by filtration to give 4.1 g (90%) of compound 15 as a white solid; TLC $R_f$ 0.09, 40/60/1 EtOAc/hexane/HOAc; $^1$H NMR ($CDCl_3$) δ1.09–2.55 (m, 4H), 1.48 (s, 9H), 3.47–3.77 (m, 2H), 4.05 (m, 2H), 4.74 (m, 1H), 5.45 (bd s, 1H), 7.35 (d, 2H), 8.30 (d, 2H).

N-FMOC-S-t-butylthiocysteineamide, Compound 16

A solution of 5.0 g (11.6 mmol) of FMOC-S-t-butylthiocysteine and 1.33 g (11.6 mmol) of N-hydroxysuccinimide in 115 mL of THF was cooled to 0° C. To the solution was added 3.58 g (17.37 mmol) of DCC. The mixture was stirred at 0° C. for 1 hour and 42.9 mL of a solution of 1.6 g of $(NH_4)HCO_3$ in 50 mL of water was added. The mixture was stirred for 4.5 hours, allowing the ice bath to gradually warm to room temperature and concentrated on a rotary evaporator to remove THF and give an aqueous phase with white solid. The mixture was stirred with 200 mL of $CH_2Cl_2$ until most of the solid dissolved, then was shaken with 100 mL of 1N HCl solution. The $CH_2Cl_2$ layer was washed with 100 mL of saturated $NaHCO_3$ solution, dried $(Na_2SO_4)$, and filtered. The filtrate was brought to a boil on a hot plate and crystallized from 300 mL of $CH_2Cl_2$/hexane to give 4.36 g (87%) of compound 16 as a white solid: mp 127°–129° C.; TLC $R_f$ 0.29, 95/5/1 $CH_2Cl_2/CH_3CN/MeOH$, $^1H$ NMR $(CDCl_3)$ δ1.36 (s, 9H), 3.06–3.24 (m, 2H), 4.25 (t, 1H), 4.55 (m, 3H), 5.56 (bd s, 1H), 5.70 (bd s, 1H), 6.23 (bd s, 1H); $^{13}C$ NMR $(CDCl_3)$ 29.8, 41.9, 47.1, 48.5, 54.2, 67.2, 120.0, 125.0, 127.1, 127.8, 141.3, 143.6, 156.1, 172.2. Analysis, Calculated: C, 61.4%; H, 6.1%; N, 6.5%. Found: C, 61.5%; H, 6.0%; N, 6.5%.

Compound 17

Water (1 6.9 mL) was added to 2.91 g (6.75 mmol) of compound 16 in 33.8 mL of dioxane and the solution was sparged with nitrogen for 5–10 minutes. The mixture was kept under a nitrogen atmosphere and 1.13 g (13.5 mmol) of $NaHCO_3$ was added followed by 1.77 mL (1.44 g, 7.09 mmol) of $PBu_3$. The mixture was stirred at room temperature for 1 hour and partitioned between 1×100 mL of 1N HCl and 2×100 mL of $CH_2Cl_2$. The $CH_2Cl_2$ layers were combined and concentrated and the resulting white solid was partially dissolved in 33.8 mL of dioxane. Water (9 mL) was added and the mixture was purged with nitrogen for 5–10 minutes. The mixture was kept under nitrogen atmosphere and 2.17 g (16.9 mmol) of $K_2CO_3$ was added followed by 2.63 g (8.1 mmol) of compound 14. The mixture was stirred for 16 hours and partitioned between 1×100 mL of 1N HCl and 2×100 mL of 10% $MeOH/CH_2Cl_2$. The $CH_2Cl_2$ layers were combined, dried with $NaSO_4$, filtered and concentrated to a semisolid residue. Purification by silica gel chromatography (1/3 $CH_3CN/CH_2Cl_2$) gave 3.2 g (80%) of compound 17 as a white solid; TLC $R_f$ 0.27, 1/3 $CH_3CN/CH_2Cl_2$. Further purification of an analytical sample was done by recrystallizing from hexane/EtOAc; mp 104–106.5° C.; $^1H$ NMR $(CDCl_3)$ δ1.47 (s, 9H), 1.49 (s, 9H), 1.96 (m, 1H), 2.11 (m, 1H), 2.69 (m, 2H), 2.88 (m, 1H), 3.03 (m, 1H), 4.29 (t, 1H), 4.36 (m, 2H), 4.50 (m, 2H), 5.21 (m, 1H), 5.49 (m, 1H), 5.81 (m, 1H), 6.54 (m, 1H), 7.34 (t, 2H), 7.42 (t, 2H), 7.61 (d, 2H), 7.80 (d, 2H); $^{13}C$ NMR (MeOH) δ26.1, 26.7, 28.2, 28.7, 34.8, 54.8, 55.7, 68.1, 80.5, 82.7, 120.9, 126.3, 128.2, 128.8, 142.6, 145.2, 160.0, 162.7, 173.4, 175.8. Analysis, Calculated for $C_{31}H_{41}N_3O_7S$: C, 62.08; H, 6.89; N, 7.01. Found: C, 62.23; H, 7.12; N, 7.39.

Compound 18

A solution of 20/1/1 $TFA/H_2O$/mercaptoethanol (23.2 mL) was added to 1.27 g (2.11 mmol) of compound 17. The mixture was stirred at room temperature for 1 hour and concentrated to a volume of about 3 mL. 50 mL of ether was added to precipitate the product. The resulting solid was washed with two more portions of ether and dried under vacuum to give 812 mg of solid. The solid was suspended in 10.6 mL of dioxane and 10.6 mL of $H_2O$. $NaHCO_3$ (355 mg, 4.22 mmol) was added to the mixture followed by a solution of 1.33 g (3.38 mmol) of compound 15 in 10.5 mL of dioxane. The mixture was allowed to stir at room temperature for 20 hours and partitioned between 100 mL of 1N HCl and 3×100 mL of $CH_2Cl_2$. The combined $CH_2Cl_2$ layers were dried $(Na_2SO_4)$, filtered and concentrated. Purification by silica gel chromatography (35×150 mm; step gradient, 5/95/1 $MeOH/CH_2CL_2/HOAc$ (1 L) to 10/95/1). Pure fractions were concentrated and the residue was triturated with ether to give 881 mg (60%) of compound 18; TLC $R_f$ 0.59, 10/90/1 $MeOH/CH_2Cl_2/HOAc$; mp 116–117.5° C.; $^1H$ NMR $(CDCl_3)$ δ1.41 (s, 9H), 2.00 (m, 2H), 2.18 (m, 2H), 2.56 (m, 1H), 2.69 (m, 1H), 2.85 (m, 2H), 3.49 (m, 2H), 3.62 (m, 2H), 3.85 (m, 2H), 4.08 (m, 1H), 4.12 (m, 1H), 4.22 (t, 1H), 4.38 (m, 1H), 4.49 (m, 2H), 4.61 (m, 2H), 7.78 (d, bd s, 1H), 6.12 (bd s, 1H), 6.43 (bd s, 1H), 7.35 (d, 2H), 7.40 (d, 2H), 7.61 (d, 2H), 7.78 (d, 2h); $^{13}C$ NMR $(CDCL_3)$ δ25.3, 27.8, 28.6, 29.4, 32.6, 35.1, 44.1, 46.9, 47.3, 52.2, 53.9, 61.2, 67.8, 80.8, 120.8, 125.7, 128.2, 129.0, 142.0, 144.5, 157.6, 157.8, 170.6, 181.2, 182.9, 183.1. Analytical, Calculated for $C_{34}H_{43}N_5O_9S$: C, 58.52; H, 6.21; N, 10.03. Found: C, 58.38, H, 6.17; N, 10.20.

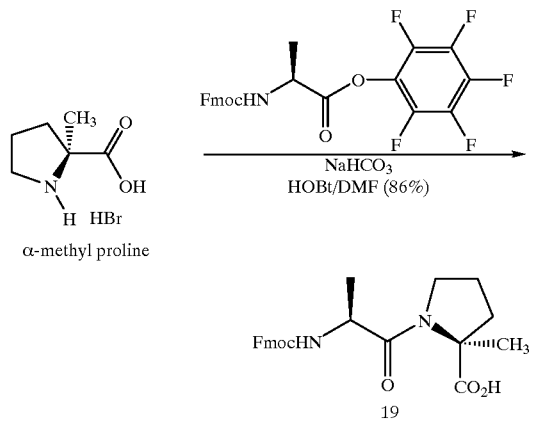

N-FMOC-L-Alanyl-L-2-methylproline, Compound 19

A solution of 2-methylproline (Seebach et al. (1983) *J. Am. Chem. Soc.* 105:5390–5398) (1.00 g, 4.76 mmol), 4.00 g (47.6 mmol) of $NaHCO_3$, and 31 mg (0.23 mmol) of HOBT in 6.9 mL of DMF was cooled to 0° C. and 3.18 g (6.66 mmol) of N-FMOC-L-alanine was added. The reaction was stirred for 1 hour at 0° C., then at room temperature for 18 hours. The mixture was partitioned between 50 mL of EtOAc and 3×50 mL of 1N HCl. The EtOAc layer was dried $(MgSO_4)$, filtered and concentrated. Purification by silica gel chromatography (step gradient 45/55/1 EtOAc/Hexane/HOAc to 47/53/1 EtOAc/Hexane/HOAc to 50/50/1 EtOAc/Hexane/HOAc) gave 1.72 g (86%) of compound 19 as a white solid. The product was concentrated several times from dioxane to remove traces of acetic acid: mp 59–60° C.; $^1H$ NMR $(CDCl_3)$ δ1.39(d, 3H), 1.93 (m, 2H), 2.06 (m, 2H), 3.78 (m, 2H), 4.22 (m, 1H), 4.40 (d, 2H), 4.56 (m, 1H), 5.09 (t, 1H), 5.69 (d, 1H), 7.32 (t, 2H), 7.42 (t, 2H), 7.62 (d, 2H), 7.78 (d, 2H); $^{13}C$ NMR $(CDCl_3)$ δ17.8, 21.8, 23.8, 37.9, 47.1, 48.5, 65.9, 67.0, 120.0, 125.1, 127.1, 127.7, 141.3, 144.1, 155.6, 172.9, 175.1.

N-FMOC-L-Leucinyl-HMPB-MBHA Resin

A solution of N-FMOC-L-leucine in 22.5 mL of $CH_2Cl_2$ and a few drops of DMF was prepared and cooled to 0° C. To the solution was added 1.71 mL (1.38 g, 10.9 mmol) of diisopropylcarbodiimide (DIC) and the mixture was stirred for 20 minutes at 0° C. The mixture was concentrated to an oil; meanwhile, enough DMF (approximately 3 mL) was added to 2.5 g (0.87 mmol/g, 2.18 mmol) HMPB-MBHA resin (Nova Biochem) to swell the resin. The concentrated oil was dissolved in a minimal amount of DMF (approximately 1 mL) and added to the swelled resin followed by a solution of 266 mg (2.18 mmol) of DMAP dissolved in approximately 1 mL of DMF. The mixture was gently rocked for 1 hour and washed (2×DMF, 2×MeOH, 2×DMF, 2×MeOH). The resin was dried under vacuum to give 2.77 g (85%) and the substitution was determined by the Geisen test to be 0.540 mmol/g.

N-FMOC-linear Peptide with t-butyl Ester on Aspartic Acid and Pmc Group on Arginine and with Thioether Insert, Compound 20

This peptide was prepared by standard FMOC synthesis on N-FMOC-L-leucinyl-HMPB-MBHA resin. Three equivalents of amino acid, HOBT and (DIC) were used for each coupling step with the exception of the coupling step of compound 18. Two equivalents of compound 18 were used with three equivalents of HOBT and diisopropylcarbodiimide. Each step was monitored by using 10 $\mu$L of bromoplieniol blue indicator. Completeness of the reaction was also assessed with a ninhlydrini test (beads turn blue for incomplete reaction with 1 mg is heated at 100° C. for 2 minutes with one drop of pyridine and one drop of 5% ninhydrin in EtOH and one drop of 80% phenol in EtOH). Thus, 1.13 mg (0.613 mmol) of resin was used to prepare the peptide. After the final coupling step, cleavage from the resin was accomplished by treatment with 15 mL of a solution of 1% trifluoroacetic acid in $CH_2Cl_2$ for 2 minutes. After 2 minutes, the solution was filtered under pressure into 30 mL of 10% pyridine in MeOH. This was repeated ten times and the filtrates which contained peptide as evidenced by HPLC (C18, gradient, 60/40/0.1 $CH_3CH/H_2O$/TFA to 90/10/0.1 $CH_3CN/H_2O$/TFA, 210 mn, 1 mL/min, 4.6 mm×250 mm column) were combined and concentrated. The concentrate was dissolved in 40 mL of 10% HOAc solution and purified by HPLC to give 0.528 g (49%) of peptide 20.

Conversion of Peptide 20 to Cyclic Peptide 21 (Removal of FMOC Group, Cyclization and Removal of Protecting Groups A solution (5 mL) of 99 $\mu$L of DBU in 10 mL of $CH_3CN$ was added to 96 mg (0.052 mmol) of peptide 20. The solution was stirred for 1 hour and concentrated to a residue. The residue was triturated with 2×10 mL of $Et_2O$ to give a white solid. The solid was dissolved in 100 mL of $CH_3CN$ and 312 $\mu$L (0.312 mmol) of 0.1 M solution of diphenylphosphorylazide (DPPA) in $CH_3CN$. The mixture was stirred for 20 hours and concentrated on a rotary evaporator. The residue was triturated with 2×50 mL of $Et_2O$ and the white opaque residue was treated with 5 mL of 92/3/2/3 TFA/anisole/EDT/$Me_2S$ for 1 hour. The product was precipitated by adding the mixture to 40 mL of $Et_2O$ in a 50 mL polypropylene centrifuge tube. The precipitate was cooled to 0° C. and centrifuged for 5 minutes at 2000 rpm. The supernatant was decanted and the pellet was washed with $Et_2O$ and recentrifuged. The pellet was dried and dissolved in 4 mL of 50/50 $CH_3CN/H_2O$. The mixture was diluted with 36 mL of $H_2O$/0.1% TFA, filtered and purified by HPLC (1" $C_{18}$ column, gradient, 10/90/0/1 $CH_3CN/H_2O$/TFA to 35/65/0.1 $CH_3CN/H_2O$/TFA, 230 nm). The pure fractions, as evidenced by HPLC, were lyophilized to give 52 mg (90%) of compound 21.

Example 13

Synthesis of Conjugates of LJP 685

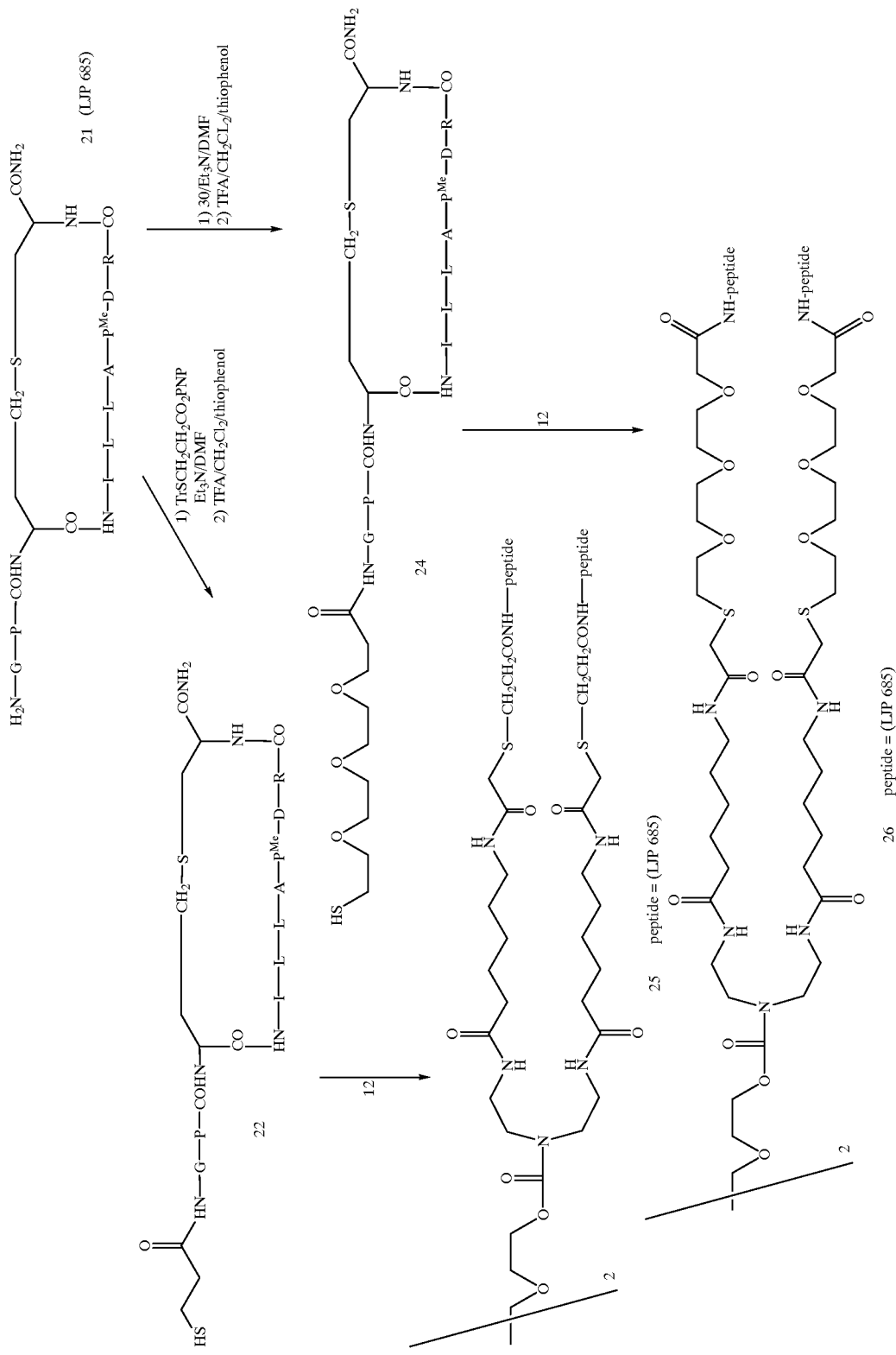

LJP 685, also referred to as compound 21, was treated with the PNP ester of 3-tritylmercaptopropionic acid and the resulting product was detritylated to give compound 22, the peptide with the free thiol linker. Reaction of an excess of compound 22 with valency platform molecule 12 produced tetravalent conjugate 25. Treatment of compound 21 with the longer linker, compound 33 (see reaction scheme below), followed by detritylation, gave compound 24. Compound 24 reacted with valency platform molecule 12 to give the tetraconjugate 26. Both conjugation reactions appeared very clean by HPLC.

Attachment of MTU Linker to LJP 685, Synthesis of Compound 24

To 15 mg (0.013 mmol) of compound 21 was added 160 μL of a solution of 29.5 mg of compound 23 and 17.5 μL of diisopropyletlhylamine in 0.5 mL of DMF. The mixture was stirred for 2 hours and precipitated from $Et_2O$. The precipitate was dried and dissolved in 650 μL of a solution of 1/1/0.05610.040 TFA/CH2Cl2/thiophenol/$Me_2S$ and the solution was allowed to stand for 1 hour. Precipitation from $Et_2O$ gave crude compound 24 which was purified by HPLC ($C_{18}$, 15–45% $CH_3CN/H_2O$, 0.1% TFA). Fractions containing pure product were lyophilized to give 8.6 mg of compound 24 as a white solid.

LJP 685-MTU-AHAB-TFG, Compound 26

To a solution of 8.6 mg ($6.3 \times 10^{-6}$ mol) of compound 24 in 630 μL of He sparged pH 8.5 200 mM borate buffer was 40 μL of a 40 mg/mL solution of compound 12 in 9/1 $MeOH/H_2O$. The mixture was stirred for 24 hours and 1 mL of 10% $HOAc/H_2O$ solution was added. The mixture was purified by HPLC ($C_{18}$, gradient 25–55% $CH_3CN/H_2O$, 0.1% TFA) to give 8.3 mg of compound 26 (LJP 685-MTU-AHAB-TEG).

Example 14

Development of Extended SH Linkers

The thiobenzoate ester, compound 28, was prepared from compound 27. Compound 28 was converted to compound 29 in portions. The thiobenzoate was removed by ethanolysis and the resulting thiol was tritylated. The ethyl ester was then hydrolyzed to give compound 29. The nitrophenyl phosphate (PNP) ester, compound 30, was prepared from compound 29. Aminotrioxoudecanoicacid ethylester, compound 31, was prepared by treatment of compound 27 with sodium azide and reduction to the amine. Amine 31 was acylated with compound 30 to provide compound 32. Hydrolysis of compound 32 was achieved by treatment with sodium hydroxide to give a free carboxylic acid. The intermediate carboxylic acid was condensed with p-nitroplhenol to give para-nitrophenyl (PNP) ester, compound 33. Linker 33 was attached to the peptide and the trityl group removed to give compound 34 which was used to produce an MTU-ATU-AHAB-TEG conjugate.

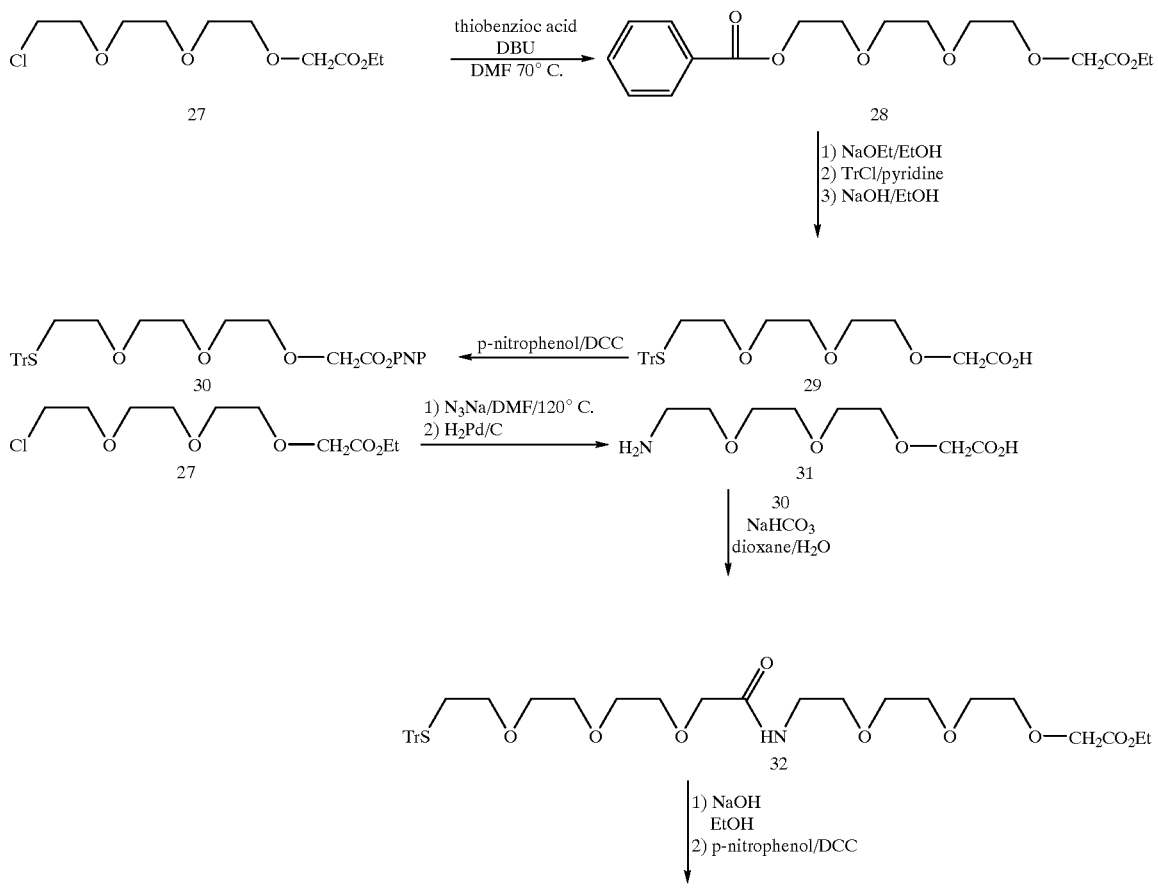

-continued
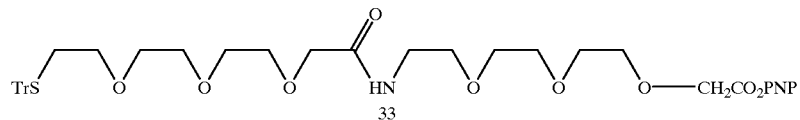
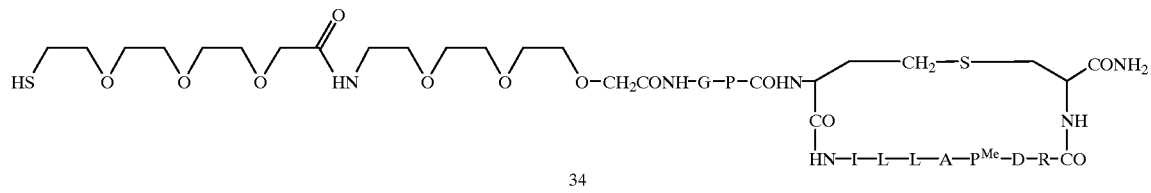
Example 15
Synthesis of a (LJP685)₄/MTU-ATU-AHAB-TEG Conjugate, Compound 35
Tetravalent conjugate 35 was prepared as shown below. The peptide with linkers attached, compound 34 was dissolved in He sparged, pH 8.5, 200 mM borate buffer. To the mixture was added 0.3 mol equivalents of platform compound 12. The mixture was stirred for 1 hour and the product was purified by HPLC.

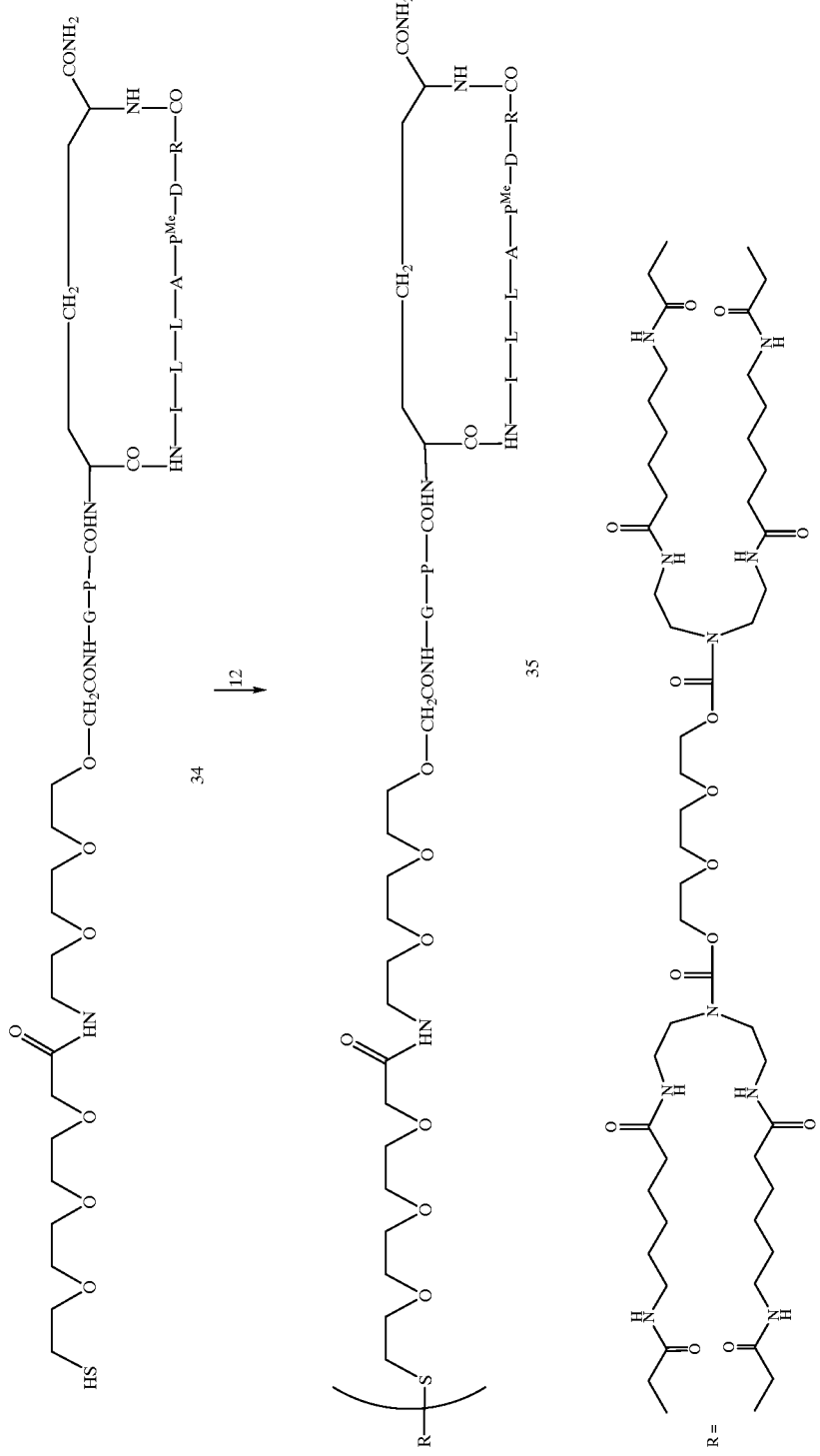

Example 16
Synthesis of a (LJP685)₄/DABA-PEG Conjugate, Compound 36

Treatment of IA-DABA-PEG with compound 24 in 8.5 borate buffer gave conjugate 36.

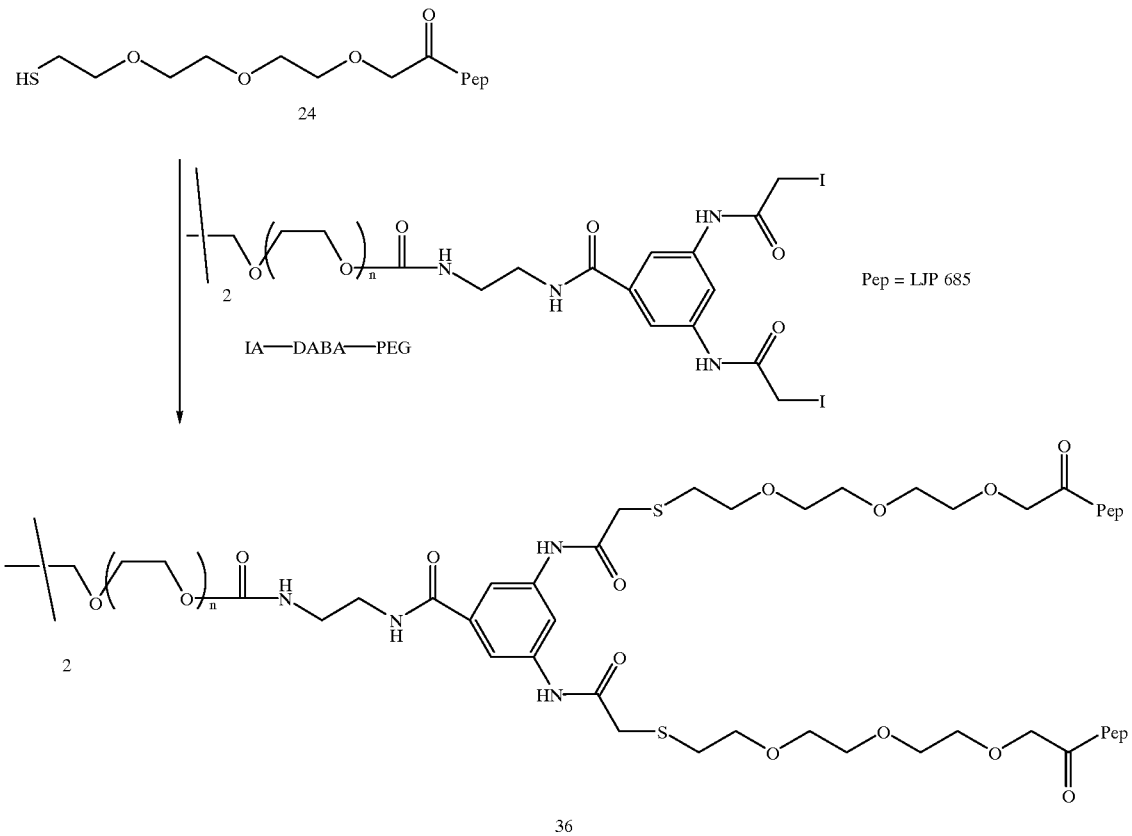

Example 17
T Cell Assay for Activation

Tritiated thymidine uptake by peptide-stimulated T cells was monitored in 96-well round bottom plates. A single-cell suspension of draining lymph node cells (mice) or isolated peripheral blood lymphocytes (human), $5\times10^5$ were mixed with between 1 and 30 μg of peptide in a final volume of 150 μL per well and incubated for 5 days at 37° C. in 5% $CO_2$. At that point, 1 micro curie of labeled thymidine was added and incubated for an additional 15–24 hours. The harvested cells were collected on filters and counted by liquid scintillation spectrometry.

Example 18
In vitro Induction of Tolerance

Figure 16:
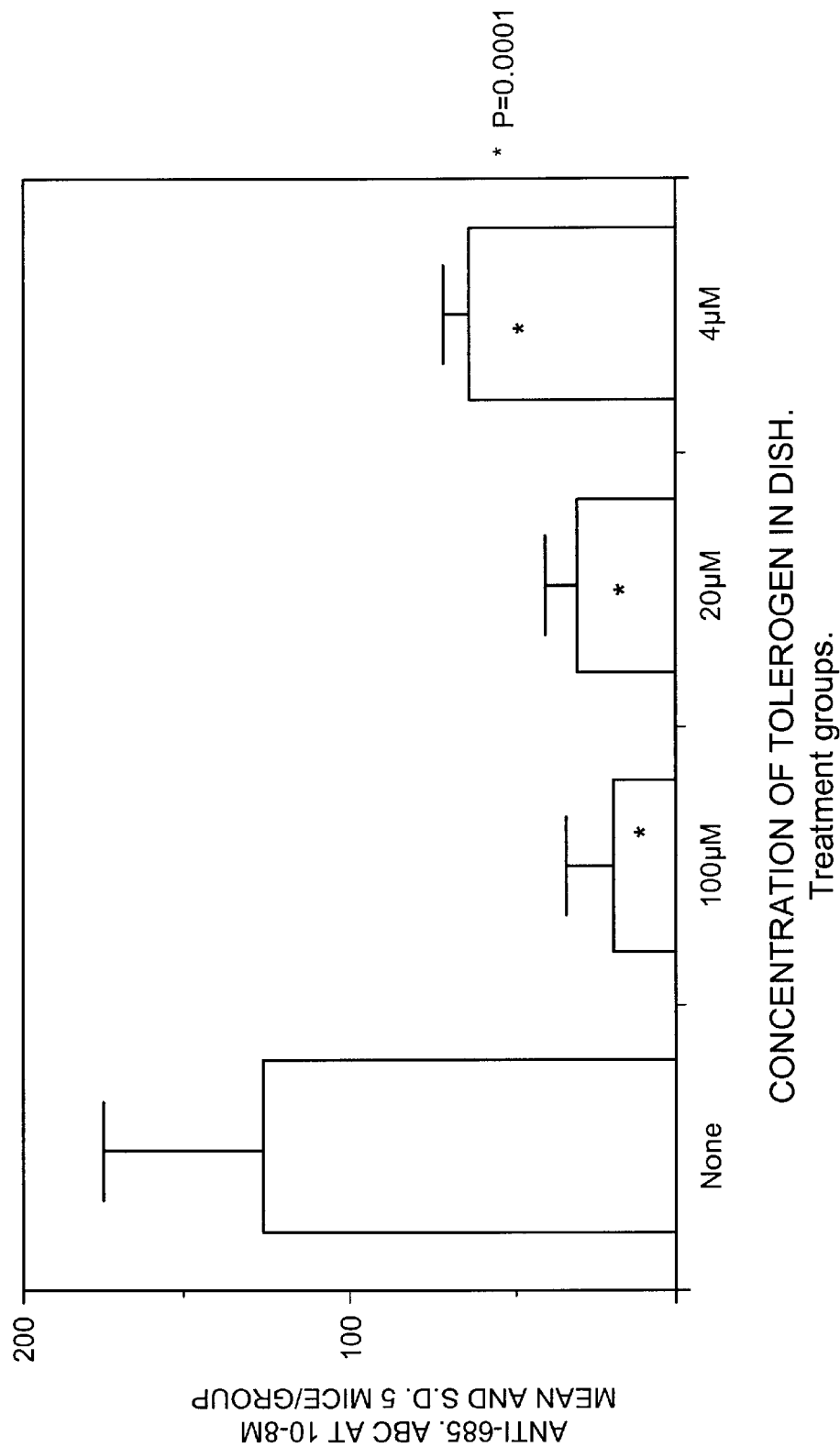
FIGS. 16 and 17 show the dose-dependent reduction in anti-685 antibody ABC at $10^8$M using spleen cells from mice immunized with LJP 685-KLH after the spleen cells were incubated with 100, 20 and 4 μM of LJP 685-MTU-DABA-PEG con As used herein "individual" denotes a member of the mammalian species and includes humans, primates, mice and domestic animals such as cattle and sheep, sports animals such as horses, and pets such as dogs and cats.
Figure 17:
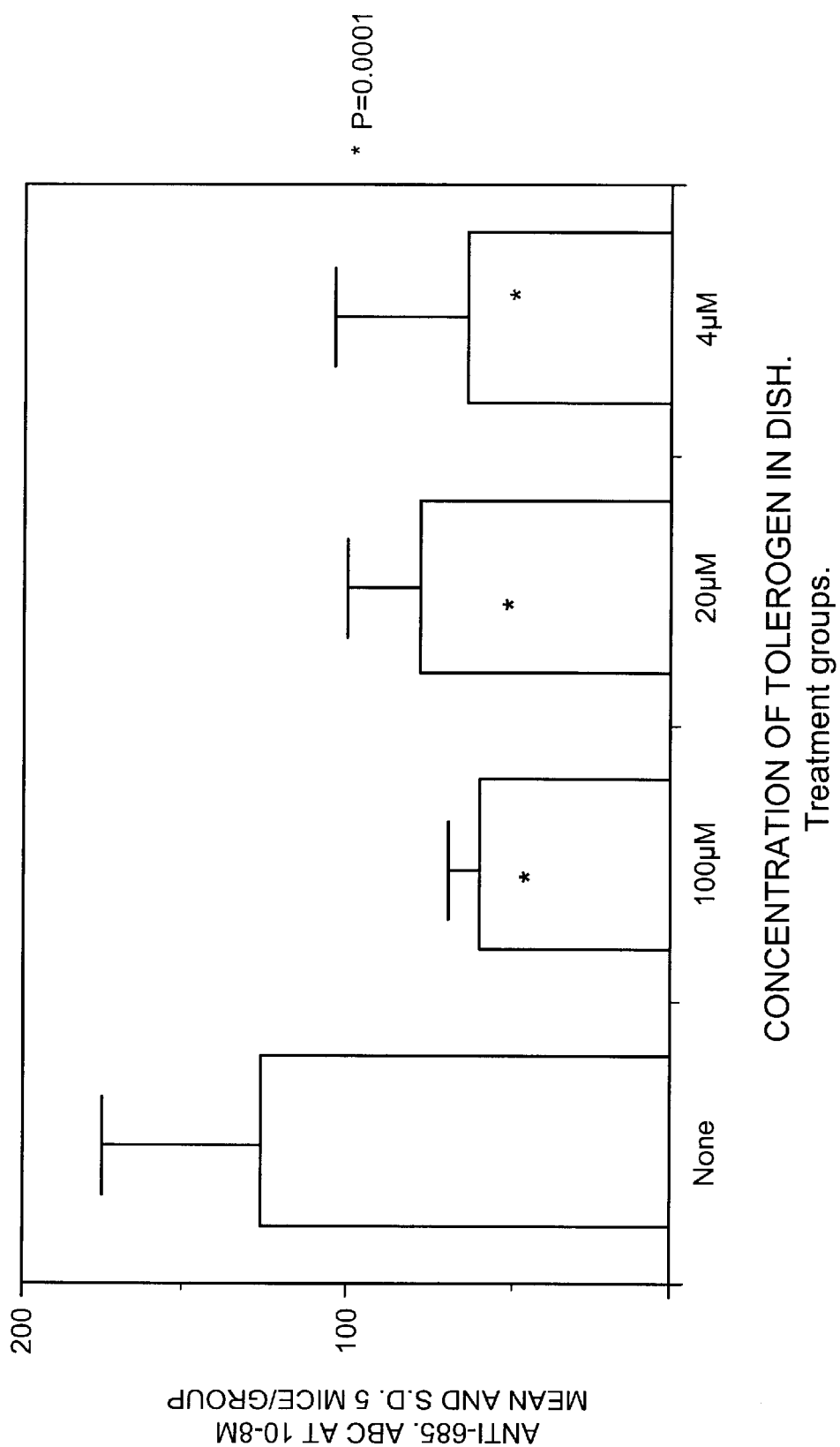

Eight groups, each containing five C57B1/6 mice, were primed with 10 μg/mouse of a conjugate of LJP685-KLH on alum plus *B. pertussis* vaccine as an adjuvant. After three weeks, spleen were harvested and single cells suspensions were prepared, washed three times with balanced salt solution and resuspended in complete RPMI-1640 medium at a concentration equivalent to one spleen/1.5 mL of medium. The cell suspension was divided into aliquots of 2.5 mL/petri dish and incubated for 2 hours at 37° C. with (LJP685)₄-DABA-PEG, compound 36, and (LJP685)₄-TEG, compound 35, in concentrations of 100 μM, 20 μM and 4 μM. One group of cells was incubated without toleragen and acted as the positive control. The cells were then washed with large volumes of balanced salt solution and resuspended in 2.5 mL of balanced salt solution. The cells were then injected into 650R irradiated syngeneic recipient mice in such a manner that all of the cells from a given treatment group were divided evenly into five recipients. All of the recipient mice, including the positive controls, were then given a booster immunization of 10 μg of LJP 685-KLH in saline, intraperitoneally. Seven days after the booster immunization, the mice were bled and their sera tested for the presence of anti-LJP 685 antibody. Treatment with either conjugate produced a significant, dose-dependent reduction of anti-LJP 685 antibodies as shown in FIGS. 16 and 17, which is measured by Antigen Binding Capacity (ABC) as described in Iverson, G. M., "Assay for in vivo adoptive immune responses," in Handbook of Experimental Immunology, Volume 2. Cellular Immunology (Weir, D. M., ed., Blackwell Scientific Publications, Palo Alto, Calif., 1986).

Example 19
NMR Solution Structure Analysis of the 5A12, CB2 and 3G3 Peptides Two peptides isolated from phage library screens using the methodology described in the examples above were subjected to NMR analysis. The original peptide has a proline in the second to last position, however, this amino acid was removed since two dimensional (2D) double quantum filtered correlated spectroscopy (DQF-COSY) NMR data suggested the presence of two different structures from the cis and trans isomers at this position. Removal of the proline gave peptides with $K_D$'S in the 50–100 nM range for binding to ACA antibodies, and the expected number of peaks in the fingerprint region of the DQF-COSY spectrum. The resulting cyclic peptides are 5A12 (GPCLILAPDRCG (SEQ ID NO:215)) AND CB2 (GPCILLARDRCG (SEQ ID NO:216)). The major difference between the peptides was the substitution of arginine for proline at position 8 which resulted in much less dispersion in the 1D 1H NMR spectrum of CB2 which was consistent with 5A12 being a more rigid peptide. The arginine substitution also produces a 0.55 kcal/mol stabilization of the ionized aspartyl carboxy group as reflected in pKa values. A structural analysis was carried out on the more ordered 5A12 peptide. Although deuterium excliange and temperature coefficient data show no evidence of hydrogen bonding, the Nuclear Overhauser Effect (NOE), Rotating Overhauser Effect (ROE) and coupling data are consistent with one structure. Distance geometry calculations yielded a family of 50 structures. The 15 best had a mean root mean square deviation (RMSD) for all atoms of 2.1±0.2 angstroms. We determined that the peptide has an oval shape with turns at opposite ends of the molecule, at the disulfide and at Proline 8 which is cis. There is also a kink in the backbone LIL region. Finally, the carboxy terminal glycine is very mobile as it is the only residue with a positive intraresidue NOE. This represents the first structural information determined about a peptide that mimics the ACA epitope on $\beta_2$-GPI.

Figure 18:
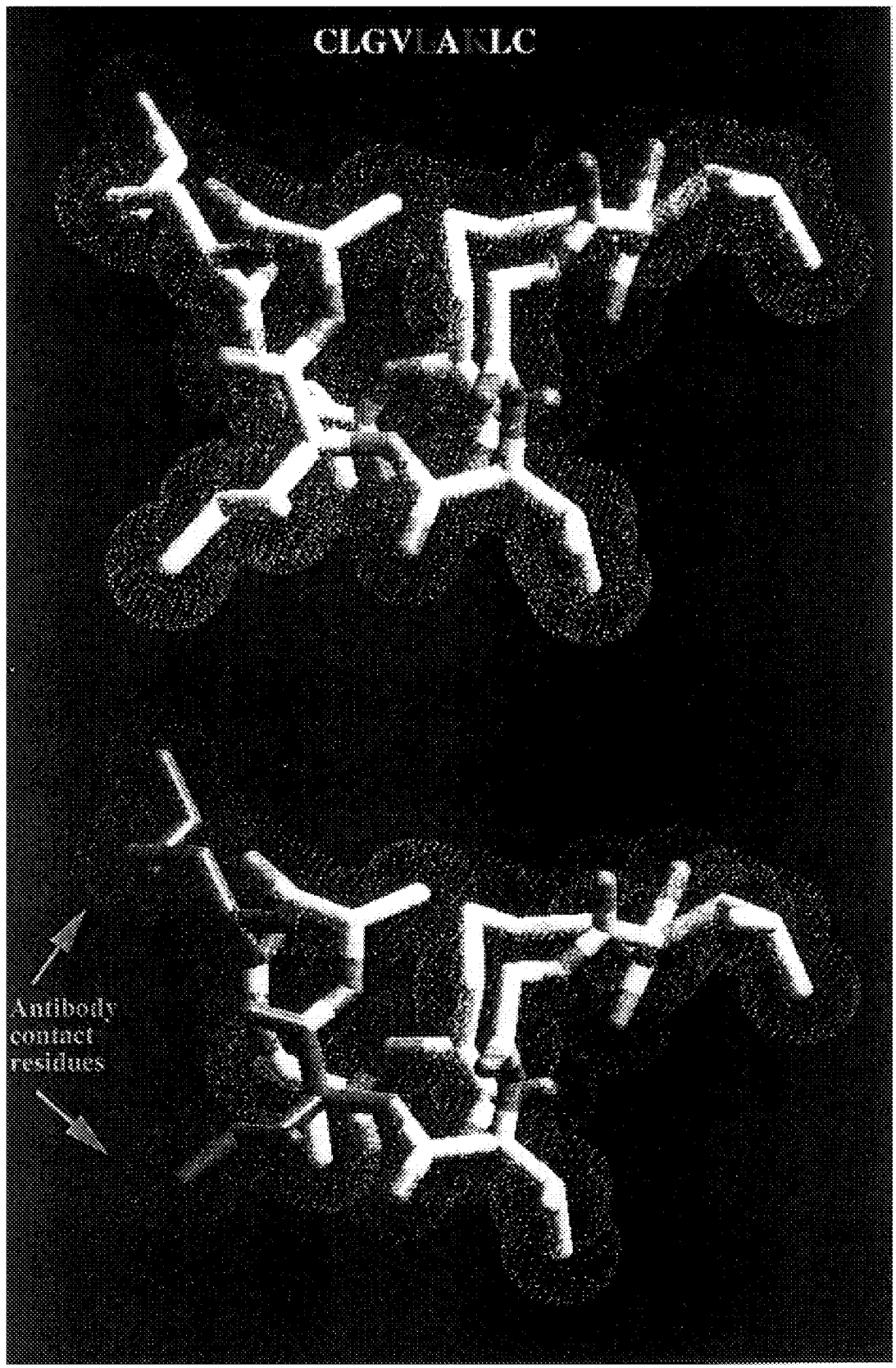
Figure 19:
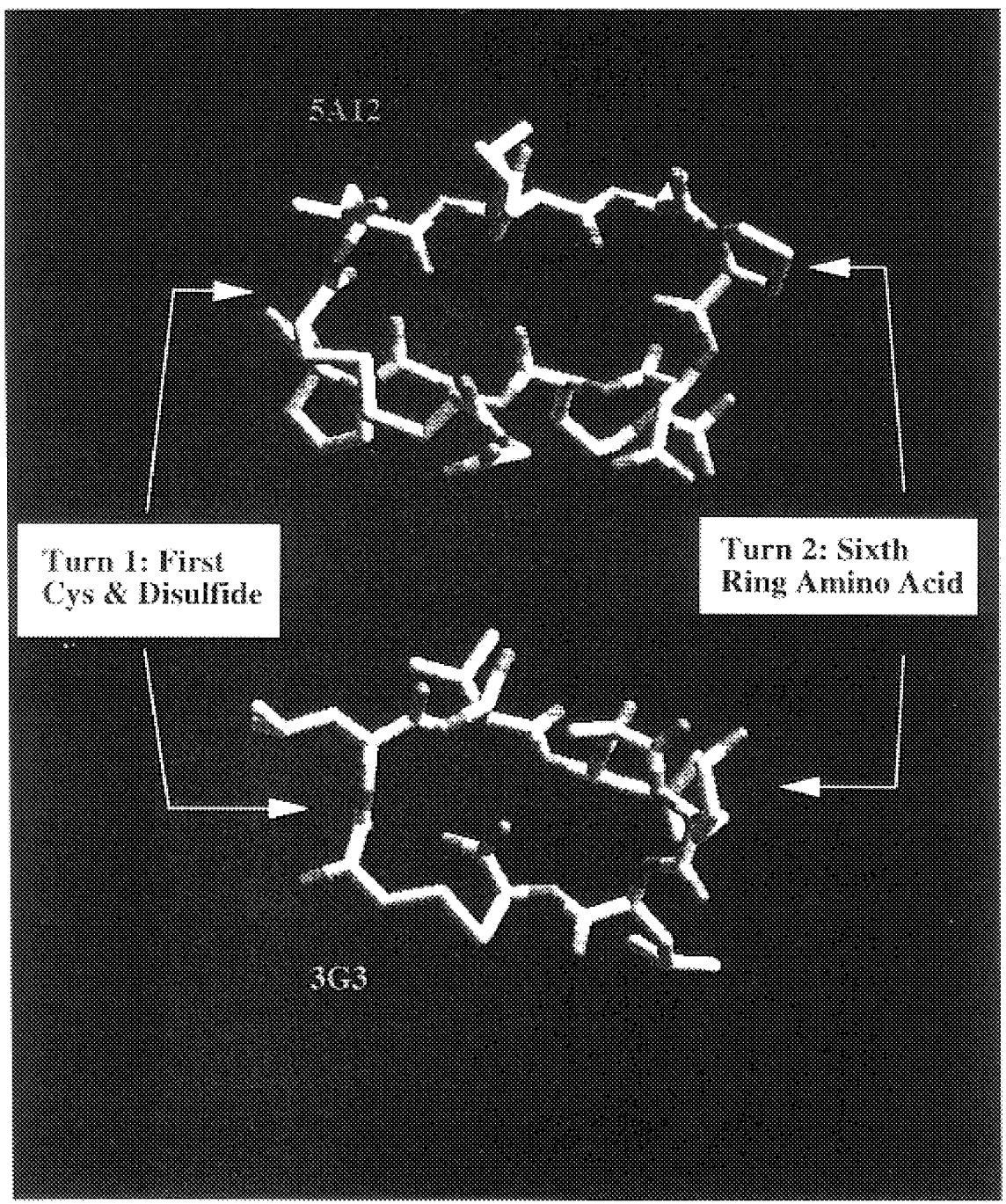

NMR data coupled with distance geometry calculations were used to determine the three dimensional structure of peptide 925 (CLGVLAKLC (SEQ ID NO:74)), a truncated version of peptide 3G3 (AGPCLGVLGKLCPG (SEQ ID NO:57)) with alanine substituted for glycine in position 6 of the 925 peptide. The structure of peptide 925 was determined in water at pH 3.8 and at 25° C. An ensemble of nine structures were calculated all of which were consistent with the NMR data. The RMSD for all non-hydrogen atoms was 2.45±0.36 angstroms when each structure was compared to the centroid. FIG. 18 displays the structure closest to the centroid of the ensemble and, therefore, is a reasonable representation of the shape of the peptide 925 molecule. FIG. 19 compares the structure of peptide 925 (labeled at the bottom of the figure as 3G3) with the structure of peptide 5A12. Both peptides have turns at approximately the same positions in the peptide sequence.

Figure 20A:
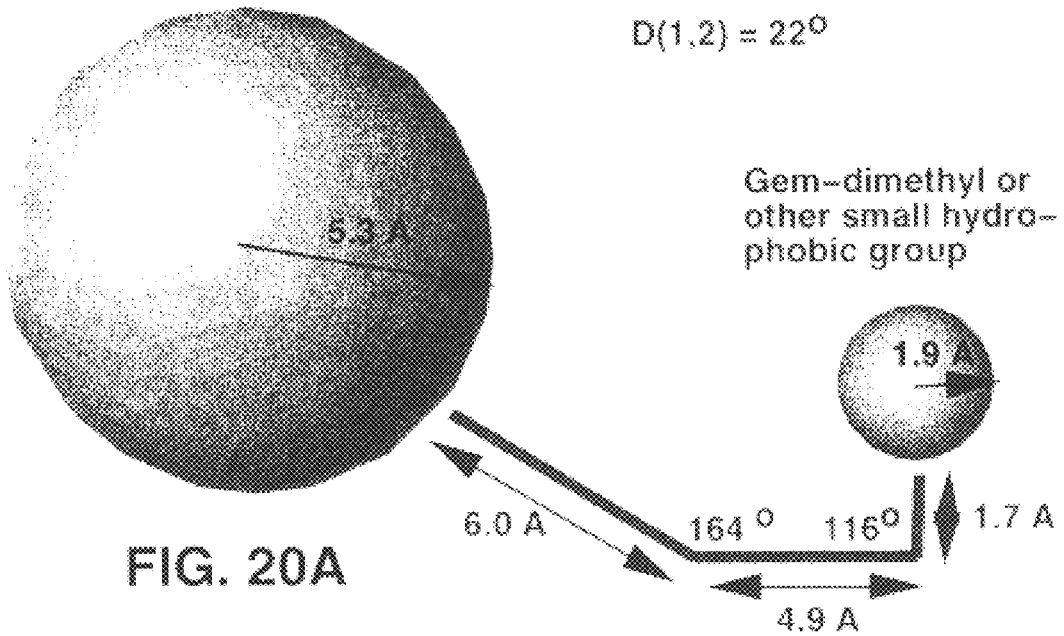
Figure 20B:
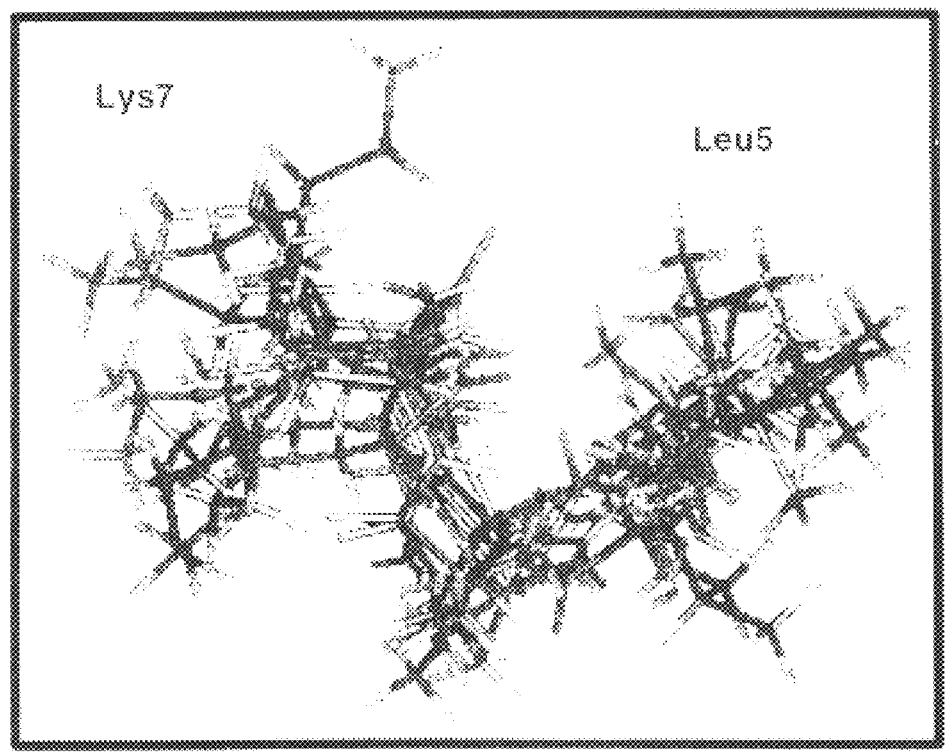

The pharmacophore of the peptides has been tentatively identified as a small hydrophobic group and a positively charged group. The gem-dimethyl and amino groups of peptide 925 are tentatively identified as the pharmacophore of this peptide as shown in FIG. 20. The hydrocarbon linkers that tether the pharmacophore groups to some scaffold have the lengths specified in FIG. 20 and the points at which these linkers are attached to the scaffold are separated by the distance specified. Finally, the dihedral angle defining the relative orientation of the two linkers was determined to be 22°.

Example 20
Synthesis of TEG Carbarnate Linker

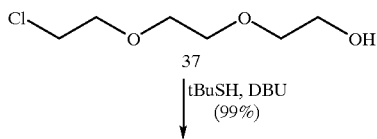

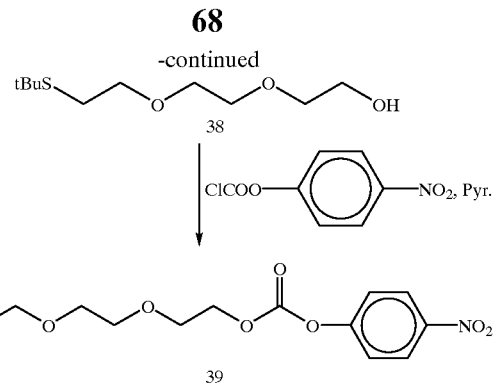

2-[2-(2-tert-Butylthioetlioxy)ethoxy]ethanol, Compound 38

To a mixture of 2-[2-(2-chloroethoxy)ethoxy]ethanol (11.0 g, 65.24 mmol) and tert-butylthiol (7.35 mL, 65.23 mmol) cooled in an ice bath was slowly added 1,8-diazabicyclo[5.4.0]undec-7-ene (DBU, 9.75 mL, 65.23 mmol). The reaction mixture was allowed to warm to room temperature and stirred overnight. This mixture was then diluted with ethyl acetate and filtered. The crude product in the filtrate was purified on a filter column eluted with ethyl acetate to give yellowish oil (14.4 g, 64.6 mmol, 99%): $^1$H NMR (300 MHz, CDCl$_3$): d 3.73 (br s, 2H), 3.69–3.60 (m, 8H), 2.75 (t, J=7.4, 2H), 2.62 (br s, 1H), 1.32 (s, 9H); $^{13}$C NMR (75 MHz, CDCl$_3$): d 72.47, 71.08, 70.33, 70.27, 61.71, 42.09, 30.95, 27.87; MS (ESI): m/e (M+1) Calcd. for C$_{10}$H$_{23}$O$_3$S: 223, obsd.: 223.

2-[2-(2-tert-Butylthioethoxy)ethoxy]ethyl p-nitroplhenyl Carbonate, Compound 39

To a solution of compound 38 (2.0 g, 8.98 mmol) and p-nitrophenol chloroformate (1.81 g, 8.98 mmol) in 5 mL of dry THF cooled in an ice bath was slowly added dry pyridine (0.73 mL, 8.98 mmol) in 1 mL of dry THF. White precipitate came out immediately. After stirred at room temperature for 15 min, the reaction mixture was diluted with 10 mL of ether and filtered. The filtrate was concentrated and used directly in the peptide synthesis without further purification.

Example 21
Synthesis of the Tetravalent Platform IA/DABA/ATEG, 46
Bis-N-(t-butoxycarbonyl)-diaminobenzoic Acid, Compound 40

A solution of 7.18 g (32.9 mmol of di-t-butyldicarbonate in 5.5 mL of MeOH was slowly added to a solution of 2.5 g (16.4 mmol) of 3,5-diaminobenzoic acid and 2.76 g (32.9 mmol) of NaHCO$_3$ in 44.5 mL of H$_2$O and 22.5 mL of MeOH, and the mixture was stirred at room temperature for 24 h. The mixture was cooled to 0°, and 6.53 g of citric acid was added, and the mixture was extracted with EtOAc. The combined EtOAc layers were dried (MgSO$_4$), filtered, and concentrated. The residue was dissolved in 40 mL of Et$_2$O and the solution was filtered through Celite. The Et$_2$O layer was extracted with two 40 mL portions of HCl. The Et$_2$O layer was dried (MgSO$_4$), filtered, and concentrated to give 3.81 g (66%) of 40 as a foamy pink solid.

N-hydroxysuccinimidyl Ester of Compound 40, Compound 41

Dicyclohexylcarbodiimide (3.34 g, 16.2 mmol) was added to a solution of 3.8 g (10.8 mmol) of compound 40 and 1.24 g (10.8 mmol) of N-hydroxysuccinimide in 55 mL of EtOAc which had been cooled to 0°, and the resulting mixture was stirred for 18 h allowing to come to room temperature. To the mixture was added 0.55 mL of acetic acid. The mixture was stirred for 30 min and placed in the freezer for 2 h. The mixture was filtered to remove solids, and the filtrate was concentrated to give 5.80 g of pink foamy solid. Purification by silica gel chromatography (60/40/1 hexane/EtOAc/HOAc) gave 4.30 g (89%) of compound 41 as a slightly pink solid.

Mono-N-(t-butoxycarbonyl)-ethylenediamine, Compound 42

A solution of 1.5 g (25.0 mmol) of ethylenediamine in 15 mL of CH$_2$Cl$_2$ was cooled to 0°, and a solution of 1.82 g (8.33 mmol) of di-t-butyldicarbonate was added slowly to the mixture. The mixture was stirred at room temperature for 18 h and filtered, and the filtrate was concentrated. Purification by silica gel chromatography (90/10/1 CH$_2$Cl$_2$/MeOH/HOAc) gave 0.98 g (67%) of compound 42 as an oil.

Bis-N-(t-butoxycarbonyl)-amino-TFG, Compound 43

To a solution of 750 mg (4.25 mmol) of compound 42 and 345 uL (337 mg, 4.25 mmol) of pyridine in 6 mL of CH$_2$Cl$_2$ was added 445 uL (559 mg, 2.02 mmol) of triethylenealycol bis-chloroformate. The mixture was stirred for 3.5 h, and the mixture was partitioned between 35 mL of CH$_2$Cl$_2$ and 35 mL of 1 N HCl. The CH$_2$Cl$_2$ layer was washed with H$_2$O, dried (Na$_2$SO$_4$), filtered and concentrated to give 1.14 g of crude compound 43 which was used directly in the next step.

Diamino-TEG bis-trifluoroacetate Salt, Compound 44

300mg (0.57 mmol) of compound 43 was dissolved in 3.5 g of CH$_2$Cl$_2$, and 3.5 mL of trifluoroacetic acid was added. The mixture was stirred for 3 h at room temperature, and the solution was concentrated to give 398 mg of crude compound 44 which was used directly in the next step.

Compound 45

A solution of 567 mg of compound 41 in 6 mL of dioxane was added to a solution of 398 mg of crude compound 44 (est. 316 mg, 0.57 mmol) and 193 mg (2.30 mmol) of NaHCO$_3$. The mixture was stirred for 3 h and acidified with 1 N HCl and partitioned between 20 mL of 1 N HCl and 30 mL of EtOAc. The combined EtOAc layers are washed with sat NaHCO$_3$ solution, dried (MgSO$_4$), filtered and concentrated to give 490 mg (86%) of crude compound 45 as a white foamy solid. Purification by silica gel chromatography (EtOAc) gave 276 mg (48%) of compound 45 as a white foamy solid.

IA/DABA/ATEG, Compound 46

A solution of 100 mg (0.1 mmol) of compound 45 was prepared, and 1 mL of trifluoroacetic acid was added, and the mixture was stirred for 1 h at room temperature. The mixture was concentrated under vacuum. The residue was triturated with Et$_2$O and dried under vacuum to give a white crystalline solid. The solid was dissolved in 1 mL of DMF, 104 uL (77 mg, 0.6 mmol) of diisopropylethylamine was added, the mixture was cooled to 0°, and 212 mg (0.6 mmol) of iodoacetic aniydride was added. The ice bath was removed, and the mixture was stirred at room temperature for 2 h. The mixture was cooled to 0°, acidified with 1 N H$_2$SO$_4$, and partitioned between 10 mL of 1 N H$_2$SO$_4$ and 6×20 mL portions of 8/2 CH$_2$Cl$_2$/MeOH. The combined organic layers were dried (MgSO$_4$), filtered, and concentrated to give 330 mg of orange oil. Purification by preparative HPLC (25 cm×22.4 mm C$_{18}$, gradient: 30%B to 40%B 0–40 min, A=H20/0.1% TFA, B=CH$_3$CN/0.1% TFA, 12 mL/min) gave 19 mg of compound 46 as a white solid.

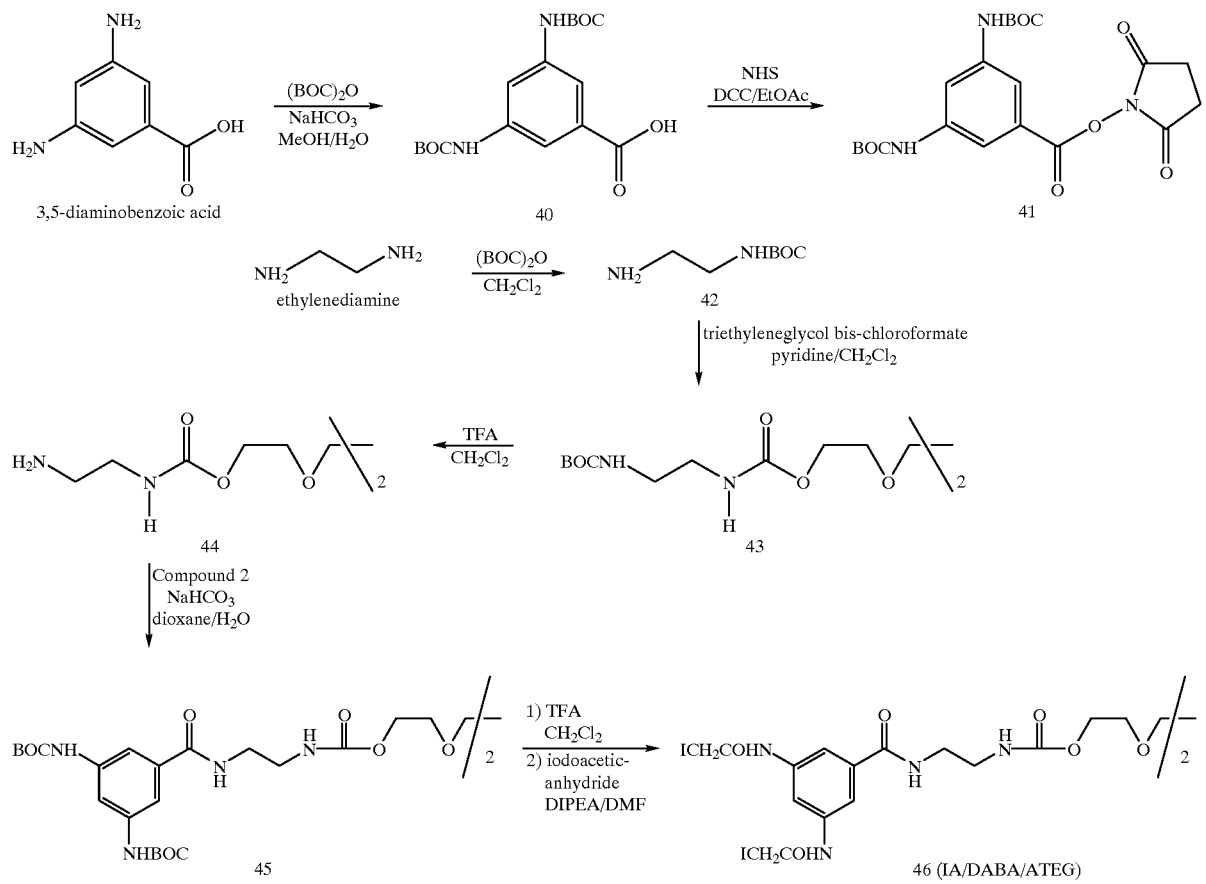

Example 22
Synthesis of the Tetravalent Platform BA/PABA/DT/TEG, 51
N-(t-butoxycarbonyl)PABA, Compound 47

A solution was prepared of 3.0 g (21.9 mmol) of p-aminobenzoic acid in 60 mL of $H_2O$. $Na_2CO_3$ (2.16 g, 25.7 mmol) was added slowly followed by 30 mL of MeOH. When all solids were dissolved, a solution of 4.77 g (21.9 mmol) of di-t-butyldicarbonate in 10 mL of MeOH was added and the mixture was stirred at room temperature for 18 h. To the mixture was added 4.92 g (25.6 mmol) of citric acid and the resulting cloudy mixture was partitioned between 200 mL of $H_2O$ and 200 mL of EtOAc. The EtOAc layer was washed successively with 200 mL of 0.1 N HCl and 200 mL of $H_2O$, dried ($Na_2SO_4$), filtered, and concentrated to yield 3.0 g (58%) of compound 47 as a white solid.

N-(t-butoxycarbonyl)PABA N-hydroxysuccinimidyl Ester, Compound 48

DCC (2.61 g, 12.6 mrnol) was added to a 0° solution of 2.0 g (8.43 mmol) of compound 47 and 0.97 g (8.43 mmol) of N-hydroxysuccinimide in 50 mL of EtOAc. The ice bath was removed, the mixture was stirred for 16 h at room temperature, and 0.5 mL of acetic acid was added. The mixture was stirred for an additional 30 min, placed in the freezer for 1.5 h, filtered, and concentrated to give 3.75 g of crude 48. Purification by silica gel chromatography (50/50 hexane/EtOAc) gave 2.53 g (90%) of compound 48 as a white solid.

Compound 49

A solution of 3.00 g (8.97 mmol) of compound 48 in 50 mL of $CH_2Cl_2$ was added dropwise over 30 min to a solution of 485 uL (4.49 mmol) of diethylenetriamine in 30 uL of $CH_2Cl_2$ which had been cooled in an ice bath. The mixture was stirred at 5–7° for 30 min then at room temperature for 16 h. The milky mixture was placed in a separatory funnel with 200 mL of $H_2O$, the pH of the $H_2O$ layer was adjusted to 10 with 3 M NaOH solution, and the mixture was extracted with 200 mL of 4/1 $CH_3Cl/MeOH$. The organic phase was dried ($Na_2SO_4$) and concentrated to give 0.971 g (40%) of compound 49 which was pure enough to be used in the following step. The aqueous layer was extracted with six 100 mL portions of 4/1 $CH_3Cl/MeOH$. The organic layers were combined, dried ($Na_2SO_4$), and concentrated to give another 1.08 g (44%) of compound 49 which required further purification. Further purification can be accomplished by silica gel chromatography (gradient, 80/20 to 70/30 $CH_3Cl/MeOH$).

Compound 50

A solution of 135 uL (0.66 mmol) of triethyleneglycol bis-chloroformate in 0.3 mL of THF was added to a 0° solution of 855 mg (1.58 mmol) of compound 49 and 275 uL (1.58 rnmol) of diisopropyletlhylamine in 13 mL of THF. The cloudy mixture cleared when the ice bath was removed. An additional 70 uL of diisopropyethylamine was added to maintain a basic pH. The mixture was stirred at room temperature for a total of 3 h and partitioned between 25 mL of $H_2O$ and 25 mL of EtOAc. The aqueous layer was extracted with a second 25 mL portion of EtOAc, and the combined EtOAc layers were dried ($Na_2CO_3$), filtered, and concentrated to give 0.986 g of crude 50. Purification by silica gel chromatography (80/4/16 $CH_3Cl$/dioxane/isopropanol) gave 516 mg (61%) of compound 50 as a white solid.

Preparation of BA/PABA/DT/TEG, Compound 51

Compound 50 (487 mg, 8.79 mmol) was dissolved in 9 mL of $CH_2Cl_2$ and 5 mL of trifluoroacetic acid. The mixture was stirred for 1.5 h and concentrated. The residue was triturated with 7 mL of $Et_2O$, and dissolved in 5 mL of MeOH and 1 mL of 48% HBr solution. The mixture was concentrated and placed under vacuum until a dry. The resulting HBr salt was dissolved in 10 mL of $H_2O$, and 191 mg (2.27 mmol) of $NaHCO_3$ was added. A solution of 591 mg (2.27 mmol) of bromoacetic anhydride in 10 mL of dioxane was added to the mixture. An additional 2 mL of dioxane was used to rinse. More $NaHCO_3$ was added as needed to maintain a basic pH. The mixture was stirred for 2 h at room temperature, and acidified with 1 N $H_2SO_4$. The mixture was extracted with 3×25 mL of EtOAc. The combined EtOAc layers were dried ($Na_2SO_4$), filtered, and concentrated to give 773 mg of an oil. Purification was accomplished by silica gel chromatography (gradient, 90/10 to 85/15 $CH_3Cl/MeOH$) to give 401 mg (77%) of 51 as a white solid.

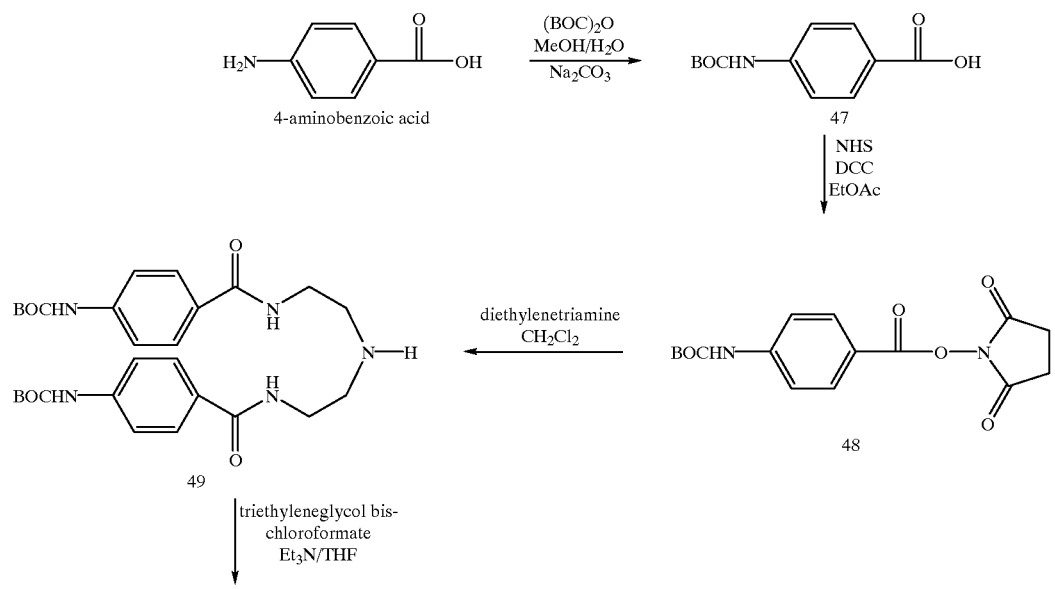

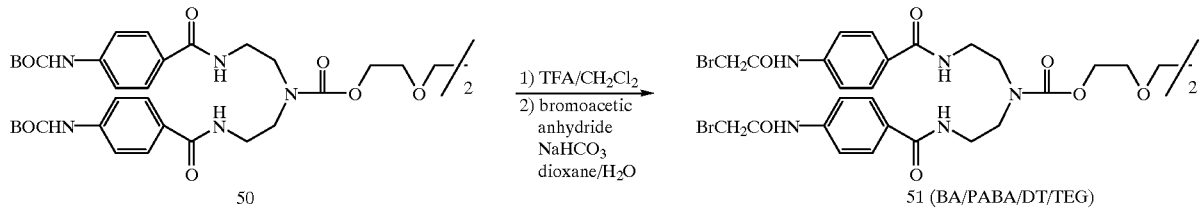

Example 23

Synthesis of the Tetravalent Platform BMP/TEG, 55

Dimethyl-5-hydroxyisophthalate, Compound 52

A solution of 2.00 g (11 mmol) of 5-hydroxyisophthalic acid and 0.5 mL of con HCl in 30 mL of MeOH was refluxed for 5 h. The mixture was concentrated and the resulting residue was dissolved in 100 mL of EtOAc. The EtOAc solution was washed successively with two 50 mL portions of 5% $NaHCO_3$ solution and two 50 mL portions of sat NaCl solution, dried ($Na_2CO_3$), filtered, and concentrated to give 2.09 g (90%) of 52 as a white crystalline solid.

Compound 53

Triethyleneglycol ditosylate 546 mg (1.19 mmol) was added to a suspension of 500 mg (2.38 mmol) of compound 52 and 395 mg (2.86 mmol) of $K_2CO_3$ in 11 mL of $CH_3CN$ and the mixture was refluxed under $N_2$ for 16 h. The mixture was concentrated, and the residue was dissolved in 25 mL of $CHCl_3$ and washed with 25 mL of $H_2O$ and 25 mL of sat NaCl solution. The $CHCl_3$ layer was dried ($Na_2SO_4$), filtered, and concentrated. Purification by silica gel chromatography (gradient, 50/50 hexane/EtOAc to 100% EtOAc) gave 93 mg (41%) of compound 53.

Compound 54

A suspension of 93 mg (0.18 mmol) of compound 53 in 4 mL of THF was stirred under a $N_2$ atmosphere whlile 1.82 mL (1.82 mmol) of a 1 M solution of $LiBHEt_3$ was added to the mixture dropwise. A clear solution was obtained which was stirred for 18 h at which time a 10% solution of HOAc in water was added until the pH was acidic. The mixture was concentrated under vacuum and the residue was dissolved in 10 mL of water. The mixture was extracted with 3×10 mL portions of EtOAc, and the combined EtOAc layers were dried ($Na_2SO_4$), filtered and concentrated. Purification was accomplished by silica gel chromatography (gradient, 90/10 to 85/15 $CH_3Cl$/MeOH) to give 20 mg (27%) of 54 as a white solid.

Compound 55

To a suspension of 20 mg (0.048 mmol) of 54 in 5 mL of $Et_2O$ and 1 mL of THF is added 9.6 uL (0.1 mmol) of $PBr_3$. The mixture is stirred for 3 h and partitioned between water and EtOAc. The EtOAc layer is dried ($Na_2SO_4$), filtered and concentrated, and the residue is purified by silica gel clhromiatograplhy ($CH_3Cl$/MeOH) to provide compound 55.

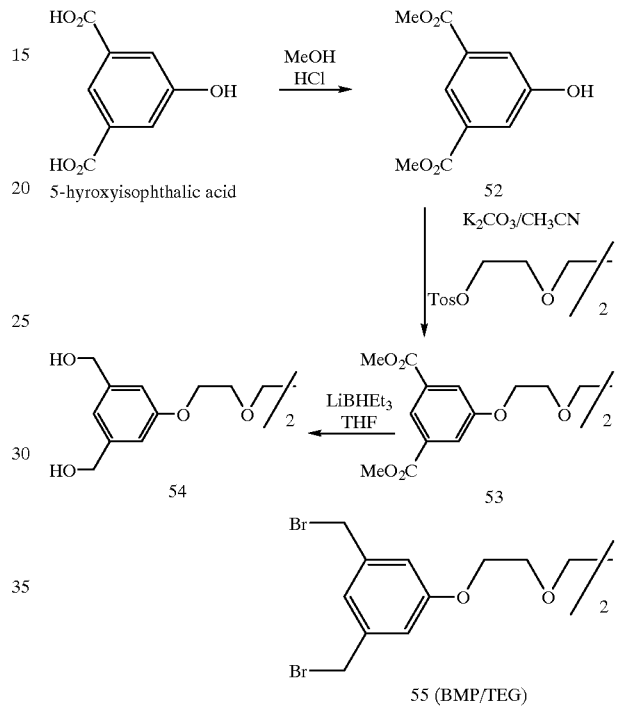

Example 24

Synthesis of the Tetravalent Platform BA/PIZ/IDA/TEG, 60

Compound 56

To a solution of 1.02 g (4.37 mmol) of N-(t-butoxycarbonyl)-iminodiacetic acid (compound 5 in U.S. Pat. No. 5,552,391, Chemically-Defined Non-Polymeric Valency Platform Molecules and Conjugates Thereof) and 1.01 g (8.75 mmol) of N-hydroxysuccinimide in 50 mL of dry THF, cooled to 0°. was added 2.26 g (10.94 mmol) of dicyclohexylcarbodiimide. The mixture was stirred for 16 h allowing to slowly warm to room temperature, and a solution of 2.22 g (10.1 mmol) of mono-CBZ-piperazine in 25 mL of THF was added to the mixture followed by 1.22 mL (887 mg, 8.75 mmol) of $Et_3N$. The mixture was stirred for 7 h at room temperature, and filtered. The filtrate was concentrated and the residue was dissolved in 125 mL of EtOAc and shaken with 2×125 mL portions of 1 N HCl, 125 mL of sat $NaHCO_3$ solution, dried ($MgSO_4$), filtered, and concentrated to give 2.39 g of a sticky solid. Purification by silica gel chromatography (95/5 $CH_2Cl_2$/MeOH) gave 1.85 g (66%) of 56.

Compound 57

To a solution of 1.74 g (2.74 mmol) of compound 56 in 10 mL of $CH_2Cl_2$ was added 10 mL of trifluoroacetic acid, and the mixture was stirred for 3 h at room temperature. The mixture was concentrated, and the residue was dissolved in 5 mL of $CH_2Cl_2$. The mixture was cooled to 0° and 100 mL of sat $NaHCO_3$ was added. The mixture was then extracted with four 100 mL portions of $CH_2Cl_2$. The $CH_2Cl_2$ layers were combined, dried ($MgSO_4$), filtered, and concentrated to give 1.46 g (99%) of 57 as a sticky hygroscopic solid which was used directly in the next step.

Compound 58

To a solution of 0.7 g (1.3 mmol) of compound 57 and 226 uL (168 mg, 1.30 mmol) of diisopropylethylamine at 0° was added a solution of 127 uL of triethyleneglycol bis-chloroformate in 4 mL of $CH_2Cl_2$, and the mixture was stirred for 3 h at room temperature. The mixture was partitioned between 80 mL of $CH_2Cl_2$ and 80 mL of 1 N HCl. The $CH_2Cl_2$ layer was washed with two 80 mL portions of water, dried ($MgSO_4$), filtered, and concentrated to give 736 mg (93%) of compound 58 as a crystalline solid.

Compound 60

Compound 58 (61 mg, 0.48 mmol) was dissolved in 3 mL of 30% HBr/HOAc and the resulting mixture was stirred at room temperature for 1 h at which time 5 mL of $Et_2O$ was added. The mixture was placed in the freezer for 1 h and centrifuged. The resulting pellet was washed with $Et_2O$ and dried to give the tetrahydrobromide salt 59 which was dissolved in 1 mL of $H_2O$. To the mixture is added 49 mg (0.58 mmol) of $NaHCO_3$ and 3 mL of dioxane. More $NaHCO_3$ is added, if needed, to make the mixture basic. The mixture is cooled to 0°, and 748 mg (2.89 mmol) of bromoacetic anhydride is added. The mixture is stirred for 2 h and partitioned between 20 mL of 1 N $H_2SO_4$ and 20 mL of 80/20 $CH_2Cl_2$/MeOH. The organic layer is dried ($Na_2SO_4$), filtered and concentrated to give crude 60 which is purified by silica gel chromatography ($CH_2Cl_2$/MeOH) to give 60.

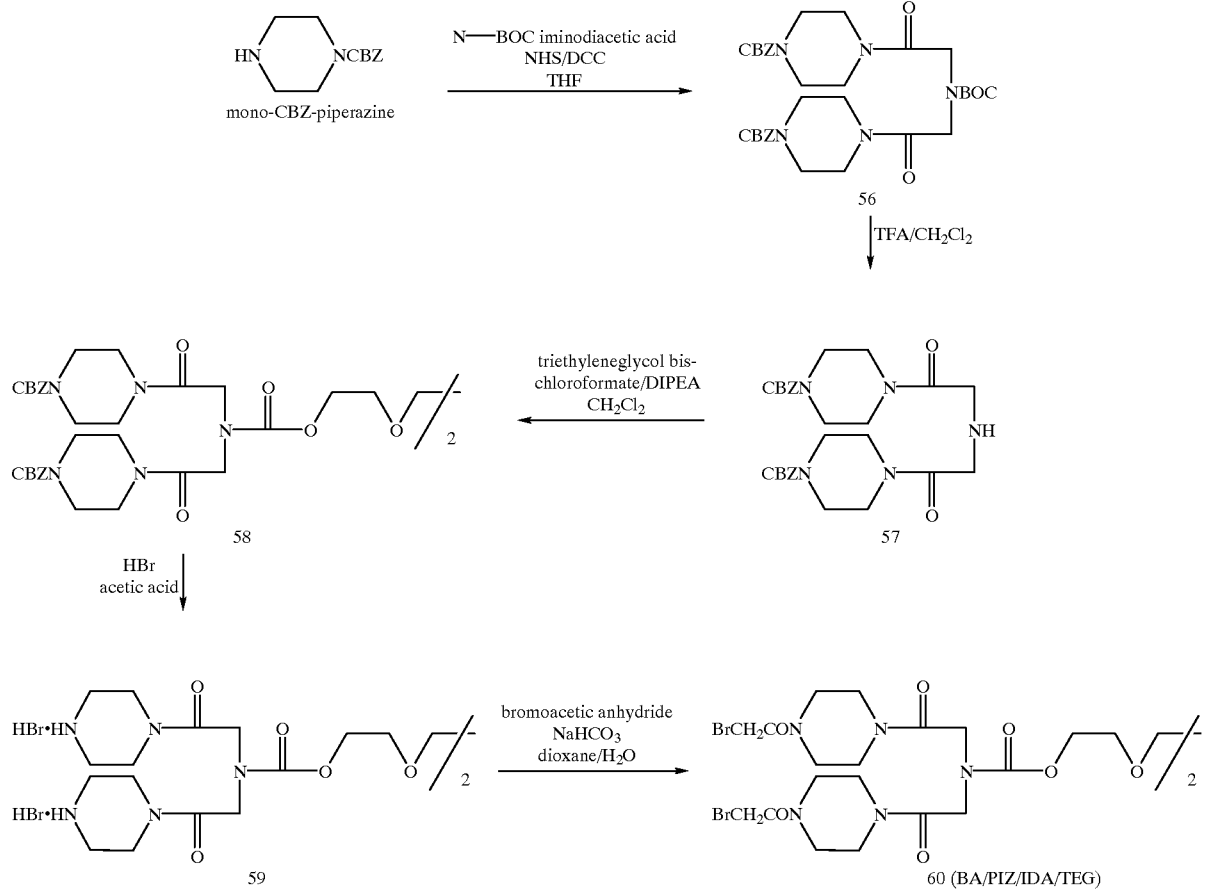

Example 25

Synthesis of the Tetravalent Platform tetrakis-BA/PIZ/PMA, 63

Compound 61

To a 0° solution of 640 mg (2.52 mmol) of pyromellitic acid and 1.16 g (10.1 mmol) of N-hydroxysuccinimiiide in 50 mL of THF was added 2.6 g (12.6 mmol) of dicyclohexylcarbodiimide, and the mixture was allowed to come to room temperature while stirring for 16 h. A solution of 2.5 g (11.3 mmol) of mono-CBZ-piperazine in 25 mL of THF was added to the mixture followed by 1.4 mL (1.02 g, 10.1 mmol) of $Et_3N$. The mixture was filtered, and the filtrate was concentrated. The residue was partitioned between 100 mL of EtOAc and 2×100 mL of 1 N HCl, and the EtOAc layer was washed with 100 mL of sat $NaHCO_3$, 100 mL of $H_2O$, 100 mL of sat $NaHCO_3$, dried ($MgSO_4$), filtered, and concentrated. Purification was accomplislhed by silica gel clhromatography (97.5/2.5 $CH_2Cl_2$/MeOH) to give 1.78 g (66%) of 63 as a white crystalline solid.

Compound 63

Compound 61 is converted to compound 63 in essentially the same manner as described for the conversion of 58 to 60 in Example 23. Purification is accomplished using silica gel chromatography.

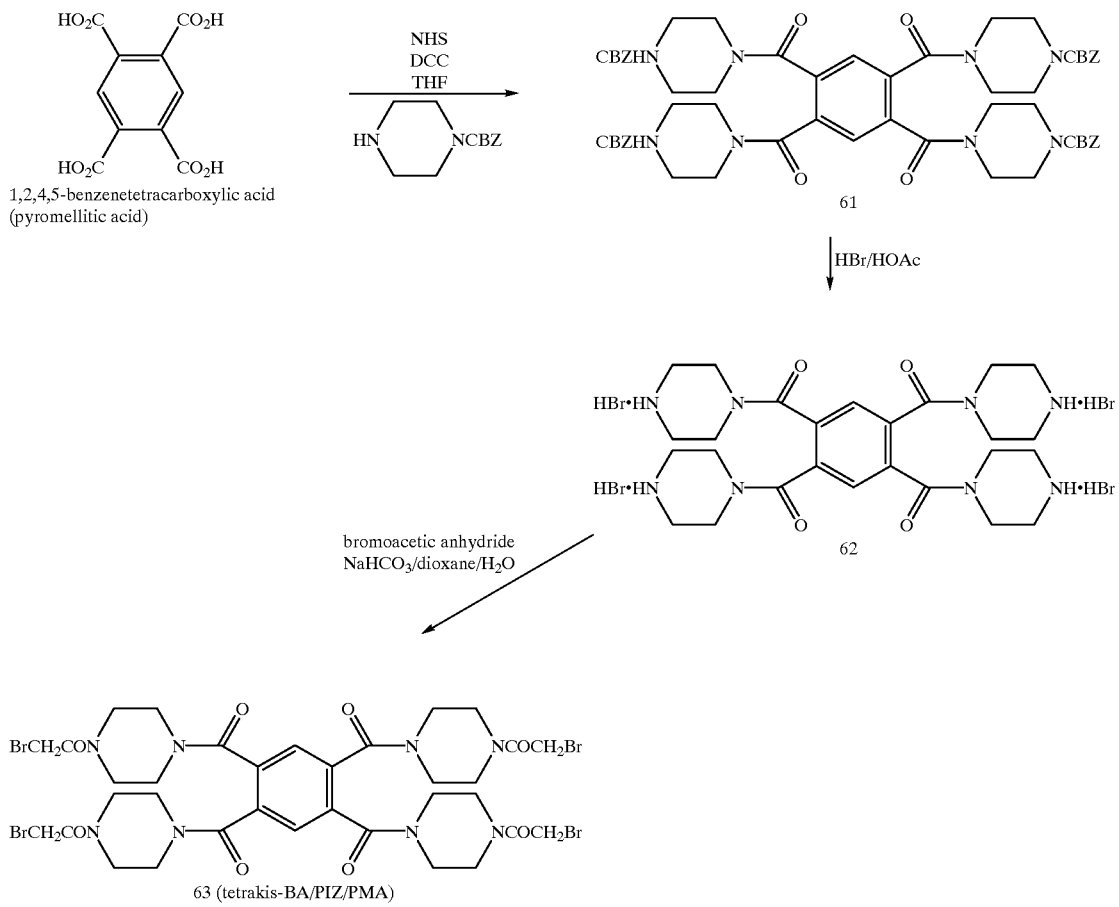

Example 26
Synthesis of the Tetravalent Platform BA/PIZ/IDA/HB/TEG, 68

Compound 64

Triethyleneglycol ditosylate (1.0 g, 2.18 mmol) was added to a solution of 725 mg (4.36 mmol) of ethyl 4-liydroxybenzoate and 723 mg (5.23 mmol) of $K_2CO_3$, and the mixture was refluxed for 16 h. The mixture was concentrated, and the residue was partitioned between 20 mL of water and 3×20 mL of $Et_2O$. The combined organic layers were washed with 2×40 mL of sat $NaHCO_3$ solution, 40 mL of sat NaCl solution. The aqueous layers were washed with $Et_2O$, and the combined $Et_2O$ layers were dried ($MgSO_4$), filtered, and concentrated. Purification by silica gel chromatogoalhy (70/30 hexanes/EtOAc) have 902 mg (93%) of 64 as a crystalline solid.

Compound 65

Compound 64 is dissolved in acetone containing 2.2 equivalents of LiOH and the mixture is stirred for 3 h (until complete as evidenced by TLC). The mixture is acidified with acetic acid and concentrated, and the residue is purified by silica gel chromatography to give 65.

Compound 66

Compound 66 is prepared similarly to the method of preparing compound 56 in example 23. Compound 65 is used instead of N-BOC-iminodiacetic acid, and compound 57 is used instead of mono-CBZ-piperazine. Purification is accomplished using silica gel chromatography.

Compound 68

Compounld 66 is converted to compound 68 in essentially the same manner as described for the conversion of 58 to 60 in Example 23. Purification is accomplished using silica gel chromatography.

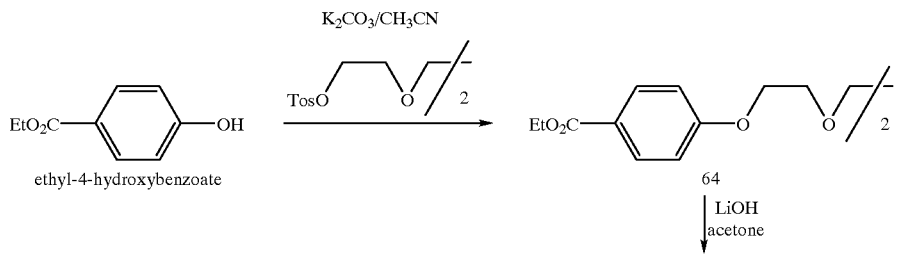

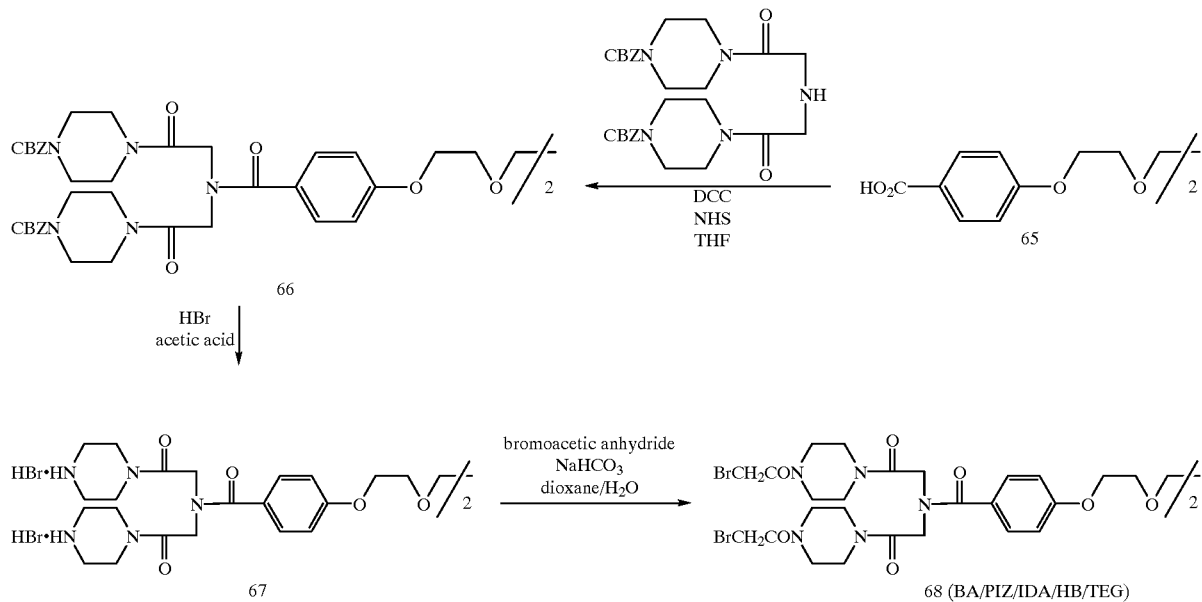

Example 27
Synthesis of the Tetravalent Platform BA/PIZ/HIP/TEG, 72
Compound 69

Compound 53 is hydrolyzed with LiOH in essentially the same manner as described for the hydrolysis of 64 in example 25 with the exception that 4.4 equivalents of LiOH is used.

Compound 70

The tetra-acid, compound 69, is converted to compound 70 in essentially the same manner as described for the conversion of pyromellitic acid to 61 in example 24 with the exception that 69 is used instead of pyromellitic acid.

Compound 72

Compound 70 is converted to compound 72 in essentially the same manner as described for the conversion of 58 to 60 in Example 23. Purification is accomplished using silica gel chromatography.

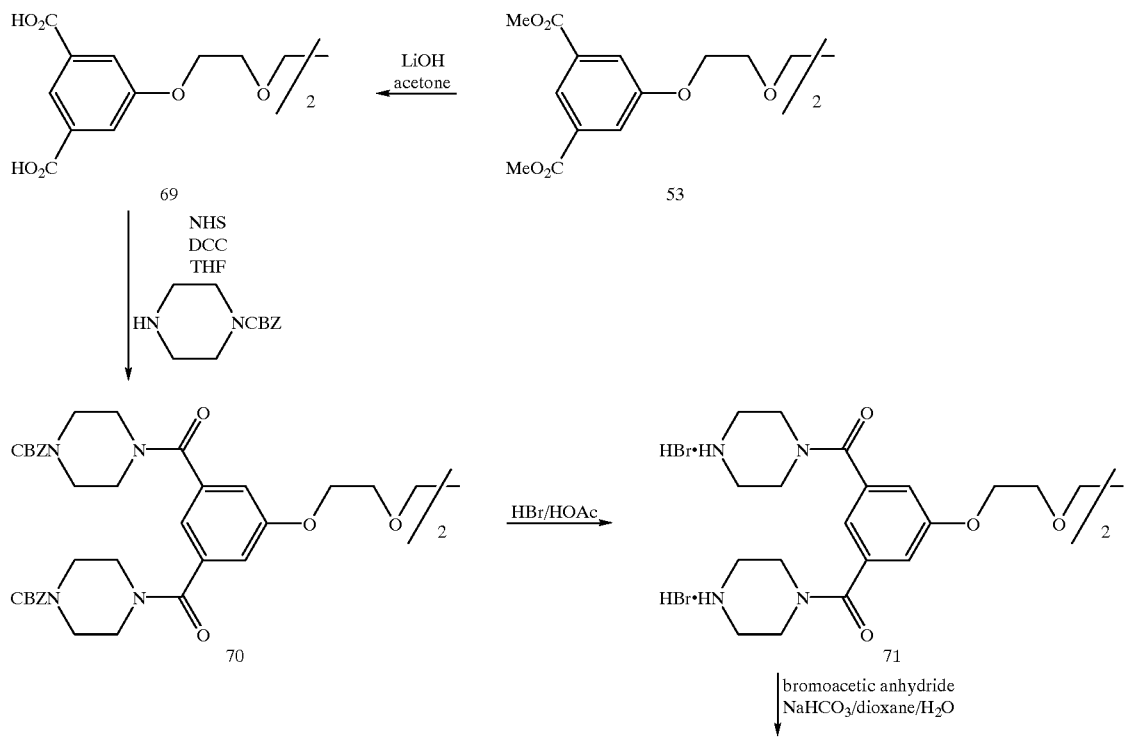

Example 28
Synthesis of Conjugates of Haloacetylated Tetravalent Compounds
Synthesis of (LJP685)$_4$/MTU/A/DABA/ATEG Conjugate Compound 73

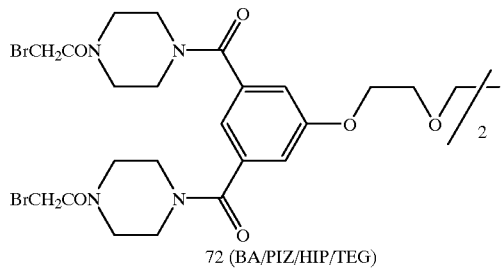

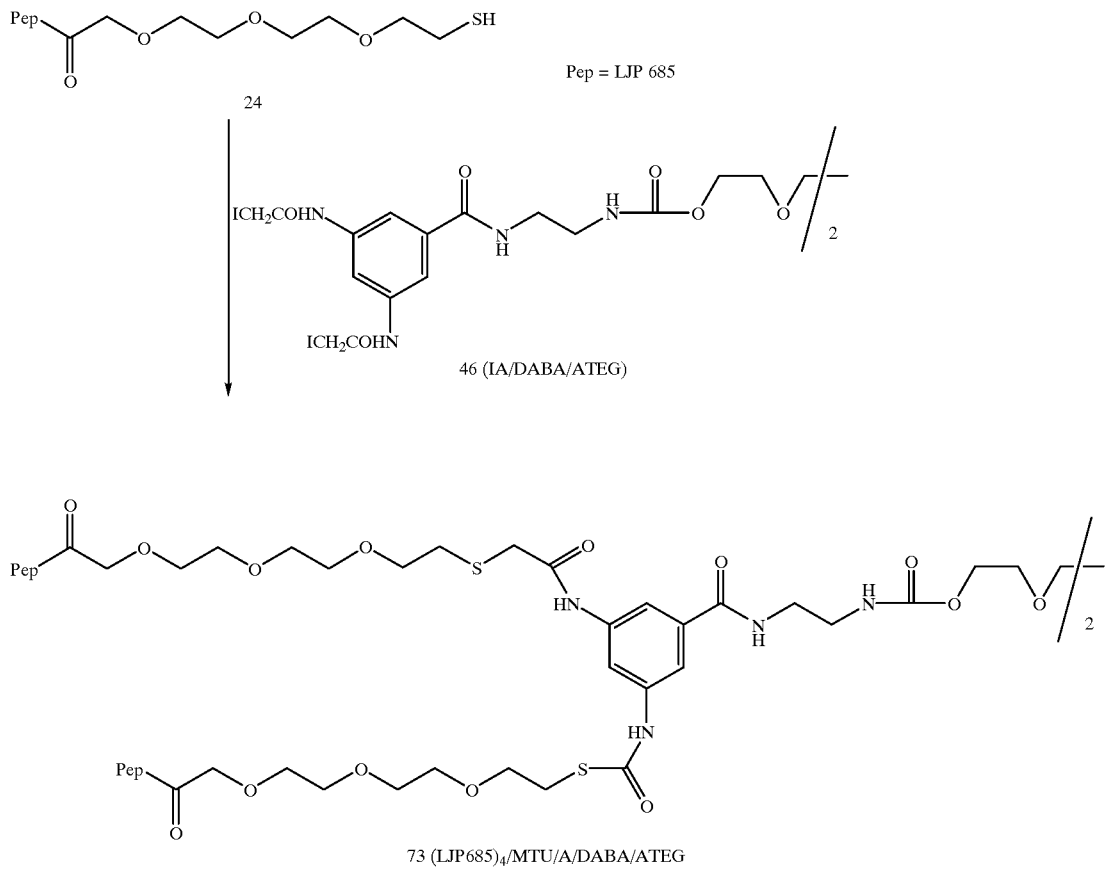

A solution was prepared of 21 mg (15.5 umol) of compound 24 in Helium sparged pH 8.5 200 mM borate buffer. To the solution was added a second solution consisting of 3.25 mg (2.6 umol) of IA/DABA/ATEG, compound 46, dissolved in 396 uL of MeOH. A precipitate formed, and 1 mL of MeOH was added to dissolve all the solids. The mixture was stirred for 18 h at room temperature, and 6 mL of 9/1 H$_2$O/HOAc was added. The mixture was diluted with 50 mL of 9/1 H$_2$O/CH$_3$CN and loaded onto an HPLC preparative column. Purification was accomplished by preparative HPLC (25 cm×22.4 mm C$_{18}$, gradient: 35%B to 45%B 0–40 min, A=H$_2$O/0.1% TFA, B=CH$_3$CN/0.1% TFA, 12 mL/min) to provide 10.8 mg (67%) of compound 73 as awhite solid after lyophilization.

Synthesis of (LJP685)$_4$/MTU Conjugates, Compounds 74, 75, 76, 77, and 78

These conjugates are prepared from platform compounds 51, 60, 63, 68, and 72, respectively, by the same reaction conditions as described above for the synthesis of conjugate 173 by substituting the appropriate platform compound for platform compound 46. Pep can be LJP685 or other relevant peptide.

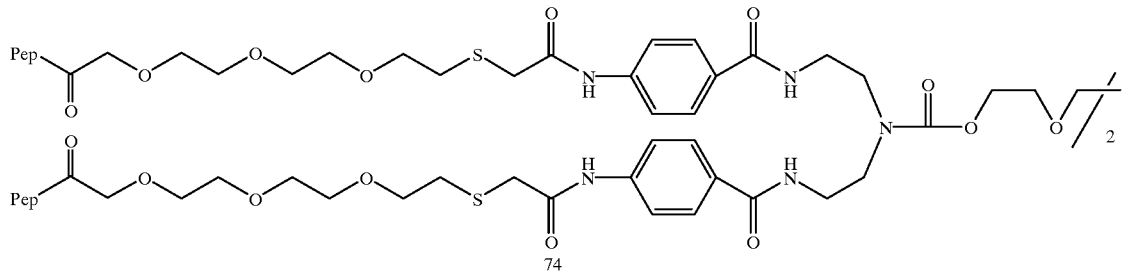

74

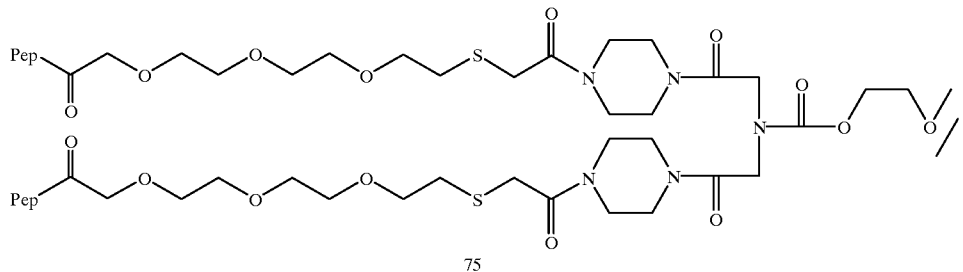

75

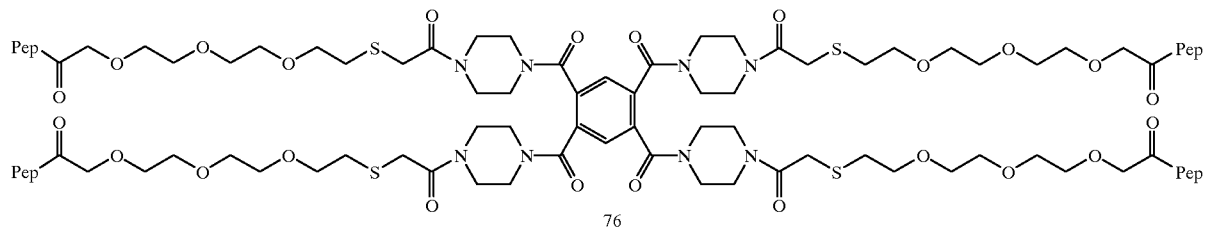

76

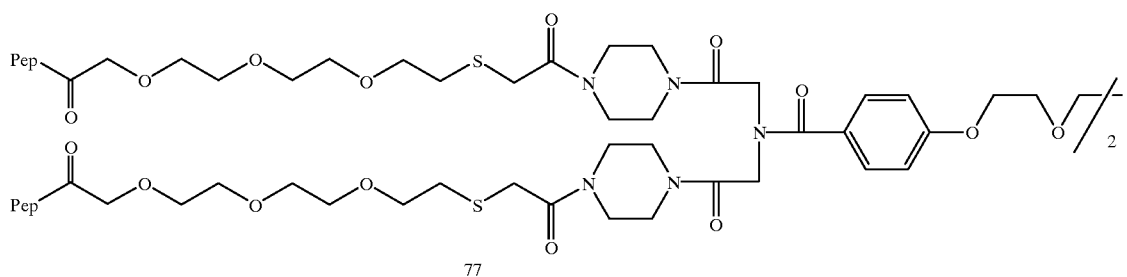

77

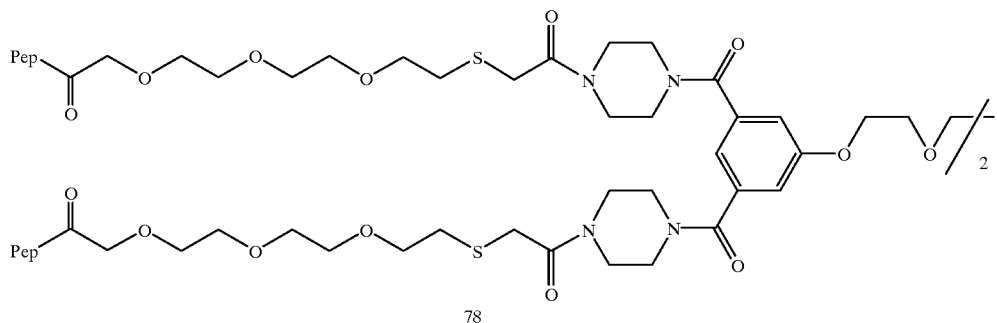

78

Example 29

Syntlesis of Conjugates Tetravalent Platform 55, Conjugate Compound 79, (LJP685)$_4$/MP/TEG A solution is prepared of four equivalents of compound 24 and five equivalents of Cs$_2$CO$_3$ in DMF. One equivaleint of BMP/TEG, platform compound 55, is added to the mixture which is then stirred for 1 h. The mixture is diluted with 80/20/10 H$_2$O/CH$_3$CN/HOAc and loaded onto a preparative HPLC column. Purification is accomplished by preparative HPLC (C$_{18}$, A=H$_2$O/0.1% TFA, B=CH$_3$CN/0.1% TFA) to give compound 79 after lyophilization. Pep can be LJP685 or other relevant peptide.

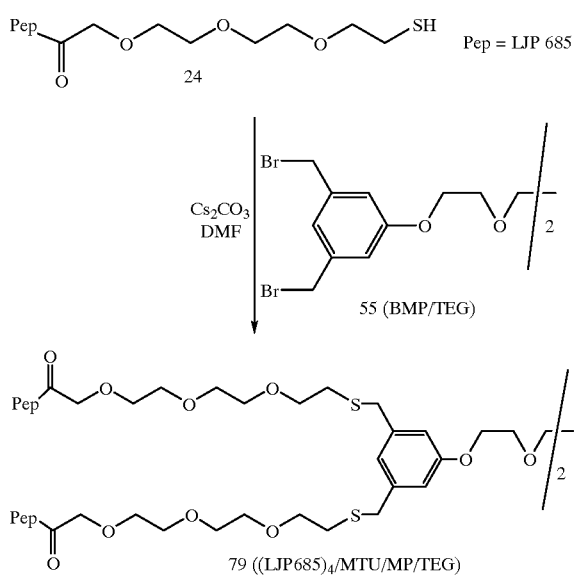

Example 30
Syntlesis of Conjuoates Tetravalent Platform tetrakis-BMB, Conjugate Compounld 80, (LJP685)₄/MTU/tetrakis-MB A solution is prepaiei of four equivalents of compound 24 and five equivalents of $Cs_2CO_3$ in DMF. One equivalent of tetrakis-bromonietliylbenzene is added to the mixture which is then stirred for 1 h. The mixture is diluted with 80/20/10 $H_2O/CH_3CN/HOAc$ and loaded onto a preparative HPLC column. Purification is accomplished by preparative HPLC ($C_{18}$, A=$H_2O$/0.1% TFA, B=$CH_3CN$/0.1% TFA) to give compound 80 after lyophilization. Pep can be LJP685 or other relevant peptide.

Example 30
Fluorescence Polarization Peptide Binding Assays Syntlhesis of FITC-GPCILLARDRCG (CB2*)

A solution of the cyclic disulfidc peptide GPCIL-LARDRCG (SEQ ID NO:216) (20.0 mg, 14.4 μmol) and fluorescein isothiocyaiiate (FITC) (5.6 mg, 14.4 μmol) in 20 mL of ACN/water (1:1), containing 20 mg sodium carbonate ($Na_2CO_3$, pH~10.5), was stirred at room temperature. The reaction was monitored by analytical HPLC. After consuming the fluorescent labeling reagent, the crude material was purified on a preparative HPLC eluted at 10 mL/min with a linear gradient from 30 to 55% B over 40 minutes whIiere A was 0.1% (v/v) TFA in $H_2O$ and B was 0.085% (v/v) TFA in CAN. The FITC peptide was obtained as a bright yellow powder after lyophilization (3.7 mg, 15% yield): MS (ESI): m/e (M+1) Calcd. for $C_{73}H_{102}N_{19}O_{20}S_3$: 1661, obsd.: 1661.

Direct Binding Fluorescence Polarization Binding Assay (dbFP)

Figure 22:
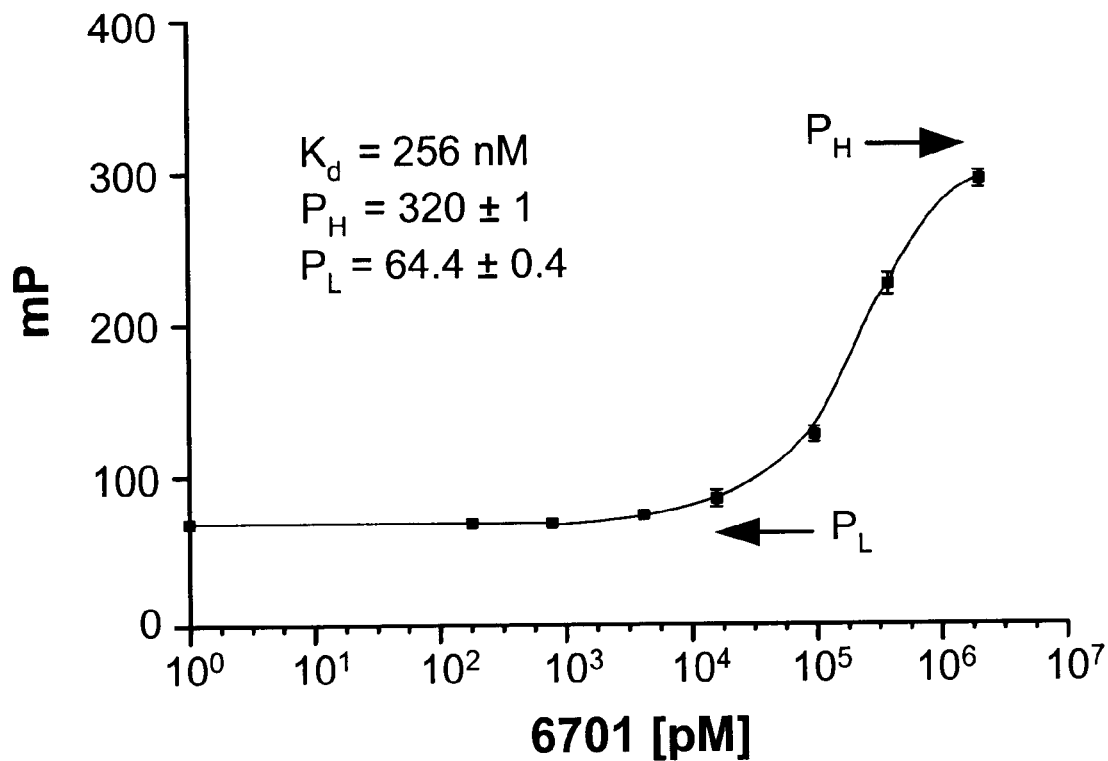
Figure 23:
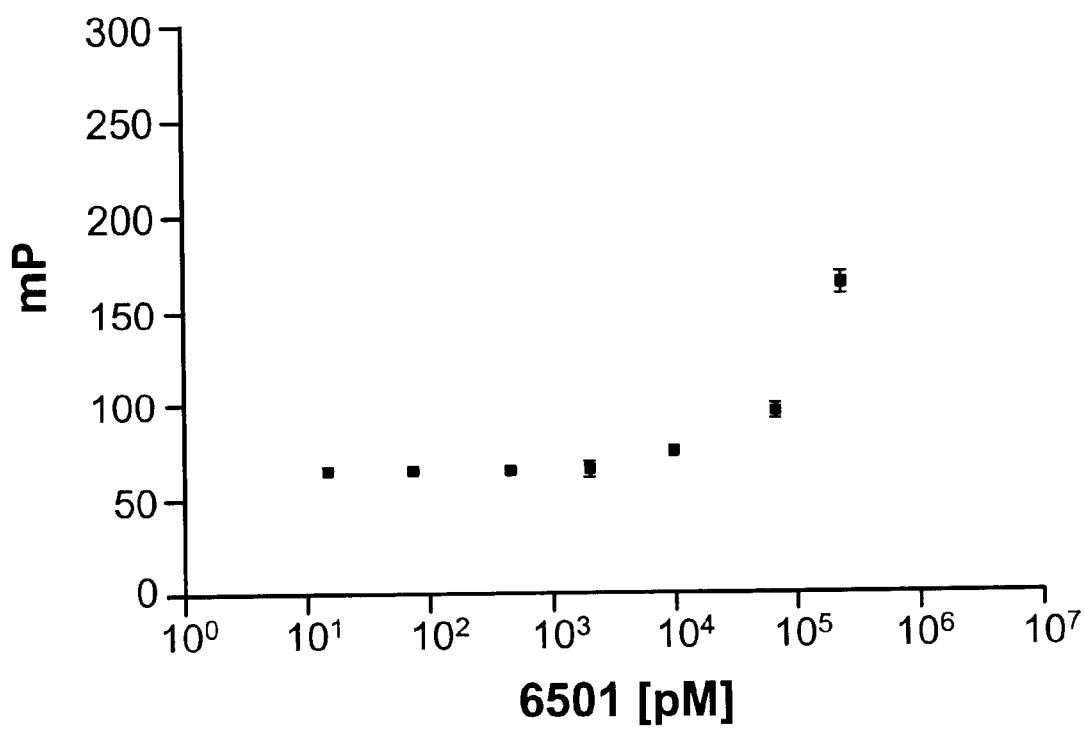

The methodology is described in PanVera Application Guide (1994), PanVera Corporation. Briefly, a trace amount of fluorescein isothiocyanate (FITC) labeled peptidc (CB2*-F) is titrated with antibody (ACA 6501 or 6701) and the polarization for the sample is plotted versus the antibody concentration. Polarization was measured with the PanVeia Beacon instrument. Data were fitted to Equation 1.

$$Y = \frac{[P_L * (K_D/R) + P_H]}{K_D/R + 1.0}$$  Equation 1 where Y is the Y-axis value (milli-polariztion units, mP), R is the total concentration of antibody receptor, $P_L$ is the polarization for free FITC-labeled peptide (F), and $P_H$ is the polarization for F complexed with R (FR). $K_D$ is the dissociation constant (reciprocal binding constant) for F from the FR complex. For these equations to be valid, it must be true that F<<R. This titration is shown in FIGS. 22 and 23 for CB2*-F binding to ACA-6701 and ACA-6501

Figure 24:
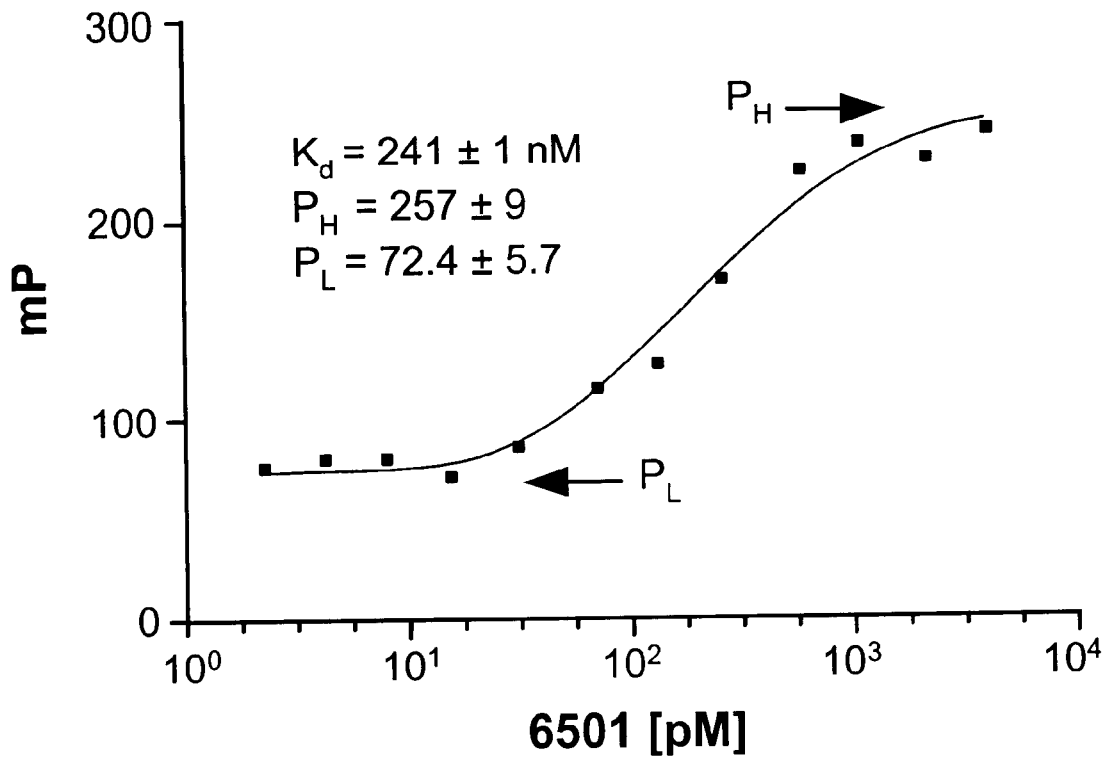
Figure 25:
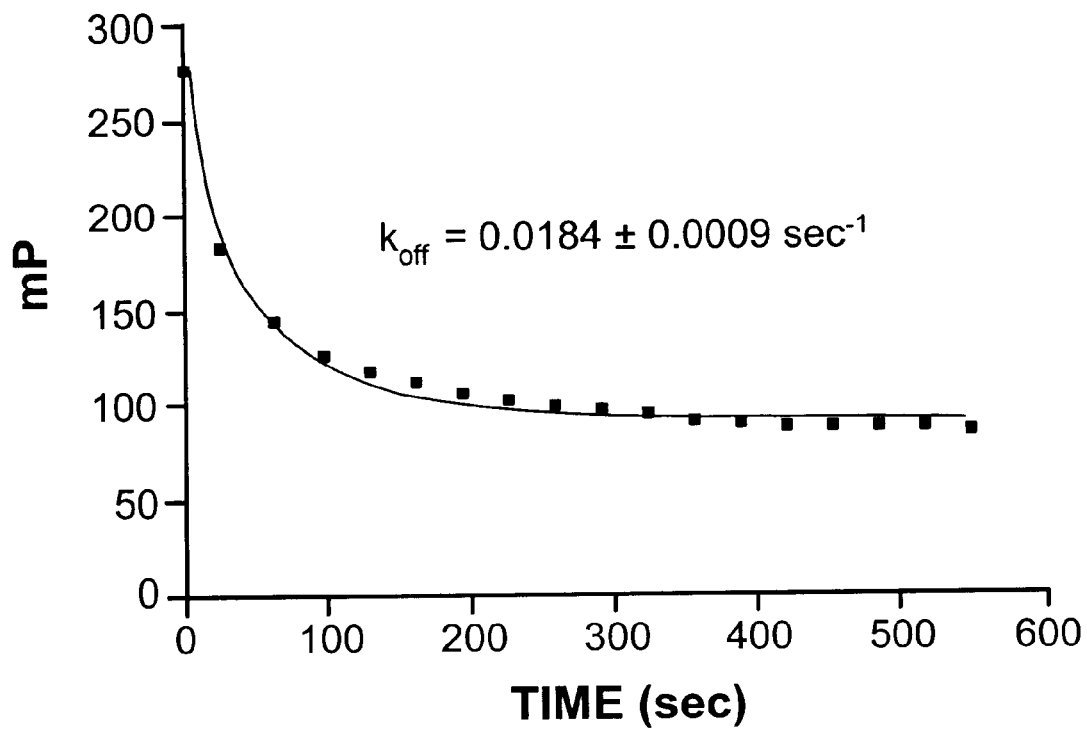

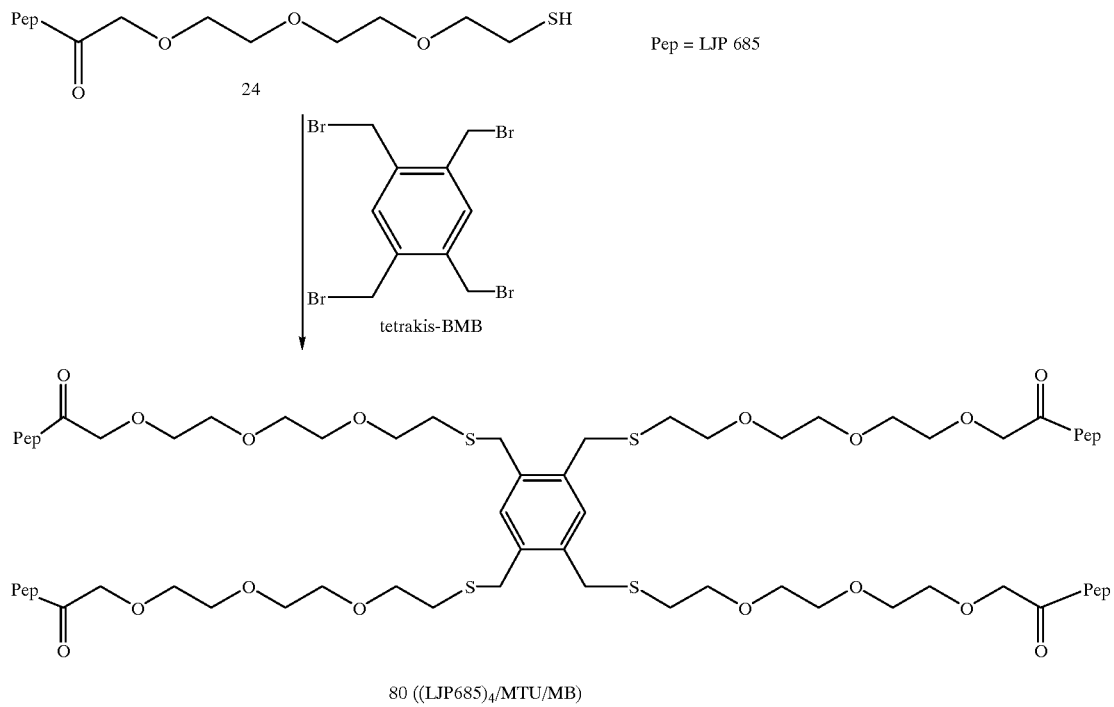

antibodies, respectively. A complete titration was not obtained with ACA-6501 as shown in FIG. 23, but a previous titration shown in FIG. 24 gave a $K_D$ of 241 nM. By adding CB2*(GPCILLARDRCG) in slight excess over antibody 6701, to displace CB2*-F from 6701 (see FIG. 25), a dissociation rate constant of $K_{off}=0.0184$ sec$^{-1}$, which corresponds to $t_{1/2}=38$ seconds, was determined for CB2*-F. Given the $K_D$ of 256 nM, this corresponds to an association rate constant of $K_{on}=3.6\times10^4$ M$^{-1}$sec$^{-1}$ (after correctings tor antibody bivalency). Thus, CB2*-F binding to ACA-6701 is limited only by diffusion of these two molecules together.

Competitive Fluorescence Polarization Assay (cFP)

The above described dbFP assay provides binding constants for FITC-labeled peptides and requires on the order of 0.5 mg of purified antibody. The cFP assay provides binding constants for peptides that lack the FITC group and it consumes less antibody, on the order of 10 µg. The cFP assay is modified from that reported in Pan Vera Applications Guide (1994) PanVera Corporation such that it consumes 50-fold less antibody. Briefly, antibody (ACA 6701) is mixed with trace FITC labeled peptide (CB2*-F) and enough time is allowed for equilibrium to be reached. This was 1 hour for ACA 6701 and CB2*-F. Increasing concentrations of the unlabeled peptide being tested (CB2* or 3B10) are then added to the tube. After each addition, sufficient time, approximately 15 minutes, is allowed for equilibrium to be reached and the mP value wag read. Although it is necessary to choose concentrations of 6701® and CB2*-F (F) such that F<<R, the concentration of R need only be high enough such that the measured polarization ($P_H$) is significantly higher than $P_L$ (see FIG. 22). This $\Delta$(mP) value should be 20 or more mP units to insure reliable results.

$$\Delta(mP)=P_H-P_L \qquad \text{Equation 2}$$

Figure 26:
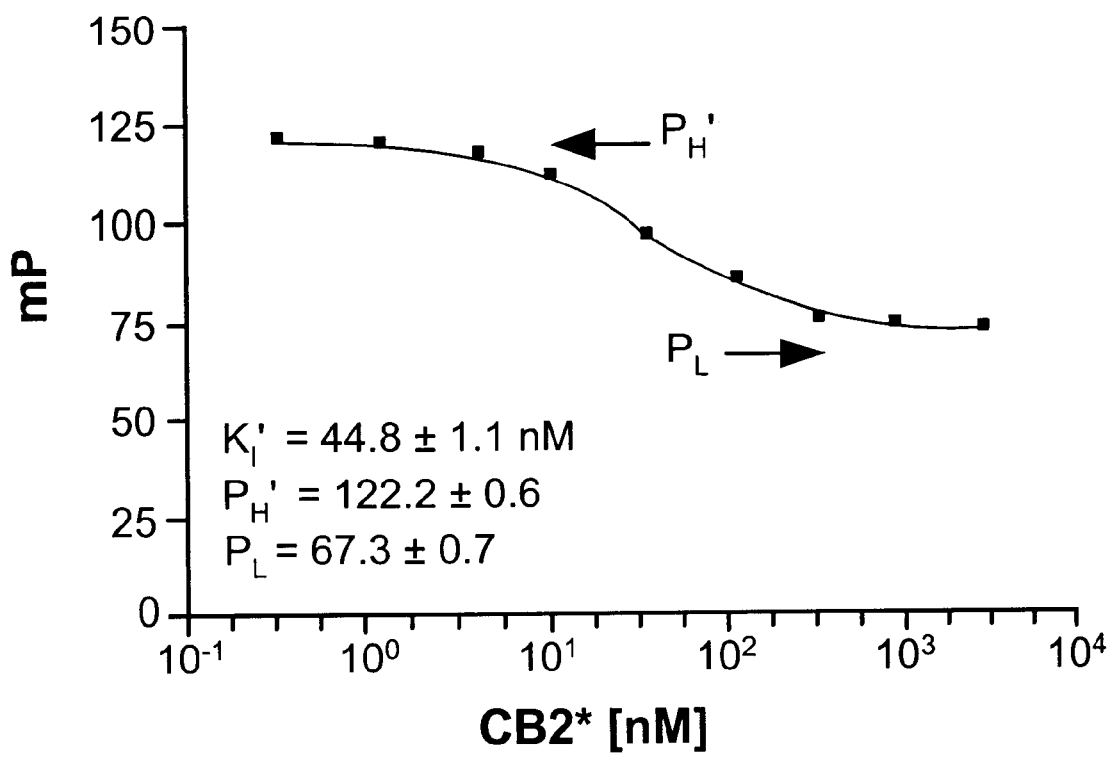
Figure 27:
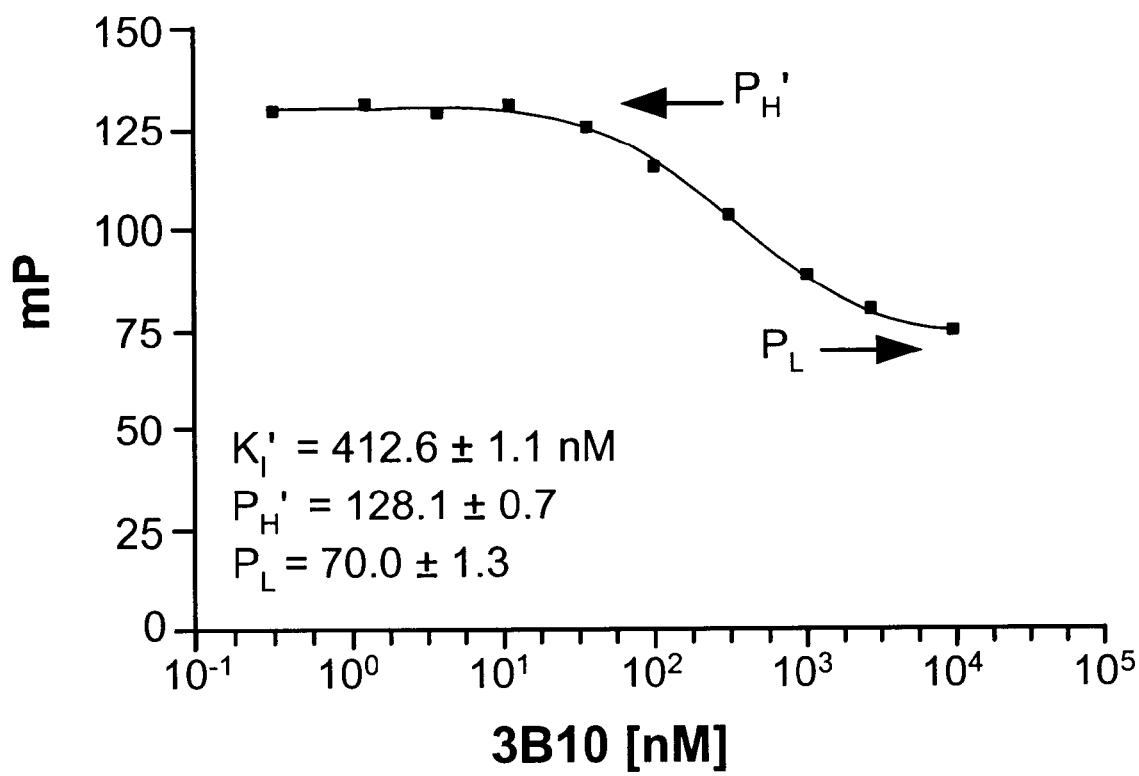

As unlabeled (no FITC) peptide (I) is added to inhibit F from binding to R, Y decreases from its maximum value of $P_H$ to a plateau of $P_L$ which should agree with that in Equation 1. These titrations are shown in FIGS. 26 and 27 for displacement of CB2*-F from ACA-6701 by CB2* and 3B10, respectively. The equation describing this titration was derided and is:

$$Y = \frac{P'_{11} + P_L*(I/K'_I)}{I/K'_I + 1.0} \qquad \text{Equation 3}$$

where $P_L$ is the same as in Equation 1, I is the concentration of unlabeled peptide competitor, and $K_I'$ is the apparent dissociation constant for that peptide. Values for these parameters were obtained by fitting cFP titration data to the above equation.

The true dissociation constant for I is obtained from Equation 4

$$K_I=K_I'/(1.0+R/K_D) \qquad \text{Equation 4}$$

where R and $K_D$ are dctlned as in Equation 1. The R/$K_D$ ratio is obtained from the values of $P_H'$ (from Equation 3) and $P_H$ and $P_L$ (from Equation 1) and using Equation 5.

$$R/K_D=(P_H'-P_L)/(P_H-P_H') \qquad \text{Equation 5}$$

In general, Equation 5 can be used to cectermine aPL antibody concentrations once the titration defined by Equation 1 is performed as a "standard curve." Thus, in addition to providing a means for determining $K_I$, this method provides a means of standardizing all aPL antibody stock solution concentrations and of analyzing their binding activity/stability over timie using only 5–10 µg of antibody per cFP assay.

Dissociation Constants Determined by dbFP and cFP

| Peptide | Antibody | Sequence | $K_D{}^a$ or $K_1$ |
|---|---|---|---|
| CB2*-F | 6501 | FITC-GPCILLARDRCG | 482 nM$^a$ |
| CB2*-F | 6701 | FITC-GPCILLARDRCG | 512 nM$^a$ |
| CB2* | 6701 | GPCILLARDRCG | 35 nM |
| 3B10 | 6701 | AGPCLLLAPDRCPG | 313 nM |

$^a$The $K_D$ values have been multiplied by 2 to correct for $K_D$ values determined from Equation 1 that do not factor in the bivalency of the antibody.

The results demonstrate that CB2*-F cross reacts with two very different aPL antibodies, ACA-6501 and ACA-6701, binding to both with equal high affinity. Removal of the FITC group improved binding of CB2* to ACA-6701 by 14-fold. Binding of a related peptide, 3B10, was 9-fold less than binding of CB2* to ACA-6701. While this result may be due to additional framework residues on 3B10, it may also be due to the substitution of a proline for arginine at position 8 in CB2*. Previous NMR structure studies of 5A12, a peptide similar to 3B10, showed that this proline that is in a turn position gives the structure rigidity. CB2 is a much more flexible peptide and it has an arginine in this position. A more flexible peptide like CB2 may be more cross-reactive because it may more readily adjust its shape to fit a given antibody binding site. The implications of drug rigidification on binding affinity are discussed in Koechler et al., p. 251, Guidebook on Molecular Modeling in Drug Design (Academic Press, N. Cohen, ed., 1996).

Example 31
Tolerance Activity of Peptide Conjugates

Two different conjugates containing the same peptide were tested for their ability to induce antigen specific tolerance in vivo. Briefly, mice were immunized with the peptide conjugated to the immlullogenic carrier Keyhole Limpet Hemocyanin (KLH) to generate peptide-specific memory B cells. Three weeks later, groups of 5 mice per group were treated with various loses of the test conjugates, one group of mice was not treated and acted as the control. Five days later, all of the mice, including the control group, were boosted with the peptide conjugated to KLH and seven days later all of the mice were bled and their sera assayed for anti-peptide antibodies using a modified Farr assay. The Antigen Binding Capacity (ABC) was calculated for each individual serum sample according to the method described in G. M. Iverson, "Assay for in vivo adoptive immune response," Volume II, Chapter 67, Handbook of Experimental Immunology (Blackwell Scientific Publications, Weir et al., eds., 4th ed., Oxford, 1986). These values were then used to determine a mean and standard deviation for all of the individuals of a group.

Figure 32:
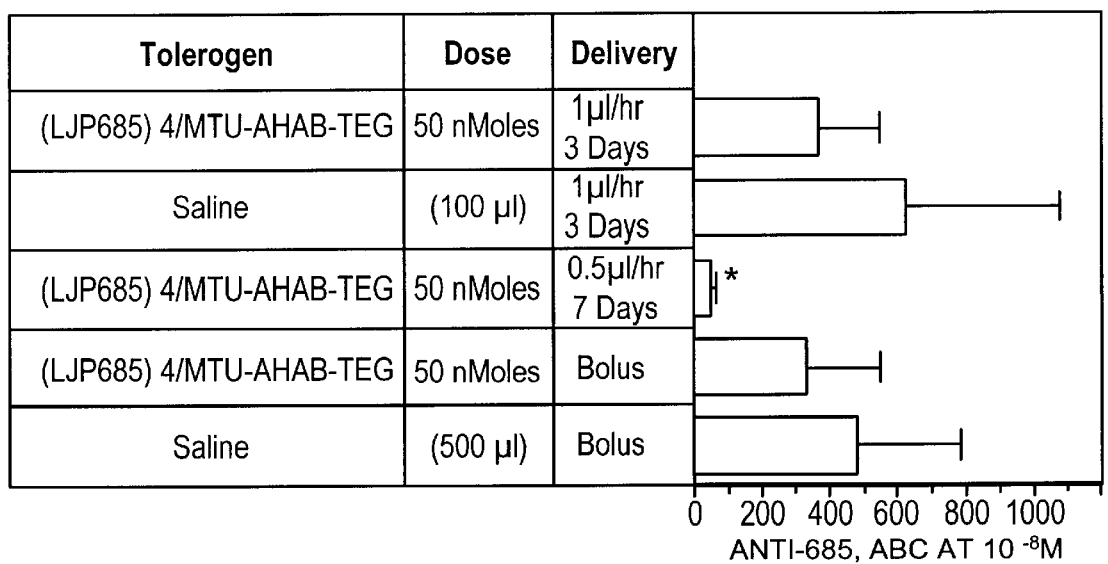

While one of the conjugates induced tolerance, the other one did not inhibit anti-peptide antibodies over the dose range tested. The most likely explanation for this difference is that the latter conjugate has a short in vivo half-life. To address this problem, a system was employed that induced tolerance in vitro, thereby negating half-life consideration, and then the cells were transferred to irradiated recipients. Briefly, spleen cells from mice primed with the peptide conjugated to KLH were harvested and incubated in complete RPMI-1640 medium for 2 hours at 37° C. with various doses of the test conjugates. One group of cells was incubated without toleragen and acted as the positive control. The cells were washed, transferred to irradiated syngeneic recipients and boosted with the peptide conjugated to KLH. Seven days later all of the mice were bled and their sera assayed for anti-peptide antibodies. The conjugate that did not induce any detectable tolerance when tested in the in vivo model did induce tolerance when tested in this in vitro model. This result supports the assumption that the difference between conjugates is due to a short half-life of the conjugate. To directly test this hypothesis, the conjugate was administered continuously by an implanted osmotic pump over a prolonged period of time. The results clearly show that this conjugate induced tolerance when administered by sustained release but not whllen administered as a bolus as shown in FIG. 32.

Figure 28:
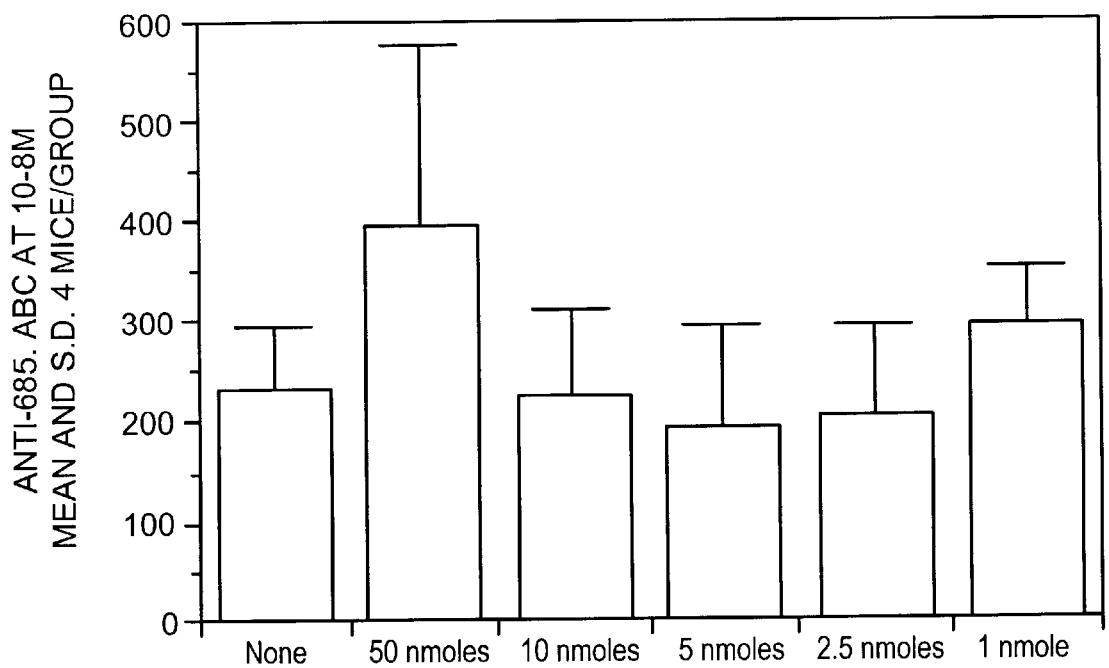

Testing of (LJP685)$_4$/MTU-AHAB-TEG for Tolerance Activity in the in vivo Model Mice were primed with LJP-685-KLH on alum plus pertussis as an adjuvant. Three weeks later, the mice were treated with a range of doses of the (LJP685)$_4$/MTU-AHAB-TEG conjugate. One group was not treated and acted as a control group. Five days later, all of the mice, including the control group, were boosted with 10 μg LJP685-KLH and seven days later the mice were bled. Their sera were analyzed for anti-LJP685 antibodies by a modified learr assay as described above. The results as shown in FIG. 28 demonstrate that the treatment with the (LJP685)$_4$/MTU-AHAB-TEG conjugate, over a dose range of 1 to 50 nmoles, had no detectable effect on the anti-LJP685 response.

Figure 29:
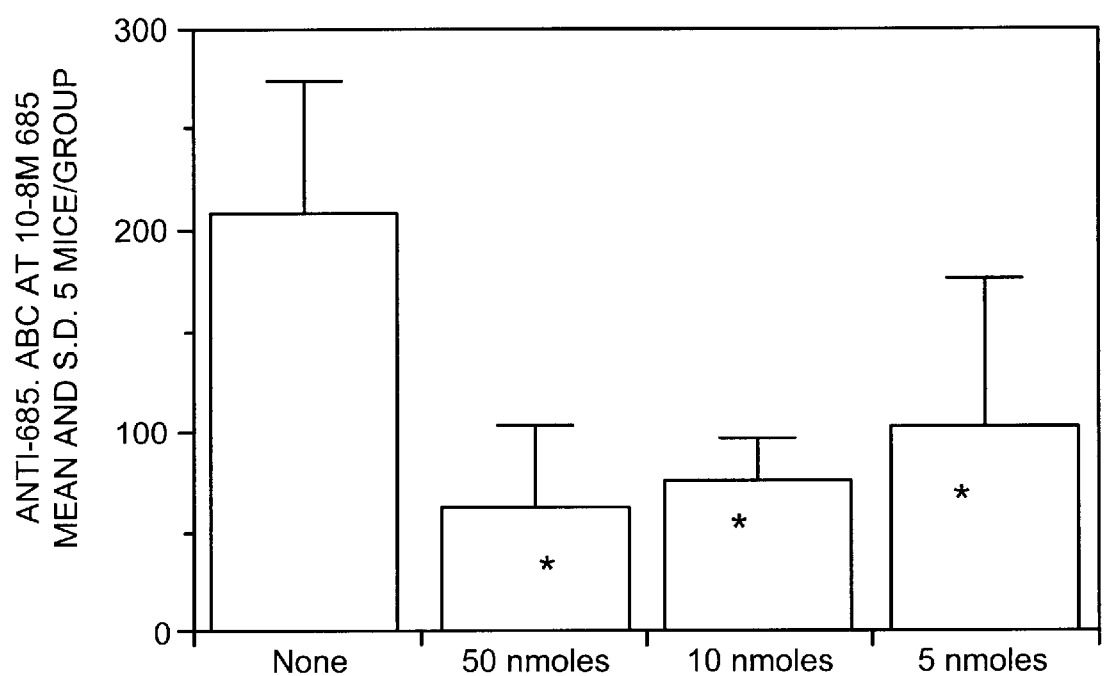

Testing the (LJP685)$_4$/MTU-DABA-TEG Conjugate for Tolerance Induction in the in vivo Model Mice were primed with LJP685-KLH on alum plus pertussis. Three weeks later, the mice were treated with 5, 10 or 50 nmoles of the (LJP685)$_4$/MTU-DABA-TEG conjugate. One group was not treated and acted as a control group. Five days later, all of the mice, including the control group, were boosted with 10 μg of LJP685-KLH and seven days later the mice were bled. Their sera were analyzed for anti-LJP685 antibodies by a modified Farr assay. The results as shown in FIG. 29 demonstrate that (LJP685)$_4$/MTU-DABA-TEG conjugate induces tolerance in the in vivo model with an ED$_{50}$ of 5 nmoles.

Figure 30:
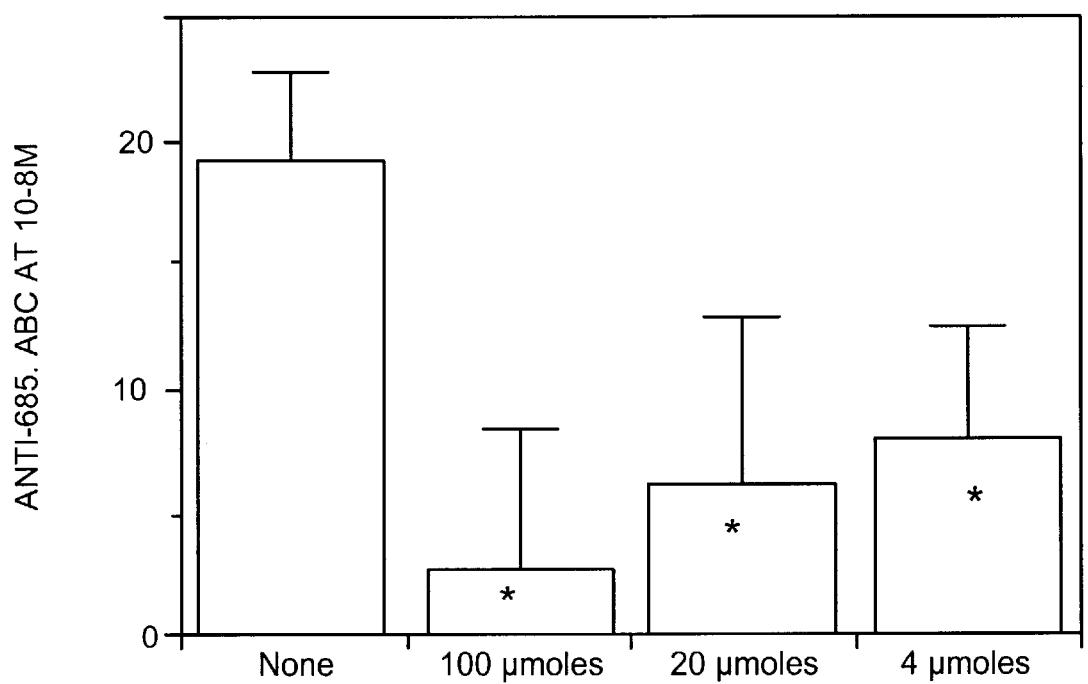

Testing the (LJP685)$_4$/MTU-AHAB-TEG Conjugate for Tolerance Induction in the in vitro Model Spleen cells from mice primed 3 weeks earlier with LJP685-KLH were harvested and incubated in complete RPMI-1640 medium for 2 hours at 37° C. with 4, 20 or 100 μM of (LJP685)$_4$/MTU-AHAB-TEG conjugate. One group of cells was incubated without toleragen and acted as a positive control group. The cells were washed, transferred to irradiated recipients and boosted with 10 μg of LJP685-KLH. Seven days later, the mice were bled and their sera were analyzed for anti-LJP685 antibodies by a modified Farr assay. The results as shown in FIG. 30 clearly illustrate that the (LJP685)$_4$/MTU-AHAB-TEG conjugate can induce tolerance when tested in the in vitro model achieving an IC$_{50}$ of <4 μM.

Figure 31:
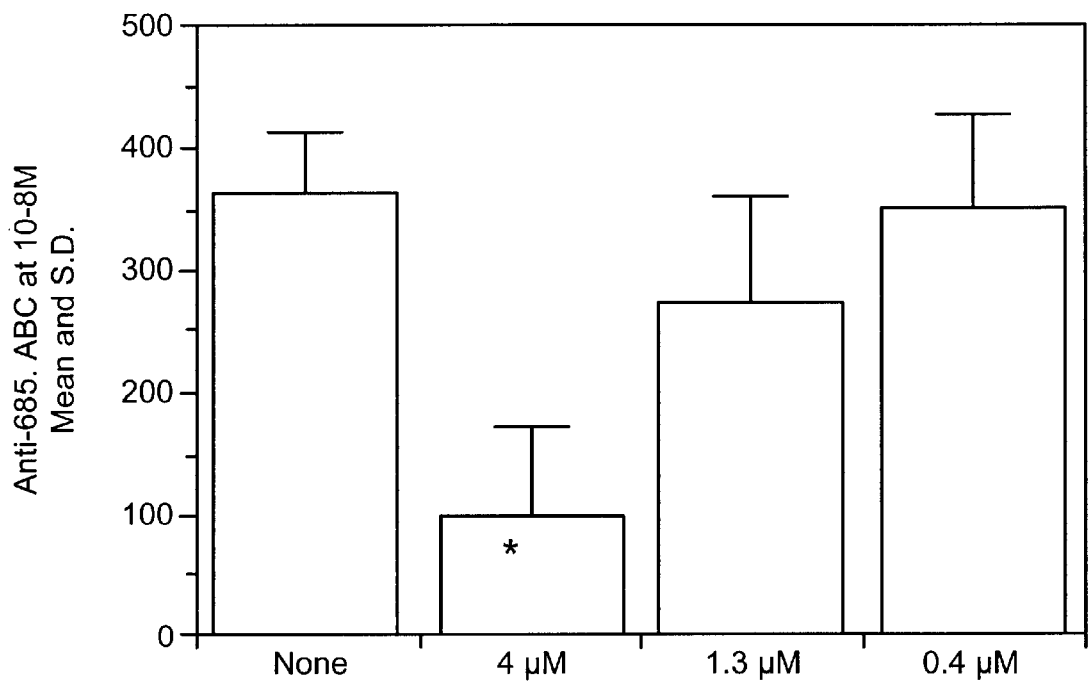

Testing the (LJP685)$_4$/MTU-DABA-TEG Conjugate for Tolerance Induction in the in vitro Model Spleen cells from mice primed 3 weeks earlier with LJP685-KLH were harvested and incubated in complete RPMI-1640 medium for 2 hours at 37° C. with 0.4, 1.3 and 4 μM of (LJP685)$_4$/MTU-DABA-TEG conjugate. One group of cells was incubated without toleragen and acted as a positive control group. The cells were washed, transferred to irradiated recipients and boosted with 10 μg of LJP685-KLH. Seven days later, the mice were bled and their sera were analyzed for anti-LJP685 antibodies by a modified Farr assay. The results as shown in FIG. 31 demonstrate that (LJP685)$_4$/MYU-DABA-TEG conjugate can induce tolerance when tested in the in vitro model, achieving an IC$_{50}$ of <4 μM.

Testing the (LJP685)$_4$/MTU-AHAB-TEG Conjugate for Tolerance Induction in vivo Using a Continuous Delivery Pump Mice were primed with LJP685-KLH on alum pertussis. Three weeks later, the mice were divided into 5 groups of five mice per group. On day 1, one group was treated with a bolus of saline and another group was treated with a bolus containing 50 nMoles of the (LJP685)$_4$/MTU-AHAB-TEG conjugate. The three remaining groups were implanted with osmotic pumps. In one group, the pumps were filled with saline and delivered at 1 μL/hour for 3 days. The two remaining groups received pumps filled with the (LJP685)$_4$/MTU-AHAB-TEG conjugate (50 nMoles). One group received pumps that deliver at 1 mL/hour for three days and the other received pumps that deliver at 0.5 μL/hour for seven days. On day 5, the pumps that deliver for three days were surgically removed. On day 7, all of the mice, including the control group, were boosted with 10 μg of LJP685-KLH. On day 10, the pumps that deliver for seven days were surgically removed. On day 14, all of the mice were bled. Their sera were analyzed for anti-LPJ685 antibodies by a modified Farr assay. The results are shown in FIG. 32.

Testing the (LJP-Peptide)$_4$/MTU-BMP-TEG Conjugate for Tolerance Induction in the in vivo Model Mice are primed with peptide -KLH on alum pertussis. Three weeks later, the mice are treated with the (LJP-peptide)$_4$/MTU-BMP-TEG conjugate, one group is not treated and acts as the control group. Five days later, all of the mice, including the control group, are boosted with 10 μg of peptide-KLH and seven days later the mice are bled. Their sera are analyzed for anti-peptide antibodies by a modified Farr assay. The results show that the (LJP-peptide)$_4$/MTU-BMP-TEG conjugate induces tolerance in the in vivo model at a potency equal to or greater than that of the (LJP685)$_4$/MTU-AHAB-TEG conjugate.

We claim:

1. Hydrophilic linkers for connecting peptides or other bioactive molecules to valency platform molecules with the formula $$R^1S(CH_2CH_2O)_nCH_2CH_2O(CH_2)_mCO_2R^2$$

wherein n=0–200, m=0 to 10, $R^1$=a protecting group, and $R^2$=aryl.

2. The linkers of claim 1 wherein m=0 to 2.

3. The linker of claim 1, wherein $R^1$ is trityl.

4. The linker of claim 1, wherein $R^2$ is 4-nitrophenyl.

5. The linker of claim 1, wherein m is 1 or 2.

SEQUENCE LISTING (1) GENERAL INFORMATION:

(iii) NUMBER OF SEQUENCES: 225

(2) INFORMATION FOR SEQ ID NO:1:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Pro Cys Leu Leu Leu Ala Pro Asp Arg Cys Pro Gly
1               5                   10

(2) INFORMATION FOR SEQ ID NO:2:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Gly Pro Cys Leu Leu Leu Ala Pro Asp Arg Cys Pro Gly
1               5                   10

(2) INFORMATION FOR SEQ ID NO:3:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Ala Gly Pro Cys Leu Leu Leu Ala Pro Asp Arg Cys Pro Gly
1               5                   10

(2) INFORMATION FOR SEQ ID NO:4:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "OTHER"
            /label= MeP;  /note= "alpha-methyl proline"

(xi) SEQUENCE DESCRIPTION: SEQ ID NO:4:

Ala Gly Xaa Cys Leu Leu Leu Ala Pro Asp Arg Cys Pro Gly
1               5                   10

(2) INFORMATION FOR SEQ ID NO:5:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 9
            (D) OTHER INFORMATION: /product= "OTHER"
                /label= MeP
                /note= "alpha-methyl proline"

(xi) SEQUENCE DESCRIPTION: SEQ ID NO:5:

Ala Gly Pro Cys Leu Leu Leu Ala Xaa Asp Arg Cys Pro Gly
1               5                   10

(2) INFORMATION FOR SEQ ID NO:6:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: group(3, 9)
            (D) OTHER INFORMATION: /product= "OTHER"
                /label= MeP
                /note= "alpha-methyl proline"

(xi) SEQUENCE DESCRIPTION: SEQ ID NO:6:

Ala Gly Xaa Cys Leu Leu Leu Ala Xaa Asp Arg Cys Pro Gly
1               5                   10

(2) INFORMATION FOR SEQ ID NO:7:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:7:

Ala Gly Pro Cys Leu Leu Leu Ala Pro Asp Arg Cys Pro Gly
1               5                   10

(2) INFORMATION FOR SEQ ID NO:8:

(i) SEQUENCE CHARACTERISTICS:
            (A) LENGTH: 4 amino acids
            (B) TYPE: amino acid
            (C) STRANDEDNESS: single
            (D) TOPOLOGY: linear (xi) SEQUENCE DESCRIPTION: SEQ ID NO:8:

Gly Ser Gly Ser
1

(2) INFORMATION FOR SEQ ID NO:9:

(i) SEQUENCE CHARACTERISTICS:
            (A) LENGTH: 9 amino acids (B) TYPE: amino acid
            (C) STRANDEDNESS: single
            (D) TOPOLOGY: linear (xi) SEQUENCE DESCRIPTION: SEQ ID NO:9:

Cys Leu Leu Leu Ala Pro Asp Arg Cys
1               5

(2) INFORMATION FOR SEQ ID NO:10:

(i) SEQUENCE CHARACTERISTICS:
            (A) LENGTH: 9 amino acids
            (B) TYPE: amino acid
            (C) STRANDEDNESS: single
            (D) TOPOLOGY: linear (vii) IMMEDIATE SOURCE:
            (A) LIBRARY: xy
            (B) CLONE: 2101

(xi) SEQUENCE DESCRIPTION: SEQ ID NO:10:

Cys Asn Ile Leu Val Leu Asp Arg Cys
1               5

(2) INFORMATION FOR SEQ ID NO:11:

(i) SEQUENCE CHARACTERISTICS:
            (A) LENGTH: 9 amino acids
            (B) TYPE: amino acid
            (C) STRANDEDNESS: single
            (D) TOPOLOGY: linear (vii) IMMEDIATE SOURCE:
            (A) LIBRARY: xyz
            (B) CLONE: 5A12

(xi) SEQUENCE DESCRIPTION: SEQ ID NO:11:

Cys Leu Ile Leu Ala Pro Asp Arg Cys
1               5

(2) INFORMATION FOR SEQ ID NO:12:

(i) SEQUENCE CHARACTERISTICS:
            (A) LENGTH: 9 amino acids
            (B) TYPE: amino acid
            (C) STRANDEDNESS: single
            (D) TOPOLOGY: linear (vii) IMMEDIATE SOURCE:
            (A) LIBRARY: xyz
            (B) CLONE: 2D7

(xi) SEQUENCE DESCRIPTION: SEQ ID NO:12:

Cys Leu Leu Leu Ala Pro Asp Arg Cys
1               5

(2) INFORMATION FOR SEQ ID NO:13:

(i) SEQUENCE CHARACTERISTICS:
            (A) LENGTH: 9 amino acids
            (B) TYPE: amino acid
            (C) STRANDEDNESS: single
            (D) TOPOLOGY: linear (vii) IMMEDIATE SOURCE:
            (A) LIBRARY: xyz
            (B) CLONE: 3B6

(xi) SEQUENCE DESCRIPTION: SEQ ID NO:13:

Cys Leu Val Leu Ala Leu Asp Arg Cys

```
1               5
```

(2) INFORMATION FOR SEQ ID NO:14:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xyz
        (B) CLONE: 3E4

(xi) SEQUENCE DESCRIPTION: SEQ ID NO:14:

```
Cys Leu Phe Val Ala Leu Asp Arg Cys
1               5
```

(2) INFORMATION FOR SEQ ID NO:15:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xyz
        (B) CLONE: 3E7

(xi) SEQUENCE DESCRIPTION: SEQ ID NO:15:

```
Cys Ile Leu Leu Ala His Asp Arg Cys
1               5
```

(2) INFORMATION FOR SEQ ID NO:16:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xyz
        (B) CLONE: 2H1

(xi) SEQUENCE DESCRIPTION: SEQ ID NO:16:

```
Cys Ile Ile Leu Ala Pro Gly Arg Cys
1               5
```

(2) INFORMATION FOR SEQ ID NO:17:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xyz
        (B) CLONE: 3C10

(xi) SEQUENCE DESCRIPTION: SEQ ID NO:17:

```
Cys Ile Leu Leu Ala Lys Asn Arg Cys
1               5
```

(2) INFORMATION FOR SEQ ID NO:18:

(i) SEQUENCE CHARACTERISTICS:
        (A) LENGTH: 9 amino acids (B) TYPE: amino acid
            (C) STRANDEDNESS: single
            (D) TOPOLOGY: linear (vii) IMMEDIATE SOURCE:
            (A) LIBRARY: xyz
            (B) CLONE: 3C5

(xi) SEQUENCE DESCRIPTION: SEQ ID NO:18:

Cys Ile Val Leu Val Pro Asp Arg Cys
1               5

(2) INFORMATION FOR SEQ ID NO:19:

(i) SEQUENCE CHARACTERISTICS:
            (A) LENGTH: 9 amino acids
            (B) TYPE: amino acid
            (C) STRANDEDNESS: single
            (D) TOPOLOGY: linear (vii) IMMEDIATE SOURCE:
            (A) LIBRARY: xyz
            (B) CLONE: 2F4

(xi) SEQUENCE DESCRIPTION: SEQ ID NO:19:

Cys Leu Val Ile Ala Leu Asp Arg Cys
1               5

(2) INFORMATION FOR SEQ ID NO:20:

(i) SEQUENCE CHARACTERISTICS:
            (A) LENGTH: 9 amino acids
            (B) TYPE: amino acid
            (C) STRANDEDNESS: single
            (D) TOPOLOGY: linear (vii) IMMEDIATE SOURCE:
            (A) LIBRARY: xyz
            (B) CLONE: 5B1

(xi) SEQUENCE DESCRIPTION: SEQ ID NO:20:

Cys Trp Phe Arg Ser Gln Ser Ser Cys
1               5

(2) INFORMATION FOR SEQ ID NO:21:

(i) SEQUENCE CHARACTERISTICS:
            (A) LENGTH: 9 amino acids
            (B) TYPE: amino acid
            (C) STRANDEDNESS: single
            (D) TOPOLOGY: linear (vii) IMMEDIATE SOURCE:
            (A) LIBRARY: xyz
            (B) CLONE: 3E11

(xi) SEQUENCE DESCRIPTION: SEQ ID NO:21:

Cys Ser Pro Ile Leu Arg Gly Asn Cys
1               5

(2) INFORMATION FOR SEQ ID NO:22:

(i) SEQUENCE CHARACTERISTICS:
            (A) LENGTH: 9 amino acids
            (B) TYPE: amino acid
            (C) STRANDEDNESS: single
            (D) TOPOLOGY: linear (vii) IMMEDIATE SOURCE:
            (A) LIBRARY: xyz
            (B) CLONE: 3E8

(xi) SEQUENCE DESCRIPTION: SEQ ID NO:22:

Cys His Lys Phe Phe Trp Leu Thr Cys
1               5

(2) INFORMATION FOR SEQ ID NO:23:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xy'z
        (B) CLONE: 2A10

(xi) SEQUENCE DESCRIPTION: SEQ ID NO:23:

Cys Thr Ile Leu Ala Pro Asp Arg Cys
1               5

(2) INFORMATION FOR SEQ ID NO:24:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xy'z
        (B) CLONE: 2G12

(xi) SEQUENCE DESCRIPTION: SEQ ID NO:24:

Cys Leu Leu Ile Thr Pro Asp Arg Cys
1               5

(2) INFORMATION FOR SEQ ID NO:25:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xy'z
        (B) CLONE: 2G11

(xi) SEQUENCE DESCRIPTION: SEQ ID NO:25:

Cys Leu Leu Ile Thr His Asp Arg Cys
1               5

(2) INFORMATION FOR SEQ ID NO:26:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xy'z
        (B) CLONE: 2F10

(xi) SEQUENCE DESCRIPTION: SEQ ID NO:26:

Cys Asn Ile Leu Val Leu Asp Arg Cys
1               5

```
(2) INFORMATION FOR SEQ ID NO:27:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xy'z
        (B) CLONE: 2E3

(xi) SEQUENCE DESCRIPTION: SEQ ID NO:27:

Cys Pro Leu Ile Thr His Asp Arg Cys
1               5

(2) INFORMATION FOR SEQ ID NO:28:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xy'z
        (B) CLONE: 2D12

(xi) SEQUENCE DESCRIPTION: SEQ ID NO:28:

Cys Leu Val Leu Ala Ala Asp Arg Cys
1               5

(2) INFORMATION FOR SEQ ID NO:29:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xy'z
        (B) CLONE: 3B10

(xi) SEQUENCE DESCRIPTION: SEQ ID NO:29:

Cys Leu Leu Leu Ala Pro Asp Arg Cys
1               5

(2) INFORMATION FOR SEQ ID NO:30:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xy'z
        (B) CLONE: 3F2

(xi) SEQUENCE DESCRIPTION: SEQ ID NO:30:

Cys Phe Phe His Phe Asp His Ser Cys
1               5

(2) INFORMATION FOR SEQ ID NO:31:

(i) SEQUENCE CHARACTERISTICS:
        (A) LENGTH: 9 amino acids
        (B) TYPE: amino acid
        (C) STRANDEDNESS: single
        (D) TOPOLOGY: linear
```

```
      (vii) IMMEDIATE SOURCE:
            (A) LIBRARY: xy'z
            (B) CLONE: 2D3

(xi) SEQUENCE DESCRIPTION: SEQ ID NO:31:

Cys Pro Leu His Thr His His Thr Cys
1               5

(2) INFORMATION FOR SEQ ID NO:32:

(i) SEQUENCE CHARACTERISTICS:
            (A) LENGTH: 9 amino acids
            (B) TYPE: amino acid
            (C) STRANDEDNESS: single
            (D) TOPOLOGY: linear (vii) IMMEDIATE SOURCE:
            (A) LIBRARY: Custom (X)6
            (B) CLONE: G11

(xi) SEQUENCE DESCRIPTION: SEQ ID NO:32:

Cys Thr Ile Leu Thr Pro Asp Arg Cys
1               5

(2) INFORMATION FOR SEQ ID NO:33:

(i) SEQUENCE CHARACTERISTICS:
            (A) LENGTH: 9 amino acids
            (B) TYPE: amino acid
            (C) STRANDEDNESS: single
            (D) TOPOLOGY: linear (vii) IMMEDIATE SOURCE:
            (A) LIBRARY: Custom (X)6
            (B) CLONE: 2H5

(xi) SEQUENCE DESCRIPTION: SEQ ID NO:33:

Cys Thr Ile Leu Thr Pro Asp Arg Cys
1               5

(2) INFORMATION FOR SEQ ID NO:34:

(i) SEQUENCE CHARACTERISTICS:
            (A) LENGTH: 9 amino acids
            (B) TYPE: amino acid
            (C) STRANDEDNESS: single
            (D) TOPOLOGY: linear (vii) IMMEDIATE SOURCE:
            (A) LIBRARY: Custom (X)6
            (B) CLONE: 2H2

(xi) SEQUENCE DESCRIPTION: SEQ ID NO:34:

Cys Thr Ile Leu Thr Leu Asp Arg Cys
1               5

(2) INFORMATION FOR SEQ ID NO:35:

(i) SEQUENCE CHARACTERISTICS:
            (A) LENGTH: 9 amino acids
            (B) TYPE: amino acid
            (C) STRANDEDNESS: single
            (D) TOPOLOGY: linear (vii) IMMEDIATE SOURCE:
            (A) LIBRARY: Custom (X)6
            (B) CLONE: 2H10

(xi) SEQUENCE DESCRIPTION: SEQ ID NO:35:
```

```
Cys Thr Leu Leu Thr Pro Asp Arg Cys
1               5

(2) INFORMATION FOR SEQ ID NO:36:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: Custom (X)6
        (B) CLONE: 2E10

(xi) SEQUENCE DESCRIPTION: SEQ ID NO:36:

Cys Ile Gln Leu Thr Pro Asp Arg Cys
1               5

(2) INFORMATION FOR SEQ ID NO:37:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: Custom (X)6
        (B) CLONE: 1B7

(xi) SEQUENCE DESCRIPTION: SEQ ID NO:37:

Cys His Leu Leu Thr Pro Asp Arg Cys
1               5

(2) INFORMATION FOR SEQ ID NO:38:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: Custom (X)6
        (B) CLONE: 2H1

(xi) SEQUENCE DESCRIPTION: SEQ ID NO:38:

Cys Leu Ile Leu Thr Pro Asp Arg Cys
1               5

(2) INFORMATION FOR SEQ ID NO:39:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: Custom (X)6
        (B) CLONE: 2H12

(xi) SEQUENCE DESCRIPTION: SEQ ID NO:39:

Cys Ser Ile Leu Ala Pro Asp Arg Cys
1               5

(2) INFORMATION FOR SEQ ID NO:40:

(i) SEQUENCE CHARACTERISTICS:
```

```
          (A) LENGTH: 9 amino acids
          (B) TYPE: amino acid
          (C) STRANDEDNESS: single
          (D) TOPOLOGY: linear (vii) IMMEDIATE SOURCE:
          (A) LIBRARY: Custom (X)6
          (B) CLONE: 1A4

(xi) SEQUENCE DESCRIPTION: SEQ ID NO:40:

Cys Asn Leu Leu Ala Leu Asp Arg Cys
1               5

(2) INFORMATION FOR SEQ ID NO:41:

(i) SEQUENCE CHARACTERISTICS:
          (A) LENGTH: 9 amino acids
          (B) TYPE: amino acid
          (C) STRANDEDNESS: single
          (D) TOPOLOGY: linear (vii) IMMEDIATE SOURCE:
          (A) LIBRARY: Custom (X)6
          (B) CLONE: 2H6

(xi) SEQUENCE DESCRIPTION: SEQ ID NO:41:

Cys Asn Leu Leu Ala Ile Asp Arg Cys
1               5

(2) INFORMATION FOR SEQ ID NO:42:

(i) SEQUENCE CHARACTERISTICS:
          (A) LENGTH: 9 amino acids
          (B) TYPE: amino acid
          (C) STRANDEDNESS: single
          (D) TOPOLOGY: linear (vii) IMMEDIATE SOURCE:
          (A) LIBRARY: Custom (X)6
          (B) CLONE: 1C3

(xi) SEQUENCE DESCRIPTION: SEQ ID NO:42:

Cys Leu Leu Leu Ala Ile Asp Arg Cys
1               5

(2) INFORMATION FOR SEQ ID NO:43:

(i) SEQUENCE CHARACTERISTICS:
          (A) LENGTH: 9 amino acids
          (B) TYPE: amino acid
          (C) STRANDEDNESS: single
          (D) TOPOLOGY: linear (vii) IMMEDIATE SOURCE:
          (A) LIBRARY: Custom (X)6
          (B) CLONE: 1D10

(xi) SEQUENCE DESCRIPTION: SEQ ID NO:43:

Cys Thr Ile Ile Thr Gln Asp Arg Cys
1               5

(2) INFORMATION FOR SEQ ID NO:44:

(i) SEQUENCE CHARACTERISTICS:
          (A) LENGTH: 9 amino acids
          (B) TYPE: amino acid
          (C) STRANDEDNESS: single
          (D) TOPOLOGY: linear (vii) IMMEDIATE SOURCE:
          (A) LIBRARY: Custom (X)6
```

(B) CLONE: 2H4

(xi) SEQUENCE DESCRIPTION: SEQ ID NO:44:

Cys Asn Ile Ile Thr Arg Asp Arg Cys
1               5

(2) INFORMATION FOR SEQ ID NO:45:

(i) SEQUENCE CHARACTERISTICS:
                (A) LENGTH: 9 amino acids
                (B) TYPE: amino acid
                (C) STRANDEDNESS: single
                (D) TOPOLOGY: linear (vii) IMMEDIATE SOURCE:
                (A) LIBRARY: Custom (X)6
                (B) CLONE: 2G12

(xi) SEQUENCE DESCRIPTION: SEQ ID NO:45:

Cys Ile Leu His Ala Ala His Arg Cys
1               5

(2) INFORMATION FOR SEQ ID NO:46:

(i) SEQUENCE CHARACTERISTICS:
                (A) LENGTH: 9 amino acids
                (B) TYPE: amino acid
                (C) STRANDEDNESS: single
                (D) TOPOLOGY: linear (vii) IMMEDIATE SOURCE:
                (A) LIBRARY: Custom (X)6
                (B) CLONE: 1A9

(xi) SEQUENCE DESCRIPTION: SEQ ID NO:46:

Cys Ser Ser Lys Ser Tyr Trp Arg Cys
1               5

(2) INFORMATION FOR SEQ ID NO:47:

(i) SEQUENCE CHARACTERISTICS:
                (A) LENGTH: 9 amino acids
                (B) TYPE: amino acid
                (C) STRANDEDNESS: single
                (D) TOPOLOGY: linear (vii) IMMEDIATE SOURCE:
                (A) LIBRARY: xy'z
                (B) CLONE: 4B11

(xi) SEQUENCE DESCRIPTION: SEQ ID NO:47:

Cys Gly Asn Ala Ala Asp Ala Arg Cys
1               5

(2) INFORMATION FOR SEQ ID NO:48:

(i) SEQUENCE CHARACTERISTICS:
                (A) LENGTH: 9 amino acids
                (B) TYPE: amino acid
                (C) STRANDEDNESS: single
                (D) TOPOLOGY: linear (vii) IMMEDIATE SOURCE:
                (A) LIBRARY: xy'z
                (B) CLONE: 4D3

(xi) SEQUENCE DESCRIPTION: SEQ ID NO:48:

Cys Thr Asn Trp Ala Asp Pro Arg Cys
1               5

(2) INFORMATION FOR SEQ ID NO:49:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xy'z
        (B) CLONE: 4C7

(xi) SEQUENCE DESCRIPTION: SEQ ID NO:49:

Cys Gly Asn Ile Ala Asp Pro Arg Cys
1               5

(2) INFORMATION FOR SEQ ID NO:50:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xy'z
        (B) CLONE: 4G7

(xi) SEQUENCE DESCRIPTION: SEQ ID NO:50:

Cys Thr Asn Leu Thr Asp Ser Arg Cys
1               5

(2) INFORMATION FOR SEQ ID NO:51:

(i) SEQUENCE CHARACTERISTICS:
        (A) LENGTH: 9 amino acids
        (B) TYPE: amino acid
        (C) STRANDEDNESS: single
        (D) TOPOLOGY: linear (vii) IMMEDIATE SOURCE:
        (A) LIBRARY: xy'z
        (B) CLONE: 4A2

(xi) SEQUENCE DESCRIPTION: SEQ ID NO:51:

Cys Gly Asn Pro Thr Asp Val Arg Cys
1               5

(2) INFORMATION FOR SEQ ID NO:52:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:52:

Gly Ile Leu Leu Asn Glu Phe Ala
1               5

(2) INFORMATION FOR SEQ ID NO:53:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:53:

```
Gly Ile Leu Thr Ile Asp Asn Leu
1               5
```

(2) INFORMATION FOR SEQ ID NO:54:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:54:

```
Gly Ile Leu Ala Leu Asp Tyr Val
1               5
```

(2) INFORMATION FOR SEQ ID NO:55:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO:55:

```
Leu Ser Asp Pro Gly Tyr Val Arg Asn Ile Phe His
1               5                   10
```

(2) INFORMATION FOR SEQ ID NO:56:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:56:

```
Leu Thr Asp Pro Arg Tyr Thr Arg Asp Ile Ser Asn Phe Thr Asp
1               5                   10                  15
```

(2) INFORMATION FOR SEQ ID NO:57:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:57:

```
Ala Gly Pro Cys Leu Gly Val Leu Gly Lys Leu Cys Pro Gly
1               5                   10
```

(2) INFORMATION FOR SEQ ID NO:58:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:58:

```
Cys Leu Gly Val Leu Gly Lys Leu Cys
1               5
```

(2) INFORMATION FOR SEQ ID NO:59:

(i) SEQUENCE CHARACTERISTICS:
    (A) LENGTH: 9 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:59:

Cys Leu Ile Leu Ala Pro Asp Arg Cys
1               5

(2) INFORMATION FOR SEQ ID NO:60:

(i) SEQUENCE CHARACTERISTICS:
    (A) LENGTH: 14 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:60:

Ala Gly Pro Cys Leu Gly Val Leu Gly Lys Leu Cys Pro Gly
1               5                   10

(2) INFORMATION FOR SEQ ID NO:61:

(i) SEQUENCE CHARACTERISTICS:
    (A) LENGTH: 13 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:61:

Gly Pro Cys Leu Gly Val Leu Gly Lys Leu Cys Pro Gly
1               5                   10

(2) INFORMATION FOR SEQ ID NO:62:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:62:

Pro Cys Leu Gly Val Leu Gly Lys Leu Cys Pro Gly
1               5                   10

(2) INFORMATION FOR SEQ ID NO:63:

(i) SEQUENCE CHARACTERISTICS:
    (A) LENGTH: 11 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:63:

Cys Leu Gly Val Leu Gly Lys Leu Cys Pro Gly
1               5                   10

```
(2) INFORMATION FOR SEQ ID NO:64:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:64:

Ala Gly Pro Cys Leu Gly Val Leu Gly Lys Leu Cys Gly
1               5                   10

(2) INFORMATION FOR SEQ ID NO:65:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:65:

Cys Leu Gly Val Leu Gly Lys Leu Cys
1               5

(2) INFORMATION FOR SEQ ID NO:66:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:66:

Cys Leu Gly Val Leu Gly Lys Leu Cys
1               5

(2) INFORMATION FOR SEQ ID NO:67:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= Hc
            /note= "Homocysteine"

(xi) SEQUENCE DESCRIPTION: SEQ ID NO:67:

Xaa Leu Gly Val Leu Gly Lys Leu Cys
1               5

(2) INFORMATION FOR SEQ ID NO:68:

(i) SEQUENCE CHARACTERISTICS:
        (A) LENGTH: 9 amino acids
        (B) TYPE: amino acid
        (C) STRANDEDNESS: single
        (D) TOPOLOGY: linear
```

(ii) MOLECULE TYPE: peptide (ix) FEATURE:
            (A) NAME/KEY: Modified-site
            (B) LOCATION: 9
            (D) OTHER INFORMATION: /product= "OTHER"
                /label= Hc
                /note= "Homocysteine"

(xi) SEQUENCE DESCRIPTION: SEQ ID NO:68:

Cys Leu Gly Val Leu Gly Lys Leu Xaa
1               5

(2) INFORMATION FOR SEQ ID NO:69:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: group(1, 9)
            (D) OTHER INFORMATION: /product= "OTHER"
                /label= Hc
                /note= "Homocysteine"

(xi) SEQUENCE DESCRIPTION: SEQ ID NO:69:

Xaa Leu Gly Val Leu Gly Lys Leu Xaa
1               5

(2) INFORMATION FOR SEQ ID NO:70:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:70:

Cys Ala Gly Val Leu Gly Lys Leu Cys
1               5

(2) INFORMATION FOR SEQ ID NO:71:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:71:

Cys Leu Ala Val Leu Gly Lys Leu Cys
1               5

(2) INFORMATION FOR SEQ ID NO:72:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:72:

Cys Leu Gly Ala Leu Gly Lys Leu Cys
1               5

(2) INFORMATION FOR SEQ ID NO:73:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:73:

Cys Leu Gly Val Ala Gly Lys Leu Cys
1               5

(2) INFORMATION FOR SEQ ID NO:74:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:74:

Cys Leu Gly Val Leu Ala Lys Leu Cys
1               5

(2) INFORMATION FOR SEQ ID NO:75:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:75:

Cys Leu Gly Val Leu Gly Ala Leu Cys
1               5

(2) INFORMATION FOR SEQ ID NO:76:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:76:

Cys Leu Gly Val Leu Gly Lys Ala Cys
1               5

(2) INFORMATION FOR SEQ ID NO:77:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:77:

Cys Gly Gly Val Leu Gly Lys Leu Cys
1               5

(2) INFORMATION FOR SEQ ID NO:78:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:78:

Cys Leu Gly Gly Leu Gly Lys Leu Cys
1               5

(2) INFORMATION FOR SEQ ID NO:79:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:79:

Cys Leu Gly Val Gly Gly Lys Leu Cys
1               5

(2) INFORMATION FOR SEQ ID NO:80:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:80:

Cys Leu Gly Val Leu Gly Gly Leu Cys
1               5

(2) INFORMATION FOR SEQ ID NO:81:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:81:

Cys Leu Gly Val Leu Gly Lys Gly Cys
1               5

(2) INFORMATION FOR SEQ ID NO:82:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:82:

Cys Ile Gly Val Leu Gly Lys Leu Cys
1               5

(2) INFORMATION FOR SEQ ID NO:83:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:83:

Cys Val Gly Val Leu Gly Lys Leu Cys
1               5

(2) INFORMATION FOR SEQ ID NO:84:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:84:

Cys Met Gly Val Leu Gly Lys Leu Cys
1               5

(2) INFORMATION FOR SEQ ID NO:85:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 2
            (D) OTHER INFORMATION: /product= "OTHER"
                /label= Cy
                /note= "cyclohexyl alanine"

(xi) SEQUENCE DESCRIPTION: SEQ ID NO:85:

Cys Xaa Gly Val Leu Gly Lys Leu Cys
1               5

(2) INFORMATION FOR SEQ ID NO:86:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 2
            (D) OTHER INFORMATION: /product= "OTHER"
                /label= tL

```
            /note= "tertiary leucine"

(xi) SEQUENCE DESCRIPTION: SEQ ID NO:86:

Cys Xaa Gly Val Leu Gly Lys Leu Cys
 1               5

(2) INFORMATION FOR SEQ ID NO:87:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "OTHER"
            /label= mL
            /note= "alpha-methyl leucine"

(xi) SEQUENCE DESCRIPTION: SEQ ID NO:87:

Cys Xaa Gly Val Leu Gly Lys Leu Cys
 1               5

(2) INFORMATION FOR SEQ ID NO:88:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "OTHER"
            /label= Iv
            /note= "alpha-methyl, alpha amino butyric acid"

(xi) SEQUENCE DESCRIPTION: SEQ ID NO:88:

Cys Xaa Gly Val Leu Gly Lys Leu Cys
 1               5

(2) INFORMATION FOR SEQ ID NO:89:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:89:

Cys Leu Gly Leu Leu Gly Lys Leu Cys
 1               5

(2) INFORMATION FOR SEQ ID NO:90:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide
```

(xi) SEQUENCE DESCRIPTION: SEQ ID NO:90:

Cys Leu Gly Ile Leu Gly Lys Leu Cys
1               5

(2) INFORMATION FOR SEQ ID NO:91:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:91:

Cys Leu Gly Met Leu Gly Lys Leu Cys
1               5

(2) INFORMATION FOR SEQ ID NO:92:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /product= "OTHER"
            /label= Cy
            /note= "homocysteine"

(xi) SEQUENCE DESCRIPTION: SEQ ID NO:92:

Cys Leu Gly Xaa Leu Gly Lys Leu Cys
1               5

(2) INFORMATION FOR SEQ ID NO:93:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /product= "OTHER"
            /label= tL
            /note= "tertiary leucine"

(xi) SEQUENCE DESCRIPTION: SEQ ID NO:93:

Cys Leu Gly Xaa Leu Gly Lys Leu Cys
1               5

(2) INFORMATION FOR SEQ ID NO:94:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide

```
        (ix) FEATURE:
              (A) NAME/KEY: Modified-site
              (B) LOCATION: 4
              (D) OTHER INFORMATION: /product= "OTHER"
                    /label= mL
                    /note= "alpha-methyl leucine"

(xi) SEQUENCE DESCRIPTION: SEQ ID NO:94:

Cys Leu Gly Xaa Leu Gly Lys Leu Cys
1               5

(2) INFORMATION FOR SEQ ID NO:95:

(i) SEQUENCE CHARACTERISTICS:
              (A) LENGTH: 9 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Modified-site
              (B) LOCATION: 4
              (D) OTHER INFORMATION: /product= "OTHER"
                    /label= Iv
                    /note= "alpha-methyl, alpha-amino butyric acid"

(xi) SEQUENCE DESCRIPTION: SEQ ID NO:95:

Cys Leu Gly Xaa Leu Gly Lys Leu Cys
1               5

(2) INFORMATION FOR SEQ ID NO:96:

(i) SEQUENCE CHARACTERISTICS:
              (A) LENGTH: 9 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO:96:

Cys Leu Gly Val Ile Gly Lys Leu Cys
1               5

(2) INFORMATION FOR SEQ ID NO:97:

(i) SEQUENCE CHARACTERISTICS:
              (A) LENGTH: 9 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO:97:

Cys Leu Gly Val Val Gly Lys Leu Cys
1               5

(2) INFORMATION FOR SEQ ID NO:98:

(i) SEQUENCE CHARACTERISTICS:
              (A) LENGTH: 9 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO:98:
```

```
Cys Leu Gly Val Met Gly Lys Leu Cys
1               5
```

(2) INFORMATION FOR SEQ ID NO:99:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /product= "OTHER"
            /label= Cy
            /note= "homocysteine"

(xi) SEQUENCE DESCRIPTION: SEQ ID NO:99:

```
Cys Leu Gly Val Xaa Gly Lys Leu Cys
1               5
```

(2) INFORMATION FOR SEQ ID NO:100:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /product= "OTHER"
            /label= tL
            /note= "tertiary leucine"

(xi) SEQUENCE DESCRIPTION: SEQ ID NO:100:

```
Cys Leu Gly Val Xaa Gly Lys Leu Cys
1               5
```

(2) INFORMATION FOR SEQ ID NO:101:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /product= "OTHER"
            /label= mL
            /note= "alpha-methyl leucine"

(xi) SEQUENCE DESCRIPTION: SEQ ID NO:101:

```
Cys Leu Gly Val Xaa Gly Lys Leu Cys
1               5
```

(2) INFORMATION FOR SEQ ID NO:102:

(i) SEQUENCE CHARACTERISTICS:
        (A) LENGTH: 9 amino acids
        (B) TYPE: amino acid

```
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /product= "OTHER"
            /label= Iv
            /note= "alpha-methyl, alpha-amino butyric acid"

(xi) SEQUENCE DESCRIPTION: SEQ ID NO:102:

Cys Leu Gly Val Xaa Gly Lys Leu Cys
1               5

(2) INFORMATION FOR SEQ ID NO:103:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:103:

Cys Leu Gly Val Leu Gly Lys Ile Cys
1               5

(2) INFORMATION FOR SEQ ID NO:104:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:104:

Cys Leu Gly Val Leu Gly Lys Val Cys
1               5

(2) INFORMATION FOR SEQ ID NO:105:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:105:

Cys Leu Gly Val Leu Gly Lys Met Cys
1               5

(2) INFORMATION FOR SEQ ID NO:106:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 8
```

```
        (D) OTHER INFORMATION: /product= "OTHER"
            /label= Cy
            /note= "homocysteine"

(xi) SEQUENCE DESCRIPTION: SEQ ID NO:106:

Cys Leu Gly Val Leu Gly Lys Xaa Cys
1               5

(2) INFORMATION FOR SEQ ID NO:107:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /product= "OTHER"
            /label= tL
            /note= "tertiary leucine"

(xi) SEQUENCE DESCRIPTION: SEQ ID NO:107:

Cys Leu Gly Val Leu Gly Lys Xaa Cys
1               5

(2) INFORMATION FOR SEQ ID NO:108:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /product= "OTHER"
            /label= mL
            /note= "alpha-methyl leucine"

(xi) SEQUENCE DESCRIPTION: SEQ ID NO:108:

Cys Leu Gly Val Leu Gly Lys Xaa Cys
1               5

(2) INFORMATION FOR SEQ ID NO:109:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /product= "OTHER"
            /label= Iv
            /note= "alpha-methyl, alpha-amino butyric acid"

(xi) SEQUENCE DESCRIPTION: SEQ ID NO:109:

Cys Leu Gly Val Leu Gly Lys Xaa Cys
1               5
```

(2) INFORMATION FOR SEQ ID NO:110:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:110:

Cys Leu Pro Val Leu Gly Lys Leu Cys
1             5

(2) INFORMATION FOR SEQ ID NO:111:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "OTHER"
            /label= mP
            /note= "alpha-methyl proline"

(xi) SEQUENCE DESCRIPTION: SEQ ID NO:111:

Cys Leu Xaa Val Leu Gly Lys Leu Cys
1             5

(2) INFORMATION FOR SEQ ID NO:112:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "OTHER"
            /label= mA
            /note= "alpha-methyl alanine"

(xi) SEQUENCE DESCRIPTION: SEQ ID NO:112:

Cys Leu Xaa Val Leu Gly Lys Leu Cys
1             5

(2) INFORMATION FOR SEQ ID NO:113:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "OTHER"
            /label= cG
            /note= "cyclo-propyl glycine"

(xi) SEQUENCE DESCRIPTION: SEQ ID NO:113:

Cys Leu Xaa Val Leu Gly Lys Leu Cys
1               5

(2) INFORMATION FOR SEQ ID NO:114:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:114:

Cys Leu Gly Val Leu Pro Lys Leu Cys
1               5

(2) INFORMATION FOR SEQ ID NO:115:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 6
        (D) OTHER INFORMATION: /product= "OTHER"
            /label= mP
            /note= "alpha-methyl proline"

(xi) SEQUENCE DESCRIPTION: SEQ ID NO:115:

Cys Leu Gly Val Leu Xaa Lys Leu Cys
1               5

(2) INFORMATION FOR SEQ ID NO:116:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 6
        (D) OTHER INFORMATION: /product= "OTHER"
            /label= mA
            /note= "alpha-methyl alanine"

(xi) SEQUENCE DESCRIPTION: SEQ ID NO:116:

Cys Leu Gly Val Leu Xaa Lys Leu Cys
1               5

(2) INFORMATION FOR SEQ ID NO:117:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:

(A) NAME/KEY: Modified-site
            (B) LOCATION: 6
            (D) OTHER INFORMATION: /product= "OTHER"
                /label= cG
                /note= "cyclopropyl glycine"

(xi) SEQUENCE DESCRIPTION: SEQ ID NO:117:

Cys Leu Gly Val Leu Xaa Lys Leu Cys
1               5

(2) INFORMATION FOR SEQ ID NO:118:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "OTHER"
            /label= dA
            /note= "D-alanine"

(xi) SEQUENCE DESCRIPTION: SEQ ID NO:118:

Cys Leu Xaa Val Leu Gly Lys Leu Cys
1               5

(2) INFORMATION FOR SEQ ID NO:119:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 6
        (D) OTHER INFORMATION: /product= "OTHER"
            /label= dA
            /note= "D-alanine"

(xi) SEQUENCE DESCRIPTION: SEQ ID NO:119:

Cys Leu Gly Val Leu Xaa Lys Leu Cys
1               5

(2) INFORMATION FOR SEQ ID NO:120:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:120:

Cys Pro Gly Val Leu Gly Lys Leu Cys
1               5

(2) INFORMATION FOR SEQ ID NO:121:

(i) SEQUENCE CHARACTERISTICS:
        (A) LENGTH: 9 amino acids
        (B) TYPE: amino acid

```
        (C) STRANDEDNESS: single
        (D) TOPOLOGY: linear (ii) MOLECULE TYPE: peptide (xi) SEQUENCE DESCRIPTION: SEQ ID NO:121:

Cys Leu Pro Val Leu Gly Lys Leu Cys
1               5

(2) INFORMATION FOR SEQ ID NO:122:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:122:

Cys Leu Gly Pro Leu Gly Lys Leu Cys
1               5

(2) INFORMATION FOR SEQ ID NO:123:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:123:

Cys Leu Gly Val Pro Gly Lys Leu Cys
1               5

(2) INFORMATION FOR SEQ ID NO:124:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:124:

Cys Leu Gly Val Leu Pro Lys Leu Cys
1               5

(2) INFORMATION FOR SEQ ID NO:125:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:125:

Cys Leu Gly Val Leu Gly Pro Leu Cys
1               5

(2) INFORMATION FOR SEQ ID NO:126:

(i) SEQUENCE CHARACTERISTICS:
        (A) LENGTH: 9 amino acids
```

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:126:

Cys Leu Gly Val Leu Gly Lys Pro Cys
1               5

(2) INFORMATION FOR SEQ ID NO:127:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 2
            (D) OTHER INFORMATION: /product= "OTHER"
                /label= pG
                /note= "phenylglycine"

(xi) SEQUENCE DESCRIPTION: SEQ ID NO:127:

Cys Xaa Gly Val Leu Gly Lys Leu Cys
1               5

(2) INFORMATION FOR SEQ ID NO:128:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "OTHER"
                /label= pG
                /note= "phenylglcine"

(xi) SEQUENCE DESCRIPTION: SEQ ID NO:128:

Cys Leu Xaa Val Leu Gly Lys Leu Cys
1               5

(2) INFORMATION FOR SEQ ID NO:129:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 4
            (D) OTHER INFORMATION: /product= "OTHER"
                /label= pG
                /note= "phenylglycine"

(xi) SEQUENCE DESCRIPTION: SEQ ID NO:129:

Cys Leu Gly Xaa Leu Gly Lys Leu Cys
1               5
```

(2) INFORMATION FOR SEQ ID NO:130:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /product= "OTHER"
            /label= pG
            /note= "phenylglycine"

(xi) SEQUENCE DESCRIPTION: SEQ ID NO:130:

Cys Leu Gly Val Xaa Gly Lys Leu Cys
1               5

(2) INFORMATION FOR SEQ ID NO:131:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 6
        (D) OTHER INFORMATION: /product= "OTHER"
            /label= pG
            /note= "phenylglycine"

(xi) SEQUENCE DESCRIPTION: SEQ ID NO:131:

Cys Leu Gly Val Leu Xaa Lys Leu Cys
1               5

(2) INFORMATION FOR SEQ ID NO:132:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 7
        (D) OTHER INFORMATION: /product= "OTHER"
            /label= pG
            /note= "phenylglycine"

(xi) SEQUENCE DESCRIPTION: SEQ ID NO:132:

Cys Leu Gly Val Leu Gly Xaa Leu Cys
1               5

(2) INFORMATION FOR SEQ ID NO:133:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
            (A) NAME/KEY: Modified-site
            (B) LOCATION: 8
            (D) OTHER INFORMATION: /product= "OTHER"
                /label= pG
                /note= "phenylglycine"

(xi) SEQUENCE DESCRIPTION: SEQ ID NO:133:

Cys Leu Gly Val Leu Gly Lys Xaa Cys
1               5

(2) INFORMATION FOR SEQ ID NO:134:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 2
            (D) OTHER INFORMATION: /product= "Aib"

(xi) SEQUENCE DESCRIPTION: SEQ ID NO:134:

Cys Xaa Gly Val Leu Gly Lys Leu Cys
1               5

(2) INFORMATION FOR SEQ ID NO:135:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "Aib"

(xi) SEQUENCE DESCRIPTION: SEQ ID NO:135:

Cys Leu Xaa Val Leu Gly Lys Leu Cys
1               5

(2) INFORMATION FOR SEQ ID NO:136:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 4
            (D) OTHER INFORMATION: /product= "Aib"

(xi) SEQUENCE DESCRIPTION: SEQ ID NO:136:

Cys Leu Gly Xaa Leu Gly Lys Leu Cys
1               5

(2) INFORMATION FOR SEQ ID NO:137:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 5
            (D) OTHER INFORMATION: /product= "Aib"

(xi) SEQUENCE DESCRIPTION: SEQ ID NO:137:

Cys Leu Gly Val Xaa Gly Lys Leu Cys
1               5

(2) INFORMATION FOR SEQ ID NO:138:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 6
            (D) OTHER INFORMATION: /product= "Aib"

(xi) SEQUENCE DESCRIPTION: SEQ ID NO:138:

Cys Leu Gly Val Leu Xaa Lys Leu Cys
1               5

(2) INFORMATION FOR SEQ ID NO:139:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 7
            (D) OTHER INFORMATION: /product= "Aib"

(xi) SEQUENCE DESCRIPTION: SEQ ID NO:139:

Cys Leu Gly Val Leu Gly Xaa Leu Cys
1               5

(2) INFORMATION FOR SEQ ID NO:140:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 8
            (D) OTHER INFORMATION: /product= "Aib"

(xi) SEQUENCE DESCRIPTION: SEQ ID NO:140:

Cys Leu Gly Val Leu Gly Lys Xaa Cys
1               5

(2) INFORMATION FOR SEQ ID NO:141:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:141:

Cys Leu Gly Val Leu Gly Arg Leu Cys
1               5

(2) INFORMATION FOR SEQ ID NO:142:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 7
        (D) OTHER INFORMATION: /product= "Orn"

(xi) SEQUENCE DESCRIPTION: SEQ ID NO:142:

Cys Leu Gly Val Leu Gly Xaa Leu Cys
1               5

(2) INFORMATION FOR SEQ ID NO:143:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 7
        (D) OTHER INFORMATION: /product= "OTHER"
            /label= mK
            /note= "N-epsilon-methyl lysine"

(xi) SEQUENCE DESCRIPTION: SEQ ID NO:143:

Cys Leu Gly Val Leu Gly Xaa Leu Cys
1               5

(2) INFORMATION FOR SEQ ID NO:144:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= dP /note= "D-proline"

(xi) SEQUENCE DESCRIPTION: SEQ ID NO:144:

Xaa Cys Leu Gly Val Leu Gly Lys Leu Cys
1               5                   10

(2) INFORMATION FOR SEQ ID NO:145:

(i) SEQUENCE CHARACTERISTICS:
      (A) LENGTH: 9 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Modified-site
      (B) LOCATION: 2
      (D) OTHER INFORMATION: /product= "OTHER"
          /label= dL
          /note= "D-leucine"

(xi) SEQUENCE DESCRIPTION: SEQ ID NO:145:

Cys Xaa Gly Val Leu Gly Lys Leu Cys
1               5

(2) INFORMATION FOR SEQ ID NO:146:

(i) SEQUENCE CHARACTERISTICS:
      (A) LENGTH: 9 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Modified-site
      (B) LOCATION: 4
      (D) OTHER INFORMATION: /product= "OTHER"
          /label= dV
          /note= "D-valine"

(xi) SEQUENCE DESCRIPTION: SEQ ID NO:146:

Cys Leu Gly Xaa Leu Gly Lys Leu Cys
1               5

(2) INFORMATION FOR SEQ ID NO:147:

(i) SEQUENCE CHARACTERISTICS:
      (A) LENGTH: 9 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Modified-site
      (B) LOCATION: 5
      (D) OTHER INFORMATION: /product= "OTHER"
          /label= dL
          /note= "D-leucine"

(xi) SEQUENCE DESCRIPTION: SEQ ID NO:147:

Cys Leu Gly Val Xaa Gly Lys Leu Cys
1               5

(2) INFORMATION FOR SEQ ID NO:148:

```
    (i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 7
        (D) OTHER INFORMATION: /product= "OTHER"
            /label= dK
            /note= "D-lysine"

(xi) SEQUENCE DESCRIPTION: SEQ ID NO:148:

Cys Leu Gly Val Leu Gly Xaa Leu Cys
1               5

(2) INFORMATION FOR SEQ ID NO:149:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /product= "OTHER"
            /label= dL
            /note= "D-leucine"

(xi) SEQUENCE DESCRIPTION: SEQ ID NO:149:

Cys Leu Gly Val Leu Gly Lys Xaa Cys
1               5

(2) INFORMATION FOR SEQ ID NO:150:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "OTHER"
            /label= dL
            /note= "D-leucine"

(ix) FEATURE:
        (A) NAME/KEY: Modified-site
        (B) LOCATION: 4
        (D) OTHER INFORMATION: /product= "OTHER"
            /label= dV
            /note= "D-valine"

(xi) SEQUENCE DESCRIPTION: SEQ ID NO:150:

Cys Xaa Gly Xaa Leu Gly Lys Leu Cys
1               5

(2) INFORMATION FOR SEQ ID NO:151:

(i) SEQUENCE CHARACTERISTICS:
        (A) LENGTH: 9 amino acids
        (B) TYPE: amino acid
```

```
            (C) STRANDEDNESS: single
            (D) TOPOLOGY: linear (ii) MOLECULE TYPE: peptide (ix) FEATURE:
            (A) NAME/KEY: Modified-site
            (B) LOCATION: group(2, 4)
            (D) OTHER INFORMATION: /product= "OTHER"
                /label= dV
                /note= "D-valine"

(xi) SEQUENCE DESCRIPTION: SEQ ID NO:151:

Cys Xaa Gly Xaa Leu Gly Lys Leu Cys
1               5

(2) INFORMATION FOR SEQ ID NO:152:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: group(2, 4)
            (D) OTHER INFORMATION: /product= "OTHER"
                /label= dL
                /note= "D-leucine"

(xi) SEQUENCE DESCRIPTION: SEQ ID NO:152:

Cys Xaa Gly Xaa Leu Gly Lys Leu Cys
1               5

(2) INFORMATION FOR SEQ ID NO:153:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 4
            (D) OTHER INFORMATION: /product= "OTHER"
                /label= dV
                /note= "D-valine"

(ix) FEATURE:
            (A) NAME/KEY: Modified-site
            (B) LOCATION: 5
            (D) OTHER INFORMATION: /product= "OTHER"
                /label= dL
                /note= "D-leucine"

(xi) SEQUENCE DESCRIPTION: SEQ ID NO:153:

Cys Leu Gly Xaa Xaa Gly Lys Leu Cys
1               5

(2) INFORMATION FOR SEQ ID NO:154:

(i) SEQUENCE CHARACTERISTICS:
            (A) LENGTH: 9 amino acids
            (B) TYPE: amino acid
            (C) STRANDEDNESS: single
            (D) TOPOLOGY: linear
```

```
        (ii) MOLECULE TYPE: peptide (ix) FEATURE:
             (A) NAME/KEY: Modified-site
             (B) LOCATION: 5
             (D) OTHER INFORMATION: /product= "OTHER"
                  /label= dV
                  /note= "D-valine"

(ix) FEATURE:
             (A) NAME/KEY: Modified-site
             (B) LOCATION: 4
             (D) OTHER INFORMATION: /product= "OTHER"
                  /label= dL
                  /note= "D-leucine"

(xi) SEQUENCE DESCRIPTION: SEQ ID NO:154:

Cys Leu Gly Xaa Xaa Gly Lys Leu Cys
1               5

(2) INFORMATION FOR SEQ ID NO:155:

(i) SEQUENCE CHARACTERISTICS:
             (A) LENGTH: 9 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY: Modified-site
             (B) LOCATION: group(4, 5)
             (D) OTHER INFORMATION: /product= "OTHER"
                  /label= dV
                  /note= "D-valine"

(xi) SEQUENCE DESCRIPTION: SEQ ID NO:155:

Cys Leu Gly Xaa Xaa Gly Lys Leu Cys
1               5

(2) INFORMATION FOR SEQ ID NO:156:

(i) SEQUENCE CHARACTERISTICS:
             (A) LENGTH: 9 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY: Modified-site
             (B) LOCATION: group(4, 5)
             (D) OTHER INFORMATION: /product= "OTHER"
                  /label= dL
                  /note= "D-leucine"

(xi) SEQUENCE DESCRIPTION: SEQ ID NO:156:

Cys Leu Gly Xaa Xaa Gly Lys Leu Cys
1               5

(2) INFORMATION FOR SEQ ID NO:157:

(i) SEQUENCE CHARACTERISTICS:
             (A) LENGTH: 9 amino acids
             (B) TYPE: amino acid
             (C) STRANDEDNESS: single
             (D) TOPOLOGY: linear (ii) MOLECULE TYPE: peptide (ix) FEATURE:
```

```
        (A) NAME/KEY: Modified-site
        (B) LOCATION: 5
        (D) OTHER INFORMATION: /product= "OTHER"
            /label= dL
            /note= "D-leucine"

(ix) FEATURE:
        (A) NAME/KEY: Modified-site
        (B) LOCATION: 7
        (D) OTHER INFORMATION: /product= "OTHER"
            /label= dK
            /note= "D-lysine"

(xi) SEQUENCE DESCRIPTION: SEQ ID NO:157:

Cys Leu Gly Val Xaa Gly Xaa Leu Cys
1               5

(2) INFORMATION FOR SEQ ID NO:158:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 7
        (D) OTHER INFORMATION: /product= "OTHER"
            /label= dL
            /note= "D-leucine"

(ix) FEATURE:
        (A) NAME/KEY: Modified-site
        (B) LOCATION: 5
        (D) OTHER INFORMATION: /product= "OTHER"
            /label= dK
            /note= "D-lysine"

(xi) SEQUENCE DESCRIPTION: SEQ ID NO:158:

Cys Leu Gly Val Xaa Gly Xaa Leu Cys
1               5

(2) INFORMATION FOR SEQ ID NO:159:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: group(5, 7)
        (D) OTHER INFORMATION: /product= "OTHER"
            /label= dL
            /note= "D-leucine"

(xi) SEQUENCE DESCRIPTION: SEQ ID NO:159:

Cys Leu Gly Val Xaa Gly Xaa Leu Cys
1               5

(2) INFORMATION FOR SEQ ID NO:160:

(i) SEQUENCE CHARACTERISTICS:
        (A) LENGTH: 9 amino acids
        (B) TYPE: amino acid
        (C) STRANDEDNESS: single
        (D) TOPOLOGY: linear
```

```
    (ii) MOLECULE TYPE: peptide (ix) FEATURE:
         (A) NAME/KEY: Modified-site
         (B) LOCATION: group(5, 7)
         (D) OTHER INFORMATION: /product= "OTHER"
             /label= dK
             /note= "D-lysine"

(xi) SEQUENCE DESCRIPTION: SEQ ID NO:160:

Cys Leu Gly Val Xaa Gly Xaa Leu Cys
1               5

(2) INFORMATION FOR SEQ ID NO:161:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Modified-site
         (B) LOCATION: 7
         (D) OTHER INFORMATION: /product= "OTHER"
             /label= dK
             /note= "D-lysine"

(ix) FEATURE:
         (A) NAME/KEY: Modified-site
         (B) LOCATION: 8
         (D) OTHER INFORMATION: /product= "OTHER"
             /label= dL
             /note= "D-leucine"

(xi) SEQUENCE DESCRIPTION: SEQ ID NO:161:

Cys Leu Gly Val Leu Gly Xaa Xaa Cys
1               5

(2) INFORMATION FOR SEQ ID NO:162:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Modified-site
         (B) LOCATION: 8
         (D) OTHER INFORMATION: /product= "OTHER"
             /label= dK
             /note= "D-lysine"

(ix) FEATURE:
         (A) NAME/KEY: Modified-site
         (B) LOCATION: 7
         (D) OTHER INFORMATION: /product= "OTHER"
             /label= dL
             /note= "D-leucine"

(xi) SEQUENCE DESCRIPTION: SEQ ID NO:162:

Cys Leu Gly Val Leu Gly Xaa Xaa Cys
1               5

(2) INFORMATION FOR SEQ ID NO:163:

(i) SEQUENCE CHARACTERISTICS:
```

(A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: group(7, 8)
            (D) OTHER INFORMATION: /product= "OTHER"
                  /label= dK
                  /note= "D-lysine"

(xi) SEQUENCE DESCRIPTION: SEQ ID NO:163:

Cys Leu Gly Val Leu Gly Xaa Xaa Cys
1               5

(2) INFORMATION FOR SEQ ID NO:164:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: group(7, 8)
            (D) OTHER INFORMATION: /product= "OTHER"
                  /label= dL
                  /note= "D-leucine"

(xi) SEQUENCE DESCRIPTION: SEQ ID NO:164:

Cys Leu Gly Val Leu Gly Xaa Xaa Cys
1               5

(2) INFORMATION FOR SEQ ID NO:165:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 6
            (D) OTHER INFORMATION: /product= "OTHER"
                  /label= dA
                  /note= "D-alanine"

(xi) SEQUENCE DESCRIPTION: SEQ ID NO:165:

Cys Leu Gly Val Leu Xaa Lys Leu Cys
1               5

(2) INFORMATION FOR SEQ ID NO:166:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 9

(D) OTHER INFORMATION: /product= "OTHER"
                /label= dC
                /note= "D-cysteine"

(xi) SEQUENCE DESCRIPTION: SEQ ID NO:166:

Cys Leu Gly Val Leu Gly Lys Leu Xaa
1               5

(2) INFORMATION FOR SEQ ID NO:167:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= nC
            /note= "N-alpha-methyl cysteine"

(xi) SEQUENCE DESCRIPTION: SEQ ID NO:167:

Xaa Leu Gly Val Leu Gly Lys Leu Cys
1               5

(2) INFORMATION FOR SEQ ID NO:168:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "OTHER"
            /label= nL
            /note= "N-alpha-methyl leucine"

(xi) SEQUENCE DESCRIPTION: SEQ ID NO:168:

Cys Xaa Gly Val Leu Gly Lys Leu Cys
1               5

(2) INFORMATION FOR SEQ ID NO:169:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "OTHER"
            /label= nG
            /note= "N-methyl glycine"

(xi) SEQUENCE DESCRIPTION: SEQ ID NO:169:

Cys Leu Xaa Val Leu Gly Lys Leu Cys
1               5

(2) INFORMATION FOR SEQ ID NO:170:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /product= "OTHER"
            /label= nV
            /note= "N-alpha-methyl valine"

(xi) SEQUENCE DESCRIPTION: SEQ ID NO:170:

Cys Leu Gly Xaa Leu Gly Lys Leu Cys
1               5

(2) INFORMATION FOR SEQ ID NO:171:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /product= "OTHER"
            /label= nL
            /note= "N-alpha-methyl leucine"

(xi) SEQUENCE DESCRIPTION: SEQ ID NO:171:

Cys Leu Gly Val Xaa Gly Lys Leu Cys
1               5

(2) INFORMATION FOR SEQ ID NO:172:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 6
        (D) OTHER INFORMATION: /product= "OTHER"
            /label= nG
            /note= "N-methyl glycine"

(xi) SEQUENCE DESCRIPTION: SEQ ID NO:172:

Cys Leu Gly Val Leu Xaa Lys Leu Cys
1               5

(2) INFORMATION FOR SEQ ID NO:173:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide

```
        (ix) FEATURE:
              (A) NAME/KEY: Modified-site
              (B) LOCATION: 7
              (D) OTHER INFORMATION: /product= "OTHER"
                    /label= nK
                    /note= "N-alpha-methyl lysine"

(xi) SEQUENCE DESCRIPTION: SEQ ID NO:173:

Cys Leu Gly Val Leu Gly Xaa Leu Cys
1               5

(2) INFORMATION FOR SEQ ID NO:174:

(i) SEQUENCE CHARACTERISTICS:
              (A) LENGTH: 9 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Modified-site
              (B) LOCATION: 8
              (D) OTHER INFORMATION: /product= "OTHER"
                    /label= nL
                    /note= "N-alpha-methyl leucine"

(xi) SEQUENCE DESCRIPTION: SEQ ID NO:174:

Cys Leu Gly Val Leu Gly Lys Xaa Cys
1               5

(2) INFORMATION FOR SEQ ID NO:175:

(i) SEQUENCE CHARACTERISTICS:
              (A) LENGTH: 9 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Modified-site
              (B) LOCATION: 9
              (D) OTHER INFORMATION: /product= "OTHER"
                    /label= nC
                    /note= "N-alpha-methyl cysteine"

(xi) SEQUENCE DESCRIPTION: SEQ ID NO:175:

Cys Leu Gly Val Leu Gly Lys Leu Xaa
1               5

(2) INFORMATION FOR SEQ ID NO:176:

(i) SEQUENCE CHARACTERISTICS:
              (A) LENGTH: 9 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO:176:

Cys Leu Gly Val Leu Gly Lys Leu Cys
1               5

(2) INFORMATION FOR SEQ ID NO:177:

(i) SEQUENCE CHARACTERISTICS:
              (A) LENGTH: 9 amino acids
```

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:177:

Cys Leu Gly Val Leu Gly Lys Leu Cys
1               5

(2) INFORMATION FOR SEQ ID NO:178:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:178:

Cys Leu Gly Val Leu Gly Lys Leu Cys
1               5

(2) INFORMATION FOR SEQ ID NO:179:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 9
            (D) OTHER INFORMATION: /product= "OTHER"
                /label= dC
                /note= "D-cysteine"

(xi) SEQUENCE DESCRIPTION: SEQ ID NO:179:

Cys Leu Gly Val Leu Gly Lys Leu Xaa
1               5

(2) INFORMATION FOR SEQ ID NO:180:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "OTHER"
                /label= dC
                /note= "D-cysteine"

(xi) SEQUENCE DESCRIPTION: SEQ ID NO:180:

Xaa Leu Gly Val Leu Gly Lys Leu Cys
1               5

(2) INFORMATION FOR SEQ ID NO:181:

(i) SEQUENCE CHARACTERISTICS:
            (A) LENGTH: 9 amino acids
            (B) TYPE: amino acid
```

```
            (C) STRANDEDNESS: single
            (D) TOPOLOGY: linear (ii) MOLECULE TYPE: peptide (ix) FEATURE:
            (A) NAME/KEY: Modified-site
            (B) LOCATION: group(1, 9)
            (D) OTHER INFORMATION: /product= "OTHER"
                /label= dC
                /note= "D-cysteine"

(xi) SEQUENCE DESCRIPTION: SEQ ID NO:181:

Xaa Leu Gly Val Leu Gly Lys Leu Xaa
1               5

(2) INFORMATION FOR SEQ ID NO:182:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "OTHER"
                /label= Hc
                /note= "homocysteine"

(xi) SEQUENCE DESCRIPTION: SEQ ID NO:182:

Xaa Leu Gly Val Leu Ala Lys Leu Cys
1               5

(2) INFORMATION FOR SEQ ID NO:183:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "OTHER"
                /label= Hc
                /note= "homocysteine"

(xi) SEQUENCE DESCRIPTION: SEQ ID NO:183:

Xaa Gly Val Leu Ala Lys Leu Cys
1               5

(2) INFORMATION FOR SEQ ID NO:184:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "OTHER"
                /label= Hc
```

/note= "homocysteine"

(xi) SEQUENCE DESCRIPTION: SEQ ID NO:184:

Xaa Leu Val Leu Ala Lys Leu Cys
1               5

(2) INFORMATION FOR SEQ ID NO:185:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Modified-site
       (B) LOCATION: 1
       (D) OTHER INFORMATION: /product= "OTHER"
           /label= Hc
           /note= "homocysteine"

(xi) SEQUENCE DESCRIPTION: SEQ ID NO:185:

Xaa Leu Gly Leu Ala Lys Leu Cys
1               5

(2) INFORMATION FOR SEQ ID NO:186:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Modified-site
       (B) LOCATION: 1
       (D) OTHER INFORMATION: /product= "OTHER"
           /label= Hc
           /note= "homocysteine"

(xi) SEQUENCE DESCRIPTION: SEQ ID NO:186:

Xaa Leu Gly Val Ala Lys Leu Cys
1               5

(2) INFORMATION FOR SEQ ID NO:187:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Modified-site
       (B) LOCATION: 1
       (D) OTHER INFORMATION: /product= "OTHER"
           /label= Hc
           /note= "homocysteine"

(xi) SEQUENCE DESCRIPTION: SEQ ID NO:187:

Xaa Leu Gly Val Leu Lys Leu Cys
1               5

(2) INFORMATION FOR SEQ ID NO:188:

```
    (i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= Hc
            /note= "homocysteine"

(xi) SEQUENCE DESCRIPTION: SEQ ID NO:188:

Xaa Leu Gly Val Leu Ala Leu Cys
1               5

(2) INFORMATION FOR SEQ ID NO:189:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= Hc
            /note= "homocysteine"

(xi) SEQUENCE DESCRIPTION: SEQ ID NO:189:

Xaa Leu Gly Val Leu Ala Lys Cys
1               5

(2) INFORMATION FOR SEQ ID NO:190:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= Hc
            /note= "homocysteine"

(xi) SEQUENCE DESCRIPTION: SEQ ID NO:190:

Xaa Val Leu Ala Lys Leu Cys
1               5

(2) INFORMATION FOR SEQ ID NO:191:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
```

```
            (B) LOCATION: 1
            (D) OTHER INFORMATION: /product= "OTHER"
                /label= Hc
                /note= "homocysteine"

(xi) SEQUENCE DESCRIPTION: SEQ ID NO:191:

Xaa Leu Ala Lys Leu Cys
1               5

(2) INFORMATION FOR SEQ ID NO:192:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= Hc
            /note= "homocysteine"

(xi) SEQUENCE DESCRIPTION: SEQ ID NO:192:

Xaa Leu Ala Lys Cys
1               5

(2) INFORMATION FOR SEQ ID NO:193:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= Hc
            /note= "homocysteine"

(ix) FEATURE:
        (A) NAME/KEY: Modified-site
        (B) LOCATION: 9
        (D) OTHER INFORMATION: /product= "OTHER"
            /label= Pe
            /note= "penicillamine"

(xi) SEQUENCE DESCRIPTION: SEQ ID NO:193:

Xaa Leu Gly Val Leu Gly Lys Leu Xaa
1               5

(2) INFORMATION FOR SEQ ID NO:194:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= Hc
```

/note= "homocysteine"

(ix) FEATURE:
            (A) NAME/KEY: Modified-site
            (B) LOCATION: 9
            (D) OTHER INFORMATION: /product= "OTHER"
                    /label= dPe
                    /note= "D-penicillamine"

(xi) SEQUENCE DESCRIPTION: SEQ ID NO:194:

Xaa Leu Gly Val Leu Gly Lys Leu Xaa
1               5

(2) INFORMATION FOR SEQ ID NO:195:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
                /label= Pe
                /note= "penicillamine"

(ix) FEATURE:
        (A) NAME/KEY: Modified-site
        (B) LOCATION: 9
        (D) OTHER INFORMATION: /product= "OTHER"
                /label= Hc
                /note= "homocysteine"

(xi) SEQUENCE DESCRIPTION: SEQ ID NO:195:

Xaa Leu Gly Val Leu Gly Lys Leu Xaa
1               5

(2) INFORMATION FOR SEQ ID NO:196:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
                /label= dPe
                /note= "D-penicillamine"

(ix) FEATURE:
        (A) NAME/KEY: Modified-site
        (B) LOCATION: 9
        (D) OTHER INFORMATION: /product= "OTHER"
                /label= Hc
                /note= "homocysteine"

(xi) SEQUENCE DESCRIPTION: SEQ ID NO:196:

Xaa Leu Gly Val Leu Gly Lys Leu Xaa
1               5

(2) INFORMATION FOR SEQ ID NO:197:

(i) SEQUENCE CHARACTERISTICS:
        (A) LENGTH: 9 amino acids

```
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: group(1, 9)
        (D) OTHER INFORMATION: /product= "OTHER"
            /label= dPe
            /note= "D-penicillamine"

(xi) SEQUENCE DESCRIPTION: SEQ ID NO:197:

Xaa Leu Gly Val Leu Gly Lys Leu Xaa
1               5

(2) INFORMATION FOR SEQ ID NO:198:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= dHc
            /note= "D-homocysteine"

(xi) SEQUENCE DESCRIPTION: SEQ ID NO:198:

Xaa Leu Gly Val Leu Gly Lys Leu Cys
1               5

(2) INFORMATION FOR SEQ ID NO:199:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= dHc
            /note= "D-homocysteine"

(ix) FEATURE:
        (A) NAME/KEY: Modified-site
        (B) LOCATION: 9
        (D) OTHER INFORMATION: /product= "OTHER"
            /label= dC
            /note= "D-cysteine"

(xi) SEQUENCE DESCRIPTION: SEQ ID NO:199:

Xaa Leu Gly Val Leu Gly Lys Leu Xaa
1               5

(2) INFORMATION FOR SEQ ID NO:200:

(i) SEQUENCE CHARACTERISTICS:
        (A) LENGTH: 9 amino acids
        (B) TYPE: amino acid
        (C) STRANDEDNESS: single
        (D) TOPOLOGY: linear
```

(ii) MOLECULE TYPE: peptide (ix) FEATURE:
             (A) NAME/KEY: Modified-site
             (B) LOCATION: 1
             (D) OTHER INFORMATION: /product= "OTHER"
                 /label= Hc
                 /note= "homocysteine"

(ix) FEATURE:
             (A) NAME/KEY: Modified-site
             (B) LOCATION: 9
             (D) OTHER INFORMATION: /product= "OTHER"
                 /label= dC
                 /note= "D-cysteine"

(xi) SEQUENCE DESCRIPTION: SEQ ID NO:200:

Xaa Leu Gly Val Leu Gly Lys Leu Xaa
1               5

(2) INFORMATION FOR SEQ ID NO:201:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
             (A) NAME/KEY: Modified-site
             (B) LOCATION: 1
             (D) OTHER INFORMATION: /product= "OTHER"
                 /label= By
                 /note= "butyroyl"

(ix) FEATURE:
             (A) NAME/KEY: Modified-site
             (B) LOCATION: 9
             (D) OTHER INFORMATION: /product= "OTHER"
                 /label= Hc
                 /note= "homocysteine"

(xi) SEQUENCE DESCRIPTION: SEQ ID NO:201:

Xaa Leu Gly Val Leu Gly Lys Leu Xaa
1               5

(2) INFORMATION FOR SEQ ID NO:202:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
             (A) NAME/KEY: Modified-site
             (B) LOCATION: 1
             (D) OTHER INFORMATION: /product= "OTHER"
                 /label= By
                 /note= "butyroyl"

(xi) SEQUENCE DESCRIPTION: SEQ ID NO:202:

Xaa Leu Gly Val Leu Gly Lys Leu Cys
1               5

(2) INFORMATION FOR SEQ ID NO:203:

(i) SEQUENCE CHARACTERISTICS:

```
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= Pp
            /note= "proprionyl"

(ix) FEATURE:
        (A) NAME/KEY: Modified-site
        (B) LOCATION: 9
        (D) OTHER INFORMATION: /product= "OTHER"
            /label= Hc
            /note= "homocysteine"

(xi) SEQUENCE DESCRIPTION: SEQ ID NO:203:

Xaa Leu Gly Val Leu Gly Lys Leu Xaa
1               5

(2) INFORMATION FOR SEQ ID NO:204:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= Pp
            /note= "proprionyl"

(xi) SEQUENCE DESCRIPTION: SEQ ID NO:204:

Xaa Leu Gly Val Leu Gly Lys Leu Cys
1               5

(2) INFORMATION FOR SEQ ID NO:205:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /label= Hc
            /note= "homocysteine"

(xi) SEQUENCE DESCRIPTION: SEQ ID NO:205:

Xaa Leu Gly Val Leu Gly Lys Leu Cys
1               5

(2) INFORMATION FOR SEQ ID NO:206:

(i) SEQUENCE CHARACTERISTICS:
        (A) LENGTH: 9 amino acids
        (B) TYPE: amino acid
        (C) STRANDEDNESS: single
```

(D) TOPOLOGY: linear (ii) MOLECULE TYPE: peptide (xi) SEQUENCE DESCRIPTION: SEQ ID NO:206:

Ser Leu Gly Val Leu Gly Lys Leu Ser
1               5

(2) INFORMATION FOR SEQ ID NO:207:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:207:

Cys Leu Gly Val Ala Gly Lys Leu Cys
1               5

(2) INFORMATION FOR SEQ ID NO:208:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:208:

Cys Leu Gly Val Leu Gly Ala Leu Cys
1               5

(2) INFORMATION FOR SEQ ID NO:209:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (xi) SEQUENCE DESCRIPTION: SEQ ID NO:209:

GGGCTGGACC CNNKCCGGGG GCTGCTG                                                27

(2) INFORMATION FOR SEQ ID NO:210:

(i) SEQUENCE CHARACTERISTICS:
          (A) LENGTH: 14 base pairs
          (B) TYPE: nucleic acid
          (C) STRANDEDNESS: single
          (D) TOPOLOGY: linear (xi) SEQUENCE DESCRIPTION: SEQ ID NO:210:

GGGTCCAGCC CCGT                                                              14

(2) INFORMATION FOR SEQ ID NO:211:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (xi) SEQUENCE DESCRIPTION: SEQ ID NO:211:

CAGCCCCCGG                                                                   10

(2) INFORMATION FOR SEQ ID NO:212:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:212:

```
Gly Ile Leu Ala Leu Asp Tyr Val Gly Gly
1               5                   10
```

(2) INFORMATION FOR SEQ ID NO:213:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:213:

```
Gly Ile Leu Thr Ile Asp Asn Leu Gly Gly
1               5                   10
```

(2) INFORMATION FOR SEQ ID NO:214:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:214:

```
Gly Ile Leu Leu Asn Glu Phe Ala Gly Gly
1               5                   10
```

(2) INFORMATION FOR SEQ ID NO:215:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:215:

```
Gly Pro Cys Leu Ile Leu Ala Pro Asp Arg Cys Gly
1               5                   10
```

(2) INFORMATION FOR SEQ ID NO:216:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:216:

```
Gly Pro Cys Ile Leu Leu Ala Arg Asp Arg Cys Gly
```

(2) INFORMATION FOR SEQ ID NO: 217:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 217:

```
Phe Ile Thr Cys Gly Pro Cys Ile Leu Leu Ala Arg Asp Arg Cys Gly
 1               5                  10                  15
```

(2) INFORMATION FOR SEQ ID NO: 218:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 218:

```
Cys Ile Leu Leu Ala Arg Asp Arg Cys
 1               5
```

(2) INFORMATION FOR SEQ ID NO: 219:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 219:

```
Ala Gly Pro Cys Leu Leu Leu Ala Pro Asp Arg Cys Pro Gly
 1               5                  10
```

(2) INFORMATION FOR SEQ ID NO: 220:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 220:

```
Ala Gly Pro Asp Asn Ile Ala Asp Pro Arg Cys Pro Gly
 1               5                  10
```

(2) INFORMATION FOR SEQ ID NO: 221:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 221:

```
Ala Gly Pro Leu Ser Asp Pro Gly Tyr Val Arg Asn Ile Phe His Pro
  1               5                  10                  15
Gly (2) INFORMATION FOR SEQ ID NO: 222:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 222:

Gly Ile Leu Ala Leu Asp Tyr Val Gly Gly
  1               5                  10

(2) INFORMATION FOR SEQ ID NO: 223:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 223:

Ala Gly Pro Ile Leu Leu Ala Arg Asp Arg Cys Pro Gly
  1               5                  10

(2) INFORMATION FOR SEQ ID NO: 224:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:  224:

Ala Gly Pro Cys Leu Ile Leu Ala Pro Asp Arg Cys Pro Gly
  1               5                  10

(2) INFORMATION FOR SEQ ID NO: 225:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:  225:

Cys Ala His Pro Asp Trp Asp Arg Cys
  1               5
```